I

US009200288B2

(12) United States Patent
Liao et al.

(10) Patent No.: US 9,200,288 B2
(45) Date of Patent: Dec. 1, 2015

(54) PRODUCTION OF 1,4-BUTANEDIOL BY RECOMBINANT MICROORGANISMS

(75) Inventors: James C. Liao, Los Angeles, CA (US); Yajun Yan, Bogart, GA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 13/639,487

(22) PCT Filed: Apr. 27, 2011

(86) PCT No.: PCT/US2011/034198
§ 371 (c)(1),
(2), (4) Date: Dec. 13, 2012

(87) PCT Pub. No.: WO2011/137192
PCT Pub. Date: Nov. 3, 2011

(65) Prior Publication Data
US 2013/0203141 A1    Aug. 8, 2013

Related U.S. Application Data

(60) Provisional application No. 61/328,301, filed on Apr. 27, 2010.

(51) Int. Cl.
| *C12N 15/70* | (2006.01) |
| *C12N 15/52* | (2006.01) |
| *C12P 7/16*  | (2006.01) |
| *C12P 7/18*  | (2006.01) |

(52) U.S. Cl.
CPC ............ *C12N 15/70* (2013.01); *C12N 15/52* (2013.01); *C12P 7/16* (2013.01); *C12P 7/18* (2013.01); *Y02E 50/10* (2013.01)

(58) Field of Classification Search
None
See application file for complete search history.

(56) References Cited

U.S. PATENT DOCUMENTS

| 4,551,433 A | 11/1985 | Deboer |
| 4,683,202 A | 7/1987 | Mullis |
| 5,426,039 A | 6/1995 | Wallace |
| 6,015,891 A | 1/2000 | Adang |

FOREIGN PATENT DOCUMENTS

| WO | 2009/023493 A1 | 2/2009 |
| WO | 2010/030711 A2 | 3/2010 |

OTHER PUBLICATIONS

Kizer L et al. Application of Functional Genomics to Pathway Optimization for Increased Isoprenoid Production. 2008. Applied and Environmental Microbiology. vol. 74, No. 10. p. 3229-3241.*
Prather KL et al. De novo biosynthetic pathways: rational design of microbial chemical factories. 2008. Current Opinion in Biotechnology. 19:468-474.*
Arnheim, N., and C. H. Levenson, "Polymerase Chain Reaction," Chemical & Engineering News 68(40):36-47, Oct. 1990.
Barringer, K. J., et al., "Blunt-End and Single-Strand Ligations by *Escherichia coli* Ligase: Influence on an In Vitro Amplification Scheme," Gene 89(1):117-122, Apr. 1990.
Cheng, S., et al., "As Increasingly Longer DNA Targets Are Amplified Reliably, New Applications for PCR Are Becoming Possible," Nature 369:684-685, Jun. 1994.
Dalphin, M. E., et al., "Transterm: a Database of Translational Signals," Nucleic Acids Research 24(1):216-218, 1996.
Guatelli, J. C., et al., "Isothermal, In Vitro Amplification of Nucleic Acids by a Multi-Enzyme Reaction Modeled After Retroviral Replication," Proceedings of the National Academy of Sciences of the United States of America (PNAS) 87(5):1874-1878, Mar. 1990.
Innis, M. A., et al., "PCR Protocols: A Guide to Methods and Applications," in M. A. Innis et al. (eds.), Academic Press, San Diego, Jan. 1990.
Kwoh, D.Y., et al., "Transcription-Based Amplification System and Detection of Amplified Human Immunodeficiency Virus Type 1 With a Bead-Based Sandwich Hybridization Format," Proceedings of the National Academy of Sciences of the United States of America (PNAS) 86(4):1173-1177, Feb. 1989.
Landegren, U., et al., "A Ligase-Mediated Gene Detection Technique," Science, 241(4869):1077-1080, Aug. 26, 1988.
Lomeli, H., et al., "Quantitative Assays Based on the Use of Replicatable Hybridization Probes," Clinical Chemistry 35(9):1826-1831, Sep. 1989.
Murray, E. E., et al., "Codon Usage in Plant Genes," Nucleic Acids Research 17:477-498, Jan. 1989.
Sooknanan, R., and L. T. Malek, "A Detection and Amplification System Uniquely Suited for RNA," Nature Biotechnology 13:563-564, 1995.
Van Brunt, J., "Amplifying Genes: PCR and Its Alternatives," Nature Biotechnology 8:291-294, 1990.
Wu, D. Y., and R. B. Wallace, "The Ligation Amplification Reaction (LAR)—Amplification of Specific DNA Sequences Using Sequential Rounds of Template-Dependent Ligation," Genomics 4(4):560-569, May 1989.
International Search Report mailed Aug. 9, 2011, issued in corresponding International Application No. PCT/US2011/034198, filed Apr. 27, 2011, 4 pages.
International Preliminary Report on Patentability and Written Opinion mailed Oct. 30, 2012, issued in corresponding International Application No. PCT/US2011/034198, filed Apr. 27, 2011, 4 pages.

* cited by examiner

*Primary Examiner* — David J Steadman
*Assistant Examiner* — Paul Holland
(74) *Attorney, Agent, or Firm* — Christensen O'Connor Johnson Kindness PLLC

(57) ABSTRACT

Provided herein are metabolically-modified microorganisms useful for producing 1,4-butanediol.

16 Claims, 5 Drawing Sheets

PRODUCTION OF 1,4-BUTANEDIOL BY RECOMBINANT MICROORGANISMS

CROSS-REFERENCE TO RELATED APPLICATION

This application claims priority to U.S. Provisional Application Ser. No. 61/328,301, filed Apr. 27, 2010, the disclosure of which is incorporated herein by reference.

STATEMENT REGARDING SEQUENCE LISTING

The sequence listing associated with this application is provided in text format in lieu of a paper copy and is hereby incorporated by reference into the specification. The name of the text file containing the sequence listing is 36584_SEQ_FINAL.txt. The text file is 316 KB; was created on 27 Apr. 2011; and is being submitted via EFS-Web with the filing of the specification.

TECHNICAL FIELD

Metabolically-modified microorganisms and methods of producing such organisms are provided. Also provided are methods of producing 1,4-butanediol by contacting a suitable substrate with a metabolically-modified microorganism and enzymatic preparations there from.

BACKGROUND 1,4-Butanediol is an industrial solvent and is used in the manufacture of some types of plastics, elastic fibers, and polyurethanes. 1,4-Butanediol is also used for the synthesis of γ-butyrolactone (GBL). 1,4-Butanediol is also used for the production of the important solvents tetrahydrofuran and butyrolactone.

World production of 1,4-butanediol is about one million metric tons per year. Almost half of it is dehydrated to tetrahydrofuran to make fibers such as Spandex.

SUMMARY

The disclosure provides methods and recombinant microorganisms for the production of 1,4-butanediol.

In some embodiments, a recombinant microorganism is provided that produces 1,4-butanediol wherein the microorganism produces at least the following metabolic intermediates: a. xylonic acid; b. 3-deoxy-D-glycero-pentulosonic acid; c. 3,4-dihydroxy-D-butanal; d. 1,2,4-butanetriol; and e. 4-hydroxybutanal.

Also provided is a recombinant microorganism that overexpresses a xylonate dehydrogenase, a xylonate dehydratase, a decarboxylase, a first alcohol dehydrogenase, a diol dehydratase, and a second alcohol dehydrogenase, as compared to the parental microorganism.

Also provided is a method of producing a recombinant microorganism that converts xylose to 1,4-butanediol, the method comprising transforming a microorganism with one or more recombinant nucleic acid sequences encoding xylonate dehydrogenase activity, xylonate dehydratase activity, decarboxylase activity, a first alcohol dehydrogenase activity, diol dehydratase activity, and a second alcohol dehydrogenase activity.

Also provided is a method of producing 1,4-butanediol, comprising: a. providing a recombinant microorganism as disclosed herein; b. culturing the microorganism in the presence of xylose under conditions suitable for the conversion of xylose to 1,4-butanediol; and c. isolating the 1,4-butanediol.

The disclosure also provides a recombinant microorganism or microorganism culture (e.g., a plurality of recombinant organisms with the same or different enzymes) that produces 1,4-butanediol comprising a recombinant metabolic pathway as set forth in FIG. 1. In one embodiment, the microorganism comprises expression of a non-natural polypeptide of the organism or over expression of an endogenous polypeptide of the organism wherein the polypeptide has an activity selected from the group consisting of xylose dehydrogenase; xylonate dehydratase; benzoylformate decarboxylase; alcohol dehydrogenase; diol dehydratase; and any combination thereof. In yet another embodiment, the microorganism comprises reduced or knocked-out expression of a polypeptide having an activity selected from the group consisting of: D-xylose isomerase (XylA); 2-keto acid aldolase (YagE and YjhH); 2-keto acid transaminase; 2-keto acid dehydrogenase; and any combination thereof.

The details of one or more embodiments of the disclosure are set forth in the accompanying drawings and the description below. Other features, objects, and advantages will be apparent from the description and drawings, and from the claims.

DESCRIPTION OF THE DRAWINGS

The accompanying drawings, which are incorporated into and constitute a part of this specification, illustrate one or more embodiments of the disclosure and, together with the detailed description, serve to explain the principles and implementations of the invention.

DETAILED DESCRIPTION

Figure 1:
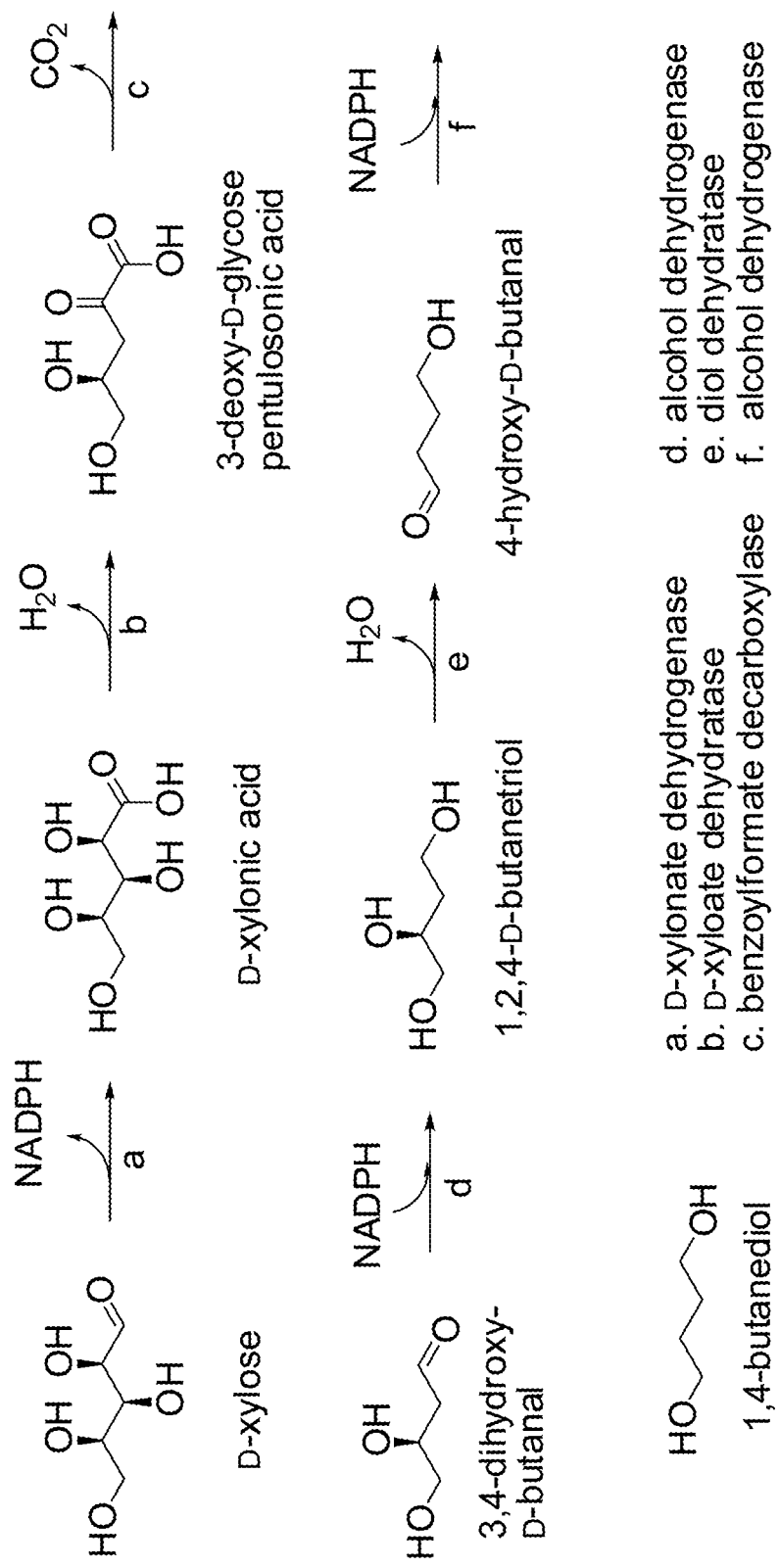
FIG. 1 shows an exemplary metabolic pathway for the production of 1,4-butanediol.

As used herein and in the appended claims, the singular forms "a," "and," and "the" include plural referents unless the context clearly dictates otherwise. Thus, for example, reference to "a polynucleotide" includes a plurality of such polynucleotides and reference to "the microorganism" includes reference to one or more microorganisms, and so forth.

Unless defined otherwise, all technical and scientific terms used herein have the same meaning as commonly understood to one of ordinary skill in the art to which this disclosure belongs. Although methods and materials similar or equivalent to those described herein can be used in the practice of the disclosed methods and compositions, the exemplary methods, devices and materials are described herein.

Any publications discussed above and throughout the text are provided solely for their disclosure prior to the filing date of the present application. Nothing herein is to be construed as an admission that the inventors are not entitled to antedate such disclosure by virtue of prior disclosure.

By "about" is meant a quantity, level, value, number, frequency, percentage, dimension, size, amount, weight, or length that varies by as much as 30, 25, 20, 25, 10, 9, 8, 7, 6, 5, 4, 3, 2, or 1% to a reference quantity, level, value, number, frequency, percentage, dimension, size, amount, weight, or length.

The disclosure provides metabolically engineered microorganisms comprising biochemical pathways for the production of 1,4-butanediol from a suitable substrate. A metabolically engineered microorganism of the disclosure comprises one or more recombinant polynucleotides within the genome of the organism or external to the genome within the organism. The microorganism can comprise a reduction, disruption, or knockout of a gene found in the wild-type organism and/or introduction of a heterologous polynucleotide.

The disclosure also includes metabolically engineered biosynthetic pathways that utilize an organism's native pathways, in part, to provide metabolic intermediates for the production of 1,4-butanediol.

In one embodiment, the disclosure provides a recombinant microorganism comprising elevated expression of at least one target enzyme as compared to a parental microorganism or encodes an enzyme not found in the parental organism. In another or further embodiment, the microorganism comprises a reduction, disruption, or knockout of at least one gene encoding an enzyme that competes with a metabolite necessary for the production of a desired metabolic intermediate. The recombinant microorganism produces at least one metabolite involved in a biosynthetic pathway for the production of 1,4-butanediol. In general, the recombinant microorganism comprises at least one recombinant metabolic pathway that comprises a target enzyme and can further include a reduction in activity or expression of an enzyme in a competitive biosynthetic pathway. The pathway acts to modify a substrate or metabolic intermediate in the production of 1,4-butanediol. The target enzyme is encoded by, and expressed from, a polynucleotide derived from a suitable biological source. In some embodiments, the polynucleotide comprises a gene derived from a bacterial or yeast source and recombinantly engineered into the microorganism of the disclosure.

In some embodiments, a recombinant microorganism is provided that produces 1,4-butanediol wherein the microorganism produces at least the following metabolic intermediates: a. xylonic acid; b. 3-deoxy-D-glycero-pentulosonic acid; c. 3,4-dihydroxy-D-butanal; d. 1,2,4-butanetriol; and e. 4-hydroxybutanal.

In some embodiments, the microorganism over-expresses a xylonate dehydrogenase, a xylonate dehydratase, a decarboxylase, a first alcohol dehydrogenase, a diol dehydratase, and a second alcohol dehydrogenase, as compared to the parental microorganism.

The xylonate dehydrogenase may be endogenous or heterologous to the parental microorganism. The xylonate dehydrogenase may be derived from, e.g., *Burkholderia fungorum* or *Caulobacter crescentus*. In some embodiments, a xylonate dehydrogenase comprises an amino acid sequence of either SEQ ID NO:2 or SEQ ID NO:4, or a conservative-substituted variant of or homologous polypeptide to either SEQ ID NO:2 or SEQ ID NO:4 having at least 70% identity to either SEQ ID NO:2 or SEQ ID NO:4 and having xylonate dehydrogenase activity. In some embodiments, the xylonate dehydrogenase comprises an amino acid sequence of either SEQ ID NO:11 or SEQ ID NO:12.

The xylonate dehydratase may be endogenous or heterologous to the parental microorganism. In some embodiments, the xylonate dehydratase is derived from *Escherichia coli*. The xylonate dehydratase may be an over-expressed endogenous *Escherichia coli* D-xylonate dehydratase associated with the yagF and yjhG loci in the *E. coli*. The xylonate dehydratase may be a heterologous D-xylonate dehydratase comprising the amino acid sequence of any one of SEQ ID NO:6, SEQ ID NO:8, or a conservative-substituted variant of or homologous polypeptide to SEQ ID NO:6 or SEQ ID NO:8 having at least 70% identity to SEQ ID NO:6 or SEQ ID NO:8 and having D-xylonate dehydratase activity.

In some embodiments, the decarboxylase is a benzoylformate decarboxylase. The benzoylformate decarboxylase may be endogenous or heterologous to the parental microorganism. In some embodiments, the benzoylformate decarboxylase is derived from *Pseudomonas pudita*. The benzoylformate decarboxylase may be a heterologous benzoylformate decarboxylase comprising the amino acid sequence of SEQ ID NO:9, or a conservative-substituted variant of or homologous polypeptide to SEQ ID NO:9 having at least 70% identity to SEQ ID NO:9 and having benzoylformate decarboxylase activity.

The first alcohol dehydrogenase or the second alcohol dehydrogenase may be endogenous or heterologous to the parental microorganism. In some embodiments, the first alcohol dehydrogenase or the second alcohol dehydrogenase is derived from *E. coli*. In some embodiments, the first alcohol dehydrogenase or the second alcohol dehydrogenase is a heterologous first alcohol dehydrogenase or a heterologous second alcohol dehydrogenase comprising the amino acid sequence of SEQ ID NO:10, or a conservative-substituted variant of or homologous polypeptide to SEQ ID NO:10 having at least 70% identity to SEQ ID NO:10 and having alcohol dehydrogenase activity. The first alcohol dehydrogenase may be the same as the second alcohol dehydrogenase. The first alcohol dehydrogenase may be different from the second alcohol dehydrogenase.

In some embodiments, the diol dehydratase is derived from *Listeria*, *Amycolatopsis*, *Klebsiella*, *Pseudomaonas*, *Salmonella*, *Lactobacillus*, or *Yersinia*.

A recombinant microorganism may comprise decreased or knocked out expression of a polypeptide that produces a flux that competes with one or more metabolic intermediates. The polypeptide that produces a flux that competes with one or more metabolic intermediates can be selected from, e.g., a. a D-xylose isomerase; b. a 2-keto acid aldolase; c. a 2-keto acid transaminase; d. a 2-keto acid dehydrogenase; and any combination thereof.

Also provided is a recombinant microorganism that over-expresses a xylonate dehydrogenase, a xylonate dehydratase, a decarboxylase, a first alcohol dehydrogenase, a diol dehydratase, and a second alcohol dehydrogenase, as compared to the parental microorganism.

A recombinant microorganism may be, for example, an *Escherichia*, a *Corynebacterium*, a *Lactobacillus*, or a *Bacillus*.

Any recombinant microorganism disclosed herein may be comprised in a host cell, such as yeast or bacteria. In some embodiments, the microorganism is comprised in a host cell selected from *Escherichia, Corynebacterium, Lactobacillus*, and *Bacillus*. In some embodiments, the microorganism is comprised in a host cell selected from *E. coli, Saccharomyces cerevisiae*, and *Pichia pastoris*.

Also provided is a method of producing a recombinant microorganism that converts xylose to 1,4-butanediol, the method comprising transforming a microorganism with one or more recombinant nucleic acid sequences encoding xylonate dehydrogenase activity, xylonate dehydratase activity, decarboxylase activity, a first alcohol dehydrogenase activity, diol dehydratase activity, and a second alcohol dehydrogenase activity.

Also provided is a method of producing 1,4-butanediol, comprising: a. providing a recombinant microorganism as disclosed herein; b. culturing the microorganism in the presence of xylose under conditions suitable for the conversion of xylose to 1,4-butanediol; and c. isolating the 1,4-butanediol.

As used herein, the term "metabolically engineered" or "metabolic engineering" involves rational pathway design and assembly of biosynthetic genes, genes associated with operons, and control elements of such polynucleotides, for the production of a desired metabolite, such as a D-xylonic acid, 3,4-dihydroxy-D-butanal, and the like as set forth in FIG. 1 in a microorganism. "Metabolically engineered" can further include optimization of metabolic flux by regulation and optimization of transcription, translation, protein stability, and protein functionality using genetic engineering and appropriate culture conditions including the reduction of, disruption, or knocking out of, a competing metabolic pathway that competes with an intermediate leading to a desired pathway. A biosynthetic gene can be heterologous to the host microorganism, either by virtue of being foreign to the host, or being modified by mutagenesis, recombination, and/or association with a heterologous expression control sequence in an endogenous host cell. In one embodiment, where the polynucleotide is xenogenetic to the host organism, the polynucleotide can be codon optimized.

The term "biosynthetic pathway", also referred to as "metabolic pathway", refers to a set of anabolic or catabolic biochemical reactions for converting (transmuting) one chemical species into another. Gene products belong to the same "metabolic pathway" if they, in parallel or in series, act on the same substrate, produce the same product, or act on or produce a metabolic intermediate (i.e., metabolite) between the same substrate and metabolite end product.

The term "substrate" or "suitable substrate" refers to any substance or compound that is converted or meant to be converted into another compound by the action of an enzyme. The term includes not only a single compound, but also combinations of compounds, such as solutions, mixtures and other materials which contain at least one substrate, or derivatives thereof. Further, the term "substrate" encompasses not only compounds that provide a carbon source suitable for use as a starting material, such as any biomass derived sugar, but also intermediate and end product metabolites used in a pathway associated with a metabolically engineered microorganism as described herein. A "biomass derived sugar" includes, but is not limited to, molecules such as glucose, sucrose, mannose, xylose, and arabinose. The term biomass derived sugar encompasses suitable carbon substrates ordinarily used by microorganisms in either D or L form.

Recombinant microorganisms provided herein can express a plurality of target enzymes involved in pathways for the production of 1,4-butanediol from using a suitable carbon substrate.

Accordingly, metabolically "engineered" or "modified" microorganisms are produced via the introduction of genetic material into a host or parental microorganism of choice thereby modifying or altering the cellular physiology and biochemistry of the microorganism. Through the introduction of genetic material the parental microorganism acquires new properties, e.g., the ability to produce a new, or greater quantities of, an intracellular metabolite. In an illustrative embodiment, the introduction of genetic material into a parental microorganism results in a new or modified ability to produce 1,4-butanediol. The genetic material introduced into the parental microorganism contains gene(s), or parts of genes, coding for one or more of the enzymes involved in a biosynthetic pathway for the production of 1,4-butanediol and can also include additional elements for the expression and/or regulation of expression of these genes, e.g., promoter sequences.

An engineered or modified microorganism can also include in the alternative, or in addition to, the introduction of a genetic material into a host or parental microorganism, the disruption, deletion, or knocking out of a gene or polynucleotide to alter the cellular physiology and biochemistry of the microorganism. Through the reduction, disruption, or knocking out of a gene or polynucleotide, the microorganism acquires new or improved properties (e.g., the ability to produced a new or greater quantities of an intracellular metabolite, improve the flux of a metabolite down a desired pathway, and/or reduce the production of undesirable by-products).

The disclosure demonstrates that the expression of one or more heterologous polynucleotide(s) or over-expression of one or more heterologous polynucleotide(s) encoding i) a polypeptide having xylose (xylonate) dehydrogenase activity and ii) a polypeptide having xylonate dehydratase activity, iii) a polypeptide having benzoylformate decarboxylase activity, iv) a polypeptide having alcohol dehydrogenase activity, and v) a polypeptide having diol dehydratase activity, will produce 1,4-butanediol.

For example, the disclosure demonstrates that with (i) over-expression or heterologous expression of a D-xylose dehydrogenase comprising the amino acid sequence of any one of SEQ ID NO:2 or SEQ ID NO:4 (See Tables 1 and 2), or a conservative-substituted variant of or homologous polypeptide to SEQ ID NO:2 or SEQ ID NO:4 having at least 70 to 99% identity to SEQ ID NO:2 or 4 and having D-xylose dehydrogenase activity (such as a xylose dehydrogenase derived from *Haloarcula marismortui, Burkholderia fugorum* LB400, *Haloferax volcanii* DS2, (see, e.g., GenBank Accession Nos. AAW78223 (SEQ ID NO:11), RBU11704 (SEQ ID NO:2), and YP_003533786 (SEQ ID NO:12), respectively, the sequence associated with the accession number is incorporated herein by reference); (ii) over-expression of the endogenous *E. coli* D-xylonate dehydratase associated with the yagF and yjhG loci in the *E. coli* or the heterologous expression of a D-xylonic acid dehydratase comprising the amino acid sequence of any one of SEQ ID NO:6 (See Table 3), SEQ ID NO:8 (See Table 4), or a conservative-substituted variant of or homologous polypeptide to SEQ ID NO:6 or SEQ ID NO:8 having at least 60% to 99% identity to SEQ ID NO:6 or 8 and having D-xylonate dehydratase activity; (iii) over-expression or heterologous expression of a decarboxylase such as, for example, a benzoylformate decarboxylase from *Pseudomonas pudita* comprising an amino acid sequence as set forth in SEQ ID NO:9 (see also Table 5) and sequences having at least 60 to 99% identity to a sequence set forth in SEQ ID NO:9 or a homology or ortholog set forth in Table 5 and having decarboxylase activity; (iv) over expression or heterologous expression of an alcohol dehydrogenase (e.g., an AdhP alcohol dehydrogenase from *E.* coli) having, for example, an amino acid sequence as set forth in SEQ ID NO:10 (see also Table 6) and sequences having at least 60 to 99% identity to a sequence set forth in SEQ ID NO:10 or a homology or ortholog set forth in Table 6 and having alcohol dehydrogenase activity; and (v) over expression or heterologous expression of a diol dehydratase (also known as "butanediol dehydratase" or "propanediol dehydratase"), 1,4-butanediol will be produced.

TABLE 1

Coding sequence for *Burkholderia fungorum* LB400 RBU11704 xylose dehydrogenase. SEQ ID NO: 1 and SEQ ID NO: 2

```
atg tat ttg ttg tca tac ccg gaa cag gtg gac tat ccg atg tcg tac    48
Met Tyr Leu Leu Ser Tyr Pro Glu Gln Val Asp Tyr Pro Met Ser Tyr

TABLE 2

Coding sequences for *Caulobacter crescentus* CB15 RC001012 xylose dehydrogenase. SEQ ID NO: 3 and SEQ ID NO 4:

```
atg tcc tca gcc atc tat ccc agc ctg aag ggc aag cgc gtc gtc atc    48
Met Ser Ser Ala Ile Tyr Pro Ser Leu Lys Gly Lys Arg Val Val Ile
 1               5                  10                  15 acc ggc ggc ggc tcg ggc atc ggg gcc ggc ctc acc gcc ggc ttc gcc    96
Thr Gly Gly Gly Ser Gly Ile Gly Ala Gly Leu Thr Ala Gly Phe Ala
                20                  25                  30 cgt cag ggc gcg gag gtg atc ttc ctc gac atc gcc gac gag gac tcc   144
Arg Gln Gly Ala Glu Val Ile Phe Leu Asp Ile Ala Asp Glu Asp Ser
            35                  40                  45 agg gct ctt gag gcc gag ctg gcc ggc tcg ccg atc ccg ccg gtc tac   192
Arg Ala Leu Glu Ala Glu Leu Ala Gly Ser Pro Ile Pro Pro Val Tyr
        50                  55                  60 aag cgc tgc gac ctg atg aac ctc gag gcg atc aag gcg gtc ttc gcc   240
Lys Arg Cys Asp Leu Met Asn Leu Glu Ala Ile Lys Ala Val Phe Ala
65                  70                  75                  80 gag atc ggc gac gtc gac gtg ctg gtc aac aac gcc ggc aat gac gac   288
Glu Ile Gly Asp Val Asp Val Leu Val Asn Asn Ala Gly Asn Asp Asp
                85                  90                  95 cgc cac aag ctg gcc gac gtg acc ggc gcc tat tgg gac gag cgg atc   336
Arg His Lys Leu Ala Asp Val Thr Gly Ala Tyr Trp Asp Glu Arg Ile
            100                 105                 110 aac gtc aac ctg cgc cac atg ctg ttc tgc acc cag gcc gtc gcg ccg   384
Asn Val Asn Leu Arg His Met Leu Phe Cys Thr Gln Ala Val Ala Pro
        115                 120                 125 ggc atg aag aag cgt ggc ggc ggg gcg gtg atc aac ttc ggt tcg atc   432
Gly Met Lys Lys Arg Gly Gly Gly Ala Val Ile Asn Phe Gly Ser Ile
130                 135                 140 agc tgg cac ctg ggg ctt gag gac ctc gtc ctc tac gaa acc gcc aag   480
Ser Trp His Leu Gly Leu Glu Asp Leu Val Leu Tyr Glu Thr Ala Lys
145                 150                 155                 160 gcc ggc atc gaa ggc atg acc cgc gcg ctg gcc cgg gag ctg ggt ccc   528
Ala Gly Ile Glu Gly Met Thr Arg Ala Leu Ala Arg Glu Leu Gly Pro
                165                 170                 175 gac gac atc cgc gtc acc tgc gtg gtg ccg ggc aac gtc aag acc aag   576
Asp Asp Ile Arg Val Thr Cys Val Val Pro Gly Asn Val Lys Thr Lys
            180                 185                 190 cgc cag gag aag tgg tac acg ccc gaa ggc gag gcc cag atc gtg gcg   624
Arg Gln Glu Lys Trp Tyr Thr Pro Glu Gly Glu Ala Gln Ile Val Ala
        195                 200                 205 gcc caa tgc ctg aag ggc cgc atc gtc ccg gag aac gtc gcc gcg ctg   672
Ala Gln Cys Leu Lys Gly Arg Ile Val Pro Glu Asn Val Ala Ala Leu
210                 215                 220 gtg ctg ttc ctg gcc tcg gat gac gcg tcg ctc tgc acc ggc cac gaa   720
Val Leu Phe Leu Ala Ser Asp Asp Ala Ser Leu Cys Thr Gly His Glu
225                 230                 235                 240 tac tgg atc gac gcc ggc tgg cgt tga                               747
Tyr Trp Ile Asp Ala Gly Trp Arg
                245
```

TABLE 3

Coding sequence for *Escherichia coli* yagF xylonate dehydratase. SEQ ID NO: 5 and SEQ ID NO: 6.

```
atg acc att gag aaa att ttc acc ccg cag gac gac gcg ttt tat gcg    48
Met Thr Ile Glu Lys Ile Phe Thr Pro Gln Asp Asp Ala Phe Tyr Ala
 1               5                  10                  15 gtg atc acc cac gcg gcg ggg ccg cag ggc gct ctg ccg ctg acc ccg    96
```

TABLE 3-continued

Coding sequence for *Escherichia coli* yagF xylonate dehydratase.
SEQ ID NO: 5 and SEQ ID NO: 6.

| | | | | | | | | | | | | |
|---|---|---|---|---|---|---|---|---|---|---|---|---|
| Val | Ile | Thr | His | Ala | Ala | Gly | Pro | Gln | Gly | Ala | Leu | Pro | Thr | Pro |
| | | | 20 | | | | 25 | | | | 30 | |

```
cag atg ctg atg gaa tct ccc agc ggc aac ctg ttc ggc atg acg cag    144
Gln Met Leu Met Glu Ser Pro Ser Gly Asn Leu Phe Gly Met Thr Gln
         35                  40                  45 aac gcc ggg atg ggc tgg gac gcc aac aag ctc acc ggc aaa gag gtg    192
Asn Ala Gly Met Gly Trp Asp Ala Asn Lys Leu Thr Gly Lys Glu Val
     50                  55                  60 ctg att atc ggc act cag ggc ggc atc cgc gcc gga gac gga cgc cca    240
Leu Ile Ile Gly Thr Gln Gly Gly Ile Arg Ala Gly Asp Gly Arg Pro
65                  70                  75                  80 atc gcg ctg ggc tac cac acc ggg cat tgg gag atc ggc atg cag atg    288
Ile Ala Leu Gly Tyr His Thr Gly His Trp Glu Ile Gly Met Gln Met
                 85                  90                  95 cag gcg gcg gcg aag gag atc acc cgc aat ggc ggg atc ccg ttc gcg    336
Gln Ala Ala Ala Lys Glu Ile Thr Arg Asn Gly Gly Ile Pro Phe Ala
            100                 105                 110 gcc ttc gtc agc gat ccg tgc gac ggg cgc tcg cag ggc acg cac ggt    384
Ala Phe Val Ser Asp Pro Cys Asp Gly Arg Ser Gln Gly Thr His Gly
        115                 120                 125 atg ttc gat tcc ctg ccg tac cgc aac gac gcg gcg atc gtg ttt cgc    432
Met Phe Asp Ser Leu Pro Tyr Arg Asn Asp Ala Ala Ile Val Phe Arg
    130                 135                 140 cgc ctg atc cgc tcc ctg ccg acg cgg cgg gcg gtg atc ggc gta gcg    480
Arg Leu Ile Arg Ser Leu Pro Thr Arg Arg Ala Val Ile Gly Val Ala
145                 150                 155                 160 acc tgc gat aaa ggg ctg ccc gcc acc atg att gcg ctg gcc gcg atg    528
Thr Cys Asp Lys Gly Leu Pro Ala Thr Met Ile Ala Leu Ala Ala Met
                165                 170                 175 cac gac ctg ccg act att ctg gtg ccg ggg ggg gcg acg ctg ccg ccg    576
His Asp Leu Pro Thr Ile Leu Val Pro Gly Gly Ala Thr Leu Pro Pro
            180                 185                 190 acc gtc ggg gaa gac gcg ggc aag gtg cag acc atc ggc gcg cgt ttc    624
Thr Val Gly Glu Asp Ala Gly Lys Val Gln Thr Ile Gly Ala Arg Phe
        195                 200                 205 gcc aac cac gaa ctc tcc ctg cag gag gcc gcc gaa ctg ggc tgt cgc    672
Ala Asn His Glu Leu Ser Leu Gln Glu Ala Ala Glu Leu Gly Cys Arg
    210                 215                 220 gcc tgc gcc tcg ccg ggc ggc ggg tgt cag ttc ctc ggc acg gcg ggc    720
Ala Cys Ala Ser Pro Gly Gly Gly Cys Gln Phe Leu Gly Thr Ala Gly
225                 230                 235                 240 acc tcg cag gtg gtc gcg gag gcg ctg ggt ctg gcg ctg ccg cac tcc    768
Thr Ser Gln Val Val Ala Glu Ala Leu Gly Leu Ala Leu Pro His Ser
                245                 250                 255 gcg ctg gcg ccg tcc ggg cag gcg gtg tgg ctg gag atc gcc cgc cag    816
Ala Leu Ala Pro Ser Gly Gln Ala Val Trp Leu Glu Ile Ala Arg Gln
            260                 265                 270 tcg gcg cgc gcg gtc agc gag ctg gat agc cgc ggc atc acc acg cgg    864
Ser Ala Arg Ala Val Ser Glu Leu Asp Ser Arg Gly Ile Thr Thr Arg
        275                 280                 285 gat atc ctc tcc gat aaa gcc atc gaa aac gcg atg gtg atc cac gcg    912
Asp Ile Leu Ser Asp Lys Ala Ile Glu Asn Ala Met Val Ile His Ala
    290                 295                 300 gcg ttc ggc ggc tcc acc aat tta ctg ctg cac att ccg gcc atc gcc    960
Ala Phe Gly Gly Ser Thr Asn Leu Leu Leu His Ile Pro Ala Ile Ala
305                 310                 315                 320 cac gcg gcg ggc tgc acg atc ccg gac gtt gag cac tgg acg cgc atc    1008
His Ala Ala Gly Cys Thr Ile Pro Asp Val Glu His Trp Thr Arg Ile
```

TABLE 3-continued

Coding sequence for *Escherichia coli* yagF xylonate dehydratase.
SEQ ID NO: 5 and SEQ ID NO: 6.

```
                    325                      330                      335
aac cgt aaa gtg ccg cgt ctg gtg agc gtg ctg ccc aac ggc ccg gac     1056
Asn Arg Lys Val Pro Arg Leu Val Ser Val Leu Pro Asn Gly Pro Asp
            340                  345                  350
tat cac ccg acc gtg cgc gcc ttc ctc gcg ggc ggc gtg ccg gag gtg     1104
Tyr His Pro Thr Val Arg Ala Phe Leu Ala Gly Gly Val Pro Glu Val
            355                  360                  365
atg ctc cac ctg cgc gac ctc ggc ctg ctg cat ctg gac gcc atg acc     1152
Met Leu His Leu Arg Asp Leu Gly Leu Leu His Leu Asp Ala Met Thr
            370                  375                  380
gtg acc ggc cag acg gtg ggc gag aac ctt gaa tgg tgg cag gcg tcc     1200
Val Thr Gly Gln Thr Val Gly Glu Asn Leu Glu Trp Trp Gln Ala Ser
385                  390                  395                  400
gag cgc cgg gcg cgc ttc cgc cag tgc ctg cgc gag cag gac ggc gta     1248
Glu Arg Arg Ala Arg Phe Arg Gln Cys Leu Arg Glu Gln Asp Gly Val
                405                  410                  415
gag ccg gat gac gtg atc ctg ccg ccg gag aag gca aaa gcg aaa ggg     1296
Glu Pro Asp Asp Val Ile Leu Pro Pro Glu Lys Ala Lys Ala Lys Gly
            420                  425                  430
ctg acc tcg acg gtc tgc ttc ccg acg ggc aac atc gct ccg gaa ggt     1344
Leu Thr Ser Thr Val Cys Phe Pro Thr Gly Asn Ile Ala Pro Glu Gly
            435                  440                  445
tcg gtg atc aag gcc acg gcg atc gac ccg tcg gtg gtg ggc gaa gat     1392
Ser Val Ile Lys Ala Thr Ala Ile Asp Pro Ser Val Val Gly Glu Asp
            450                  455                  460
ggc gta tac cac cac acc ggc cgg gtg cgg gtg ttt gtc tcg gaa gcg     1440
Gly Val Tyr His His Thr Gly Arg Val Arg Val Phe Val Ser Glu Ala
465                  470                  475                  480
cag gcg atc aag gcg atc aag cgg gaa gag att gtg cag ggc gat atc     1488
Gln Ala Ile Lys Ala Ile Lys Arg Glu Glu Ile Val Gln Gly Asp Ile
                485                  490                  495
atg gtg gtg atc ggc ggc ggg ccg tcc ggc acc ggc atg gaa gag acc     1536
Met Val Val Ile Gly Gly Gly Pro Ser Gly Thr Gly Met Glu Glu Thr
            500                  505                  510
tac cag ctc acc tcc gcg cta aag cat atc tcg tgg ggc aag acg gtg     1584
Tyr Gln Leu Thr Ser Ala Leu Lys His Ile Ser Trp Gly Lys Thr Val
            515                  520                  525
tcg ctc atc acc gat gcg cgc ttc tcg ggc gtg tcg acg ggc gcc tgc     1632
Ser Leu Ile Thr Asp Ala Arg Phe Ser Gly Val Ser Thr Gly Ala Cys
            530                  535                  540
ttc ggc cac gtg tcg ccg gag gcg ctg gcg ggc ggg ccg att ggc aag     1680
Phe Gly His Val Ser Pro Glu Ala Leu Ala Gly Gly Pro Ile Gly Lys
545                  550                  555                  560
ctg cgc gat aac gac atc atc gag att gcc gtg gat cgt ctg acg tta     1728
Leu Arg Asp Asn Asp Ile Ile Glu Ile Ala Val Asp Arg Leu Thr Leu
                565                  570                  575
act ggc agc gtg aac ttc atc ggc acc gcg gac aac ccg ctg acg ccg     1776
Thr Gly Ser Val Asn Phe Ile Gly Thr Ala Asp Asn Pro Leu Thr Pro
                580                  585                  590
gaa gag ggc gcg cgc gag ctg gcg cgg cgg cag acg cac ccg gac ctg     1824
Glu Glu Gly Ala Arg Glu Leu Ala Arg Arg Gln Thr His Pro Asp Leu
595                  600                  605
cac gcc cac gac ttt ttg ccg gac gac acc cgg ctg tgg gcg gca ctg     1872
His Ala His Asp Phe Leu Pro Asp Asp Thr Arg Leu Trp Ala Ala Leu
                610                  615                  620
cag tcg gtg agc ggc ggc acc tgg aaa ggc tgt att tat gac acc gat     1920
Gln Ser Val Ser Gly Gly Thr Trp Lys Gly Cys Ile Tyr Asp Thr Asp
625                  630                  635                  640
```

TABLE 3-continued

Coding sequence for *Escherichia coli* yagF xylonate dehydratase.
SEQ ID NO: 5 and SEQ ID NO: 6.

| | | | | | | | | | | | | | | | | |
|---|---|---|---|---|---|---|---|---|---|---|---|---|---|---|---|---|
| aaa | att | atc | gag | gta | att | aac | gcc | ggt | aaa | aaa | gcg | ctc | gga | att | taa | 1968 |
| Lys | Ile | Ile | Glu | Val | Ile | Asn | Ala | Gly | Lys | Lys | Ala | Leu | Gly | Ile | | |
| | | | 645 | | | | 650 | | | | 655 | | | | | |

TABLE 4

Coding sequences for *E. coli* yjhG xylonate dehydratase.
SEQ ID NO: 7 and SEQ ID NO: 8

| | | | | | | | | | | | | | | | | |
|---|---|---|---|---|---|---|---|---|---|---|---|---|---|---|---|---|
| atg | tct | gtt | cgc | aat | att | ttt | gct | gac | gag | agc | cac | gat | att | tac | acc | 48 |
| Met | Ser | Val | Arg | Asn | Ile | Phe | Ala | Asp | Glu | Ser | His | Asp | Ile | Tyr | Thr | |
| 1 | | | | 5 | | | | 10 | | | | 15 | | | | |
| gtc | aga | acg | cac | gcc | gat | ggc | ccg | gac | ggc | gaa | ctc | cca | tta | acc | gca | 96 |
| Val | Arg | Thr | His | Ala | Asp | Gly | Pro | Asp | Gly | Glu | Leu | Pro | Leu | Thr | Ala | |
| | | | 20 | | | | 25 | | | | 30 | | | | | |
| gag | atg | ctt | atc | aac | cgc | ccg | agc | ggg | gat | ctg | ttc | ggt | atg | acc | atg | 144 |
| Glu | Met | Leu | Ile | Asn | Arg | Pro | Ser | Gly | Asp | Leu | Phe | Gly | Met | Thr | Met | |
| | | 35 | | | | 40 | | | | 45 | | | | | | |
| aat | gcc | gga | atg | ggt | tgg | tct | ccg | gac | gag | ctg | gat | cgg | gac | ggt | att | 192 |
| Asn | Ala | Gly | Met | Gly | Trp | Ser | Pro | Asp | Glu | Leu | Asp | Arg | Asp | Gly | Ile | |
| | 50 | | | | 55 | | | | 60 | | | | | | | |
| tta | ctg | ctc | agt | aca | ctc | ggt | ggc | tta | cgc | ggc | gca | gac | ggt | aaa | ccc | 240 |
| Leu | Leu | Leu | Ser | Thr | Leu | Gly | Gly | Leu | Arg | Gly | Ala | Asp | Gly | Lys | Pro | |
| 65 | | | | 70 | | | | 75 | | | | 80 | | | | |
| gtg | gcg | ctg | gcg | ttg | cac | cag | ggg | cat | tac | gaa | ctg | gac | atc | cag | atg | 288 |
| Val | Ala | Leu | Ala | Leu | His | Gln | Gly | His | Tyr | Glu | Leu | Asp | Ile | Gln | Met | |
| | | | | 85 | | | | 90 | | | | 95 | | | | |
| aaa | gcg | gcg | gcc | gag | gtt | att | aaa | gcc | aac | cat | gcc | ctg | ccc | tat | gcc | 336 |
| Lys | Ala | Ala | Ala | Glu | Val | Ile | Lys | Ala | Asn | His | Ala | Leu | Pro | Tyr | Ala | |
| | | | 100 | | | | 105 | | | | 110 | | | | | |
| gtg | tac | gtc | tcc | gat | cct | tgt | gac | ggg | cgt | act | cag | ggt | aca | acg | ggg | 384 |
| Val | Tyr | Val | Ser | Asp | Pro | Cys | Asp | Gly | Arg | Thr | Gln | Gly | Thr | Thr | Gly | |
| | | | 115 | | | | 120 | | | | 125 | | | | | |
| atg | ttt | gat | tcg | cta | cca | tac | cga | aat | gac | gca | tcg | atg | gta | atg | cgc | 432 |
| Met | Phe | Asp | Ser | Leu | Pro | Tyr | Arg | Asn | Asp | Ala | Ser | Met | Val | Met | Arg | |
| | | 130 | | | | 135 | | | | 140 | | | | | | |
| cgc | ctt | att | cgc | tct | ctg | ccc | gac | gcg | aaa | gca | gtt | att | ggt | gtg | gcg | 480 |
| Arg | Leu | Ile | Arg | Ser | Leu | Pro | Asp | Ala | Lys | Ala | Val | Ile | Gly | Val | Ala | |
| 145 | | | | 150 | | | | 155 | | | | 160 | | | | |
| agt | tgc | gat | aag | ggg | ctt | ccg | gcc | acc | atg | atg | gca | ctc | gcc | gcg | cag | 528 |
| Ser | Cys | Asp | Lys | Gly | Leu | Pro | Ala | Thr | Met | Met | Ala | Leu | Ala | Ala | Gln | |
| | | | | 165 | | | | 170 | | | | 175 | | | | |
| cac | aac | atc | gca | acc | gtg | ctg | gtc | ccc | ggc | ggc | gcg | acg | ctg | ccc | gca | 576 |
| His | Asn | Ile | Ala | Thr | Val | Leu | Val | Pro | Gly | Gly | Ala | Thr | Leu | Pro | Ala | |
| | | | 180 | | | | 185 | | | | 190 | | | | | |
| aag | gat | gga | gaa | gac | aac | ggc | aag | gtg | caa | acc | att | ggc | gca | cgc | ttc | 624 |
| Lys | Asp | Gly | Glu | Asp | Asn | Gly | Lys | Val | Gln | Thr | Ile | Gly | Ala | Arg | Phe | |
| | | | 195 | | | | 200 | | | | 205 | | | | | |
| gcc | aat | ggc | gaa | tta | tct | cta | cag | gac | gca | cgc | cgt | gcg | ggc | tgt | aaa | 672 |
| Ala | Asn | Gly | Glu | Leu | Ser | Leu | Gln | Asp | Ala | Arg | Arg | Ala | Gly | Cys | Lys | |
| | | 210 | | | | 215 | | | | 220 | | | | | | |
| gcc | tgt | gcc | tct | tcc | ggc | ggc | tgt | caa | ttt | ttg | ggc | act | gcc | ggg | | 720 |
| Ala | Cys | Ala | Ser | Ser | Gly | Gly | Cys | Gln | Phe | Leu | Gly | Thr | Ala | Gly | | |
| 225 | | | | 230 | | | | 235 | | | | 240 | | | | |
| aca | tct | cag | gtg | gtg | gcc | gaa | gga | ttg | gga | ctg | gca | atc | cca | cat | tca | 768 |
| Thr | Ser | Gln | Val | Val | Ala | Glu | Gly | Leu | Gly | Leu | Ala | Ile | Pro | His | Ser | |
| | | | | 245 | | | | 250 | | | | 255 | | | | |

TABLE 4-continued

Coding sequences for *E. coli* yjhG xylonate dehydratase.
SEQ ID NO: 7 and SEQ ID NO: 8

| gcc ctg gcc cct tcc ggt gag cct gtg tgg cgg gag atc gcc aga gct | 816 |
|---|---|
| Ala Leu Ala Pro Ser Gly Glu Pro Val Trp Arg Glu Ile Ala Arg Ala | |
|           260                   265                  270 | |
| tcc gcg cga gct gcg ctg aac ctg agt caa aaa ggc atc acc acc cgg | 864 |
| Ser Ala Arg Ala Ala Leu Asn Leu Ser Gln Lys Gly Ile Thr Thr Arg | |
|         275                   280                  285 | |
| gaa att ctc acc gat aaa gcg ata gag aat gcg atg acg gtc cat gcc | 912 |
| Glu Ile Leu Thr Asp Lys Ala Ile Glu Asn Ala Met Thr Val His Ala | |
|           290                   295                300 | |
| gcg ttc ggt ggt tca aca aac ctg ctg tta cac atc ccg gca att gct | 960 |
| Ala Phe Gly Gly Ser Thr Asn Leu Leu Leu His Ile Pro Ala Ile Ala | |
| 305                  310                   315                320 | |
| cac cag gca ggt tgc cat atc ccg acc gtt gat gac tgg atc cgc atc | 1008 |
| His Gln Ala Gly Cys His Ile Pro Thr Val Asp Asp Trp Ile Arg Ile | |
|                    325                  330                335 | |
| aac aag cgc gtg ccc cga ctg gtg agc gta ctg cct aat ggc ccg gtt | 1056 |
| Asn Lys Arg Val Pro Arg Leu Val Ser Val Leu Pro Asn Gly Pro Val | |
|                   340                   345                  350 | |
| tat cat cca acg gtc aat gcc ttt atg gca ggt ggt gtg ccg gaa gtc | 1104 |
| Tyr His Pro Thr Val Asn Ala Phe Met Ala Gly Gly Val Pro Glu Val | |
|                    355                  360                365 | |
| atg ttg cat ctg cgc agc ctc gga ttg ttg cat gaa gac gtt atg acg | 1152 |
| Met Leu His Leu Arg Ser Leu Gly Leu Leu His Glu Asp Val Met Thr | |
| 370                  375                   380 | |
| gtt acc ggc agc acg ctg aaa gaa aac ctc gac tgg tgg gag cac tcc | 1200 |
| Val Thr Gly Ser Thr Leu Lys Glu Asn Leu Asp Trp Trp Glu His Ser | |
| 385                  390                   395                400 | |
| gaa cgg cgt cag cgg ttc aag caa ctc ctg ctc gat cag gaa caa atc | 1248 |
| Glu Arg Arg Gln Arg Phe Lys Gln Leu Leu Leu Asp Gln Glu Gln Ile | |
|                   405                  410                415 | |
| aac gct gac gaa gtg atc atg tct ccg cag caa gca aaa gcg cgc gga | 1296 |
| Asn Ala Asp Glu Val Ile Met Ser Pro Gln Gln Ala Lys Ala Arg Gly | |
|           420                   425                430 | |
| tta acc tca act atc acc ttc ccg gtg ggc aat att gcg cca gaa ggt | 1344 |
| Leu Thr Ser Thr Ile Thr Phe Pro Val Gly Asn Ile Ala Pro Glu Gly | |
|                   435                  440                445 | |
| tcg gtg atc aaa tcc acc gcc att gac ccc tcg atg att gat gag caa | 1392 |
| Ser Val Ile Lys Ser Thr Ala Ile Asp Pro Ser Met Ile Asp Glu Gln | |
|           450                   455                460 | |
| ggt atc tat tac cat aaa ggt gtg gcg aag gtt tat ctg tcc gag aaa | 1440 |
| Gly Ile Tyr Tyr His Lys Gly Val Ala Lys Val Tyr Leu Ser Glu Lys | |
| 465                  470                   475                480 | |
| agt gcg att tac gat atc aaa cat gac aag atc aag gcg ggc gat att | 1488 |
| Ser Ala Ile Tyr Asp Ile Lys His Asp Lys Ile Lys Ala Gly Asp Ile | |
|                   485                  490                495 | |
| ctg gtc att att ggc gtt gga cct tca ggt aca ggg atg gaa gaa acc | 1536 |
| Leu Val Ile Ile Gly Val Gly Pro Ser Gly Thr Gly Met Glu Glu Thr | |
|           500                   505                510 | |
| tac cag gtt acc agt gcc ctg aag cat ctg tca tac ggt aag cat gtt | 1584 |
| Tyr Gln Val Thr Ser Ala Leu Lys His Leu Ser Tyr Gly Lys His Val | |
|                   515                  520                525 | |
| tcg tta atc acc gat gca cgt ttc tcg ggc gtt tct act ggc gcg tgc | 1632 |
| Ser Leu Ile Thr Asp Ala Arg Phe Ser Gly Val Ser Thr Gly Ala Cys | |
|           530                   535                540 | |
| atc ggc cat gtg ggg cca gaa gcg ctg gcc gga ggc ccc atc ggt aaa | 1680 |
| Ile Gly His Val Gly Pro Glu Ala Leu Ala Gly Gly Pro Ile Gly Lys | |
| 545                  550                   555                560 | |
| tta cgc acc ggg gat tta att gaa att aaa att gat tgt cgc gag ctt | 1728 |

TABLE 4-continued

Coding sequences for *E. coli* yjhG xylonate dehydratase.
SEQ ID NO: 7 and SEQ ID NO: 8

| Leu | Arg | Thr | Gly | Asp | Leu | Ile | Glu | Ile | Lys | Ile | Asp | Cys | Arg | Glu | Leu | |
|---|---|---|---|---|---|---|---|---|---|---|---|---|---|---|---|---|
| | | | | 565 | | | | | 570 | | | | | 575 | | |
| cac | ggc | gaa | gtc | aat | ttc | ctc | gga | acc | cgt | agc | gat | gaa | caa | tta | cct | 1776 |
| His | Gly | Glu | Val | Asn | Phe | Leu | Gly | Thr | Arg | Ser | Asp | Glu | Gln | Leu | Pro | |
| | | | 580 | | | | | 585 | | | | | 590 | | | |
| tca | cag | gag | gag | gca | act | gca | ata | tta | aat | gcc | aga | ccc | agc | cat | cag | 1824 |
| Ser | Gln | Glu | Glu | Ala | Thr | Ala | Ile | Leu | Asn | Ala | Arg | Pro | Ser | His | Gln | |
| | | | | 595 | | | | | 600 | | | | | 605 | | |
| gat | tta | ctt | ccc | gat | cct | gaa | ttg | cca | gat | gat | acc | cgg | cta | tgg | gca | 1872 |
| Asp | Leu | Leu | Pro | Asp | Pro | Glu | Leu | Pro | Asp | Asp | Thr | Arg | Leu | Trp | Ala | |
| | 610 | | | | | 615 | | | | | 620 | | | | | |
| atg | ctt | cag | gcc | gtg | agt | ggt | ggg | aca | tgg | acc | ggt | tgt | att | tat | gat | 1920 |
| Met | Leu | Gln | Ala | Val | Ser | Gly | Gly | Thr | Trp | Thr | Gly | Cys | Ile | Tyr | Asp | |
| 625 | | | | | 630 | | | | | 635 | | | | | 640 | |
| gta | aac | aaa | att | ggc | gcg | gct | ttg | cgc | gat | ttt | atg | aat | aaa | aac | tga | 1968 |
| Val | Asn | Lys | Ile | Gly | Ala | Ala | Leu | Arg | Asp | Phe | Met | Asn | Lys | Asn | | |
| | | | | 645 | | | | | 650 | | | | | 655 | | |

TABLE 5

Amino acid sequence for *Pseudomonas pudita* benzoylformate decarboxylase.

(SEQ ID NO: 9)
MASVHGTTYELLRRQGIDTVFGNPGSNELPFLKDFPEDFRYILALQEAC

VVGIADGYAQASRKPAFINLHSAAGTGNAMGALSNAWNSHSPLIVTAGQ

QTRAMIGVEALLTNVDAANLPRPLVKWSYEPASAAEVPHAMSRAIHMAS

MAPQGPVYLSVPYDDWDKDADPQSHHLFDRHVSSSVRLNDQDLDILVKA

LNSASNPAIVLGPDVDAANANADCVMLAERLKAPVWVAPSAPRCPFPTR

HPCFRGLMPAGIAAISQLLEGHDVVLVIGAPVFRYHQYDPGQYLKPGTR

TABLE 5-continued

Amino acid sequence for *Pseudomonas pudita* benzoylformate decarboxylase.

LISVTCDPLEAARAPMGDAIVADIGAMASALANLVEESSRQLPTAAPEP

AKVDQDAGRLHPETVFDTLNDMAPENAIYLNESTSTTAQMWQRLNMRNP

GSYYFCAAGGLGFALPAAIGVQLAEPERQVIAVIGDGSANYSISALWTA

AQYNIPTIFVIMNNGTYGALRWFAGVLEAENVPGLDVPGIDFRALAKGY

GVQALKADNLEQLKGSLQEALSAKGPVLIEVSTVSPVK

Other amino acid sequences having benzoylformate decarboxylase activity that can be used in the methods and compositions of the disclosure include:

| SEQ ID NO: | ACCESSION NO. | DESCRIPTION |
|---|---|---|
| 13 | ABN80423.1 | benzoylformate decarboxylase (*Pseudomonas stutzeri*) |
| 14 | YP_002546713.1 | benzoylformate decarboxylase (*Agrobacterium radiobacter* K84) |
| 15 | YP_001350945.1 | benzoylformate decarboxylase (*Pseudomonas aeruginosa* PA7) |
| 16 | NP_253588.1 | benzoylformate decarboxylase (*Pseudomonas aeruginosa* PAO1) |
| 17 | YP_793369.1 | benzoylformate decarboxylase (*Pseudomonas aeruginosa* UCBPP-PA14) |
| 18 | ZP_04937527.1 | benzoylformate decarboxylase (*Pseudomonas aeruginosa* 2192) |
| 19 | ZP_01367918.1 | hypothetical protein PaerPA_01005073 (*Pseudomonas aeruginosa* PACS2) |
| 20 | YP_002442865.1 | benzoylformate decarboxylase (*Pseudomonas aeruginosa* LESB58) |
| 21 | CAK95977.1 | benzoylformate decarboxylase (*Pseudomonas putida*) |
| 22 | CAK95976.1 | benzoylformate decarboxylase (*Pseudomonas putida*) |
| 23 | YP_260581.1 | benzoylformate decarboxylase (*Pseudomonas fluorescens* Pf-5) |
| 24 | ZP_06547677.1 | benzoylformate decarboxylase (*Klebsiella* sp. 1_1_55) |
| 25 | YP_555151.1 | benzoylformate decarboxylase (*Burkholderia xenovorans* LB400) |
| 26 | YP_002363219.1 | benzoylformate decarboxylase (*Methylocella silvestris* BL2) |
| 27 | YP_831380.1 | benzoylformate decarboxylase (*Arthrobacter* sp. FB24) |
| 28 | YP_572370.1 | benzoylformate decarboxylase (*Chromohalobacter salexigens* DSM 3043) |
| 29 | YP_702946.1 | benzoylformate decarboxylase (*Rhodococcus jostii* RHA1) |
| 30 | YP_702758.1 | benzoylformate decarboxylase (*Rhodococcus jostii* RHA1) |
| 31 | YP_001105345.1 | benzoylformate decarboxylase (*Saccharopolyspora erythraea* NRRL 2338) |
| 32 | ZP_06526521.1 | benzoylformate decarboxylase (*Streptomyces lividans* TK24) |
| 33 | NP_631486.1 | benzoylformate decarboxylase (*Streptomyces coelicolor* A3(2)) |
| 34 | ZP_05521701.1 | benzoylformate decarboxylase (*Streptomyces lividans* TK24) |
| 35 | CAJ89675.1 | putative decarboxylase (*Streptomyces ambofaciens* ATCC 23877) |

| SEQ ID NO: | ACCESSION NO. | DESCRIPTION |
|---|---|---|
| 36 | ZP_04996569.1 | benzoylformate decarboxylase (*Streptomyces* sp. Mg1) |
| 37 | ZP_05915352.1 | benzoylformate decarboxylase (*Brevibacterium linens* BL2) |
| 38 | YP_885985.1 | benzoylformate decarboxylase (*Mycobacterium smegmatis* str. MC2 155) |
| 39 | ZP_05973486.1 | benzoylformate decarboxylase (*Providencia rustigianii* DSM 4541) |
| 40 | YP_002754411.1 | benzoylformate decarboxylase (*Acidobacterium capsulatum* ATCC 51196) |
| 41 | YP_002954549.1 | putative benzoylformate decarboxylase (*Desulfovibrio magneticus* RS-1) |
| 42 | ZP_03572222.1 | benzoylformate decarboxylase (bfd) (bfdc) (*Burkholderia multivorans* CGD2M) |
| 43 | ZP_03584382.1 | benzoylformate decarboxylase (*Burkholderia multivorans* CGD1) |
| 44 | YP_001578906.1 | benzoylformate decarboxylase (*Burkholderia multivorans* ATCC 17616) |
| 45 | YP_001242472.1 | benzoylformate decarboxylase (*Bradyrhizobium* sp. BTAi1) |
| 46 | NP_773888.1 | benzoylformate decarboxylase (*Bradyrhizobium japonicum* USDA 110) |
| 47 | YP_002231898.1 | benzoylformate decarboxylase (*Burkholderia cenocepacia* J2315) |
| 48 | ZP_04940696.1 | Pyruvate decarboxylase (*Burkholderia cenocepacia* PC184) |
| 49 | YP_836226.1 | benzoylformate decarboxylase (*Burkholderia cenocepacia* HI2424) |
| 50 | YP_001765890.1 | benzoylformate decarboxylase (*Burkholderia cenocepacia* MC0-3) |
| 51 | NP_773056.1 | benzoylformate decarboxylase (*Bradyrhizobium japonicum* USDA 110) |
| 52 | NP_946955.1 | benzoylformate decarboxylase (*Rhodopseudomonas palustris* CGA009) |
| 53 | YP_370152.1 | benzoylformate decarboxylase (*Burkholderia* sp. 383) |
| 54 | YP_001562574.1 | benzoylformate decarboxylase (*Delftia acidovorans* SPH-1) |
| 55 | YP_001203568.1 | benzoylformate decarboxylase (*Bradyrhizobium* sp. ORS278) |

TABLE 6

Amino acid sequence of ADHP alcohol dehydrogenase (*E. coli*)

(SEQ ID NO: 10)
MQNIIRKGGTMKAAVVTKDHHVDVTYKTLRSLKHGEALLKMECCGVCHT

DLHVKNGDFGDKTGVILGHEGIGVVAEVGPGVTSLKPGDRASVAWFYEG

CGHCEYCNSGNETLCRSVKNAGYSVDGGMAEECIVVADYAVKVPDGLDS

AAASSITCAGVTTYKAVKLSKIRPGQWIAIYGLGGLGNLALQYAKNVFN

AKVIAIDVNDEQLKLATEMGADLAINSHTEDAAKIVQEKTGGAHAAVVT

AVAKAAFNSAVDAVRAGGRVVAVGLPPESMSLDIPRLVLDGIEVVGSLV

GTRQDLTEAFQFAAEGKVVPKVALRPLADINTIFTEMEEGKIRGRMVID

FRH

Other sequence having alcohol dehydrogenase activity that may be used in the methods and compositions of the disclosure include, but are not limited to:

| SEQ ID NO: | ACCESSION NO. | DESCRIPTION |
|---|---|---|
| 56 | YP_002292842.1 | alcohol dehydrogenase (*Escherichia coli* SE11) |
| 57 | BAB35505.1 | alcohol dehydrogenase (*Escherichia coli* O157:H7 str. *Sakai*) |
| 58 | ACI83654.1 | alcohol dehydrogenase (*Escherichia coli*, str. TB182A) |
| 59 | YP_540705.1 | alcohol dehydrogenase (*Escherichia coli* UTI89) |
| 60 | ABB61735.1 | alcohol dehydrogenase (*Shigella dysenteriae* Sd197) |
| 61 | AP_002101.1 | alcohol dehydrogenase, 1-propanol preferring (*Escherichia coli* str. K-12 substr. W3110) |
| 62 | YP_001462749.1 | alcohol dehydrogenase (*Escherichia coli* E24377A) |
| 63 | NP_310109.2 | alcohol dehydrogenase (*Escherichia coli* O157:H7 str. *Sakai*) |
| 64 | YP_002382641.1 | alcohol dehydrogenase (*Escherichia fergusonii* ATCC 35469) |
| 65 | NP_753808.2 | alcohol dehydrogenase (*Escherichia coli* CFT073) |
| 66 | ZP_06653399.1 | alcohol dehydrogenase (*Escherichia coli* B354) |
| 67 | NP_707612.1 | alcohol dehydrogenase (*Shigella flexneri* 2a str. 301) |
| 68 | YP_002329135.1 | alcohol dehydrogenase (*Escherichia coli* O127:H6 str. E2348/69) |
| 69 | BAI54933.1 | alcohol dehydrogenase (*Escherichia coli* SE15) |
| 70 | YP_669388.1 | alcohol dehydrogenase (*Escherichia coli* 536) |
| 71 | YP_403226.2 | alcohol dehydrogenase (*Shigella dysenteriae* Sd197) |
| 72 | NP_455923.1 | alcohol dehydrogenase (*Salmonella enterica* subsp. *enterica* serovar *Typhi* str. CT18) |
| 73 | YP_001587957.1 | alcohol dehydrogenase (*Salmonella enterica* subsp. *enterica* serovar *Paratyphi B* str. SPB7) |
| 74 | YP_002040815.1 | alcohol dehydrogenase (*Salmonella enterica* subsp. *enterica* serovar *Newport* str. SL254) |
| 75 | YP_150561.1 | alcohol dehydrogenase (*Salmonella enterica* subsp. *enterica* serovar *Paratyphi A* str. ATCC 9150) |

| SEQ ID NO: | ACCESSION NO. | DESCRIPTION |
| --- | --- | --- |
| 76 | ZP_03359218.1 | alcohol dehydrogenase (*Salmonella enterica* subsp. *enterica* serovar *Typhi* str. E02-1180) |
| 77 | YP_002637737.1 | alcohol dehydrogenase (*Salmonella enterica* subsp. *enterica* serovar *Paratyphi* C strain RKS4594) |
| 78 | ZP_05967726.2 | alcohol dehydrogenase, propanol-preferring (*Enterobacter cancerogenus* ATCC 35316) |

The term diol dehydratase refers to a polypeptide (or polypeptides) having an enzyme activity that catalyzes the conversion of 1,2,4-D-butanetriol to 4-hydroxy-D-butanal. Diol dehydratase may utilize the cofactor adenosyl cobalamin. For example, a diol dehydratase useful in the methods and compositions of the disclosure can be selected from 2,3-butanediol dehydratase, 3,4-hexanediol dehydratase, 4,5-octanediol dehydratase, 5,6-decanediol dehydratase, 6,7-dodecanediol dehydratase, 7,8-tetradecanediol dehydratase, 8,9-hexadecanediol dehydratase, 2,5-dimethyl-3,4-hexanediol dehydratase, 3,6-dimethyl-4,5-octanediol dehydratase, 2,7-dimethyl-4,5-octanediol dehydratase, 2,9-dimethyl-5,6-decanediol dehydratase, 1,4-diphenyl-2,3-butanediol dehydratase, bis-1,4-(4-hydroxyphenyl)-2,3-butanediol dehydratase, 1,4-diindole-2,3-butanediol dehydratase, 1,2-cyclopentanediol dehydratase, 2,3-pentanediol dehydratase, 2,3-hexanediol dehydratase, 2,3-heptanediol dehydratase, 2,3-octanediol dehydratase, 2,3-nonanediol dehydratase, 4-methyl-2,3-pentanediol dehydratase, 4-methyl-2,3-hexanediol dehydratase, 5-methyl-2,3-hexanediol dehydratase, 6-methyl-2,3-heptanediol dehydratase, 1-phenyl-2,3-butanediol dehydratase, 1-(4-hydroxyphenyl)-2,3-butanediol dehydratase, 1-indole-2,3-butanediol dehydratase, 3,4-heptanediol dehydratase, 3,4-octanediol dehydratase, 3,4-nonanediol dehydratase, 3,4-decanediol dehydratase, 3,4-undecanediol dehydratase, 2-methyl-3,4-hexanediol dehydratase, 5-methyl-3,4-heptanediol dehydratase, 6-methyl-3,4-heptanediol dehydratase, 7-methyl-3,4-octanediol dehydratase, 1-phenyl-2,3-pentanediol dehydratase, 1-(4-hydroxyphenyl)-2,3-pentanediol dehydratase, 1-indole-2,3-pentanediol dehydratase, 4,5-nonanediol dehydratase, 4,5-decanediol dehydratase, 4,5-undecanediol dehydratase, 4,5-dodecanediol dehydratase, 2-methyl-3,4-heptanediol dehydratase, 3-methyl-4,5-octanediol dehydratase, 2-methyl-4,5-octanediol dehydratase, 8-methyl-4,5-nonanediol dehydratase, 1-phenyl-2,3-hexanediol dehydratase, 1-(4-hydroxyphenyl)-2,3-hexanediol dehydratase, 1-indole-2,3-hexanediol dehydratase, 5,6-undecanediol dehydratase, 5,6-undecanediol dehydratase, 5,6-tridecanediol dehydratase, 2-methyl-3,4-octanediol dehydratase, 3-methyl-4,5-nonanediol dehydratase, 2-methyl-4,5-nonanediol dehydratase, 2-methyl-5,6-decanediol dehydratase, 1-phenyl-2,3-heptanediol dehydratase, 1-(4-hydroxyphenyl)-2,3-heptanediol dehydratase, 1-indole-2,3-heptanediol dehydratase, 6,7-tridecanediol dehydratase, 6,7-tetradecanediol dehydratase, 2-methyl-3,4-nonanediol dehydratase, 3-methyl-4,5-decanediol dehydratase, 2-methyl-4,5-decanediol dehydratase, 2-methyl-5,6-undecanediol dehydratase, 1-phenyl-2,3-octanediol dehydratase, 1-(4-hydroxyphenyl)-2,3-octanediol dehydratase, 1-indole-2,3-octanediol dehydratase, 7,8-pentadecanediol dehydratase, 2-methyl-3,4-decanediol dehydratase, 3-methyl-4,5-undecanediol dehydratase, 2-methyl-4,5-undecanediol dehydratase, 2-methyl-5,6-dodecanediol dehydratase, 1-phenyl-2,3-nonanediol dehydratase, 1-(4-hydroxyphenyl)-2,3-nonanediol dehydratase, 1-indole-2,3-nonanediol dehydratase, 2-methyl-3,4-undecanediol dehydratase, 3-methyl-4,5-dodecanediol dehydratase, 2-methyl-4,5-dodecanediol dehydratase, 2-methyl-5,6-tridecanediol dehydratase, 1-phenyl-2,3-decanediol dehydratase, 1-(4-hydroxyphenyl)-2,3-decanediol dehydratase, 1-indole-2,3-decanediol dehydratase, 2,5-dimethyl-3,4-heptanediol dehydratase, 2,6-dimethyl-3,4-heptanediol dehydratase, 2,7-dimethyl-3,4-octanediol dehydratase, 1-phenyl-4-methyl-2,3-pentanediol dehydratase, 1-(4-hydroxyphenyl)-4-methyl-2,3-pentanediol dehydratase, 1-indole-4-methyl-2,3-pentanediol dehydratase, 2,6-dimethyl-4,5-octanediol dehydratase, 3,8-dimethyl-4,5-nonanediol dehydratase, 1-phenyl-4-methyl-2,3-hexanediol dehydratase, 1-(4-hydroxyphenyl)-4-methyl-2,3-hexanediol dehydratase, 1-indole-4-methyl-2,3-hexanediol dehydratase, 2,8-dimethyl-4,5-nonanediol dehydratase, 1-phenyl-5-methyl-2,3-hexanediol dehydratase, 1-(4-hydroxyphenyl)-5-methyl-2,3-hexanediol dehydratase, 1-indole-5-methyl-2,3-hexanediol dehydratase, 1-phenyl-6-methyl-2,3-heptanediol dehydratase, 1-(4-hydroxyphenyl)-6-methyl-2,3-heptanediol dehydratase, 1-indole-6-methyl-2,3-heptanediol dehydratase, 1-(4-hydroxyphenyl)-4-phenyl-2,3-butanediol dehydratase, 1-indole-4-phenyl-2,3-butanediol dehydratase, 1-indole-4-(4-hydroxyphenyl)-2,3-butanediol dehydratase, 1,10-diamino-5,6-decanediol dehydratase, 1,4-di(4-hydroxyphenyl)-2,3-butanediol, and 2,3-hexanediol-1,6-dicarboxylic acid dehydratase. The diol dehydratase can be one characterized, for example from *Listeria, Amycolatopsis, Klebsiella, Pseudomaonas, Salmonella, Lactobacillus, Yersinia*, and the like.

An "alcohol dehydrogenase" refers to any alcohol dehydrogenase enzyme having a catalytic activity that converts 3,4-dihydroxy-D-butanal to D-1,2,4-butanetriol, e.g., an AdhP, or an AdhE or a YiaY, type of alcohol dehydrogenase. An alcohol dehydrogenase also refers to an enzyme having a catalytic activity that converts 4-hydroxy-D-butanal to 1,4-butanediol.

Microorganisms provided herein are modified to produce metabolites in quantities not available in the parental microorganism. A "metabolite" refers to any substance produced by metabolism or a substance necessary for, or taking part in, a particular metabolic process. A metabolite can be an organic compound that is a starting material (e.g., D-xylonic acid), an intermediate (e.g., 3,4-dihydroxy-D-butanal), or an end product (e.g., 1,4-butanediol) of metabolism. Metabolites can be used to construct more complex molecules, or they can be broken down into simpler ones. Intermediate metabolites can be synthesized from other metabolites, for example, to be used to make more complex substances, or broken down into simpler compounds, often with the release of chemical energy.

Exemplary metabolites include D-xylose, D-xylonic acid, 3-deoxy-D-glycero-pentulosonic acid, 3,4-dihydroxy-D-butanal, 1,2,4-D-butanetriol, 4-hydroxy-D-butanal, and 1,4-butanediol. For example, as shown in FIG. 1, a recombinant microorganism can be metabolically engineered to provide elevated expression or heterologous expression of enzymes useful in the production of 1,4-butanediol. For example, xylose is converted to xylonic acid by a xylose dehydrogenase. 3-Deoxy-D-glycero-pentulosonic acid is produced by xylonate dehydratase from xylonic acid. 3-Deoxy-D-glycero-pentulosonoic acid is further converted by a decarboxylase to 3,4-dihydroxy-D-butanal. 3,4-Dihydroxy-D-butanal is then reduced to 1,2,4-D-butanetriol by a dehydrogenase. 1,2,4-D-butanetriol is further dehydrated into 4-hydroxy-D-butanal by a dehydratase. 4-hydroxy-D-butanal was then reduced to 1,4-butanediol by a dehydrogenase.

In addition, it can be advantageous to decrease or remove expression of enzymes that compete with a metabolite used in the production of 1,4-butanediol. For example, the enzyme D-xylose isomerase (XylA) can be reduced or knocked out to prevent flux of the substrate xylose to D-xylulose by the activity of the D-xylose isomerase. Alternatively, or in addition, the enzyme 2-keto acid aldolase (YagE and YjhH) can be reduced or knocked out to prevent flux of the metabolite 3-deoxy-D-glycero-pentulsonic acid to pyruvic acid. Alternatively, or in addition, the enzyme 2-keto acid transaminase can be reduced or knocked out to prevent flux of the metabolite 3-deoxy-D-glycero-pentulsonic acid to 2-amino-2,3-dideoxy-L-pentanoic acid. Alternatively, or in addition, the enzyme 2-keto acid dehydrogenase may be reduced or knocked out to prevent flux of the metabolite 3-deoxy-D-glycero-pentulsonic acid to 3-deoxy-D-glycero-pentanoic acid.

The disclosure identifies specific genes and enzymes useful in the methods, compositions, and organisms for the production of 1,4-butanediol, or intermediates thereof; however it will be recognized that absolute identity to such genes or polypeptides is not necessary. For example, changes in a particular gene or polynucleotide comprising a sequence encoding a polypeptide or enzyme can be performed and screened for activity. Typically such changes comprise conservative mutations and/or silent mutations. Such modified or mutated polynucleotides and polypeptides can be screened for expression of a functional enzyme activity using methods known in the art.

Due to the inherent degeneracy of the genetic code, other polynucleotides which encode substantially the same or a functionally equivalent polypeptide can also be used to clone and express the polynucleotides encoding such enzymes.

As will be understood by those of skill in the art, it can be advantageous to modify a coding sequence to enhance its expression in a particular host. The genetic code is redundant with 64 possible codons, but most organisms typically use a subset of these codons. The codons that are utilized most often in a species are called optimal codons, and those not utilized very often are classified as rare or low-usage codons. Codons can be substituted to reflect the preferred codon usage of the host, a process sometimes called "codon optimization" or "controlling for species codon bias."

Optimized coding sequences containing codons preferred by a particular prokaryotic or eukaryotic host (see also, Murray et al. (1989) *Nucl. Acids Res.* 17:477-508) can be prepared, for example, to increase the rate of translation or to produce recombinant RNA transcripts having desirable properties, such as a longer half-life, as compared with transcripts produced from a non-optimized sequence. Translation stop codons can also be modified to reflect host preference. For example, typical stop codons for *S. cerevisiae* and mammals are UAA and UGA, respectively. The typical stop codon for monocotyledonous plants is UGA, whereas insects and *E. coli* commonly use UAA as the stop codon (Dalphin et al. (1996) *Nucl. Acids Res.* 24:216-218). Methodology for optimizing a nucleotide sequence for expression in a plant is provided, for example, in U.S. Pat. No. 6,015,891, and the references cited therein.

Those of skill in the art will recognize that, due to the degenerate nature of the genetic code, a variety of DNA compounds differing in their nucleotide sequences can be used to encode a given amino acid sequence (e.g., enzyme) of the disclosure. The native DNA sequence encoding the biosynthetic enzymes described above are referenced herein merely to illustrate an embodiment of the disclosure, and the disclosure includes DNA compounds of any sequence that encode the amino acid sequences of the polypeptides and proteins of the enzymes utilized in the methods of the disclosure. In similar fashion, a polypeptide can typically tolerate one or more amino acid substitutions, deletions, and insertions in its amino acid sequence without loss or significant loss of a desired activity. The disclosure includes such polypeptides with different amino acid sequences than the specific proteins described herein so long as the modified or variant polypeptides have the enzymatic anabolic or catabolic activity of the reference polypeptide. Furthermore, the amino acid sequences encoded by the DNA sequences shown herein merely illustrate embodiments of the disclosure.

In addition, homologs of enzymes useful for generating metabolites are encompassed by the microorganisms and methods provided herein. The term "homologs" used with respect to an original enzyme or gene of a first family or species refers to distinct enzymes or genes of a second family or species which are determined by functional, structural, or genomic analyses to be an enzyme or gene of the second family or species which corresponds to the original enzyme or gene of the first family or species. Most often, homologs will have functional, structural, or genomic similarities. Techniques are known by which homologs of an enzyme or gene can readily be cloned using genetic probes and PCR. Identity of cloned sequences as homolog can be confirmed using functional assays and/or by genomic mapping of the genes.

A protein has "homology" or is "homologous" to a second protein if the nucleic acid sequence that encodes the protein has a similar sequence to the nucleic acid sequence that encodes the second protein. Alternatively, a protein has homology to a second protein if the two proteins have "similar" amino acid sequences. (Thus, the term "homologous proteins" is defined to mean that the two proteins have similar amino acid sequences).

As used herein, two proteins (or a region of the proteins) are substantially homologous when the amino acid sequences have at least about 30%, 40%, 50% 60%, 65%, 70%, 75%, 80%, 85%, 90%, 91%, 92%, 93%, 94%, 95%, 96%, 97%, 98%, or 99% identity. To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In one embodiment, the length of a reference sequence aligned for comparison purposes is at least 30%, typically at least 40%, more typically at least 50%, even more typically at least 60%, and even more typically at least 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

When "homologous" is used in reference to proteins or peptides, it is recognized that residue positions that are not identical often differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of homology may be adjusted upwards to correct for the conservative nature of the substitution. Means for making this adjustment are well known to those of skill in the art. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). In addition, the following five groups each contain amino acids that are conservative substitutions for one another: 1) Serine (S), Threonine (T); 2) Asparagine (N), Glutamine (Q); 3) Arginine (R), Lysine (K); 4) Isoleucine (I), Leucine (L), Methionine (M), Alanine (A), Valine (V), and 5) Phenylalanine (F), Tyrosine (Y), Tryptophan (W).

Sequence homology for polypeptides, which is also referred to as percent sequence identity, is typically measured using sequence analysis software. See, e.g., the Sequence Analysis Software Package of the Genetics Computer Group (GCG), University of Wisconsin Biotechnology Center, 910 University Avenue, Madison, Wis. 53705. Protein analysis software matches similar sequences using measure of homology assigned to various substitutions, deletions, and other modifications, including conservative amino acid substitutions. For instance, GCG contains programs such as "Gap" and "Bestfit" which can be used with default parameters to determine sequence homology or sequence identity between closely related polypeptides, such as homologous polypeptides from different species of organisms or between a wild type protein and a mutein thereof. See, e.g., GCG Version 6.1.

A typical algorithm used comparing a molecule sequence to a database containing a large number of sequences from different organisms is the computer program BLAST, as is known in the art, especially blastp or tblastn. Typical parameters for BLASTp are: Expectation value: 10 (default); Filter: seg (default); Cost to open a gap: 11 (default); Cost to extend a gap: 1 (default); Max. alignments: 100 (default); Word size: 11 (default); No. of descriptions: 100 (default); Penalty Matrix: BLOWSUM62.

When searching a database containing sequences from a large number of different organisms, it is typical to compare amino acid sequences. Database searching using amino acid sequences can be measured by algorithms other than blastp known in the art. For instance, polypeptide sequences can be compared using FASTA, a program in GCG Version 6.1. FASTA provides alignments and percent sequence identity of the regions of the best overlap between the query and search sequences. For example, percent sequence identity between amino acid sequences can be determined using FASTA with its default parameters (a word size of 2 and the PAM250 scoring matrix), as provided in GCG Version 6.1, hereby incorporated herein by reference.

The disclosure provides accession numbers for various genes and/or proteins, homologs, and variants useful in the generation of recombinant microorganism described herein. In addition, the nucleotide and amino acid sequences corresponding to the accession numbers are provided in the attached Sequence Listing. It is to be understood that homologs and variants described herein are exemplary and non-limiting. Additional homologs, variants, and polynucleotide and/or amino acid sequences are available to those of skill in the art using various databases including, for example, the National Center for Biotechnology Information (NCBI) access to which is available on the World-Wide-Web.

It is understood that a range of microorganisms can be modified to include a recombinant metabolic pathway suitable for the production of 1,4-butanediol. It is also understood that various microorganisms can act as "sources" for genetic material encoding target enzymes suitable for use in a recombinant microorganism provided herein. The term "microorganism" includes prokaryotic and eukaryotic microbial species from the Domains Archaea, Bacteria, and Eucarya, the latter including yeast and filamentous fungi, protozoa, algae, or higher Protista. The terms "microbial cells" and "microbes" are used interchangeably with the term microorganism.

The term "prokaryotes" is art recognized and refers to cells which contain no nucleus or other cell organelles. The prokaryotes are generally classified in one of two domains, the Bacteria and the Archaea. The definitive difference between organisms of the Archaea and Bacteria domains is based on fundamental differences in the nucleotide base sequence in the 16S ribosomal RNA.

The term "Archaea" refers to a categorization of organisms of the division Mendosicutes, typically found in unusual environments and distinguished from the rest of the prokaryotes by several criteria, including the number of ribosomal proteins and the lack of muramic acid in cell walls. On the basis of ssrRNA analysis, the Archaea consist of two phylogenetically-distinct groups: Crenarchaeota and Euryarchaeota. On the basis of their physiology, the Archaea can be organized into three types: methanogens (prokaryotes that produce methane); extreme halophiles (prokaryotes that live at very high concentrations of salt ((NaCl)); and extreme (hyper) thermophilus (prokaryotes that live at very high temperatures). Besides the unifying archaeal features that distinguish them from Bacteria (i.e., no murein in cell wall, ester-linked membrane lipids, and the like), these prokaryotes exhibit unique structural or biochemical attributes which adapt them to their particular habitats. The Crenarchaeota consists mainly of hyperthermophilic sulfur-dependent prokaryotes and the Euryarchaeota contains the methanogens and extreme halophiles.

"Bacteria", or "eubacteria", refers to a domain of prokaryotic organisms. Bacteria include at least 11 distinct groups as follows: (1) Gram-positive (gram+) bacteria, of which there are two major subdivisions: (1) high G+C group (*Actinomycetes, Mycobacteria, Micrococcus*, others) (2) low G+C group (*Bacillus, Clostridia, Lactobacillus*, Staphylococci, Streptococci, Mycoplasmas); (2) Proteobacteria, e.g., Purple photosynthetic+non-photosynthetic Gram-negative bacteria (includes most "common" Gram-negative bacteria); (3) Cyanobacteria, e.g., oxygenic phototrophs; (4) Spirochetes and related species; (5) Planctomyces; (6) *Bacteroides*, Flavobacteria; (7) *Chlamydia*; (8) Green sulfur bacteria; (9) Green non-sulfur bacteria (also anaerobic phototrophs); (10) Radioresistant micrococci and relatives; and (11) Thermotoga and Thermosipho thermophiles.

"Gram-negative bacteria" include cocci, nonenteric rods, and enteric rods. The genera of Gram-negative bacteria include, for example, *Neisseria, Spirillum, Pasteurella, Brucella, Yersinia, Francisella, Haemophilus, Bordetella, Escherichia, Salmonella, Shigella, Klebsiella, Proteus, Vibrio, Pseudomonas, Bacteroides, Acetobacter, Aerobacter, Agrobacterium, Azotobacter, Spirilla, Serratia, Vibrio, Rhizobium, Chlamydia, Rickettsia, Treponema,* and *Fusobacterium*.

"Gram positive bacteria" include cocci, nonsporulating rods, and sporulating rods. The genera of gram positive bacteria include, for example, *Actinomyces, Bacillus, Clostridium, Corynebacterium, Erysipelothrix, Lactobacillus, Listeria, Mycobacterium, Myxococcus, Nocardia, Staphylococcus, Streptococcus,* and *Streptomyces.*

The term "recombinant microorganism" and "recombinant host cell" are used interchangeably herein and refer to microorganisms that have been genetically modified to express or over-express endogenous polynucleotides, or to express non-endogenous polynucleotides, such as those included in a vector, or which have a reduction in expression of an endogenous gene. The polynucleotide generally encodes a target enzyme involved in a metabolic pathway for producing a desired metabolite as described above. Accordingly, recombinant microorganisms described herein have been genetically engineered to express or over-express target enzymes not previously expressed or over-expressed by a parental microorganism. It is understood that the terms "recombinant microorganism" and "recombinant host cell" refer not only to the particular recombinant microorganism but to the progeny or potential progeny of such a microorganism.

A "parental microorganism" refers to a cell used to generate a recombinant microorganism. The term "parental microorganism" describes a cell that occurs in nature, i.e., a "wild-type" cell that has not been genetically modified. The term "parental microorganism" also describes a cell that has been genetically modified but which does not express or over-express a target enzyme, e.g., an enzyme involved in the biosynthetic pathway for the production of a desired metabolite. For example, a wild-type microorganism can be genetically modified to express or over express a first target enzyme such as a xylose dehydrogenase. This microorganism can act as a parental microorganism in the generation of a microorganism modified to express or over-express a second target enzyme, e.g., xylonate dehydratase. In turn, the microorganism modified to express or over express, e.g., a xylose dehydrogenase and a xylonate dehydratase can be modified to express or over express a third target enzyme, e.g., a benzoylformate decarboxylase. Accordingly, a parental microorganism functions as a reference cell for successive genetic modification events. Each modification event can be accomplished by introducing a nucleic acid molecule into the reference cell. The introduction facilitates the expression or over-expression of a target enzyme. It is understood that the term "facilitates" encompasses the activation of endogenous polynucleotides encoding a target enzyme through genetic modification of, e.g., a promoter sequence in a parental microorganism. It is further understood that the term "facilitates" encompasses the introduction of exogenous polynucleotides encoding a target enzyme into a parental microorganism.

In another embodiment a method of producing a recombinant microorganism that converts a suitable carbon substrate to 1,4-butanediol is provided. The method includes transforming a microorganism with one or more recombinant polynucleotides encoding polypeptides that include, for example, D-xylonate dehydrogenase, D-xylonate dehydratase, benzoylformate decarboxylase, diol dehydratase, and an alcohol dehydrogenase. Polynucleotides that encode enzymes useful for generating metabolites including homologs, variants, fragments, related fusion proteins, or functional equivalents thereof, are used in recombinant nucleic acid molecules that direct the expression of such polypeptides in appropriate host cells, such as bacterial or yeast cells. It is understood that the addition of sequences which do not alter the encoded activity of a polynucleotide, such as the addition of a non-functional or non-coding sequence, is a conservative variation of the basic nucleic acid. The "activity" of an enzyme is a measure of its ability to catalyze a reaction resulting in a metabolite, i.e., to "function", and may be expressed as the rate at which the metabolite of the reaction is produced. For example, enzyme activity can be represented as the amount of metabolite produced per unit of time or per unit of enzyme (e.g., concentration or weight), or in terms of affinity or dissociation constants.

A "protein" or "polypeptide", which terms are used interchangeably herein, comprises one or more chains of chemical building blocks called amino acids that are linked together by chemical bonds called peptide bonds. An "enzyme" means any substance, composed wholly or largely of protein, that catalyzes or promotes, more or less specifically, one or more chemical or biochemical reactions. A "native" or "wild-type" protein, enzyme, polynucleotide, gene, or cell, means a protein, enzyme, polynucleotide, gene, or cell that occurs in nature.

It is understood that the polynucleotides described above include "genes" and that the nucleic acid molecules described above include "vectors" or "plasmids." Accordingly, the term "gene", also called a "structural gene" refers to a polynucleotide that codes for a particular sequence of amino acids, which comprise all or part of one or more proteins or enzymes, and can include regulatory (non-transcribed) DNA sequences, such as promoter sequences, which determine, for example, the conditions under which the gene is expressed. The transcribed region of the gene can include untranslated regions, including introns, 5'-untranslated region (UTR), and 3'-UTR, as well as the coding sequence. The term "nucleic acid" or "recombinant nucleic acid" refers to polynucleotides such as deoxyribonucleic acid (DNA), and, where appropriate, ribonucleic acid (RNA). The term "expression" with respect to a gene sequence refers to transcription of the gene and, as appropriate, translation of the resulting mRNA transcript to a protein. Thus, as will be clear from the context, expression of a protein results from transcription and translation of an open reading frame sequence.

The term "operon" refers to two or more genes which are transcribed as a single transcriptional unit from a common promoter. In some embodiments, the genes comprising the operon are contiguous genes. It is understood that transcription of an entire operon can be modified (i.e., increased, decreased, or eliminated) by modifying the common promoter. Alternatively, any gene or combination of genes in an operon can be modified to alter the function or activity of the encoded polypeptide. The modification can result in an increase in the activity of the encoded polypeptide. Further, the modification can impart new activities on the encoded polypeptide. Exemplary new activities include the use of alternative substrates and/or the ability to function in alternative environmental conditions.

A "vector" is any means by which a nucleic acid can be propagated and/or transferred between organisms, cells, or cellular components. Vectors can include viruses, bacteriophages, pro-viruses, plasmids, phagemids, transposons, and artificial chromosomes, such as YACs (yeast artificial chromosomes), BACs (bacterial artificial chromosomes), PLACs (plant artificial chromosomes), and the like, that are "episomes," that is, that replicate autonomously or can integrate into a chromosome of a host cell. A vector can also be a naked RNA polynucleotide, a naked DNA polynucleotide, a polynucleotide composed of both DNA and RNA within the same strand, a poly-lysine-conjugated DNA or RNA, a peptide-conjugated DNA or RNA, a liposome-conjugated DNA, or the like, that are not episomal in nature, or it can be an organism which comprises one or more of the above polynucleotide constructs such as an *agrobacterium* or a bacterium.

"Transformation" refers to the process by which a vector is introduced into a host cell. Transformation (or transduction, or transfection), can be achieved by any one of a number of means including electroporation, microinjection, biolistics (or particle bombardment-mediated delivery), or *agrobacterium* mediated transformation.

The disclosure provides nucleic acid molecules in the form of recombinant DNA expression vectors or plasmids, as described in more detail below, that encode one or more target enzymes. Generally, such vectors can either replicate in the cytoplasm of the host microorganism or integrate into the chromosomal DNA of the host microorganism. In either case, the vector can be a stable vector (i.e., the vector remains present over many cell divisions, even if only with selective pressure) or a transient vector (i.e., the vector is gradually lost by host microorganisms with increasing numbers of cell divisions). The disclosure provides DNA molecules in isolated (i.e., not pure, but existing in a preparation in an abundance and/or concentration not found in nature) and purified (i.e., substantially free of contaminating materials or substantially free of materials with which the corresponding DNA would be found in nature) forms.

Provided herein are methods for the heterologous expression of one or more of the biosynthetic genes involved in 1,4-butanediol biosynthesis and recombinant DNA expression vectors useful in the method. Thus, included within the scope of the disclosure are recombinant expression vectors that include such nucleic acids. The term "expression vector" refers to a nucleic acid that can be introduced into a host microorganism or cell-free transcription and translation system. An expression vector can be maintained permanently or transiently in a microorganism, whether as part of the chromosomal or other DNA in the microorganism or in any cellular compartment, such as a replicating vector in the cytoplasm. An expression vector also comprises a promoter that drives expression of an RNA, which typically is translated into a polypeptide in the microorganism or cell extract. For efficient translation of RNA into protein, the expression vector also typically contains a ribosome-binding site sequence positioned upstream of the start codon of the coding sequence of the gene to be expressed. Other elements, such as enhancers, secretion signal sequences, transcription termination sequences, and one or more marker genes by which host microorganisms containing the vector can be identified and/or selected, may also be present in an expression vector. Selectable markers, i.e., genes that confer antibiotic resistance or sensitivity, are used and confer a selectable phenotype on transformed cells when the cells are grown in an appropriate selective medium.

The various components of an expression vector can vary widely, depending on the intended use of the vector and the host cell(s) in which the vector is intended to replicate or drive expression. Expression vector components suitable for the expression of genes and maintenance of vectors in *E. coli*, yeast, *Streptomyces*, and other commonly used cells are widely known and commercially available. For example, suitable promoters for inclusion in the expression vectors of the disclosure include those that function in eukaryotic or prokaryotic host microorganisms. Promoters can comprise regulatory sequences that allow for regulation of expression relative to the growth of the host microorganism or that cause the expression of a gene to be turned on or off in response to a chemical or physical stimulus. For *E. coli* and certain other bacterial host cells, promoters derived from genes for biosynthetic enzymes, antibiotic-resistance conferring enzymes, and phage proteins can be used and include, for example, the galactose, lactose (lac), maltose, tryptophan (trp), beta-lactamase (bla), bacteriophage lambda PL, and T5 promoters. In addition, synthetic promoters, such as the tac promoter (U.S. Pat. No. 4,551,433), can also be used. For *E. coli* expression vectors, it is useful to include an *E. coli* origin of replication, such as from pUC, p1P, p1, pBR, and the like.

Thus, recombinant expression vectors contain at least one expression system, which, in turn, is composed of at least a portion of polyketide synthase (PKS) and/or other biosynthetic gene coding sequences operably linked to a promoter and optionally termination sequences that operate to effect expression of the coding sequence in compatible host cells. The host cells are modified by transformation with the recombinant DNA expression vectors of the disclosure to contain the expression system sequences either as extrachromosomal elements or integrated into the chromosome.

A nucleic acid of the disclosure can be amplified using cDNA, mRNA or alternatively, genomic DNA, as a template and appropriate oligonucleotide primers according to standard PCR amplification techniques as known in the art. The nucleic acid so amplified can be cloned into an appropriate vector and characterized by DNA sequence analysis. Furthermore, oligonucleotides corresponding to nucleotide sequences can be prepared by standard synthetic techniques, e.g., using an automated DNA synthesizer.

It is also understood that an isolated nucleic acid molecule encoding a polypeptide homologous to the enzymes described herein can be created by introducing one or more nucleotide substitutions, additions, or deletions into the nucleotide sequence encoding the particular polypeptide, such that one or more amino acid substitutions, additions, or deletions are introduced into the encoded protein. Mutations can be introduced into the polynucleotide by standard techniques, such as site-directed mutagenesis and PCR-mediated mutagenesis. In contrast to those positions where it may be desirable to make a non-conservative amino acid substitutions (see above), in some positions it is preferable to make conservative amino acid substitutions.

In another embodiment a method for producing 1,4-butanediol is provided. The method includes culturing a recombinant microorganism as provided herein in the presence of a suitable substrate and under conditions suitable for the conversion of the substrate to 1,4-butanediol or an intermediate which can be further converted to 1,4-butanediol. The 1,4-butanediol produced by a microorganism provided herein can be detected by any method known to the skilled artisan. Such methods include mass spectrometry. Culture conditions suitable for the growth and maintenance can be modified to accommodate the requirements of each microorganism.

As previously discussed, general texts which describe molecular biological techniques useful herein, including the use of vectors, promoters and many other relevant topics, include Berger and Kimmel, Guide to Molecular Cloning Techniques, Methods in Enzymology Volume 152, (Academic Press, Inc., San Diego, Calif.) ("Berger"); Sambrook et al., Molecular Cloning: A Laboratory Manual, 2d ed., Vol. 1-3, Cold Spring Harbor Laboratory, Cold Spring Harbor, N.Y., 1989 ("Sambrook"); and Current Protocols in Molecular Biology, F. M. Ausubel et al., eds., Current Protocols, a joint venture between Greene Publishing Associates, Inc. and John Wiley & Sons, Inc., (supplemented through 1999) ("Ausubel"). Examples of protocols sufficient to direct persons of skill through in vitro amplification methods, including the polymerase chain reaction (PCR), the ligase chain reaction (LCR), Qβ-replicase amplification and other RNA polymerase mediated techniques (e.g., NASBA), e.g., for the production of the homologous nucleic acids of the disclosure are found in Berger, Sambrook, and Ausubel, as well as in Mullis et al. (1987) U.S. Pat. No. 4,683,202; Innis et al., eds. (1990) PCR Protocols: A Guide to Methods and Applications (Academic Press Inc. San Diego, Calif.) ("Innis"); Arnheim & Levinson (Oct. 1, 1990) *C&EN* 36-47; Kwoh et al. (1989) *Proc. Natl. Acad. Sci. USA* 86:1173; Guatelli et al. (1990) *Proc. Nat'l Acad. Sci. USA* 87:1874; Lomell et al. (1989) *J. Clin. Chem.* 35:1826; Landegren et al. (1988) *Science* 241: 1077-1080; Van Brunt (1990) Biotechnology 8:291-294; Wu and Wallace (1989) Gene 4:560; Barringer et al. (1990) Gene 89:117; and Sooknanan and Malek (1995) *Biotechnology* 13:563-564. Improved methods for cloning in vitro amplified nucleic acids are described in Wallace et al., U.S. Pat. No. 5,426,039. Improved methods for amplifying large nucleic acids by PCR are summarized in Cheng et al. (1994) *Nature* 369:684-685 and the references cited therein, in which PCR amplicons of up to 40 kb are generated. One of skill will appreciate that essentially any RNA can be converted into a double stranded DNA suitable for restriction digestion, PCR expansion, and sequencing using reverse transcriptase and a polymerase. See, e.g., Ausubel, Sambrook and Berger, all supra.

Appropriate culture conditions are conditions of culture medium pH, ionic strength, nutritive content, and the like; temperature; oxygen/$CO_2$/nitrogen content; humidity; and other culture conditions that permit production of the compound by the host microorganism, i.e., by the metabolic action of the microorganism. Appropriate culture conditions are well known to the skilled artisan for the various microorganisms that can serve as host cells.

EXAMPLES

Figure 2:
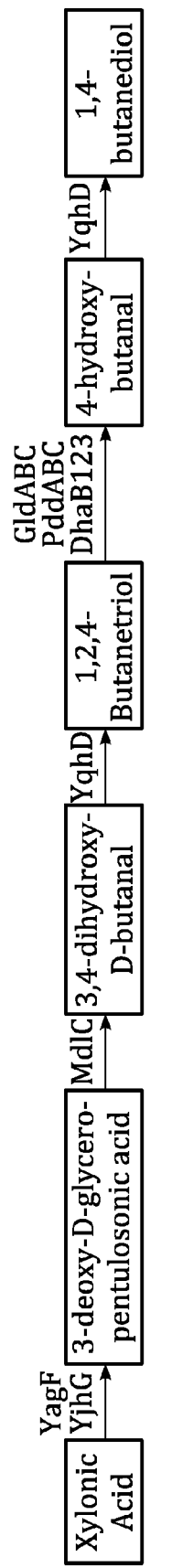
FIG. 2 shows an exemplary metabolic pathway for the production of 1,4-butanediol. Xylose can be converted to 1,4-butanediol through the action of enzymes expressed by *E. coli* (YagF, YjhG, and each YqhD) and by the heterologous expression of enzymes from other microorganisms (MdlC, GldABC, PddABC, and DhaB124). Enzymes: Xdh (xylose dehydrogenase from *Caulobacter crescentus*), YagF and YjhG (xylonate dehydratases from *E. coli*), MdlC (benzoylformate decarboxylase from *Pseudomonas putida*), GldABC (diol dehydratase from *Klebsiella pneumoniae*), PddABC (diol dehydratase from *Klebsiella oxytoca*), and DhaB123 (diol dehydratase from *Clostridium butryicum*), YqhD (alcohol dehydrogenase from *E. coli*).

*Escherichia coli* strain JCL16 (BW25113/F' [traD36, proAB+, lacIqZΔM15Tn10]) was successfully modified to produce 1,4-butanediol from D-xylonic acid using the pathway illustrated in FIG. 2.

Figure 3:
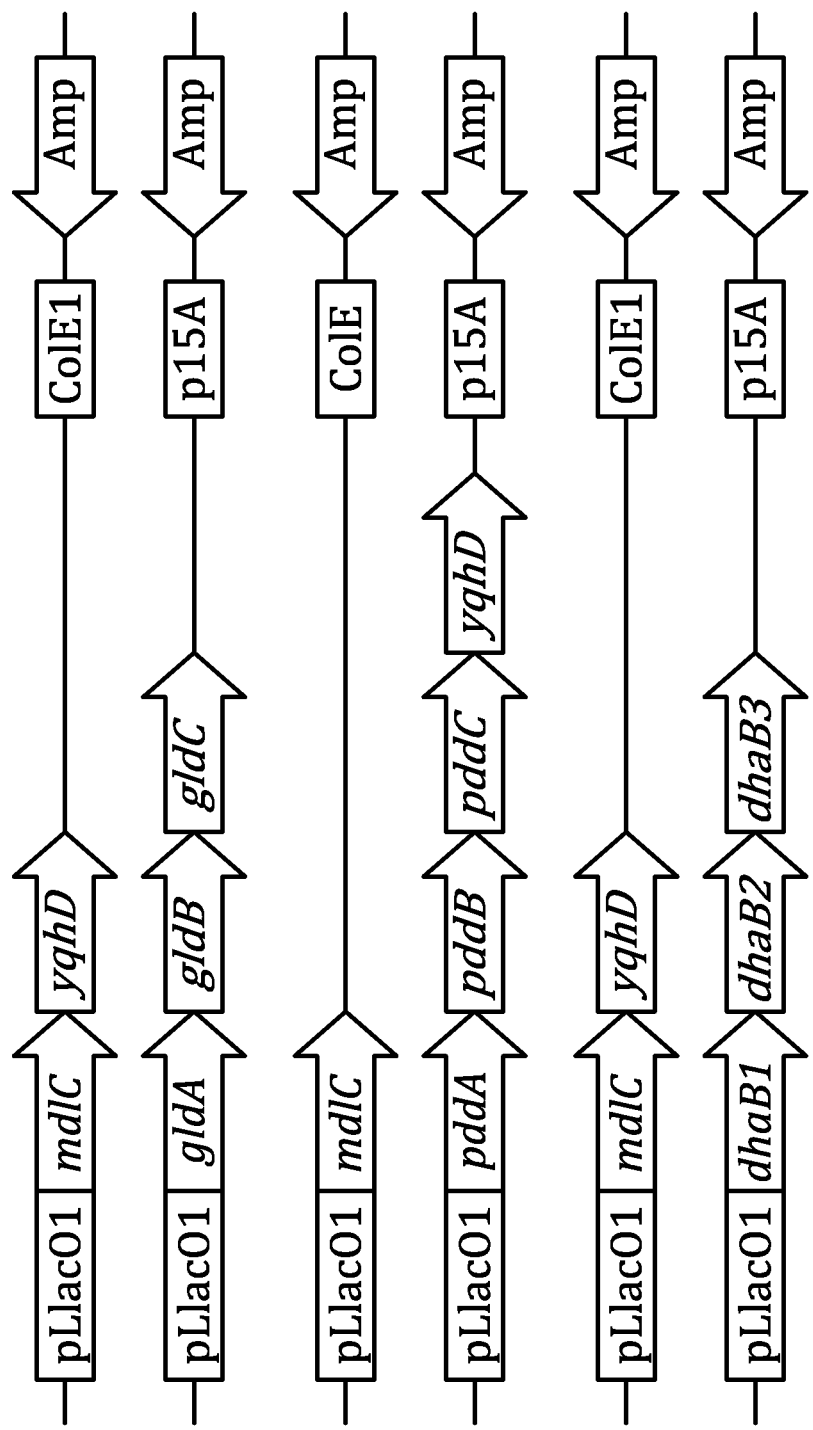
FIG. 3 shows exemplary plasmid pairs transformed into JCL16 for 1,4-butanediol production from D-xylonic acid.

In addition to the genes already expressed by *E. coli* (eg., yagF, yjhG, and yqhD), the benzoylformate decarboxylase of *Pseudomonas putida* (mdlC) and the diol dehydratases from *Klebsiella pneumoniae* (gldABC), *Klebsiella oxytoca* (pddABC), or *Clostridium butyricum* (dhaB123) were expressed heterologously behind the PLlacO1 inducible promoter (FIG. 3).

Figure 4:
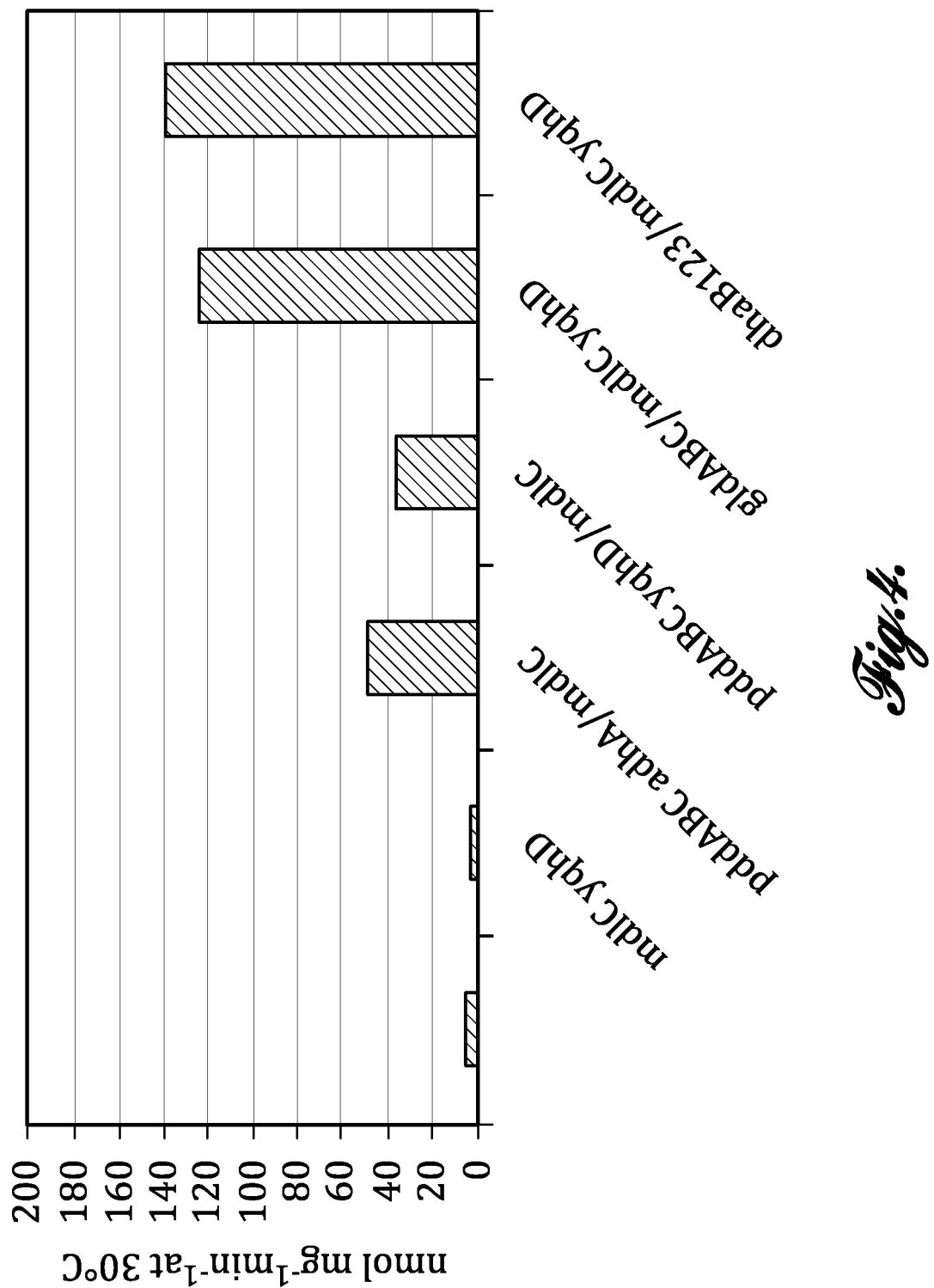
FIG. 4 is a graph showing enzymatic activity of diol dehydratases PddABC, GldABC, and DhaB123. Diol dehydratase activity with 1,2,4-butanetriol was determined by a coupled reaction measuring the oxidation of NADPH in the presence of excess alcohol dehydrogenase.

Diol dehydratases do not naturally utilize 1,2,4-butanetriol as a substrate. To illustrate that the diol dehydratases are able to utilize 1,2,4-butanetriol, diol dehydratase activity was determined. All of the diol dehydratases examined, GldABC, PddABC, and DhaB123, demonstrated activity with 1,2,4-butanetriol as a substrate, with GldABC and DhaB123 having the most significant activity (FIG. 4).

To examine 1,4-butanediol production, fresh transformants were grown overnight in LB at 37° C. Ampicillin (120 μg/L) and Kanamycin (50 μg/L) were added for plasmid maintenance. From these overnights, 100 μl were subcultured into 20 ml of fermentation media (per Liter: 20 g Bacto tryptone, 10 g Bacto yeast extract, 5 g NaCl, 3.75 g $K_2HPO_4$, 0.24 g $MgSO_4$, and 0.34 g thiamine hydrochloride). The cells were incubated at 37° C. until the cells reached an OD600 ~0.4-0.6, at which point IPTG (1 mM), D-xylonic acid (2% wt/vol), and coenzyme B 12 (0.5 mg/L) were added to the cultures. The cultures were then grown at 30° C. at 250 rpm.

Figure 5:
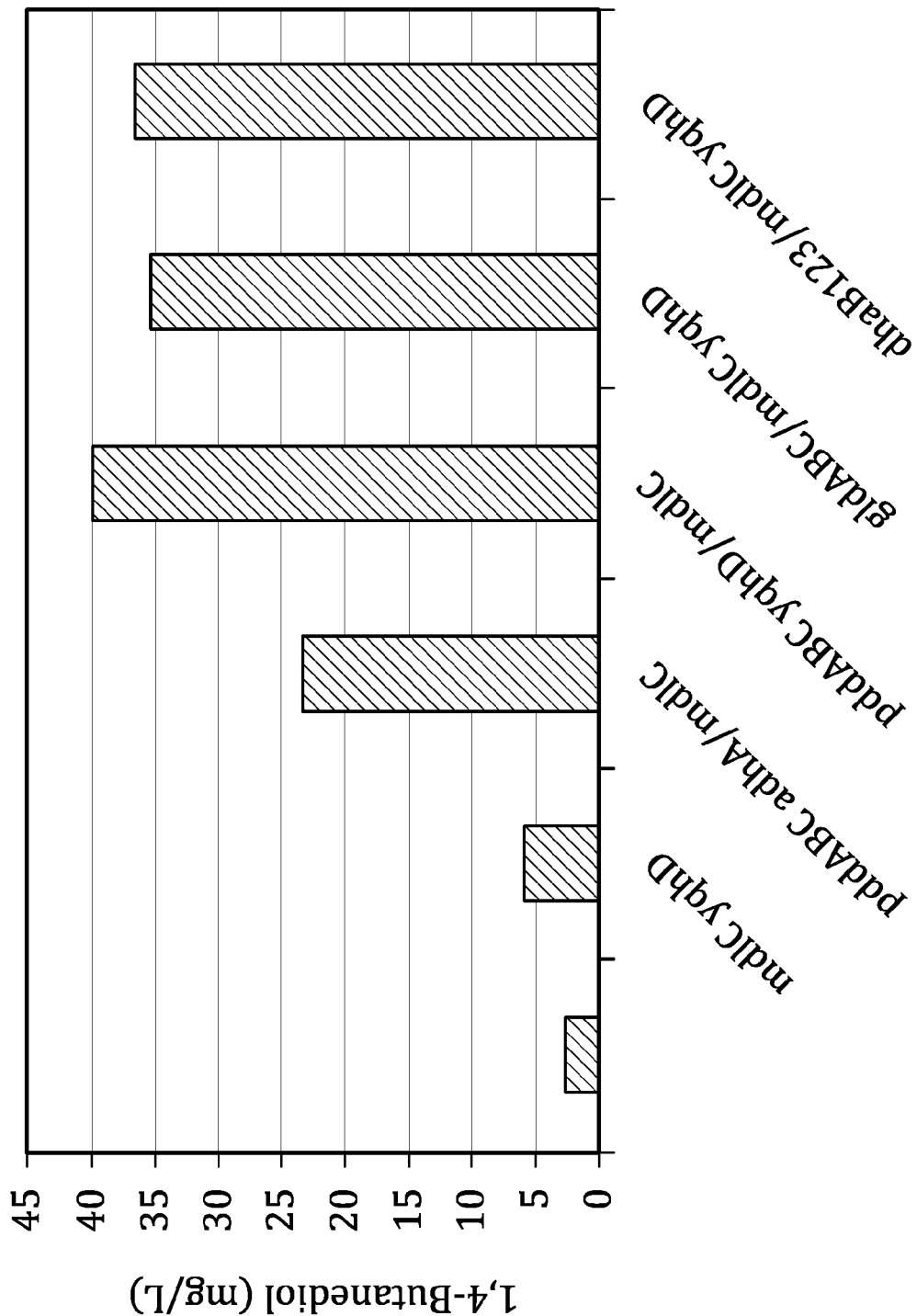
FIG. 5 is a graph showing 1,4-butanediol production from D-xylonic acid. The JCL16 strains were grown in 20 ml with 20 g/L of D-xylonic acid at 30° C. for 24 hours.

After 24 hr, 1,4-butanediol was observed for all of the strains expressing mdlC, yqhDladhA, and one of the diol dehydratases (gldABC, pddABC, or dhaB123) (FIG. 5). This production was not observed for the strain that did not contain the plasmids, nor for the strain expressing mdlC yqhD, which did not express one of the diol dehydratases.

A number of embodiments of the invention have been described. Nevertheless, it will be understood that various modifications may be made without departing from the spirit and scope of the invention. Accordingly, other embodiments are within the scope of the following claims.

---

SEQUENCE LISTING

<160> NUMBER OF SEQ ID NOS: 78

<210> SEQ ID NO 1
<211> LENGTH: 807
<212> TYPE: DNA
<213> ORGANISM: Burkholderia fungorum
<220> FEATURE:
<221> NAME/KEY: CDS
<222> LOCATION: (1)..(807)

<400> SEQUENCE: 1

```
atg tat ttg ttg tca tac ccg gaa cag gtg gac tat ccg atg tcg tac      48
Met Tyr Leu Leu Ser Tyr Pro Glu Gln Val Asp Tyr Pro Met Ser Tyr
1               5                   10                  15 gca atc tat ccc agc ctc tca ggc aaa acg gtt gtc atc acc ggc ggc      96
Ala Ile Tyr Pro Ser Leu Ser Gly Lys Thr Val Val Ile Thr Gly Gly
            20                  25                  30 ggc agc ggc atc ggc gcc gcg atg gtc gaa gct ttc gcc cgg cag ggc     144
Gly Ser Gly Ile Gly Ala Ala Met Val Glu Ala Phe Ala Arg Gln Gly
```

```
                35                  40                  45
gcg cga gtt ttc ttc ctc gac gtc gct gag gac gat tcg ctg gcg ttg      192
Ala Arg Val Phe Phe Leu Asp Val Ala Glu Asp Asp Ser Leu Ala Leu
 50                  55                  60 cag caa tcg ctg agc gac gcg cct cac ccg ccg ttg ttc cgc cgc tgc      240
Gln Gln Ser Leu Ser Asp Ala Pro His Pro Pro Leu Phe Arg Arg Cys
 65                  70                  75                  80 gat ctg cgc agc gtc gat gcg atc cac agt gcg ttt gcc ggg atc gtc      288
Asp Leu Arg Ser Val Asp Ala Ile His Ser Ala Phe Ala Gly Ile Val
                 85                  90                  95 gag atc gcc ggg ccg atc gag gta ctc gtc aac aac gct ggc aac gac      336
Glu Ile Ala Gly Pro Ile Glu Val Leu Val Asn Asn Ala Gly Asn Asp
            100                 105                 110 gac cgg cat gaa gtc gac gcc atc acg ccg gcc tat tgg gac gag cgc      384
Asp Arg His Glu Val Asp Ala Ile Thr Pro Ala Tyr Trp Asp Glu Arg
        115                 120                 125 atg gcc gtg aac ctg cgg cac cag ttc ttc tgc gcg cag gcc gca gcg      432
Met Ala Val Asn Leu Arg His Gln Phe Phe Cys Ala Gln Ala Ala Ala
130                 135                 140 gcc ggc atg cgc aag atc ggg cgc ggc gtg atc ctg aat ctt ggc tcg      480
Ala Gly Met Arg Lys Ile Gly Arg Gly Val Ile Leu Asn Leu Gly Ser
145                 150                 155                 160 gtt tcc tgg cac ctc gcg ttg ccg aac ctc gcg atc tac atg agc gcg      528
Val Ser Trp His Leu Ala Leu Pro Asn Leu Ala Ile Tyr Met Ser Ala
                165                 170                 175 aag gcc ggt atc gaa ggg ctg acc cgg ggc ctc gcg cgc gat ctc ggc      576
Lys Ala Gly Ile Glu Gly Leu Thr Arg Gly Leu Ala Arg Asp Leu Gly
            180                 185                 190 gcc gcc ggc atc cgc gtg aac tgc att att ccc ggc gcg gtg cgg act      624
Ala Ala Gly Ile Arg Val Asn Cys Ile Ile Pro Gly Ala Val Arg Thr
        195                 200                 205 ccc cgt cag atg cag ctc tgg cag tcg ccc gag agc gaa gcg aag ctc      672
Pro Arg Gln Met Gln Leu Trp Gln Ser Pro Glu Ser Glu Ala Lys Leu
210                 215                 220 gtc gcc agc caa tgt ctg cgt ttg cgt atc gaa cct gag cat gtc gcg      720
Val Ala Ser Gln Cys Leu Arg Leu Arg Ile Glu Pro Glu His Val Ala
225                 230                 235                 240 cgc atg gcg ttg ttt ctt gcg tcc gac gat gcg tcg cgt tgc tca ggg      768
Arg Met Ala Leu Phe Leu Ala Ser Asp Asp Ala Ser Arg Cys Ser Gly
                245                 250                 255 cgg gat tat ttc gtc gac gcc ggg tgg tac gga gaa tga              807
Arg Asp Tyr Phe Val Asp Ala Gly Trp Tyr Gly Glu
            260                 265

<210> SEQ ID NO 2
<211> LENGTH: 268
<212> TYPE: PRT
<213> ORGANISM: Burkholderia fungorum

<400> SEQUENCE: 2

Met Tyr Leu Leu Ser Tyr Pro Glu Gln Val Asp Tyr Pro Met Ser Tyr
 1               5                  10                  15

Ala Ile Tyr Pro Ser Leu Ser Gly Lys Thr Val Ile Thr Gly Gly
            20                  25                  30

Gly Ser Gly Ile Gly Ala Ala Met Val Glu Ala Phe Ala Arg Gln Gly
        35                  40                  45

Ala Arg Val Phe Phe Leu Asp Val Ala Glu Asp Asp Ser Leu Ala Leu
 50                  55                  60

Gln Gln Ser Leu Ser Asp Ala Pro His Pro Pro Leu Phe Arg Arg Cys
```

```
                    65                  70                  75                  80
Asp Leu Arg Ser Val Asp Ala Ile His Ser Ala Phe Ala Gly Ile Val
                    85                  90                  95

Glu Ile Ala Gly Pro Ile Glu Val Leu Val Asn Asn Ala Gly Asn Asp
                100                 105                 110

Asp Arg His Glu Val Asp Ala Ile Thr Pro Ala Tyr Trp Asp Glu Arg
                115                 120                 125

Met Ala Val Asn Leu Arg His Gln Phe Phe Cys Ala Gln Ala Ala Ala
            130                 135                 140

Ala Gly Met Arg Lys Ile Gly Arg Gly Val Ile Leu Asn Leu Gly Ser
145                 150                 155                 160

Val Ser Trp His Leu Ala Leu Pro Asn Leu Ala Ile Tyr Met Ser Ala
                165                 170                 175

Lys Ala Gly Ile Glu Gly Leu Thr Arg Gly Leu Ala Arg Asp Leu Gly
            180                 185                 190

Ala Ala Gly Ile Arg Val Asn Cys Ile Ile Pro Gly Ala Val Arg Thr
        195                 200                 205

Pro Arg Gln Met Gln Leu Trp Gln Ser Pro Glu Ser Glu Ala Lys Leu
    210                 215                 220

Val Ala Ser Gln Cys Leu Arg Leu Arg Ile Glu Pro Glu His Val Ala
225                 230                 235                 240

Arg Met Ala Leu Phe Leu Ala Ser Asp Asp Ala Ser Arg Cys Ser Gly
                245                 250                 255

Arg Asp Tyr Phe Val Asp Ala Gly Trp Tyr Gly Glu
            260                 265

<210> SEQ ID NO 3
<211> LENGTH: 747
<212> TYPE: DNA
<213> ORGANISM: Caulobacter crescentus
<220> FEATURE:
<221> NAME/KEY: CDS
<222> LOCATION: (1)..(747)

<400> SEQUENCE: 3 atg tcc tca gcc atc tat ccc agc ctg aag ggc aag cgc gtc gtc atc      48
Met Ser Ser Ala Ile Tyr Pro Ser Leu Lys Gly Lys Arg Val Val Ile
1               5                   10                  15 acc ggc ggc ggc tcg ggc atc ggg gcc ggc ctc acc gcc ggc ttc gcc      96
Thr Gly Gly Gly Ser Gly Ile Gly Ala Gly Leu Thr Ala Gly Phe Ala
                20                  25                  30 cgt cag ggc gcg gag gtg atc ttc ctc gac atc gcc gac gag gac tcc     144
Arg Gln Gly Ala Glu Val Ile Phe Leu Asp Ile Ala Asp Glu Asp Ser
            35                  40                  45 agg gct ctt gag gcc gag ctg gcc ggc tcg ccg atc ccg ccg gtc tac     192
Arg Ala Leu Glu Ala Glu Leu Ala Gly Ser Pro Ile Pro Pro Val Tyr
        50                  55                  60 aag cgc tgc gac ctg atg aac ctc gag gcg atc aag gcg gtc ttc gcc     240
Lys Arg Cys Asp Leu Met Asn Leu Glu Ala Ile Lys Ala Val Phe Ala
65                  70                  75                  80 gag atc ggc gac gtc gac gtg ctg gtc aac aac gcc ggc aat gac gac     288
Glu Ile Gly Asp Val Asp Val Leu Val Asn Asn Ala Gly Asn Asp Asp
                85                  90                  95 cgc cac aag ctg gcc gac gtg acc ggc gcc tat tgg gac gag cgg atc     336
Arg His Lys Leu Ala Asp Val Thr Gly Ala Tyr Trp Asp Glu Arg Ile
                100                 105                 110 aac gtc aac ctg cgc cac atg ctg ttc tgc acc cag gcc gtc gcg ccg     384
Asn Val Asn Leu Arg His Met Leu Phe Cys Thr Gln Ala Val Ala Pro
```

```
                       115                 120                 125
ggc atg aag aag cgt ggc ggg gcg gtg atc aac ttc ggt tcg atc      432
Gly Met Lys Lys Arg Gly Gly Ala Val Ile Asn Phe Gly Ser Ile
    130                 135                 140 agc tgg cac ctg ggg ctt gag gac ctc gtc ctc tac gaa acc gcc aag  480
Ser Trp His Leu Gly Leu Glu Asp Leu Val Leu Tyr Glu Thr Ala Lys
145                 150                 155                 160 gcc ggc atc gaa ggc atg acc cgc gcg ctg gcc cgg gag ctg ggt ccc  528
Ala Gly Ile Glu Gly Met Thr Arg Ala Leu Ala Arg Glu Leu Gly Pro
                165                 170                 175 gac gac atc cgc gtc acc tgc gtg gtg ccg ggc aac gtc aag acc aag  576
Asp Asp Ile Arg Val Thr Cys Val Val Pro Gly Asn Val Lys Thr Lys
            180                 185                 190 cgc cag gag aag tgg tac acg ccc gaa ggc gag gcc cag atc gtg gcg  624
Arg Gln Glu Lys Trp Tyr Thr Pro Glu Gly Glu Ala Gln Ile Val Ala
        195                 200                 205 gcc caa tgc ctg aag ggc cgc atc gtc ccg gag aac gtc gcc gcg ctg  672
Ala Gln Cys Leu Lys Gly Arg Ile Val Pro Glu Asn Val Ala Ala Leu
    210                 215                 220 gtg ctg ttc ctg gcc tcg gat gac gcg tcg ctc tgc acc ggc cac gaa  720
Val Leu Phe Leu Ala Ser Asp Asp Ala Ser Leu Cys Thr Gly His Glu
225                 230                 235                 240 tac tgg atc gac gcc ggc tgg cgt tga                              747
Tyr Trp Ile Asp Ala Gly Trp Arg
                245

<210> SEQ ID NO 4
<211> LENGTH: 248
<212> TYPE: PRT
<213> ORGANISM: Caulobacter crescentus

<400> SEQUENCE: 4

Met Ser Ser Ala Ile Tyr Pro Ser Leu Lys Gly Lys Arg Val Val Ile
1               5                   10                  15

Thr Gly Gly Gly Ser Gly Ile Gly Ala Gly Leu Thr Ala Gly Phe Ala
                20                  25                  30

Arg Gln Gly Ala Glu Val Ile Phe Leu Asp Ile Ala Asp Glu Asp Ser
            35                  40                  45

Arg Ala Leu Glu Ala Glu Leu Ala Gly Ser Pro Ile Pro Pro Val Tyr
        50                  55                  60

Lys Arg Cys Asp Leu Met Asn Leu Glu Ala Ile Lys Ala Val Phe Ala
65                  70                  75                  80

Glu Ile Gly Asp Val Asp Val Leu Val Asn Asn Ala Gly Asn Asp Asp
                85                  90                  95

Arg His Lys Leu Ala Asp Val Thr Gly Ala Tyr Trp Asp Glu Arg Ile
            100                 105                 110

Asn Val Asn Leu Arg His Met Leu Phe Cys Thr Gln Ala Val Ala Pro
        115                 120                 125

Gly Met Lys Lys Arg Gly Gly Ala Val Ile Asn Phe Gly Ser Ile
    130                 135                 140

Ser Trp His Leu Gly Leu Glu Asp Leu Val Leu Tyr Glu Thr Ala Lys
145                 150                 155                 160

Ala Gly Ile Glu Gly Met Thr Arg Ala Leu Ala Arg Glu Leu Gly Pro
                165                 170                 175

Asp Asp Ile Arg Val Thr Cys Val Val Pro Gly Asn Val Lys Thr Lys
            180                 185                 190

Arg Gln Glu Lys Trp Tyr Thr Pro Glu Gly Glu Ala Gln Ile Val Ala
```

-continued

```
                195                 200                 205
Ala Gln Cys Leu Lys Gly Arg Ile Val Pro Glu Asn Val Ala Ala Leu
            210                 215                 220

Val Leu Phe Leu Ala Ser Asp Asp Ala Ser Leu Cys Thr Gly His Glu
225                 230                 235                 240

Tyr Trp Ile Asp Ala Gly Trp Arg
                245

<210> SEQ ID NO 5
<211> LENGTH: 1968
<212> TYPE: DNA
<213> ORGANISM: Escherichia coli
<220> FEATURE:
<221> NAME/KEY: CDS
<222> LOCATION: (1)..(1968)

<400> SEQUENCE: 5 atg acc att gag aaa att ttc acc ccg cag gac gac gcg ttt tat gcg      48
Met Thr Ile Glu Lys Ile Phe Thr Pro Gln Asp Asp Ala Phe Tyr Ala
1               5                   10                  15 gtg atc acc cac gcg gcg ggg ccg cag ggc gct ctg ccg ctg acc ccg      96
Val Ile Thr His Ala Ala Gly Pro Gln Gly Ala Leu Pro Leu Thr Pro
            20                  25                  30 cag atg ctg atg gaa tct ccc agc ggc aac ctg ttc ggc atg acg cag     144
Gln Met Leu Met Glu Ser Pro Ser Gly Asn Leu Phe Gly Met Thr Gln
        35                  40                  45 aac gcc ggg atg ggc tgg gac gcc aac aag ctc acc ggc aaa gag gtg     192
Asn Ala Gly Met Gly Trp Asp Ala Asn Lys Leu Thr Gly Lys Glu Val
    50                  55                  60 ctg att atc ggc act cag ggc ggc atc cgc gcc gga gac gga cgc cca     240
Leu Ile Ile Gly Thr Gln Gly Gly Ile Arg Ala Gly Asp Gly Arg Pro
65                  70                  75                  80 atc gcg ctg ggc tac cac acc ggg cat tgg gag atc ggc atg cag atg     288
Ile Ala Leu Gly Tyr His Thr Gly His Trp Glu Ile Gly Met Gln Met
                85                  90                  95 cag gcg gcg gcg aag gag atc acc cgc aat ggc ggg atc ccg ttc gcg     336
Gln Ala Ala Ala Lys Glu Ile Thr Arg Asn Gly Gly Ile Pro Phe Ala
            100                 105                 110 gcc ttc gtc agc gat ccg tgc gac ggg cgc tcg cag ggc acg cac ggt     384
Ala Phe Val Ser Asp Pro Cys Asp Gly Arg Ser Gln Gly Thr His Gly
        115                 120                 125 atg ttc gat tcc ctg ccg tac cgc aac gac gcg gcg atc gtg ttt cgc     432
Met Phe Asp Ser Leu Pro Tyr Arg Asn Asp Ala Ala Ile Val Phe Arg
    130                 135                 140 cgc ctg atc cgc tcc ctg ccg acg cgg cgg gcg gtg atc ggc gta gcg     480
Arg Leu Ile Arg Ser Leu Pro Thr Arg Arg Ala Val Ile Gly Val Ala
145                 150                 155                 160 acc tgc gat aaa ggg ctg ccc gcc acc atg att gcg ctg gcc gcg atg     528
Thr Cys Asp Lys Gly Leu Pro Ala Thr Met Ile Ala Leu Ala Ala Met
                165                 170                 175 cac gac ctg ccg act att ctg gtg ccg ggc ggg gcg acg ctg ccg ccg     576
His Asp Leu Pro Thr Ile Leu Val Pro Gly Gly Ala Thr Leu Pro Pro
            180                 185                 190 acc gtc ggg gaa gac gcg ggc aag gtg cag acc atc ggc gcg cgt ttc     624
Thr Val Gly Glu Asp Ala Gly Lys Val Gln Thr Ile Gly Ala Arg Phe
        195                 200                 205 gcc aac cac gaa ctc tcc ctg cag gag gcc gcc gaa ctg ggc tgt cgc     672
Ala Asn His Glu Leu Ser Leu Gln Glu Ala Ala Glu Leu Gly Cys Arg
    210                 215                 220 gcc tgc gcc tcg ccg ggc ggc ggg tgt cag ttc ctc ggc acg gcg ggc     720
```

-continued

| | | | | | | | | | | | | | | | |
|---|---|---|---|---|---|---|---|---|---|---|---|---|---|---|---|
| Ala | Cys | Ala | Ser | Pro | Gly | Gly | Gly | Cys | Gln | Phe | Leu | Gly | Thr | Ala | Gly |
| 225 | | | | 230 | | | | | 235 | | | | | 240 | |

| acc | tcg | cag | gtg | gtc | gcg | gag | gcg | ctg | ggt | ctg | gcg | ctg | ccg | cac | tcc | 768 |
|---|---|---|---|---|---|---|---|---|---|---|---|---|---|---|---|---|
| Thr | Ser | Gln | Val | Val | Ala | Glu | Ala | Leu | Gly | Leu | Ala | Leu | Pro | His | Ser | |
| | | | | 245 | | | | | 250 | | | | | 255 | | |

| gcg | ctg | gcg | ccg | tcc | ggg | cag | gcg | gtg | tgg | ctg | gag | atc | gcc | cgc | cag | 816 |
|---|---|---|---|---|---|---|---|---|---|---|---|---|---|---|---|---|
| Ala | Leu | Ala | Pro | Ser | Gly | Gln | Ala | Val | Trp | Leu | Glu | Ile | Ala | Arg | Gln | |
| | | | 260 | | | | | 265 | | | | | 270 | | | |

| tcg | gcg | cgc | gcg | gtc | agc | gag | ctg | gat | agc | cgc | ggc | atc | acc | acg | cgg | 864 |
|---|---|---|---|---|---|---|---|---|---|---|---|---|---|---|---|---|
| Ser | Ala | Arg | Ala | Val | Ser | Glu | Leu | Asp | Ser | Arg | Gly | Ile | Thr | Thr | Arg | |
| | | | 275 | | | | | 280 | | | | | 285 | | | |

| gat | atc | ctc | tcc | gat | aaa | gcc | atc | gaa | aac | gcg | atg | gtg | atc | cac | gcg | 912 |
|---|---|---|---|---|---|---|---|---|---|---|---|---|---|---|---|---|
| Asp | Ile | Leu | Ser | Asp | Lys | Ala | Ile | Glu | Asn | Ala | Met | Val | Ile | His | Ala | |
| | | 290 | | | | | 295 | | | | | 300 | | | | |

| gcg | ttc | ggc | ggc | tcc | acc | aat | tta | ctg | ctg | cac | att | ccg | gcc | atc | gcc | 960 |
|---|---|---|---|---|---|---|---|---|---|---|---|---|---|---|---|---|
| Ala | Phe | Gly | Gly | Ser | Thr | Asn | Leu | Leu | Leu | His | Ile | Pro | Ala | Ile | Ala | |
| 305 | | | | 310 | | | | | 315 | | | | | 320 | | |

| cac | gcg | gcg | ggc | tgc | acg | atc | ccg | gac | gtt | gag | cac | tgg | acg | cgc | atc | 1008 |
|---|---|---|---|---|---|---|---|---|---|---|---|---|---|---|---|---|
| His | Ala | Ala | Gly | Cys | Thr | Ile | Pro | Asp | Val | Glu | His | Trp | Thr | Arg | Ile | |
| | | | 325 | | | | | 330 | | | | | 335 | | | |

| aac | cgt | aaa | gtg | ccg | cgt | ctg | gtg | agc | gtg | ctg | ccc | aac | ggc | ccg | gac | 1056 |
|---|---|---|---|---|---|---|---|---|---|---|---|---|---|---|---|---|
| Asn | Arg | Lys | Val | Pro | Arg | Leu | Val | Ser | Val | Leu | Pro | Asn | Gly | Pro | Asp | |
| | | | 340 | | | | | 345 | | | | | 350 | | | |

| tat | cac | ccg | acc | gtg | cgc | gcc | ttc | ctc | gcg | ggc | ggc | gtg | ccg | gag | gtg | 1104 |
|---|---|---|---|---|---|---|---|---|---|---|---|---|---|---|---|---|
| Tyr | His | Pro | Thr | Val | Arg | Ala | Phe | Leu | Ala | Gly | Gly | Val | Pro | Glu | Val | |
| | | | 355 | | | | | 360 | | | | | 365 | | | |

| atg | ctc | cac | ctg | cgc | gac | ctc | ggc | ctg | ctg | cat | ctg | gac | gcc | atg | acc | 1152 |
|---|---|---|---|---|---|---|---|---|---|---|---|---|---|---|---|---|
| Met | Leu | His | Leu | Arg | Asp | Leu | Gly | Leu | Leu | His | Leu | Asp | Ala | Met | Thr | |
| | | 370 | | | | | 375 | | | | | 380 | | | | |

| gtg | acc | ggc | cag | acg | gtg | ggc | gag | aac | ctt | gaa | tgg | tgg | cag | gcg | tcc | 1200 |
|---|---|---|---|---|---|---|---|---|---|---|---|---|---|---|---|---|
| Val | Thr | Gly | Gln | Thr | Val | Gly | Glu | Asn | Leu | Glu | Trp | Trp | Gln | Ala | Ser | |
| 385 | | | | 390 | | | | | 395 | | | | | 400 | | |

| gag | cgc | cgg | gcg | cgc | ttc | cgc | cag | tgc | ctg | cgc | gag | cag | gac | ggc | gta | 1248 |
|---|---|---|---|---|---|---|---|---|---|---|---|---|---|---|---|---|
| Glu | Arg | Arg | Ala | Arg | Phe | Arg | Gln | Cys | Leu | Arg | Glu | Gln | Asp | Gly | Val | |
| | | | 405 | | | | | 410 | | | | | 415 | | | |

| gag | ccg | gat | gac | gtg | atc | ctg | ccg | ccg | gag | aag | gca | aaa | gcg | aaa | ggg | 1296 |
|---|---|---|---|---|---|---|---|---|---|---|---|---|---|---|---|---|
| Glu | Pro | Asp | Asp | Val | Ile | Leu | Pro | Pro | Glu | Lys | Ala | Lys | Ala | Lys | Gly | |
| | | | 420 | | | | | 425 | | | | | 430 | | | |

| ctg | acc | tcg | acg | gtc | tgc | ttc | ccg | acg | ggc | aac | atc | gct | ccg | gaa | ggt | 1344 |
|---|---|---|---|---|---|---|---|---|---|---|---|---|---|---|---|---|
| Leu | Thr | Ser | Thr | Val | Cys | Phe | Pro | Thr | Gly | Asn | Ile | Ala | Pro | Glu | Gly | |
| | | | 435 | | | | | 440 | | | | | 445 | | | |

| tcg | gtg | atc | aag | gcc | acg | gcg | atc | gac | ccg | tcg | gtg | gtg | ggc | gaa | gat | 1392 |
|---|---|---|---|---|---|---|---|---|---|---|---|---|---|---|---|---|
| Ser | Val | Ile | Lys | Ala | Thr | Ala | Ile | Asp | Pro | Ser | Val | Val | Gly | Glu | Asp | |
| | 450 | | | | | 455 | | | | | 460 | | | | | |

| ggc | gta | tac | cac | cac | acc | ggc | cgg | gtg | cgg | gtg | ttt | gtc | tcg | gaa | gcg | 1440 |
|---|---|---|---|---|---|---|---|---|---|---|---|---|---|---|---|---|
| Gly | Val | Tyr | His | His | Thr | Gly | Arg | Val | Arg | Val | Phe | Val | Ser | Glu | Ala | |
| 465 | | | | 470 | | | | | 475 | | | | | 480 | | |

| cag | gcg | atc | aag | gcg | atc | aag | cgg | gaa | gag | att | gtg | cag | ggc | gat | atc | 1488 |
|---|---|---|---|---|---|---|---|---|---|---|---|---|---|---|---|---|
| Gln | Ala | Ile | Lys | Ala | Ile | Lys | Arg | Glu | Glu | Ile | Val | Gln | Gly | Asp | Ile | |
| | | | 485 | | | | | 490 | | | | | 495 | | | |

| atg | gtg | gtg | atc | ggc | ggc | ggg | ccg | tcc | ggc | acc | ggc | atg | gaa | gag | acc | 1536 |
|---|---|---|---|---|---|---|---|---|---|---|---|---|---|---|---|---|
| Met | Val | Val | Ile | Gly | Gly | Gly | Pro | Ser | Gly | Thr | Gly | Met | Glu | Glu | Thr | |
| | | | 500 | | | | | 505 | | | | | 510 | | | |

| tac | cag | ctc | acc | tcc | gcg | cta | aag | cat | atc | tcg | tgg | ggc | aag | acg | gtg | 1584 |
|---|---|---|---|---|---|---|---|---|---|---|---|---|---|---|---|---|
| Tyr | Gln | Leu | Thr | Ser | Ala | Leu | Lys | His | Ile | Ser | Trp | Gly | Lys | Thr | Val | |
| | | | 515 | | | | | 520 | | | | | 525 | | | |

| tcg | ctc | atc | acc | gat | gcg | cgc | ttc | tcg | ggc | gtg | tcg | acg | ggc | gcc | tgc | 1632 |
|---|---|---|---|---|---|---|---|---|---|---|---|---|---|---|---|---|
| Ser | Leu | Ile | Thr | Asp | Ala | Arg | Phe | Ser | Gly | Val | Ser | Thr | Gly | Ala | Cys | |
| | 530 | | | | | 535 | | | | | 540 | | | | | |

```
ttc ggc cac gtg tcg ccg gag gcg ctg gcg ggc ggg ccg att ggc aag    1680
Phe Gly His Val Ser Pro Glu Ala Leu Ala Gly Gly Pro Ile Gly Lys
545                 550                 555                 560 ctg cgc gat aac gac atc atc gag att gcc gtg gat cgt ctg acg tta    1728
Leu Arg Asp Asn Asp Ile Ile Glu Ile Ala Val Asp Arg Leu Thr Leu
                565                 570                 575 act ggc agc gtg aac ttc atc ggc acc gcg gac aac ccg ctg acg ccg    1776
Thr Gly Ser Val Asn Phe Ile Gly Thr Ala Asp Asn Pro Leu Thr Pro
            580                 585                 590 gaa gag ggc gcg cgt gag ctg gcg cgg cgg cag acg cac ccg gac ctg    1824
Glu Glu Gly Ala Arg Glu Leu Ala Arg Arg Gln Thr His Pro Asp Leu
        595                 600                 605 cac gcc cac gac ttt ttg ccg gac gac acc cgg ctg tgg gcg gca ctg    1872
His Ala His Asp Phe Leu Pro Asp Asp Thr Arg Leu Trp Ala Ala Leu
    610                 615                 620 cag tcg gtg agc ggc ggc acc tgg aaa ggc tgt att tat gac acc gat    1920
Gln Ser Val Ser Gly Gly Thr Trp Lys Gly Cys Ile Tyr Asp Thr Asp
625                 630                 635                 640 aaa att atc gag gta att aac gcc ggt aaa aaa gcg ctc gga att taa    1968
Lys Ile Ile Glu Val Ile Asn Ala Gly Lys Lys Ala Leu Gly Ile
                645                 650                 655

<210> SEQ ID NO 6
<211> LENGTH: 655
<212> TYPE: PRT
<213> ORGANISM: Escherichia coli

<400> SEQUENCE: 6

Met Thr Ile Glu Lys Ile Phe Thr Pro Gln Asp Asp Ala Phe Tyr Ala
1               5                   10                  15

Val Ile Thr His Ala Ala Gly Pro Gln Gly Ala Leu Pro Leu Thr Pro
            20                  25                  30

Gln Met Leu Met Glu Ser Pro Ser Gly Asn Leu Phe Gly Met Thr Gln
        35                  40                  45

Asn Ala Gly Met Gly Trp Asp Ala Asn Lys Leu Thr Gly Lys Glu Val
    50                  55                  60

Leu Ile Ile Gly Thr Gln Gly Gly Ile Arg Ala Gly Asp Gly Arg Pro
65                  70                  75                  80

Ile Ala Leu Gly Tyr His Thr Gly His Trp Glu Ile Gly Met Gln Met
                85                  90                  95

Gln Ala Ala Ala Lys Glu Ile Thr Arg Asn Gly Gly Ile Pro Phe Ala
            100                 105                 110

Ala Phe Val Ser Asp Pro Cys Asp Gly Arg Ser Gln Gly Thr His Gly
        115                 120                 125

Met Phe Asp Ser Leu Pro Tyr Arg Asn Asp Ala Ala Ile Val Phe Arg
    130                 135                 140

Arg Leu Ile Arg Ser Leu Pro Thr Arg Arg Ala Val Ile Gly Val Ala
145                 150                 155                 160

Thr Cys Asp Lys Gly Leu Pro Ala Thr Met Ile Ala Leu Ala Ala Met
                165                 170                 175

His Asp Leu Pro Thr Ile Leu Val Pro Gly Gly Ala Thr Leu Pro Pro
            180                 185                 190

Thr Val Gly Glu Asp Ala Gly Lys Val Gln Thr Ile Gly Ala Arg Phe
        195                 200                 205

Ala Asn His Glu Leu Ser Leu Gln Glu Ala Ala Glu Leu Gly Cys Arg
    210                 215                 220

Ala Cys Ala Ser Pro Gly Gly Gly Cys Gln Phe Leu Gly Thr Ala Gly
```

```
            225                 230                 235                 240
        Thr Ser Gln Val Val Ala Glu Ala Leu Gly Leu Ala Leu Pro His Ser
                        245                 250                 255

Ala Leu Ala Pro Ser Gly Gln Ala Val Trp Leu Glu Ile Ala Arg Gln
                        260                 265                 270

Ser Ala Arg Ala Val Ser Glu Leu Asp Ser Arg Gly Ile Thr Thr Arg
                        275                 280                 285

Asp Ile Leu Ser Asp Lys Ala Ile Glu Asn Ala Met Val Ile His Ala
                        290                 295                 300

Ala Phe Gly Gly Ser Thr Asn Leu Leu Leu His Ile Pro Ala Ile Ala
        305                 310                 315                 320

His Ala Ala Gly Cys Thr Ile Pro Asp Val Glu His Trp Thr Arg Ile
                        325                 330                 335

Asn Arg Lys Val Pro Arg Leu Val Ser Val Leu Pro Asn Gly Pro Asp
                        340                 345                 350

Tyr His Pro Thr Val Arg Ala Phe Leu Ala Gly Gly Val Pro Glu Val
                        355                 360                 365

Met Leu His Leu Arg Asp Leu Gly Leu Leu His Leu Asp Ala Met Thr
                        370                 375                 380

Val Thr Gly Gln Thr Val Gly Glu Asn Leu Glu Trp Trp Gln Ala Ser
        385                 390                 395                 400

Glu Arg Arg Ala Arg Phe Arg Gln Cys Leu Arg Glu Gln Asp Gly Val
                        405                 410                 415

Glu Pro Asp Asp Val Ile Leu Pro Pro Glu Lys Ala Lys Ala Lys Gly
                        420                 425                 430

Leu Thr Ser Thr Val Cys Phe Pro Thr Gly Asn Ile Ala Pro Glu Gly
                        435                 440                 445

Ser Val Ile Lys Ala Thr Ala Ile Asp Pro Ser Val Val Gly Glu Asp
                        450                 455                 460

Gly Val Tyr His His Thr Gly Arg Val Arg Val Phe Val Ser Glu Ala
        465                 470                 475                 480

Gln Ala Ile Lys Ala Ile Lys Arg Glu Glu Ile Val Gln Gly Asp Ile
                        485                 490                 495

Met Val Val Ile Gly Gly Gly Pro Ser Gly Thr Gly Met Glu Glu Thr
                        500                 505                 510

Tyr Gln Leu Thr Ser Ala Leu Lys His Ile Ser Trp Gly Lys Thr Val
                        515                 520                 525

Ser Leu Ile Thr Asp Ala Arg Phe Ser Gly Val Ser Thr Gly Ala Cys
                        530                 535                 540

Phe Gly His Val Ser Pro Glu Ala Leu Ala Gly Gly Pro Ile Gly Lys
        545                 550                 555                 560

Leu Arg Asp Asn Asp Ile Ile Glu Ile Ala Val Asp Arg Leu Thr Leu
                        565                 570                 575

Thr Gly Ser Val Asn Phe Ile Gly Thr Ala Asp Asn Pro Leu Thr Pro
                        580                 585                 590

Glu Glu Gly Ala Arg Glu Leu Ala Arg Arg Gln Thr His Pro Asp Leu
                        595                 600                 605

His Ala His Asp Phe Leu Pro Asp Asp Thr Arg Leu Trp Ala Ala Leu
                        610                 615                 620

Gln Ser Val Ser Gly Gly Thr Trp Lys Gly Cys Ile Tyr Asp Thr Asp
        625                 630                 635                 640

Lys Ile Ile Glu Val Ile Asn Ala Gly Lys Lys Ala Leu Gly Ile
                        645                 650                 655
```

<210> SEQ ID NO 7
<211> LENGTH: 1968
<212> TYPE: DNA
<213> ORGANISM: Escherichia coli
<220> FEATURE:
<221> NAME/KEY: CDS
<222> LOCATION: (1)..(1968)

<400> SEQUENCE: 7

| | | | | | | | | | | | | | | | | |
|---|---|---|---|---|---|---|---|---|---|---|---|---|---|---|---|---|
| atg | tct | gtt | cgc | aat | att | ttt | gct | gac | gag | agc | cac | gat | att | tac | acc | 48 |
| Met | Ser | Val | Arg | Asn | Ile | Phe | Ala | Asp | Glu | Ser | His | Asp | Ile | Tyr | Thr | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| gtc | aga | acg | cac | gcc | gat | ggc | ccg | gac | ggc | gaa | ctc | cca | tta | acc | gca | 96 |
| Val | Arg | Thr | His | Ala | Asp | Gly | Pro | Asp | Gly | Glu | Leu | Pro | Leu | Thr | Ala | |
| | | | 20 | | | | | 25 | | | | | 30 | | | |

| | | | | | | | | | | | | | | | | |
|---|---|---|---|---|---|---|---|---|---|---|---|---|---|---|---|---|
| gag | atg | ctt | atc | aac | cgc | ccg | agc | ggg | gat | ctg | ttc | ggt | atg | acc | atg | 144 |
| Glu | Met | Leu | Ile | Asn | Arg | Pro | Ser | Gly | Asp | Leu | Phe | Gly | Met | Thr | Met | |
| | | | 35 | | | | | 40 | | | | | 45 | | | |

| | | | | | | | | | | | | | | | | |
|---|---|---|---|---|---|---|---|---|---|---|---|---|---|---|---|---|
| aat | gcc | gga | atg | ggt | tgg | tct | ccg | gac | gag | ctg | gat | cgg | gac | ggt | att | 192 |
| Asn | Ala | Gly | Met | Gly | Trp | Ser | Pro | Asp | Glu | Leu | Asp | Arg | Asp | Gly | Ile | |
| | 50 | | | | | 55 | | | | | 60 | | | | | |

| | | | | | | | | | | | | | | | | |
|---|---|---|---|---|---|---|---|---|---|---|---|---|---|---|---|---|
| tta | ctg | ctc | agt | aca | ctc | ggt | ggc | tta | cgc | ggc | gca | gac | ggt | aaa | ccc | 240 |
| Leu | Leu | Leu | Ser | Thr | Leu | Gly | Gly | Leu | Arg | Gly | Ala | Asp | Gly | Lys | Pro | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| gtg | gcg | ctg | gcg | ttg | cac | cag | ggg | cat | tac | gaa | ctg | gac | atc | cag | atg | 288 |
| Val | Ala | Leu | Ala | Leu | His | Gln | Gly | His | Tyr | Glu | Leu | Asp | Ile | Gln | Met | |
| | | | | 85 | | | | | 90 | | | | | 95 | | |

| | | | | | | | | | | | | | | | | |
|---|---|---|---|---|---|---|---|---|---|---|---|---|---|---|---|---|
| aaa | gcg | gcg | gcc | gag | gtt | att | aaa | gcc | aac | cat | gcc | ctg | ccc | tat | gcc | 336 |
| Lys | Ala | Ala | Ala | Glu | Val | Ile | Lys | Ala | Asn | His | Ala | Leu | Pro | Tyr | Ala | |
| | | | 100 | | | | | 105 | | | | | 110 | | | |

| | | | | | | | | | | | | | | | | |
|---|---|---|---|---|---|---|---|---|---|---|---|---|---|---|---|---|
| gtg | tac | gtc | tcc | gat | cct | tgt | gac | ggg | cgt | act | cag | ggt | aca | acg | ggg | 384 |
| Val | Tyr | Val | Ser | Asp | Pro | Cys | Asp | Gly | Arg | Thr | Gln | Gly | Thr | Thr | Gly | |
| | | | 115 | | | | | 120 | | | | | 125 | | | |

| | | | | | | | | | | | | | | | | |
|---|---|---|---|---|---|---|---|---|---|---|---|---|---|---|---|---|
| atg | ttt | gat | tcg | cta | cca | tac | cga | aat | gac | gca | tcg | atg | gta | atg | cgc | 432 |
| Met | Phe | Asp | Ser | Leu | Pro | Tyr | Arg | Asn | Asp | Ala | Ser | Met | Val | Met | Arg | |
| | | | 130 | | | | | 135 | | | | | 140 | | | |

| | | | | | | | | | | | | | | | | |
|---|---|---|---|---|---|---|---|---|---|---|---|---|---|---|---|---|
| cgc | ctt | att | cgc | tct | ctg | ccc | gac | gcg | aaa | gca | gtt | att | ggt | gtg | gcg | 480 |
| Arg | Leu | Ile | Arg | Ser | Leu | Pro | Asp | Ala | Lys | Ala | Val | Ile | Gly | Val | Ala | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| agt | tgc | gat | aag | ggg | ctt | ccg | gcc | acc | atg | atg | gca | ctc | gcc | gcg | cag | 528 |
| Ser | Cys | Asp | Lys | Gly | Leu | Pro | Ala | Thr | Met | Met | Ala | Leu | Ala | Ala | Gln | |
| | | | 165 | | | | | 170 | | | | | 175 | | | |

| | | | | | | | | | | | | | | | | |
|---|---|---|---|---|---|---|---|---|---|---|---|---|---|---|---|---|
| cac | aac | atc | gca | acc | gtg | ctg | gtc | ccc | ggc | ggc | gcg | acg | ctg | ccc | gca | 576 |
| His | Asn | Ile | Ala | Thr | Val | Leu | Val | Pro | Gly | Gly | Ala | Thr | Leu | Pro | Ala | |
| | | | 180 | | | | | 185 | | | | | 190 | | | |

| | | | | | | | | | | | | | | | | |
|---|---|---|---|---|---|---|---|---|---|---|---|---|---|---|---|---|
| aag | gat | gga | gaa | gac | aac | ggc | aag | gtg | caa | acc | att | ggc | gca | cgc | ttc | 624 |
| Lys | Asp | Gly | Glu | Asp | Asn | Gly | Lys | Val | Gln | Thr | Ile | Gly | Ala | Arg | Phe | |
| | | | 195 | | | | | 200 | | | | | 205 | | | |

| | | | | | | | | | | | | | | | | |
|---|---|---|---|---|---|---|---|---|---|---|---|---|---|---|---|---|
| gcc | aat | ggc | gaa | tta | tct | cta | cag | gac | gca | cgc | cgt | gcg | ggc | tgt | aaa | 672 |
| Ala | Asn | Gly | Glu | Leu | Ser | Leu | Gln | Asp | Ala | Arg | Arg | Ala | Gly | Cys | Lys | |
| | | | 210 | | | | | 215 | | | | | 220 | | | |

| | | | | | | | | | | | | | | | | |
|---|---|---|---|---|---|---|---|---|---|---|---|---|---|---|---|---|
| gcc | tgt | gcc | tct | tcc | ggc | ggc | ggc | tgt | caa | ttt | ttg | ggc | act | gcc | ggg | 720 |
| Ala | Cys | Ala | Ser | Ser | Gly | Gly | Gly | Cys | Gln | Phe | Leu | Gly | Thr | Ala | Gly | |
| 225 | | | | | 230 | | | | | 235 | | | | | 240 | |

| | | | | | | | | | | | | | | | | |
|---|---|---|---|---|---|---|---|---|---|---|---|---|---|---|---|---|
| aca | tct | cag | gtg | gtg | gcc | gaa | gga | ttg | gga | ctg | gca | atc | cca | cat | tca | 768 |
| Thr | Ser | Gln | Val | Val | Ala | Glu | Gly | Leu | Gly | Leu | Ala | Ile | Pro | His | Ser | |
| | | | 245 | | | | | 250 | | | | | 255 | | | |

| | | | | | | | | | | | | | | | | |
|---|---|---|---|---|---|---|---|---|---|---|---|---|---|---|---|---|
| gcc | ctg | gcc | cct | tcc | ggt | gag | cct | gtg | tgg | cgg | gag | atc | gcc | aga | gct | 816 |
| Ala | Leu | Ala | Pro | Ser | Gly | Glu | Pro | Val | Trp | Arg | Glu | Ile | Ala | Arg | Ala | |
| | | | 260 | | | | | 265 | | | | | 270 | | | |

```
tcc gcg cga gct gcg ctg aac ctg agt caa aaa ggc atc acc acc cgg      864
Ser Ala Arg Ala Ala Leu Asn Leu Ser Gln Lys Gly Ile Thr Thr Arg
        275                 280                 285 gaa att ctc acc gat aaa gcg ata gag aat gcg atg acg gtc cat gcc      912
Glu Ile Leu Thr Asp Lys Ala Ile Glu Asn Ala Met Thr Val His Ala
    290                 295                 300 gcg ttc ggt ggt tca aca aac ctg ctg tta cac atc ccg gca att gct      960
Ala Phe Gly Gly Ser Thr Asn Leu Leu Leu His Ile Pro Ala Ile Ala
305                 310                 315                 320 cac cag gca ggt tgc cat atc ccg acc gtt gat gac tgg atc cgc atc     1008
His Gln Ala Gly Cys His Ile Pro Thr Val Asp Asp Trp Ile Arg Ile
                325                 330                 335 aac aag cgc gtg ccc cga ctg gtg agc gta ctg cct aat ggc ccg gtt     1056
Asn Lys Arg Val Pro Arg Leu Val Ser Val Leu Pro Asn Gly Pro Val
            340                 345                 350 tat cat cca acg gtc aat gcc ttt atg gca ggt ggt gtg ccg gaa gtc     1104
Tyr His Pro Thr Val Asn Ala Phe Met Ala Gly Gly Val Pro Glu Val
        355                 360                 365 atg ttg cat ctg cgc agc ctc gga ttg ttg cat gaa gac gtt atg acg     1152
Met Leu His Leu Arg Ser Leu Gly Leu Leu His Glu Asp Val Met Thr
    370                 375                 380 gtt acc ggc agc acg ctg aaa gaa aac ctc gac tgg tgg gag cac tcc     1200
Val Thr Gly Ser Thr Leu Lys Glu Asn Leu Asp Trp Trp Glu His Ser
385                 390                 395                 400 gaa cgg cgt cag cgg ttc aag caa ctc ctg ctc gat cag gaa caa atc     1248
Glu Arg Arg Gln Arg Phe Lys Gln Leu Leu Leu Asp Gln Glu Gln Ile
                405                 410                 415 aac gct gac gaa gtg atc atg tct ccg cag caa gca aaa gcg cgc gga     1296
Asn Ala Asp Glu Val Ile Met Ser Pro Gln Gln Ala Lys Ala Arg Gly
            420                 425                 430 tta acc tca act atc acc ttc ccg gtg ggc aat att gcg cca gaa ggt     1344
Leu Thr Ser Thr Ile Thr Phe Pro Val Gly Asn Ile Ala Pro Glu Gly
        435                 440                 445 tcg gtg atc aaa tcc acc gcc att gac ccc tcg atg att gat gag caa     1392
Ser Val Ile Lys Ser Thr Ala Ile Asp Pro Ser Met Ile Asp Glu Gln
    450                 455                 460 ggt atc tat tac cat aaa ggt gtg gcg aag gtt tat ctg tcc gag aaa     1440
Gly Ile Tyr Tyr His Lys Gly Val Ala Lys Val Tyr Leu Ser Glu Lys
465                 470                 475                 480 agt gcg att tac gat atc aaa cat gac aag atc aag gcg ggc gat att     1488
Ser Ala Ile Tyr Asp Ile Lys His Asp Lys Ile Lys Ala Gly Asp Ile
                485                 490                 495 ctg gtc att att ggc gtt gga cct tca ggt aca ggg atg gaa gaa acc     1536
Leu Val Ile Ile Gly Val Gly Pro Ser Gly Thr Gly Met Glu Glu Thr
            500                 505                 510 tac cag gtt acc agt gcc ctg aag cat ctg tca tac ggt aag cat gtt     1584
Tyr Gln Val Thr Ser Ala Leu Lys His Leu Ser Tyr Gly Lys His Val
        515                 520                 525 tcg tta atc acc gat gca cgt ttc tcg ggc gtt tct act ggc gcg tgc     1632
Ser Leu Ile Thr Asp Ala Arg Phe Ser Gly Val Ser Thr Gly Ala Cys
    530                 535                 540 atc ggc cat gtg ggg cca gaa gcg ctg gcc gga ggc ccc atc ggt aaa     1680
Ile Gly His Val Gly Pro Glu Ala Leu Ala Gly Gly Pro Ile Gly Lys
545                 550                 555                 560 tta cgc acc ggg gat tta att gaa att aaa att gat tgt cgc gag ctt     1728
Leu Arg Thr Gly Asp Leu Ile Glu Ile Lys Ile Asp Cys Arg Glu Leu
                565                 570                 575 cac ggc gaa gtc aat ttc ctc gga acc cgt agc gat gaa caa tta cct     1776
His Gly Glu Val Asn Phe Leu Gly Thr Arg Ser Asp Glu Gln Leu Pro
```

-continued

```
                580                 585                 590
tca cag gag gag gca act gca ata tta aat gcc aga ccc agc cat cag    1824
Ser Gln Glu Glu Ala Thr Ala Ile Leu Asn Ala Arg Pro Ser His Gln
            595                 600                 605 gat tta ctt ccc gat cct gaa ttg cca gat gat acc cgg cta tgg gca    1872
Asp Leu Leu Pro Asp Pro Glu Leu Pro Asp Asp Thr Arg Leu Trp Ala
610                 615                 620 atg ctt cag gcc gtg agt ggt ggg aca tgg acc ggt tgt att tat gat    1920
Met Leu Gln Ala Val Ser Gly Gly Thr Trp Thr Gly Cys Ile Tyr Asp
625                 630                 635                 640 gta aac aaa att ggc gcg gct ttg cgc gat ttt atg aat aaa aac tga    1968
Val Asn Lys Ile Gly Ala Ala Leu Arg Asp Phe Met Asn Lys Asn
                645                 650                 655

<210> SEQ ID NO 8
<211> LENGTH: 655
<212> TYPE: PRT
<213> ORGANISM: Escherichia coli

<400> SEQUENCE: 8

Met Ser Val Arg Asn Ile Phe Ala Asp Glu Ser His Asp Ile Tyr Thr
1               5                   10                  15

Val Arg Thr His Ala Asp Gly Pro Asp Gly Glu Leu Pro Leu Thr Ala
            20                  25                  30

Glu Met Leu Ile Asn Arg Pro Ser Gly Asp Leu Phe Gly Met Thr Met
        35                  40                  45

Asn Ala Gly Met Gly Trp Ser Pro Asp Glu Leu Asp Arg Asp Gly Ile
    50                  55                  60

Leu Leu Leu Ser Thr Leu Gly Gly Leu Arg Gly Ala Asp Gly Lys Pro
65                  70                  75                  80

Val Ala Leu Ala Leu His Gln Gly His Tyr Glu Leu Asp Ile Gln Met
                85                  90                  95

Lys Ala Ala Ala Glu Val Ile Lys Ala Asn His Ala Leu Pro Tyr Ala
            100                 105                 110

Val Tyr Val Ser Asp Pro Cys Asp Gly Arg Thr Gln Gly Thr Thr Gly
        115                 120                 125

Met Phe Asp Ser Leu Pro Tyr Arg Asn Asp Ala Ser Met Val Met Arg
    130                 135                 140

Arg Leu Ile Arg Ser Leu Pro Asp Ala Lys Ala Val Ile Gly Val Ala
145                 150                 155                 160

Ser Cys Asp Lys Gly Leu Pro Ala Thr Met Met Ala Leu Ala Ala Gln
                165                 170                 175

His Asn Ile Ala Thr Val Leu Val Pro Gly Gly Ala Thr Leu Pro Ala
            180                 185                 190

Lys Asp Gly Glu Asp Asn Gly Lys Val Gln Thr Ile Gly Ala Arg Phe
        195                 200                 205

Ala Asn Gly Glu Leu Ser Leu Gln Asp Ala Arg Arg Ala Gly Cys Lys
    210                 215                 220

Ala Cys Ala Ser Ser Gly Gly Cys Gln Phe Leu Gly Thr Ala Gly
225                 230                 235                 240

Thr Ser Gln Val Val Ala Glu Gly Leu Gly Leu Ala Ile Pro His Ser
                245                 250                 255

Ala Leu Ala Pro Ser Gly Glu Pro Val Trp Arg Glu Ile Ala Arg Ala
            260                 265                 270

Ser Ala Arg Ala Ala Leu Asn Leu Ser Gln Lys Gly Ile Thr Thr Arg
        275                 280                 285
```

Glu Ile Leu Thr Asp Lys Ala Ile Glu Asn Ala Met Thr Val His Ala
    290                 295                 300

Ala Phe Gly Gly Ser Thr Asn Leu Leu His Ile Pro Ala Ile Ala
305                 310                 315                 320

His Gln Ala Gly Cys His Ile Pro Thr Val Asp Asp Trp Ile Arg Ile
                325                 330                 335

Asn Lys Arg Val Pro Arg Leu Val Ser Val Leu Pro Asn Gly Pro Val
                340                 345                 350

Tyr His Pro Thr Val Asn Ala Phe Met Ala Gly Val Pro Glu Val
                355                 360                 365

Met Leu His Leu Arg Ser Gly Leu Leu His Glu Asp Val Met Thr
    370                 375                 380

Val Thr Gly Ser Thr Leu Lys Glu Asn Leu Asp Trp Trp Glu His Ser
385                 390                 395                 400

Glu Arg Arg Gln Arg Phe Lys Gln Leu Leu Asp Gln Glu Gln Ile
                405                 410                 415

Asn Ala Asp Glu Val Ile Met Ser Pro Gln Gln Ala Lys Ala Arg Gly
                420                 425                 430

Leu Thr Ser Thr Ile Thr Phe Pro Val Gly Asn Ile Ala Pro Glu Gly
                435                 440                 445

Ser Val Ile Lys Ser Thr Ala Ile Asp Pro Ser Met Ile Asp Glu Gln
450                 455                 460

Gly Ile Tyr Tyr His Lys Gly Val Ala Lys Val Tyr Leu Ser Glu Lys
465                 470                 475                 480

Ser Ala Ile Tyr Asp Ile Lys His Asp Lys Ile Lys Ala Gly Asp Ile
                485                 490                 495

Leu Val Ile Ile Gly Val Gly Pro Ser Gly Thr Gly Met Glu Glu Thr
                500                 505                 510

Tyr Gln Val Thr Ser Ala Leu Lys His Leu Ser Tyr Gly Lys His Val
    515                 520                 525

Ser Leu Ile Thr Asp Ala Arg Phe Ser Gly Val Ser Thr Gly Ala Cys
530                 535                 540

Ile Gly His Val Gly Pro Glu Ala Leu Ala Gly Gly Pro Ile Gly Lys
545                 550                 555                 560

Leu Arg Thr Gly Asp Leu Ile Glu Ile Lys Ile Asp Cys Arg Glu Leu
                565                 570                 575

His Gly Glu Val Asn Phe Leu Gly Thr Arg Ser Asp Glu Gln Leu Pro
                580                 585                 590

Ser Gln Glu Glu Ala Thr Ala Ile Leu Asn Ala Arg Pro Ser His Gln
                595                 600                 605

Asp Leu Leu Pro Asp Pro Glu Leu Pro Asp Asp Thr Arg Leu Trp Ala
610                 615                 620

Met Leu Gln Ala Val Ser Gly Gly Thr Trp Thr Gly Cys Ile Tyr Asp
625                 630                 635                 640

Val Asn Lys Ile Gly Ala Ala Leu Arg Asp Phe Met Asn Lys Asn
                645                 650                 655

<210> SEQ ID NO 9
<211> LENGTH: 528
<212> TYPE: PRT
<213> ORGANISM: Pseudomonas pudita

<400> SEQUENCE: 9

Met Ala Ser Val His Gly Thr Thr Tyr Glu Leu Leu Arg Arg Gln Gly

-continued

```
1               5                   10                  15
Ile Asp Thr Val Phe Gly Asn Pro Gly Ser Asn Glu Leu Pro Phe Leu
                20                  25                  30

Lys Asp Phe Pro Glu Asp Phe Arg Tyr Ile Leu Ala Leu Gln Glu Ala
                35                  40                  45

Cys Val Val Gly Ile Ala Asp Gly Tyr Ala Gln Ala Ser Arg Lys Pro
 50                  55                  60

Ala Phe Ile Asn Leu His Ser Ala Ala Gly Thr Gly Asn Ala Met Gly
 65                  70                  75                  80

Ala Leu Ser Asn Ala Trp Asn Ser His Ser Pro Leu Ile Val Thr Ala
                 85                  90                  95

Gly Gln Gln Thr Arg Ala Met Ile Gly Val Glu Ala Leu Leu Thr Asn
                100                 105                 110

Val Asp Ala Ala Asn Leu Pro Arg Pro Leu Val Lys Trp Ser Tyr Glu
                115                 120                 125

Pro Ala Ser Ala Ala Glu Val Pro His Ala Met Ser Arg Ala Ile His
                130                 135                 140

Met Ala Ser Met Ala Pro Gln Gly Pro Val Tyr Leu Ser Val Pro Tyr
145                 150                 155                 160

Asp Asp Trp Asp Lys Asp Ala Asp Pro Gln Ser His His Leu Phe Asp
                165                 170                 175

Arg His Val Ser Ser Ser Val Arg Leu Asn Asp Gln Asp Leu Asp Ile
                180                 185                 190

Leu Val Lys Ala Leu Asn Ser Ala Ser Asn Pro Ala Ile Val Leu Gly
                195                 200                 205

Pro Asp Val Asp Ala Ala Asn Ala Asn Ala Asp Cys Val Met Leu Ala
210                 215                 220

Glu Arg Leu Lys Ala Pro Val Trp Val Ala Pro Ser Ala Pro Arg Cys
225                 230                 235                 240

Pro Phe Pro Thr Arg His Pro Cys Phe Arg Gly Leu Met Pro Ala Gly
                245                 250                 255

Ile Ala Ala Ile Ser Gln Leu Leu Glu Gly His Asp Val Val Leu Val
                260                 265                 270

Ile Gly Ala Pro Val Phe Arg Tyr His Gln Tyr Asp Pro Gly Gln Tyr
                275                 280                 285

Leu Lys Pro Gly Thr Arg Leu Ile Ser Val Thr Cys Asp Pro Leu Glu
                290                 295                 300

Ala Ala Arg Ala Pro Met Gly Asp Ala Ile Val Ala Asp Ile Gly Ala
305                 310                 315                 320

Met Ala Ser Ala Leu Ala Asn Leu Val Glu Glu Ser Ser Arg Gln Leu
                325                 330                 335

Pro Thr Ala Ala Pro Glu Pro Ala Lys Val Asp Gln Asp Ala Gly Arg
                340                 345                 350

Leu His Pro Glu Thr Val Phe Asp Thr Leu Asn Asp Met Ala Pro Glu
                355                 360                 365

Asn Ala Ile Tyr Leu Asn Glu Ser Thr Ser Thr Thr Ala Gln Met Trp
                370                 375                 380

Gln Arg Leu Asn Met Arg Asn Pro Gly Ser Tyr Tyr Phe Cys Ala Ala
385                 390                 395                 400

Gly Gly Leu Gly Phe Ala Leu Pro Ala Ala Ile Gly Val Gln Leu Ala
                405                 410                 415

Glu Pro Glu Arg Gln Val Ile Ala Val Ile Gly Asp Gly Ser Ala Asn
                420                 425                 430
```

```
Tyr Ser Ile Ser Ala Leu Trp Thr Ala Ala Gln Tyr Asn Ile Pro Thr
        435                 440                 445

Ile Phe Val Ile Met Asn Asn Gly Thr Tyr Gly Ala Leu Arg Trp Phe
450                 455                 460

Ala Gly Val Leu Glu Ala Glu Asn Val Pro Gly Leu Asp Val Pro Gly
465                 470                 475                 480

Ile Asp Phe Arg Ala Leu Ala Lys Gly Tyr Gly Val Gln Ala Leu Lys
                485                 490                 495

Ala Asp Asn Leu Glu Gln Leu Lys Gly Ser Leu Gln Glu Ala Leu Ser
                500                 505                 510

Ala Lys Gly Pro Val Leu Ile Glu Val Ser Thr Val Ser Pro Val Lys
    515                 520                 525
```

<210> SEQ ID NO 10
<211> LENGTH: 346
<212> TYPE: PRT
<213> ORGANISM: Escherichia coli

<400> SEQUENCE: 10

```
Met Gln Asn Ile Ile Arg Lys Gly Gly Thr Met Lys Ala Ala Val Val
1               5                   10                  15

Thr Lys Asp His His Val Asp Val Thr Tyr Lys Thr Leu Arg Ser Leu
            20                  25                  30

Lys His Gly Glu Ala Leu Leu Lys Met Glu Cys Cys Gly Val Cys His
        35                  40                  45

Thr Asp Leu His Val Lys Asn Gly Asp Phe Gly Asp Lys Thr Gly Val
50                  55                  60

Ile Leu Gly His Glu Gly Ile Gly Val Val Ala Glu Val Gly Pro Gly
65                  70                  75                  80

Val Thr Ser Leu Lys Pro Gly Asp Arg Ala Ser Val Ala Trp Phe Tyr
                85                  90                  95

Glu Gly Cys Gly His Cys Glu Tyr Cys Asn Ser Gly Asn Glu Thr Leu
            100                 105                 110

Cys Arg Ser Val Lys Asn Ala Gly Tyr Ser Val Asp Gly Gly Met Ala
        115                 120                 125

Glu Glu Cys Ile Val Val Ala Asp Tyr Ala Val Lys Val Pro Asp Gly
    130                 135                 140

Leu Asp Ser Ala Ala Ala Ser Ser Ile Thr Cys Ala Gly Val Thr Thr
145                 150                 155                 160

Tyr Lys Ala Val Lys Leu Ser Lys Ile Arg Pro Gly Gln Trp Ile Ala
                165                 170                 175

Ile Tyr Gly Leu Gly Gly Leu Gly Asn Leu Ala Leu Gln Tyr Ala Lys
            180                 185                 190

Asn Val Phe Asn Ala Lys Val Ile Ala Ile Asp Val Asn Asp Glu Gln
        195                 200                 205

Leu Lys Leu Ala Thr Glu Met Gly Ala Asp Leu Ala Ile Asn Ser His
    210                 215                 220

Thr Glu Asp Ala Ala Lys Ile Val Gln Glu Lys Thr Gly Gly Ala His
225                 230                 235                 240

Ala Ala Val Val Thr Ala Val Ala Lys Ala Ala Phe Asn Ser Ala Val
                245                 250                 255

Asp Ala Val Arg Ala Gly Gly Arg Val Val Ala Val Gly Leu Pro Pro
            260                 265                 270

Glu Ser Met Ser Leu Asp Ile Pro Arg Leu Val Leu Asp Gly Ile Glu
```

```
                275                 280                 285
Val Val Gly Ser Leu Val Gly Thr Arg Gln Asp Leu Thr Glu Ala Phe
        290                 295                 300

Gln Phe Ala Ala Glu Gly Lys Val Val Pro Lys Val Ala Leu Arg Pro
305                 310                 315                 320

Leu Ala Asp Ile Asn Thr Ile Phe Thr Glu Met Glu Glu Gly Lys Ile
                325                 330                 335

Arg Gly Arg Met Val Ile Asp Phe Arg His
                340                 345

<210> SEQ ID NO 11
<211> LENGTH: 360
<212> TYPE: PRT
<213> ORGANISM: Haloarcula marismortui

<400> SEQUENCE: 11

Met Asn Val Asp Ala Leu Thr Gly Gly Phe Asp Arg Arg Asp Trp Gln
1               5                   10                  15

Glu Gln Thr Ala Thr Asp Asn Pro Val Arg Phe Ala Met Ile Gly Val
                20                  25                  30

Gly Trp Trp Thr Thr Glu Gln Ala Met Pro Ala Val Ala Ala Gly Asp
        35                  40                  45

Leu Cys Glu Thr Thr Val Leu Val Ser Ser Asp Arg Glu Lys Ala Ala
50                  55                  60

Asp Val Ala Ala Asp Ser Glu Thr Val Glu His Ala Ile Thr Tyr Glu
65                  70                  75                  80

Glu Phe His Asp Gly Ala Ala Ser Asp Ala Tyr Asp Ala Val Tyr Ile
                85                  90                  95

Val Thr Pro Asn Ala Leu His Leu Pro Tyr Val Glu Thr Ala Ala Glu
            100                 105                 110

Leu Asp Lys Ala Ile Leu Cys Glu Lys Pro Met Glu Ala Thr Ile Glu
        115                 120                 125

Arg Ala Glu Arg Met Val Glu Val Cys Asp Glu His Asp Ala Thr Leu
130                 135                 140

Met Ile Ala Tyr Arg Met His Thr Glu Pro Ala Val Arg Ala Lys
145                 150                 155                 160

Asp Leu Ile Asp Glu Gly Tyr Ile Gly Glu Pro Leu Phe Val His Gly
                165                 170                 175

Asn Met Thr Glu Pro Ile Leu Glu Leu Val Pro Asp Pro Asp Gln Trp
            180                 185                 190

Arg Leu Asp Gly Glu Leu Ser Gly Gly Cys Ala Val Met Asp Ile Gly
        195                 200                 205

Ile Tyr Pro Leu Asn Thr Ser Arg Phe Leu Leu Asp Ala Asp Pro Val
210                 215                 220

Ala Val Arg Gly Thr Val Ala Ser Val Gln Glu Glu Phe Ala Asp Val
225                 230                 235                 240

Pro Asp Glu His Gly Ala Phe Gln Leu Asp Phe Pro Gly His Val Tyr
                245                 250                 255

Ala Val Cys Thr Ala Ser Gln Asn Ala His Leu Asp Ser His Ile Ser
            260                 265                 270

Val Leu Gly Thr Glu Gly Lys Val Arg Val Glu Pro Ala Phe Tyr Pro
        275                 280                 285

Trp Asp Asp Arg Ala Leu Gln Leu Ser His Glu Gly Thr Thr Val Glu
290                 295                 300
```

```
Ile Asp Phe Glu Gln Ile Asp Gln Met Glu Glu Phe Glu Tyr Phe
305                 310                 315                 320

Ala His Cys Leu Leu Thr Asp Thr Glu Pro Tyr Ala Asp Gly Glu His
                325                 330                 335

Gly Leu Val Asp Ile Asn Thr Ile Lys Ser Val Tyr Glu Ala Ser Glu
                340                 345                 350

Thr Glu Ser Thr Val Arg Leu Asp
            355                 360

<210> SEQ ID NO 12
<211> LENGTH: 357
<212> TYPE: PRT
<213> ORGANISM: Haloferax volcanii

<400> SEQUENCE: 12

Met Ser Leu Glu Ala Phe Leu Asp Asp Phe Glu Arg Arg Asn Trp Gln
1               5                   10                  15

Arg Val Ser Asp Gly Thr Val Arg Ile Ala Val Ile Gly Leu Gly Trp
                20                  25                  30

Trp Thr Val Asp Gln Ala Ile Pro Ala Ile Asp Ala Ser Gly Leu Cys
            35                  40                  45

Glu Thr Thr Val Thr Val Ser Ser Thr Ser Glu Lys Ala Lys Arg Val
    50                  55                  60

Ala Ala Gly Val Glu Thr Ala Thr His Gly Leu Ser Tyr Asp Glu Phe
65                  70                  75                  80

His Ala Gly Glu Ala Ala Asp Ala Tyr Asp Ala Val Tyr Ile Cys Ser
                85                  90                  95

Pro Asn Ala Leu His Leu Pro Tyr Ala Arg Thr Ala Ala Glu Leu Gly
            100                 105                 110

Lys Ala Val Leu Cys Glu Lys Pro Ile Glu Ala Ser Ser Glu Arg Gly
        115                 120                 125

Gln Gln Met Val Asp Ala Cys Asp Glu Ala Gly Val Pro Leu Ile Val
    130                 135                 140

Gly Tyr Arg Met His Thr Glu Pro Ala Ile Arg Arg Ala Arg Lys Leu
145                 150                 155                 160

Ile Arg Asp Gly Val Ile Gly Asp Pro Val His Ala Ile Gly Thr Asn
                165                 170                 175

Ser Gln Ala Met Leu Glu Leu Ile Ser Asp Pro Asn Gln Trp Arg Leu
            180                 185                 190

Asp Pro Glu Leu Ala Gly Pro Gly Ala Thr Val Thr Asp Ile Gly Ile
        195                 200                 205

Tyr Pro Leu Asn Thr Cys Arg Phe Leu Leu Asp Ser Asp Pro Val Ala
    210                 215                 220

Ala Gln Ala Phe Met Gln Ser Ser His Asp Ala Phe Gln Val Pro
225                 230                 235                 240

Asp Glu His Ser Ser Phe Met Val Glu Phe Asp Asp Gly Thr Tyr Leu
                245                 250                 255

Ala Ala Thr Ala Ser Gln Asn Ala Gln Ala Thr Thr Ser Leu Arg Ile
            260                 265                 270

Val Gly Thr Asn Gly Glu Ile Leu Val Glu Pro Ala Phe His Met Glu
        275                 280                 285

Thr Glu Ile Arg Val Thr Arg Asp Asp Val Ser Val Thr Leu Asp Thr
    290                 295                 300

Pro Gln Val Asn Gln Met Thr Glu Leu Phe Asp Tyr Ala Ala Asp Arg
305                 310                 315                 320
```

```
Ile Leu Thr Asp Ala Pro Ile Gly Pro Asp Gly Glu His Gly Val Leu
            325                 330                 335

Asp Met Arg Leu Ile Glu Ala Val Tyr Glu Ala Gly Glu Ser Gly Arg
        340                 345                 350

Val Val Thr Leu Asp
            355

<210> SEQ ID NO 13
<211> LENGTH: 526
<212> TYPE: PRT
<213> ORGANISM: Pseudomonas stutzeri

<400> SEQUENCE: 13

Met Ala Ser Val His Ser Ile Thr Tyr Glu Leu Leu Arg Arg Gln Gly
1               5                   10                  15

Ile Asp Thr Val Phe Gly Asn Pro Gly Ser Asn Glu Leu Pro Phe Leu
            20                  25                  30

Lys Asp Phe Pro Glu Asp Phe Arg Tyr Ile Leu Ala Leu Gln Glu Ala
        35                  40                  45

Cys Val Val Gly Ile Ala Asp Gly Tyr Ala Gln Ala Ser Arg Lys Pro
    50                  55                  60

Ala Phe Ile Asn Leu His Ser Ala Ala Gly Thr Gly Asn Ala Met Gly
65                  70                  75                  80

Ala Met Ser Asn Ala Trp Asn Cys His Ser Pro Leu Ile Val Thr Ala
                85                  90                  95

Gly Gln Gln Asn Arg Ala Met Ile Gly Val Glu Ala Leu Leu Thr Asn
            100                 105                 110

Val Asp Ala Ala Ser Leu Pro Arg Pro Leu Val Lys Trp Ser Tyr Glu
        115                 120                 125

Pro Ala Ser Ala Ala Glu Val Pro His Ala Met Ser Arg Ala Ile His
    130                 135                 140

Met Ala Ser Met Ala Pro Arg Gly Pro Val Tyr Leu Ser Val Pro Tyr
145                 150                 155                 160

Asp Asp Trp Asp Lys Glu Ala Asp Pro Gln Ser His His Leu Tyr Asp
                165                 170                 175

Arg Ser Val Asn Ser Ala Val Arg Leu Asn Asp Gln Asp Leu Glu Val
            180                 185                 190

Leu Val Glu Ala Leu Asn Ser Ala Ser Asn Pro Ala Ile Val Leu Gly
        195                 200                 205

Pro Asp Val Asp Ser Ala Asn Ala Asn Ala Asp Cys Val Thr Leu Ala
    210                 215                 220

Glu Arg Leu Lys Ala Pro Val Trp Val Ala Pro Ser Ala Pro Arg Cys
225                 230                 235                 240

Pro Phe Pro Thr Arg His Pro Cys Phe Arg Gly Leu Met Pro Ala Gly
                245                 250                 255

Ile Ala Ala Ile Ser Gln Leu Leu Glu Gly His Asp Val Leu Val Val
            260                 265                 270

Ile Gly Ala Pro Val Phe Arg Tyr His Gln Tyr Asp Pro Gly Gln Tyr
        275                 280                 285

Leu Lys Pro Gly Thr Arg Leu Ile Ser Ile Thr Cys Asp Pro Leu Glu
    290                 295                 300

Ala Ala Arg Ala Pro Met Gly Asp Ala Ile Val Ala Asp Ile Gly Thr
305                 310                 315                 320

Met Thr Ala Ala Leu Ala Ser Arg Ile Gly Glu Ser Glu Arg Gln Leu
```

```
                        325                 330                 335
        Pro Ala Val Leu Pro Ser Pro Glu Arg Val Asn Gln Asp Ala Gly Arg
                        340                 345                 350

Leu Arg Pro Glu Thr Val Phe Asp Thr Leu Asn Glu Met Ala Pro Glu
                    355                 360                 365

Asp Ala Ile Tyr Leu Asn Glu Ser Thr Ser Thr Ala Gln Met Trp
            370                 375                 380

Gln Arg Leu Asn Met Arg Asn Pro Gly Ser Tyr Tyr Phe Cys Ala Ala
        385                 390                 395                 400

Gly Gly Leu Gly Phe Ala Leu Pro Ala Ala Ile Gly Val Gln Leu Ala
                        405                 410                 415

Glu Pro Asp Arg Gln Val Ile Ala Val Ile Gly Asp Gly Ser Ala Asn
                        420                 425                 430

Tyr Ser Ile Ser Ala Leu Trp Thr Ala Ala His Tyr Asn Ile Pro Ala
                    435                 440                 445

Ile Phe Leu Ile Met Asn Asn Gly Thr Tyr Gly Ala Leu Arg Trp Phe
                        450                 455                 460

Ala Gly Val Leu Glu Ala Glu Asn Val Pro Gly Leu Asp Val Pro Gly
        465                 470                 475                 480

Ile Asp Phe Cys Ala Ile Ala Lys Gly Tyr Gly Ile Pro Ala Leu Lys
                        485                 490                 495

Ala Asp Asn Leu Glu Gln Leu Lys Gly Ser Ile His Glu Ala Leu Ser
                    500                 505                 510

Ala Lys Gly Pro Val Leu Ile Glu Val Ser Thr Val Ser Leu
                    515                 520                 525

<210> SEQ ID NO 14
<211> LENGTH: 527
<212> TYPE: PRT
<213> ORGANISM: Agrobacterium radiobacter

<400> SEQUENCE: 14

Met Lys Thr Val Arg Glu Ala Thr Tyr Glu Leu Leu Arg Ser Val Gly
1               5                   10                  15

Leu Thr Thr Val Phe Gly Asn Pro Gly Ser Asn Glu Leu Pro Phe Leu
                20                  25                  30

Asn Gly Phe Pro Ala Asp Phe Arg Tyr Ile Leu Gly Leu His Glu Gly
            35                  40                  45

Val Val Val Gly Met Ala Asp Gly Tyr Ala Gln Ala Thr Gly Asn Ala
        50                  55                  60

Ser Leu Val Asn Leu His Ser Ala Ala Gly Thr Gly Asn Gly Met Gly
65                  70                  75                  80

Ala Leu Ala Asn Ala Trp Asn Ser His Thr Pro Ile Ile Val Thr Ala
                85                  90                  95

Gly Gln Gln Thr Arg Ala Met Ile Gly Ala Glu Pro Leu Leu Ala Asn
                100                 105                 110

Val Asp Ala Ala Met Leu Pro Arg Pro Leu Val Lys Trp Ser Tyr Glu
            115                 120                 125

Pro Ala Ser Ala Ser Glu Val Pro His Ala Phe Ser Arg Ala Tyr His
        130                 135                 140

Ile Ala Glu Leu Pro Ala Lys Gly Pro Val Tyr Leu Ser Ile Pro Tyr
145                 150                 155                 160

Asn Asp Trp Glu Gln Pro Ala Gly Pro Phe Ser Asp Ala Val Asn Met
                165                 170                 175
```

```
Arg Lys Val Glu Ala Ala Gly Met Pro Asp Glu His Arg Leu Ala Ala
            180                 185                 190

Leu Leu Asp Arg Ile Ala Ser Ala Arg Asn Pro Val Ile Val Leu Gly
        195                 200                 205

Pro Asp Val Asp Ala Ala Arg Ala Asn Ser Tyr Ala Val Thr Leu Ala
    210                 215                 220

Glu Lys Ile Ala Ala Pro Val Trp Val Ala Pro Ser Ala Pro Arg Cys
225                 230                 235                 240

Pro Phe Pro Thr Thr His Gln Asn Phe Arg Gly Leu Leu Pro Ala Gly
            245                 250                 255

Ile Ala Ser Ile Ser Arg Leu Leu Ser Gly His Asp Leu Ile Leu Val
        260                 265                 270

Phe Gly Ala Pro Val Phe Arg Tyr His Gln Tyr Asp Pro Gly Ala Trp
    275                 280                 285

Leu Pro Glu Gly Ala Ser Leu Ile Ser Val Thr Cys Asp Ala Leu Glu
290                 295                 300

Ala Ala Arg Ala Pro Met Gly Asp Ala Ile Val Gly Asp Val Gly Gly
305                 310                 315                 320

Val Leu Lys Arg Leu Cys Glu Arg Val Val Ala Gly Ala Arg Ala Asp
            325                 330                 335

Leu Glu Ala Leu Pro Arg Pro Glu Arg Ala Pro Ala Ser Ser Gly Ala
        340                 345                 350

Leu Leu Pro Glu Ala Val Phe Asp Ile Leu Asp Asp Leu Ala Pro Glu
    355                 360                 365

Asn Ala Ile Tyr Leu Asn Glu Ser Thr Ser Thr Thr Ala Ala Leu Trp
370                 375                 380

Glu Arg Leu Arg Met Arg Gln Pro Gly Ser Tyr Tyr Phe Ala Ala
385                 390                 395                 400

Gly Gly Leu Gly Phe Ala Met Pro Ala Ser Val Gly Val Gln Leu Ala
            405                 410                 415

Glu Pro Glu Arg Arg Val Ile Ala Ile Gly Asp Gly Ser Ala Asn
        420                 425                 430

Tyr Gly Ile Gln Ala Leu Trp Thr Ala Ala Gln Tyr Lys Ile Pro Thr
    435                 440                 445

Ile Phe Ile Ile Met Lys Asn Gly Thr Tyr Gly Ala Leu Arg Trp Phe
450                 455                 460

Ala Gly Val Leu Lys Val Glu Asn Val Pro Gly Leu Asp Val Pro Asp
465                 470                 475                 480

Ile Asp Phe Gln Ala Leu Ala Thr Gly Tyr Gly Val Lys Ala His Arg
            485                 490                 495

Ala Arg Asn Ala Glu Glu Phe Lys His Ala Leu Thr Glu Ala Leu Ser
        500                 505                 510

Ser Asp Thr Pro Ile Leu Ile Glu Val Leu Thr Lys His Gly Gly
    515                 520                 525

<210> SEQ ID NO 15
<211> LENGTH: 549
<212> TYPE: PRT
<213> ORGANISM: Pseudomonas aeruginosa

<400> SEQUENCE: 15

Met Ile Asp Tyr Arg Ala Ala Ala Thr Val Ala Gln Ile Gln Glu Thr
1               5                   10                  15

Thr Leu Lys Ala Cys Met Lys Thr Val His Ser Ala Ser Tyr Glu Ile
            20                  25                  30
```

```
Leu Arg Arg His Gly Leu Thr Thr Val Phe Gly Asn Pro Gly Ser Asn
         35                  40                  45

Glu Leu Pro Phe Leu Arg Asp Phe Pro Glu Asp Phe Arg Tyr Ile Leu
 50                  55                  60

Gly Leu His Glu Gly Ala Val Gly Met Ala Asp Gly Phe Ala Leu
 65                  70                  75                  80

Ala Ser Gly Arg Pro Ala Phe Val Asn Leu His Ala Ala Gly Thr
                 85                  90                  95

Gly Asn Gly Met Gly Ala Leu Thr Asn Ala Trp Tyr Ser His Ser Pro
                100                 105                 110

Leu Val Ile Ser Ala Gly Gln Gln Val Arg Ser Met Ile Gly Val Glu
        115                 120                 125

Ala Met Leu Ala Asn Val Glu Ala Gly Gln Leu Pro Lys Pro Leu Val
        130                 135                 140

Lys Trp Ser His Glu Pro Ala Cys Ala Gln Asp Val Pro Arg Ala Leu
145                 150                 155                 160

Ser Gln Ala Ile Gln Ile Ala Ser Leu Pro Pro Arg Ala Pro Val Tyr
                    165                 170                 175

Leu Ser Ile Pro Tyr Asp Asp Trp Ala Gln Pro Ala Pro Ala Gly Val
            180                 185                 190

Glu His Leu Ala Ala Arg Gln Val Ser Gly Ala Ala Leu Pro Ala Pro
        195                 200                 205

Ala Leu Leu Ala Glu Leu Gly Glu Arg Leu Ser Arg Ser Arg Asn Pro
        210                 215                 220

Val Leu Val Leu Gly Pro Asp Val Asp Gly Ala Asn Ala Asn Gly Leu
225                 230                 235                 240

Ala Val Gln Leu Ala Glu Lys Leu Arg Met Pro Ala Trp Val Ala Pro
                    245                 250                 255

Ser Ala Ser Arg Cys Pro Phe Pro Thr Arg His Pro Cys Phe Arg Gly
                260                 265                 270

Val Leu Pro Ala Ala Ile Ala Gly Ile Ser Arg Leu Leu Asp Gly His
        275                 280                 285

Asp Leu Ile Leu Val Val Gly Ala Pro Val Phe Arg Tyr His Gln Phe
        290                 295                 300

Ala Pro Gly Asp Tyr Leu Pro Ala Gly Ala Glu Leu Val Gln Ile Thr
305                 310                 315                 320

Cys Asp Pro Gly Glu Ala Ala Arg Ala Pro Met Gly Asp Ala Leu Val
                325                 330                 335

Gly Asp Ile Gly Leu Ser Leu Glu Ala Leu Leu Glu Gln Val Arg Pro
                340                 345                 350

Ser Ala Arg Pro Leu Pro Glu Ala Leu Pro Arg Pro Ala Leu Ala
                355                 360                 365

Glu Glu Gly Gly Pro Leu Arg Pro Glu Thr Val Phe Asp Val Ile Asp
370                 375                 380

Ala Leu Ala Pro Arg Asp Ala Ile Phe Val Lys Glu Ser Thr Ser Thr
385                 390                 395                 400

Val Thr Ala Phe Trp Gln Arg Val Glu Met Arg Glu Pro Gly Ser Tyr
                    405                 410                 415

Phe Phe Pro Ala Ala Gly Gly Leu Gly Phe Gly Leu Pro Ala Ala Val
                420                 425                 430

Gly Ala Gln Leu Ala Gln Pro Arg Arg Gln Val Ile Gly Ile Ile Gly
                435                 440                 445
```

```
Asp Gly Ser Ala Asn Tyr Gly Ile Thr Ala Leu Trp Ser Ala Ala Gln
    450                 455                 460

Tyr Arg Val Pro Ala Val Phe Ile Ile Leu Lys Asn Gly Thr Tyr Gly
465                 470                 475                 480

Ala Leu Arg Trp Phe Ala Gly Val Leu Glu Val Pro Asp Ala Pro Gly
            485                 490                 495

Leu Asp Val Pro Gly Leu Asp Phe Cys Ala Ile Ala Arg Gly Tyr Gly
        500                 505                 510

Val Glu Ala Leu His Ala Ala Thr Arg Glu Glu Leu Glu Ser Ala Leu
    515                 520                 525

Lys Gln Ala Leu Ala Ala Asp Arg Pro Val Leu Ile Glu Val Pro Thr
530                 535                 540

Gln Thr Ile Glu Pro
545

<210> SEQ ID NO 16
<211> LENGTH: 528
<212> TYPE: PRT
<213> ORGANISM: Pseudomonas aeruginosa

<400> SEQUENCE: 16

Met Lys Thr Val His Ser Ala Ser Tyr Glu Ile Leu Arg Arg His Gly
1               5                   10                  15

Leu Thr Val Phe Gly Asn Pro Gly Ser Asn Glu Leu Pro Phe Leu
            20                  25                  30

Lys Asp Phe Pro Glu Asp Phe Arg Tyr Ile Leu Gly Leu His Glu Gly
            35                  40                  45

Ala Val Val Gly Met Ala Asp Gly Phe Ala Leu Ala Ser Gly Arg Pro
    50                  55                  60

Ala Phe Val Asn Leu His Ala Ala Gly Thr Gly Asn Gly Met Gly
65                  70                  75                  80

Ala Leu Thr Asn Ala Trp Tyr Ser His Ser Pro Leu Val Ile Thr Ala
                85                  90                  95

Gly Gln Gln Val Arg Ser Met Ile Gly Val Glu Ala Met Leu Ala Asn
            100                 105                 110

Val Asp Ala Gly Gln Leu Pro Lys Pro Leu Val Lys Trp Ser His Glu
        115                 120                 125

Pro Ala Cys Ala Gln Asp Val Pro Arg Ala Leu Ser Gln Ala Ile Gln
    130                 135                 140

Thr Ala Ser Leu Pro Pro Arg Ala Pro Val Tyr Leu Ser Ile Pro Tyr
145                 150                 155                 160

Asp Asp Trp Ala Gln Pro Ala Pro Ala Gly Val Glu His Leu Ala Ala
                165                 170                 175

Arg Gln Val Ser Gly Ala Ala Leu Pro Ala Pro Ala Leu Leu Ala Glu
            180                 185                 190

Leu Gly Glu Arg Leu Ser Arg Ser Arg Asn Pro Val Leu Val Leu Gly
        195                 200                 205

Pro Asp Val Asp Gly Ala Asn Ala Asn Gly Leu Ala Val Glu Leu Ala
    210                 215                 220

Glu Lys Leu Arg Met Pro Ala Trp Val Ala Pro Ser Ala Ser Arg Cys
225                 230                 235                 240

Pro Phe Pro Thr Arg His Ala Cys Phe Arg Gly Val Leu Pro Ala Ala
                245                 250                 255

Ile Ala Gly Ile Ser Arg Leu Leu Asp Gly His Asp Leu Ile Leu Val
            260                 265                 270
```

```
Val Gly Ala Pro Val Phe Arg Tyr His Gln Phe Ala Pro Gly Asp Tyr
        275                 280                 285

Leu Pro Ala Gly Ala Glu Leu Val Gln Val Thr Cys Asp Pro Gly Glu
290                 295                 300

Ala Ala Arg Ala Pro Met Gly Asp Ala Leu Val Gly Asp Ile Ala Leu
305                 310                 315                 320

Thr Leu Glu Ala Leu Leu Glu Gln Val Arg Pro Ser Ala Arg Pro Leu
                325                 330                 335

Pro Glu Ala Leu Pro Arg Pro Ala Leu Ala Glu Glu Gly Gly Pro
            340                 345                 350

Leu Arg Pro Glu Thr Val Phe Asp Val Ile Asp Ala Leu Ala Pro Arg
                355                 360                 365

Asp Ala Ile Phe Val Lys Glu Ser Thr Ser Thr Val Thr Ala Phe Trp
370                 375                 380

Gln Arg Val Glu Met Arg Glu Pro Gly Ser Tyr Phe Phe Pro Ala Ala
385                 390                 395                 400

Gly Gly Leu Gly Phe Gly Leu Pro Ala Ala Val Gly Ala Gln Leu Ala
                405                 410                 415

Gln Pro Arg Arg Gln Val Ile Gly Ile Ile Gly Asp Gly Ser Ala Asn
            420                 425                 430

Tyr Gly Ile Thr Ala Leu Trp Ser Ala Ala Gln Tyr Arg Val Pro Ala
                435                 440                 445

Val Phe Ile Ile Leu Lys Asn Gly Thr Tyr Gly Ala Leu Arg Trp Phe
450                 455                 460

Ala Gly Val Leu Glu Val Pro Asp Ala Pro Gly Leu Asp Val Pro Gly
465                 470                 475                 480

Leu Asp Phe Cys Ala Ile Ala Arg Gly Tyr Gly Val Glu Ala Leu His
                485                 490                 495

Ala Ala Thr Arg Glu Glu Leu Glu Gly Ala Leu Lys His Ala Leu Ala
            500                 505                 510

Ala Asp Arg Pro Val Leu Ile Glu Val Pro Thr Gln Thr Ile Glu Pro
                515                 520                 525

<210> SEQ ID NO 17
<211> LENGTH: 528
<212> TYPE: PRT
<213> ORGANISM: Pseudomonas aeruginosa

<400> SEQUENCE: 17

Met Lys Thr Val His Ser Ala Ser Tyr Glu Ile Leu Arg Arg His Gly
1               5                   10                  15

Leu Thr Thr Val Phe Gly Asn Pro Gly Ser Asn Glu Leu Pro Phe Leu
                20                  25                  30

Lys Asp Phe Pro Glu Asp Phe Arg Tyr Ile Leu Gly Leu His Glu Gly
            35                  40                  45

Ala Val Val Gly Met Ala Asp Gly Phe Ala Leu Ala Ser Gly Arg Pro
        50                  55                  60

Ala Phe Val Asn Leu His Ala Ala Ala Gly Thr Gly Asn Gly Met Gly
65                  70                  75                  80

Ala Leu Thr Asn Ala Trp Tyr Ser His Ser Pro Leu Val Ile Thr Ala
                85                  90                  95

Gly Gln Gln Val Arg Ser Met Ile Gly Val Glu Ala Met Leu Ala Asn
            100                 105                 110

Val Asp Ala Gly Gln Leu Pro Lys Pro Leu Val Lys Trp Ser His Glu
```

```
            115                 120                 125
Pro Ala Cys Ala Gln Asp Val Pro Arg Ala Leu Ser Gln Ala Ile Gln
130                 135                 140

Thr Ala Ser Leu Pro Pro Arg Ala Pro Val Tyr Leu Ser Ile Pro Tyr
145                 150                 155                 160

Asp Asp Trp Ala Gln Pro Ala Pro Ala Gly Val Glu His Leu Ala Ala
                165                 170                 175

Arg Gln Val Ser Gly Ala Ala Leu Pro Ala Pro Ala Leu Leu Ala Glu
            180                 185                 190

Leu Gly Glu Arg Leu Ser Arg Ser Arg Asn Pro Val Leu Val Leu Gly
        195                 200                 205

Pro Asp Val Asp Gly Ala Asn Ala Asn Gly Leu Ala Val Gln Leu Ala
210                 215                 220

Glu Lys Leu Arg Met Pro Ala Trp Val Ala Pro Ser Ala Ser Arg Cys
225                 230                 235                 240

Pro Phe Pro Thr Arg His Ala Cys Phe Arg Gly Val Leu Pro Ala Ala
                245                 250                 255

Ile Ala Gly Ile Ser Arg Leu Leu Asp Gly His Asp Leu Ile Leu Val
            260                 265                 270

Val Gly Ala Pro Val Phe Arg Tyr His Gln Phe Ala Pro Gly Asp Tyr
        275                 280                 285

Leu Pro Ala Gly Ala Glu Leu Val Gln Val Thr Cys Asp Pro Gly Glu
290                 295                 300

Ala Ala Arg Ala Pro Met Gly Asp Ala Leu Val Gly Asp Ile Ala Leu
305                 310                 315                 320

Thr Leu Glu Ala Leu Leu Glu Gln Val Arg Pro Ser Ala Arg Pro Leu
                325                 330                 335

Pro Glu Ala Leu Pro Arg Pro Pro Ala Leu Ala Glu Glu Gly Gly Pro
            340                 345                 350

Leu Arg Pro Glu Thr Val Phe Asp Val Ile Asp Ala Leu Ala Pro Arg
        355                 360                 365

Asp Ala Ile Phe Val Lys Glu Ser Thr Ser Thr Val Thr Ala Phe Trp
370                 375                 380

Gln Arg Val Glu Met Arg Glu Pro Gly Ser Tyr Phe Phe Pro Ala Ala
385                 390                 395                 400

Gly Gly Leu Gly Phe Gly Leu Pro Ala Ala Val Gly Ala Gln Leu Ala
                405                 410                 415

Gln Pro Arg Arg Gln Val Ile Gly Ile Ile Gly Asp Gly Ser Ala Asn
            420                 425                 430

Tyr Gly Ile Thr Ala Leu Trp Ser Ala Ala Gln Tyr Arg Val Pro Ala
        435                 440                 445

Val Phe Ile Ile Leu Lys Asn Gly Thr Tyr Gly Ala Leu Arg Trp Phe
450                 455                 460

Ala Gly Val Leu Glu Val Pro Asp Ala Pro Gly Leu Asp Val Pro Gly
465                 470                 475                 480

Leu Asp Phe Cys Ala Ile Ala Arg Gly Tyr Gly Val Glu Ala Leu His
                485                 490                 495

Ala Ala Thr Arg Glu Glu Leu Glu Ser Ala Leu Lys His Ala Leu Ala
            500                 505                 510

Ala Asp Arg Pro Val Leu Ile Glu Val Pro Thr Gln Thr Ile Glu Pro
        515                 520                 525

<210> SEQ ID NO 18
```

```
<211> LENGTH: 528
<212> TYPE: PRT
<213> ORGANISM: Pseudomonas aeruginosa

<400> SEQUENCE: 18

Met Lys Thr Val His Ser Ala Ser Tyr Glu Ile Leu Arg Arg His Gly
1               5                   10                  15

Leu Thr Thr Val Phe Gly Asn Pro Gly Ser Asn Glu Leu Pro Phe Leu
            20                  25                  30

Lys Asp Phe Pro Glu Asp Phe Arg Tyr Ile Leu Gly Leu His Glu Gly
        35                  40                  45

Ala Val Val Gly Met Ala Asp Gly Phe Ala Leu Ala Ser Gly Arg Pro
    50                  55                  60

Ala Phe Val Asn Leu His Ala Ala Gly Thr Gly Asn Gly Met Gly
65                  70                  75                  80

Ala Leu Thr Asn Ala Trp Tyr Ser His Ser Pro Leu Val Ile Thr Ala
                85                  90                  95

Gly Gln Gln Val Arg Ser Met Ile Gly Val Glu Ala Met Leu Ala Asn
            100                 105                 110

Val Asp Ala Gly Gln Leu Pro Lys Pro Leu Val Lys Trp Ser His Glu
        115                 120                 125

Pro Ala Cys Ala Gln Asp Val Pro Arg Ala Leu Ser Gln Ala Ile Gln
    130                 135                 140

Thr Ala Ser Leu Pro Pro Arg Ala Pro Val Tyr Leu Ser Ile Pro Tyr
145                 150                 155                 160

Asp Asp Trp Ala Gln Pro Ala Pro Val Gly Val Glu His Leu Ala Ala
                165                 170                 175

Arg Gln Val Ser Gly Ala Ala Leu Pro Ala Pro Ala Leu Leu Ala Glu
            180                 185                 190

Leu Gly Glu Arg Leu Ser Arg Ser Arg Asn Pro Val Leu Val Leu Gly
        195                 200                 205

Pro Asp Val Asp Gly Ala Asn Ala Asn Gly Leu Ala Val Glu Leu Ala
    210                 215                 220

Glu Lys Leu Arg Met Pro Ala Trp Val Ala Pro Ser Ala Ser Arg Cys
225                 230                 235                 240

Pro Phe Pro Thr Arg His Ala Cys Phe Arg Gly Val Leu Pro Ala Ala
                245                 250                 255

Ile Ala Gly Ile Ser Arg Leu Leu Asp Gly His Asp Leu Ile Leu Val
            260                 265                 270

Val Gly Ala Pro Val Phe Arg Tyr His Gln Phe Ala Pro Gly Asp Tyr
        275                 280                 285

Leu Pro Ala Gly Ala Glu Leu Val Gln Val Thr Cys Asp Pro Gly Glu
    290                 295                 300

Ala Ala Arg Ala Pro Met Gly Asp Ala Leu Val Gly Asp Ile Ala Leu
305                 310                 315                 320

Thr Leu Glu Ala Leu Leu Glu Gln Val Arg Pro Ser Ala Arg Pro Leu
                325                 330                 335

Pro Glu Ala Leu Pro Arg Pro Ala Leu Ala Glu Glu Gly Gly Pro
            340                 345                 350

Leu Arg Pro Glu Thr Val Phe Asp Val Ile Asp Ala Leu Ala Pro Arg
        355                 360                 365

Asp Ala Ile Phe Val Lys Glu Ser Thr Ser Thr Val Thr Ala Phe Trp
    370                 375                 380

Gln Arg Val Glu Met Arg Glu Pro Gly Ser Tyr Phe Phe Pro Ala Ala
```

```
                385                 390                 395                 400
Gly Gly Leu Gly Phe Gly Leu Pro Ala Ala Val Gly Ala Gln Leu Ala
                405                 410                 415

Gln Pro Arg Arg Gln Val Ile Gly Ile Ile Gly Asp Gly Ser Ala Asn
        420                 425                 430

Tyr Gly Ile Thr Ala Leu Trp Ser Ala Ala Gln Tyr Arg Val Pro Ala
            435                 440                 445

Val Phe Ile Ile Leu Lys Asn Gly Thr Tyr Gly Ala Leu Arg Trp Phe
        450                 455                 460

Ala Gly Val Leu Glu Val Pro Asp Ala Pro Gly Leu Asp Val Pro Gly
465                 470                 475                 480

Leu Asp Phe Cys Ala Ile Ala Arg Gly Tyr Gly Val Glu Ala Leu His
                485                 490                 495

Ala Ala Thr Arg Glu Glu Leu Glu Ser Ala Leu Lys His Ala Leu Ala
                500                 505                 510

Ala Asp Arg Pro Val Leu Ile Glu Val Pro Thr Gln Thr Ile Glu Pro
            515                 520                 525
```

<210> SEQ ID NO 19
<211> LENGTH: 528
<212> TYPE: PRT
<213> ORGANISM: Pseudomonas aeruginosa

<400> SEQUENCE: 19

```
Met Lys Thr Val His Ser Ala Ser Tyr Glu Ile Leu Arg Arg His Gly
1               5                   10                  15

Leu Thr Thr Val Phe Gly Asn Pro Gly Ser Asn Glu Leu Pro Phe Leu
            20                  25                  30

Lys Asp Phe Pro Glu Asp Phe Arg Tyr Ile Leu Gly Leu His Glu Gly
        35                  40                  45

Ala Val Val Gly Met Ala Asp Gly Phe Ala Leu Ala Ser Gly Arg Pro
    50                  55                  60

Ala Phe Val Asn Leu His Ala Ala Gly Thr Gly Asn Gly Met Gly
65                  70                  75                  80

Ala Leu Thr Asn Ala Trp Tyr Ser His Ser Pro Leu Val Ile Thr Ala
                85                  90                  95

Gly Gln Gln Val Arg Ser Met Ile Gly Val Glu Ala Met Leu Ala Asn
            100                 105                 110

Val Asp Ala Gly Gln Leu Pro Lys Pro Leu Val Lys Trp Ser His Glu
        115                 120                 125

Pro Ala Cys Ala Gln Asp Val Pro Arg Ala Leu Ser Gln Ala Ile Gln
    130                 135                 140

Thr Ala Ser Leu Pro Pro Arg Ala Pro Val Tyr Leu Ser Ile Pro Tyr
145                 150                 155                 160

Asp Asp Trp Ala Gln Pro Ala Pro Ala Gly Val Glu His Leu Ala Ala
                165                 170                 175

Arg Gln Val Ser Gly Ala Ala Leu Pro Ala Pro Ala Leu Leu Ala Glu
            180                 185                 190

Leu Gly Glu Arg Leu Ser Arg Ser Arg Asn Pro Val Leu Val Leu Gly
        195                 200                 205

Pro Asp Val Asp Gly Ala Asn Ala Asn Gly Leu Ala Val Glu Leu Ala
    210                 215                 220

Glu Lys Leu Arg Met Pro Ala Trp Val Ala Pro Ser Ala Ser Arg Cys
225                 230                 235                 240
```

```
Pro Phe Pro Thr Arg His Ala Cys Phe Arg Gly Val Leu Pro Ala Ala
            245                 250                 255

Ile Ala Gly Ile Ser Arg Leu Leu Asp Gly His Asp Leu Ile Leu Val
        260                 265                 270

Val Gly Ala Pro Val Phe Arg Tyr His Gln Phe Ala Pro Gly Asp Tyr
        275                 280                 285

Leu Pro Ala Gly Ala Glu Leu Val Gln Val Thr Cys Asp Pro Gly Glu
        290                 295                 300

Ala Ala Arg Ala Pro Met Gly Asp Ala Leu Val Gly Asp Ile Ala Leu
305                 310                 315                 320

Thr Leu Glu Ala Leu Leu Glu Gln Val Arg Pro Ser Ala Arg Pro Leu
                325                 330                 335

Pro Glu Ala Leu Pro Arg Pro Ala Leu Ala Glu Glu Gly Gly Pro
        340                 345                 350

Leu Arg Pro Glu Thr Val Phe Asp Val Ile Asp Ala Leu Ala Pro Arg
        355                 360                 365

Asp Ala Ile Phe Val Lys Glu Ser Thr Ser Thr Val Thr Ala Phe Trp
        370                 375                 380

Gln Arg Val Glu Met Arg Glu Pro Gly Ser Tyr Phe Phe Pro Ala Ala
385                 390                 395                 400

Gly Gly Leu Gly Phe Gly Leu Pro Ala Ala Val Gly Ala Gln Leu Ala
                405                 410                 415

Gln Pro Arg Arg Gln Val Ile Gly Ile Ile Gly Asp Gly Ser Ala Asn
                420                 425                 430

Tyr Gly Ile Thr Ala Leu Trp Ser Ala Ala Gln Tyr Arg Val Pro Ala
                435                 440                 445

Val Phe Ile Ile Leu Lys Asn Gly Thr Tyr Gly Ala Leu Arg Trp Phe
    450                 455                 460

Ala Gly Val Leu Glu Val Pro Asp Ala Pro Gly Leu Asp Val Pro Gly
465                 470                 475                 480

Leu Asp Phe Cys Ala Ile Ala Arg Gly Tyr Gly Val Glu Ala Leu His
                485                 490                 495

Ala Ala Thr Arg Glu Glu Leu Glu Ser Ala Leu Lys His Ala Leu Ala
                500                 505                 510

Ala Asp Arg Pro Val Leu Ile Glu Val Pro Thr Gln Thr Ile Glu Pro
                515                 520                 525

<210> SEQ ID NO 20
<211> LENGTH: 528
<212> TYPE: PRT
<213> ORGANISM: Pseudomonas aeruginosa

<400> SEQUENCE: 20

Met Lys Thr Val His Ser Ala Ser Tyr Glu Ile Leu Arg Arg His Gly
1               5                   10                  15

Leu Thr Thr Val Phe Gly Asn Pro Gly Ser Asn Glu Leu Pro Phe Leu
            20                  25                  30

Lys Asp Phe Pro Glu Asp Phe Arg Tyr Ile Leu Gly Leu His Glu Gly
        35                  40                  45

Ala Val Val Gly Met Ala Asp Gly Phe Ala Leu Ala Ser Gly Arg Pro
    50                  55                  60

Ala Phe Val Asn Leu His Ala Ala Gly Thr Gly Asn Gly Met Gly
65                  70                  75                  80

Ala Leu Thr Asn Ala Trp Tyr Ser His Ser Pro Leu Val Ile Thr Ala
                85                  90                  95
```

```
Gly Gln Gln Val Arg Ser Met Ile Gly Val Glu Ala Met Leu Ala Asn
            100                 105                 110

Val Asp Ala Gly Gln Leu Pro Lys Pro Leu Val Lys Trp Ser His Glu
        115                 120                 125

Pro Ala Cys Ala Gln Asp Val Pro Arg Ala Leu Ser Gln Ala Ile Gln
    130                 135                 140

Thr Ala Ser Leu Pro Pro Arg Ala Pro Val Tyr Leu Ser Ile Pro Tyr
145                 150                 155                 160

Asp Asp Trp Ala Gln Pro Ala Pro Val Gly Val Glu His Leu Ala Ala
                165                 170                 175

Arg Gln Val Ser Gly Ala Ala Leu Pro Ala Pro Ala Leu Leu Ala Glu
                180                 185                 190

Leu Gly Glu Arg Leu Ser Arg Ser Arg Asn Pro Val Leu Val Leu Gly
                195                 200                 205

Pro Asp Val Asp Gly Ala Asn Ala Asn Gly Leu Ala Val Glu Leu Ala
    210                 215                 220

Glu Lys Leu Arg Met Pro Ala Trp Val Ala Pro Ser Ala Ser Arg Cys
225                 230                 235                 240

Pro Phe Pro Thr Arg His Ala Cys Phe Arg Gly Val Leu Pro Ala Ala
                245                 250                 255

Ile Ala Gly Ile Ser Arg Leu Leu Asp Gly His Asp Leu Ile Leu Val
                260                 265                 270

Val Gly Ala Pro Val Phe Arg Tyr His Gln Phe Ala Pro Gly Asp Tyr
                275                 280                 285

Leu Pro Ala Gly Ala Glu Leu Val Gln Val Thr Cys Asp Pro Gly Glu
    290                 295                 300

Ala Ala Arg Ala Pro Met Gly Asp Ala Leu Val Gly Asp Ile Ala Leu
305                 310                 315                 320

Thr Leu Glu Ala Leu Leu Glu Gln Val Arg Pro Ser Ala Arg Pro Leu
                325                 330                 335

Pro Glu Ala Leu Pro Arg Pro Pro Ala Leu Ala Glu Glu Gly Gly Pro
                340                 345                 350

Leu Arg Pro Glu Thr Val Phe Asp Val Ile Asp Ala Leu Ala Pro Arg
                355                 360                 365

Asp Ala Ile Phe Val Lys Glu Ser Thr Ser Thr Val Thr Ala Phe Trp
    370                 375                 380

Gln Arg Val Glu Met Arg Glu Pro Gly Ser Tyr Phe Phe Pro Ala Ala
385                 390                 395                 400

Gly Gly Leu Gly Phe Gly Leu Pro Ala Ala Val Gly Ala Gln Leu Ala
                405                 410                 415

Gln Pro Arg Arg Gln Val Ile Gly Ile Ile Gly Asp Gly Ser Ala Asn
                420                 425                 430

Tyr Gly Ile Thr Ala Leu Trp Ser Ala Ala Gln Tyr Arg Val Pro Ala
                435                 440                 445

Val Phe Ile Ile Leu Lys Asn Gly Thr Tyr Gly Ala Leu Arg Trp Phe
    450                 455                 460

Ala Gly Val Leu Glu Val Pro Asp Ala Pro Gly Leu Asp Val Pro Gly
465                 470                 475                 480

Leu Asp Phe Cys Ala Ile Val Arg Gly Tyr Gly Val Glu Ala Leu His
                485                 490                 495

Ala Ala Thr Arg Glu Glu Leu Glu Ser Ala Leu Lys His Ala Leu Ala
                500                 505                 510
```

```
Ala Asp Arg Pro Val Leu Ile Glu Val Pro Thr Gln Thr Ile Glu Pro
            515                 520                 525
```

<210> SEQ ID NO 21
<211> LENGTH: 528
<212> TYPE: PRT
<213> ORGANISM: Pseudomonas putida

<400> SEQUENCE: 21

```
Met Lys Thr Val His Gly Ala Thr Tyr Asp Ile Leu Arg Gln His Gly
1               5                   10                  15

Leu Thr Thr Ile Phe Gly Asn Pro Gly Ser Asn Glu Leu Pro Phe Leu
            20                  25                  30

Lys Gly Phe Pro Glu Asp Phe Arg Tyr Ile Leu Gly Leu His Glu Gly
        35                  40                  45

Ala Val Val Gly Met Ala Asp Gly Tyr Ala Leu Ala Ser Gly Gln Pro
    50                  55                  60

Thr Phe Val Asn Leu His Ala Ala Gly Thr Gly Asn Gly Met Gly
65                  70                  75                  80

Ala Leu Thr Asn Ala Trp Tyr Ser His Ser Pro Leu Val Ile Thr Ala
                85                  90                  95

Gly Gln Gln Val Arg Ser Met Ile Gly Val Glu Ala Met Leu Ala Asn
            100                 105                 110

Val Asp Ala Ala Gln Leu Pro Lys Pro Leu Val Lys Trp Ser His Glu
        115                 120                 125

Pro Ala Thr Ala Gln Asp Val Pro Arg Ala Leu Ser Gln Ala Ile His
    130                 135                 140

Thr Ala Asn Leu Pro Pro Arg Gly Pro Val Tyr Val Ser Ile Pro Tyr
145                 150                 155                 160

Asp Asp Trp Ala Cys Glu Ala Pro Ser Gly Val Glu His Leu Ala Arg
                165                 170                 175

Arg Gln Val Ser Ser Ala Gly Leu Pro Ser Pro Ala Gln Leu Gln His
            180                 185                 190

Leu Cys Glu Arg Leu Ala Ala Ala Arg Asn Pro Val Leu Val Leu Gly
        195                 200                 205

Pro Asp Val Asp Gly Ser Ala Ala Asn Gly Leu Ala Val Gln Leu Ala
    210                 215                 220

Glu Lys Leu Arg Met Pro Ala Trp Val Ala Pro Ser Ala Ser Arg Cys
225                 230                 235                 240

Pro Phe Pro Thr Arg His Ala Cys Phe Arg Gly Val Leu Pro Ala Ala
                245                 250                 255

Ile Ala Gly Ile Ser His Asn Leu Ala Gly His Asp Leu Ile Leu Val
            260                 265                 270

Val Gly Ala Pro Val Phe Arg Tyr His Gln Phe Ala Pro Gly Asn Tyr
        275                 280                 285

Leu Pro Ala Gly Cys Glu Leu Leu His Leu Thr Cys Asp Pro Gly Glu
    290                 295                 300

Ala Ala Arg Ala Pro Met Gly Asp Ala Leu Val Gly Asp Ile Ala Leu
305                 310                 315                 320

Thr Leu Glu Ala Val Leu Asp Gly Val Pro Gln Ser Val Arg Gln Met
                325                 330                 335

Pro Thr Ala Leu Pro Ala Glu Pro Val Ala Asp Asp Gly Gly Leu
            340                 345                 350

Leu Arg Pro Glu Thr Val Phe Asp Leu Leu Asn Ala Leu Ala Pro Lys
        355                 360                 365
```

```
Asp Ala Ile Tyr Val Lys Glu Ser Thr Ser Thr Val Gly Ala Phe Trp
            370                 375                 380

Arg Arg Val Glu Met Arg Glu Pro Gly Ser Tyr Phe Phe Pro Ala Ala
385                 390                 395                 400

Gly Gly Leu Gly Phe Gly Leu Pro Ala Ala Val Gly Val Gln Leu Ala
                405                 410                 415

Ser Pro Gly Arg Gln Val Ile Gly Val Ile Gly Asp Gly Ser Ala Asn
                420                 425                 430

Tyr Gly Ile Thr Ala Leu Trp Thr Ala Ala Gln Tyr Asn Ile Pro Val
            435                 440                 445

Val Phe Ile Ile Leu Lys Asn Gly Thr Tyr Gly Ala Leu Arg Trp Phe
            450                 455                 460

Ala Asp Val Leu Asp Val Asn Asp Ala Pro Gly Leu Asp Val Pro Gly
465                 470                 475                 480

Leu Asp Phe Cys Ala Ile Ala Arg Gly Tyr Gly Val Gln Ala Val His
                485                 490                 495

Ala Ala Thr Gly Ser Ala Phe Ala Gln Ala Leu Arg Glu Ala Leu Glu
                500                 505                 510

Ser Asp Arg Pro Val Leu Ile Glu Val Pro Thr Gln Thr Ile Glu Pro
            515                 520                 525
```

<210> SEQ ID NO 22
<211> LENGTH: 525
<212> TYPE: PRT
<213> ORGANISM: Pseudomonas pudita

<400> SEQUENCE: 22

```
Met Lys Thr Val His Gly Ala Thr Tyr Asp Ile Leu Arg Gln His Gly
1               5                   10                  15

Leu Thr Thr Ile Phe Gly Asn Pro Gly Ser Asn Glu Leu Pro Phe Leu
                20                  25                  30

Lys Gly Phe Pro Glu Asp Phe Arg Tyr Ile Leu Gly Leu His Glu Gly
            35                  40                  45

Ala Val Val Gly Met Ala Asp Gly Tyr Ala Leu Ala Ser Gly Gln Pro
50                  55                  60

Thr Phe Val Asn Leu His Ala Ala Gly Thr Gly Asn Gly Met Gly
65                  70                  75                  80

Ala Leu Thr Asn Ala Trp Tyr Ser His Ser Pro Leu Val Ile Thr Ala
                85                  90                  95

Gly Gln Gln Val Arg Ser Met Ile Gly Val Glu Ala Met Leu Ala Asn
            100                 105                 110

Val Asp Ala Ala Gln Leu Pro Lys Pro Leu Val Lys Trp Ser His Glu
            115                 120                 125

Pro Ala Thr Ala Gln Asp Val Pro Arg Ala Leu Ser Gln Ala Ile His
130                 135                 140

Thr Ala Asn Leu Pro Pro Arg Gly Pro Val Tyr Val Ser Ile Pro Tyr
145                 150                 155                 160

Asp Asp Trp Ala Cys Glu Ala Pro Ser Gly Val Glu His Leu Ala Arg
                165                 170                 175

Arg Gln Val Ser Ser Ala Gly Leu Pro Ser Pro Ala Gln Leu Gln His
            180                 185                 190

Leu Cys Glu Arg Leu Ala Ala Ala Arg Asn Pro Val Leu Val Leu Gly
            195                 200                 205

Pro Asp Val Asp Gly Ser Ala Ala Asn Gly Leu Ala Val Gln Leu Ala
```

```
            210                 215                 220
Glu Lys Leu Arg Met Pro Ala Trp Val Ala Pro Ser Ala Ser Arg Cys
225                 230                 235                 240

Pro Phe Pro Thr Arg His Ala Cys Phe Arg Gly Val Leu Pro Ala Ala
                245                 250                 255

Ile Ala Gly Ile Ser His Asn Leu Ala Gly His Asp Leu Ile Leu Val
                    260                 265                 270

Val Gly Ala Pro Val Phe Arg Tyr His Gln Phe Ala Pro Gly Asn Tyr
                275                 280                 285

Leu Pro Ala Gly Cys Glu Leu Leu His Leu Thr Cys Asp Pro Gly Glu
            290                 295                 300

Ala Ala Arg Ala Pro Met Gly Asp Ala Leu Val Gly Asp Ile Ala Leu
305                 310                 315                 320

Thr Leu Glu Ala Val Leu Asp Gly Val Pro Gln Ser Val Arg Gln Met
                325                 330                 335

Pro Thr Ala Leu Pro Ala Ala Glu Pro Val Ala Asp Asp Gly Gly Leu
                340                 345                 350

Leu Arg Pro Glu Thr Val Phe Asp Leu Leu Asn Ala Leu Ala Pro Lys
            355                 360                 365

Asp Ala Ile Tyr Val Lys Glu Ser Thr Ser Thr Val Gly Ala Phe Trp
            370                 375                 380

Arg Arg Val Glu Met Arg Glu Pro Gly Ser Tyr Phe Phe Pro Ala Ala
385                 390                 395                 400

Gly Gly Leu Gly Phe Gly Leu Pro Ala Ala Val Gly Val Gln Leu Ala
                    405                 410                 415

Ser Pro Gly Arg Gln Val Ile Gly Val Ile Gly Asp Gly Ser Ala Asn
                420                 425                 430

Tyr Gly Ile Thr Ala Leu Trp Thr Ala Ala Gln Tyr Asn Ile Pro Val
            435                 440                 445

Val Phe Ile Ile Leu Lys Asn Gly Thr Tyr Gly Ala Leu Arg Trp Phe
            450                 455                 460

Ala Asp Val Leu Asp Val Asn Asp Ala Pro Gly Leu Asp Val Pro Gly
465                 470                 475                 480

Leu Asp Phe Cys Ala Ile Ala Arg Gly Tyr Gly Val Gln Ala Val His
                    485                 490                 495

Ala Ala Thr Gly Ser Ala Phe Gln Ala Leu Arg Glu Ala Leu Glu
                500                 505                 510

Ser Asp Arg Pro Val Leu Ile Cys Ala Ala Ser Ser Arg
            515                 520                 525

<210> SEQ ID NO 23
<211> LENGTH: 528
<212> TYPE: PRT
<213> ORGANISM: Pseudomonas fluorescens

<400> SEQUENCE: 23

Met Lys Thr Val His Ser Ala Ser Tyr Asp Ile Leu Arg Gln Gln Gly
1               5                   10                  15

Leu Thr Thr Val Phe Gly Asn Pro Gly Ser Asn Glu Leu Pro Phe Leu
                20                  25                  30

Lys Gly Phe Pro Glu Asp Phe Arg Tyr Ile Leu Gly Leu His Glu Gly
            35                  40                  45

Ala Val Val Gly Met Ala Asp Gly Phe Ala Leu Ala Ser Gly Gln Pro
        50                  55                  60
```

```
Ala Phe Val Asn Leu His Ala Ala Gly Thr Gly Asn Gly Met Gly
 65                  70                  75                  80

Ala Leu Thr Asn Ala Trp Tyr Ser His Ser Pro Leu Val Ile Thr Ala
                 85                  90                  95

Gly Gln Gln Val Arg Ser Met Ile Gly Val Glu Ala Met Leu Ala Asn
            100                 105                 110

Val Asp Ala Pro Gln Leu Pro Lys Pro Leu Val Lys Trp Ser Ala Glu
        115                 120                 125

Pro Ala Cys Ala Glu Asp Val Pro Arg Ala Leu Ser Gln Ala Ile His
    130                 135                 140

Met Ala Asn Gln Ala Pro Lys Gly Pro Val Tyr Leu Ser Ile Pro Tyr
145                 150                 155                 160

Asp Asp Trp Ala Arg Pro Ala Pro Ala Gly Val Glu His Leu Ala Arg
                165                 170                 175

Arg Gln Val Ala Thr Ala Gly Leu Pro Ser Ala Ala Gln Leu Arg Ser
            180                 185                 190

Leu Val Gln Arg Leu Ala Ala Ala Arg Asn Pro Val Leu Val Leu Gly
        195                 200                 205

Pro Asp Val Asp Gly Ser Arg Ser Asn His Leu Ala Val Gln Leu Ala
    210                 215                 220

Glu Lys Leu Arg Met Pro Ala Trp Val Ala Pro Ser Ala Ser Arg Cys
225                 230                 235                 240

Pro Phe Pro Thr Arg His Pro Ser Phe Arg Gly Val Leu Pro Ala Ala
                245                 250                 255

Ile Ala Gly Ile Ser Arg Cys Leu Ala Asp His Asp Leu Ile Leu Val
            260                 265                 270

Val Gly Ala Pro Val Phe Arg Tyr His Gln Phe Ala Pro Gly Asp Tyr
        275                 280                 285

Leu Pro Ala Gly Thr Glu Leu Leu His Ile Thr Cys Asp Pro Gly Glu
    290                 295                 300

Ala Ala Arg Ala Pro Met Gly Asp Ala Leu Val Gly Asp Ile Val Glu
305                 310                 315                 320

Thr Leu Gln Ala Leu Val Trp Ala Leu Pro Asp Cys Asp Arg Pro Gln
                325                 330                 335

Pro Gln Ala Leu Pro Pro Ala Ala Pro Val Glu Glu Leu Gly Gly Leu
            340                 345                 350

Leu Arg Pro Glu Thr Val Phe Asp Val Ile Asp Glu Leu Ala Pro Lys
        355                 360                 365

Asp Ala Ile Tyr Val Lys Glu Ser Thr Ser Thr Val Gly Ala Phe Trp
    370                 375                 380

Gln Arg Val Glu Met Arg Glu Pro Gly Ser Tyr Tyr Phe Pro Ala Ala
385                 390                 395                 400

Gly Gly Leu Gly Phe Gly Leu Pro Ala Ala Val Gly Val Gln Leu Ala
                405                 410                 415

Arg Pro Glu Arg Arg Val Ile Gly Val Ile Gly Asp Gly Ser Ala Asn
            420                 425                 430

Tyr Gly Ile Thr Ala Leu Trp Thr Ala Ala Gln Tyr Gln Ile Pro Val
        435                 440                 445

Val Phe Ile Ile Leu Lys Asn Gly Thr Tyr Gly Ala Leu Arg Trp Phe
    450                 455                 460

Ala Gly Val Leu Gln Val Ser Asp Ala Pro Gly Leu Asp Val Pro Gly
465                 470                 475                 480

Leu Asp Phe Cys Ala Ile Gly Arg Gly Tyr Gly Val His Ser Val Gln
```

```
            485                 490                 495
Ala Asn Thr Arg Glu Ala Phe Ala Gln Ala Leu Ser Glu Ala Leu Ala
                500                 505                 510

Gly Asp Arg Pro Val Leu Ile Glu Val Pro Thr Leu Thr Ile Glu Pro
                515                 520                 525

<210> SEQ ID NO 24
<211> LENGTH: 529
<212> TYPE: PRT
<213> ORGANISM: Klebsiella sp.

<400> SEQUENCE: 24

Met Lys Thr Ile His Ser Ala Ala Tyr Ala Leu Leu Arg Arg His Gly
1               5                   10                  15

Met Thr Thr Ile Phe Gly Asn Pro Gly Ser Asn Glu Leu Pro Phe Leu
                20                  25                  30

Lys Ser Phe Pro Glu Asp Phe Gln Tyr Val Leu Gly Leu His Glu Gly
            35                  40                  45

Ala Val Val Gly Met Ala Asp Gly Tyr Ala Leu Ala Ser Gly Lys Pro
        50                  55                  60

Ala Phe Val Asn Leu His Ala Ala Gly Thr Gly Asn Gly Met Gly Gly
65                  70                  75                  80

Ala Leu Thr Asn Ser Trp Tyr Ser His Ser Pro Leu Val Ile Thr Ala
                85                  90                  95

Gly Gln Gln Val Arg Pro Met Ile Gly Val Glu Ala Met Leu Ala Asn
            100                 105                 110

Val Asp Ala Thr Gln Leu Pro Lys Pro Leu Val Lys Trp Ser Tyr Glu
        115                 120                 125

Pro Ala Asn Ala Gln Asp Val Pro Arg Ala Leu Ser Gln Ala Ile His
    130                 135                 140

Tyr Ala Asn Thr Thr Pro Lys Ala Pro Val Tyr Leu Ser Ile Pro Tyr
145                 150                 155                 160

Asp Asp Trp Asp Gln Pro Ser Gly Pro Gly Val Glu His Leu Ile Glu
                165                 170                 175

Arg Asp Val Gln Thr Ala Gly Thr Pro Asp Ala Arg Gln Leu Gln Val
            180                 185                 190

Leu Val Gln Gln Val Gln Asp Ala Arg Asn Pro Val Leu Val Leu Gly
        195                 200                 205

Pro Asp Val Asp Ala Thr Leu Ser Asn Asp His Ala Val Ala Leu Ala
    210                 215                 220

Asp Lys Leu Arg Met Pro Val Trp Ile Ala Pro Ser Ala Ser Arg Cys
225                 230                 235                 240

Pro Phe Pro Thr Arg His Pro Ser Phe Arg Gly Val Leu Pro Ala Ala
                245                 250                 255

Ile Ala Gly Ile Ser Lys Thr Leu Gln Gly His Asp Leu Ile Ile Val
            260                 265                 270

Val Gly Ala Pro Val Phe Arg Tyr His Gln Phe Ala Pro Gly Asp Tyr
        275                 280                 285

Leu Pro Val Gly Ala Gln Leu Leu His Ile Thr Ser Asp Pro Leu Glu
    290                 295                 300

Ala Thr Arg Ala Pro Met Gly His Ala Leu Val Gly Asp Ile Arg Glu
305                 310                 315                 320

Thr Leu Arg Val Leu Ala Glu Glu Val Val Gln Gln Ser Arg Pro Tyr
                325                 330                 335
```

-continued

```
Pro Glu Ala Leu Ala Ala Pro Glu Cys Val Thr Asp Glu Pro His His
            340                 345                 350

Leu His Pro Glu Thr Leu Phe Asp Val Leu Asp Ala Val Ala Pro His
    355                 360                 365

Asp Ala Ile Tyr Val Lys Glu Ser Thr Ser Thr Thr Thr Ala Phe Trp
370                 375                 380

Gln Arg Met Asn Leu Arg His Pro Gly Ser Tyr Tyr Phe Pro Ala Ala
385                 390                 395                 400

Gly Gly Leu Gly Phe Gly Leu Pro Ala Ala Val Gly Val Gln Leu Ala
            405                 410                 415

Gln Pro Gln Arg Arg Val Val Ala Leu Ile Gly Asp Gly Ser Ala Asn
            420                 425                 430

Tyr Gly Ile Thr Ala Leu Trp Thr Ala Ala Gln Tyr Arg Ile Pro Val
            435                 440                 445

Val Phe Ile Ile Leu Lys Asn Gly Thr Tyr Gly Ala Leu Arg Trp Phe
    450                 455                 460

Ala Gly Val Leu Lys Ala Glu Asp Ser Pro Gly Leu Asp Val Pro Gly
465                 470                 475                 480

Leu Asp Phe Cys Ala Ile Ala Lys Gly Tyr Gly Val Lys Ala Val His
            485                 490                 495

Thr Asp Thr Arg Asp Ser Phe Glu Ala Ala Leu Arg Thr Ala Leu Asp
            500                 505                 510

Ala Asn Glu Pro Thr Val Ile Glu Val Pro Thr Leu Thr Ile Gln Pro
            515                 520                 525

His
```

<210> SEQ ID NO 25
<211> LENGTH: 522
<212> TYPE: PRT
<213> ORGANISM: Burkholderia xenovorans

<400> SEQUENCE: 25

```
Met Lys Thr Val Gln His Ala Ala Tyr Glu Ile Leu Arg Arg His Gly
1               5                   10                  15

Leu Thr Thr Ile Phe Gly Asn Pro Gly Ser Asn Glu Leu Pro Phe Leu
            20                  25                  30

Lys His Phe Pro Ser Asp Phe Arg Tyr Ile Leu Gly Leu His Glu Gly
        35                  40                  45

Val Val Thr Gly Met Ala Asp Gly Tyr Ala Gln Ala Thr Gly Asn Pro
    50                  55                  60

Ala Phe Val Asn Leu His Ser Ala Ala Gly Thr Gly Asn Ala Met Gly
65                  70                  75                  80

Ala Leu Ala Asn Ala Trp Asn Ser His Thr Pro Leu Val Val Thr Ser
                85                  90                  95

Gly Gln Gln Val Arg Ser Thr Ile Gly Met Glu Pro Leu Leu Ala Asn
            100                 105                 110

Val Asp Ala Val Asn Leu Pro Arg Pro Leu Val Lys Trp Ser Thr Glu
        115                 120                 125

Pro Ala Ser Ala Glu Asp Val Pro Arg Ser Phe Ala Gln Ala Ile His
    130                 135                 140

Ile Ala Arg Thr Pro Ala Thr Gly Pro Val Tyr Leu Ser Ile Pro Tyr
145                 150                 155                 160

Asp Asp Trp Asp Gln Pro Ala Pro Glu Tyr Ala His Tyr Leu Ala Ala
                165                 170                 175
```

```
Arg Glu Val Gly Leu Pro Ser Glu Ala Ile Leu Gln Ala Leu Ala Asp
            180                 185                 190
Arg Leu Gln Arg Ala Thr Asn Pro Val Leu Val Leu Gly Pro Asp Val
        195                 200                 205
Asp Ala Gln His Ala Asn Glu Ser Ala Val Ala Leu Ala Glu Arg Leu
    210                 215                 220
Lys Met Pro Ala Trp Met Ala Pro Ser Ala Pro Arg Cys Ser Phe Pro
225                 230                 235                 240
Thr Thr His Ala Cys Phe Arg Gly Val Leu Pro Ala Gly Ile Ala Ser
                245                 250                 255
Ile Ser Arg Leu Leu Asp Gly His Asp Leu Ile Leu Val Val Gly Ala
            260                 265                 270
Pro Val Phe Arg Tyr His Gln Tyr Glu Pro Gly Ala Leu Leu Pro Ala
        275                 280                 285
Gly Ala Glu Leu Val Ser Ile Thr Cys Asp Val Leu Glu Ala Ala Arg
    290                 295                 300
Ala Pro Met Gly Asp Ala Ile Val Ala Asp Ile Ala Leu Thr Leu Glu
305                 310                 315                 320
Ala Leu Ala Ala Arg Ala Glu Pro Ala Ala Arg Pro Met Pro Val Ala
                325                 330                 335
Val Ala Arg Pro Ala Ala Ala Ala Glu Thr Pro Gly Pro Leu Ala Pro
            340                 345                 350
Glu Arg Val Phe Asp Ile Val Asp Ala Ile Ala Pro Arg Asp Ala Ile
        355                 360                 365
Tyr Val Asn Glu Ser Thr Ser Thr Thr Asn Leu Met Trp Gln Arg Leu
    370                 375                 380
Arg Met Thr Ser Gln Gly Ser Tyr Tyr Phe Ala Ala Gly Gly Leu
385                 390                 395                 400
Gly Phe Ala Met Pro Ala Ala Ala Gly Ile Gln Leu Ala Gln Pro Gly
                405                 410                 415
Arg Arg Val Ile Gly Ile Ile Gly Asp Gly Ser Ala Asn Tyr Gly Ile
            420                 425                 430
Thr Ala Leu Trp Thr Ala Ala Gln Tyr Ser Ile Pro Thr Ile Phe Ile
        435                 440                 445
Ile Met Lys Asn Gly Thr Tyr Gly Ala Leu Arg Trp Phe Ala Gly Val
    450                 455                 460
Leu Gly Val Glu Asp Val Pro Gly Leu Tyr Val Pro Gly Ile Asp Phe
465                 470                 475                 480
Cys Ala Leu Ala Arg Gly Tyr Gly Val Glu Ala Leu His Ala Asp Ser
                485                 490                 495
Gly Ala Ser Leu Thr Val Ala Leu Glu Arg Ala Leu Ser Ser Ser Arg
            500                 505                 510
Pro Thr Leu Ile Glu Val Glu Thr Leu Ala
        515                 520

<210> SEQ ID NO 26
<211> LENGTH: 528
<212> TYPE: PRT
<213> ORGANISM: Methylocella sylvestris

<400> SEQUENCE: 26

Met Thr Thr Ile Arg His Leu Thr Tyr Asp Leu Leu Arg Arg His Gly
1               5                   10                  15
Val Thr Thr Ile Phe Gly Asn Pro Gly Ser Asn Glu Leu Leu Phe Leu
            20                  25                  30
```

```
Glu Asp Phe Pro Ser Asp Phe Arg Tyr Ile Leu Ala Leu His Glu Gly
         35                  40                  45

Ala Ala Ile Gly Met Ala Asp Gly Tyr Ala Gln Ala Thr Gly His Thr
     50                  55                  60

Gly Phe Val Asn Leu His Ser Ala Ala Gly Thr Gly Asn Ala Met Gly
 65              70                  75                  80

Gly Phe Ala Asn Ala Trp Asn Ala His Thr Pro Leu Val Val Thr Ala
                 85                  90                  95

Gly Gln Gln Val Arg Ala Met Met Gly Ile Glu Pro Leu Leu Thr Asn
                100                 105                 110

Ile Asp Ala Thr Thr Leu Pro Lys Pro Leu Val Lys Trp Ser Cys Glu
         115                 120                 125

Pro Ala Arg Ala Glu Asp Val Pro Leu Ala Ile Ser Arg Ala Leu His
         130                 135                 140

Leu Ser Ala Leu Pro Ala Pro Gly Pro Val Tyr Leu Ser Ile Pro Tyr
145                 150                 155                 160

Asp Asp Trp Asp Lys Pro Ala Glu Pro Glu Ser Leu Arg Leu Leu Lys
                 165                 170                 175

Arg Ala Val Ser Ala Ala Gly Ala Leu Asp Ala Gly Ala Leu Ala Ala
                 180                 185                 190

Leu Ala Ala Arg Leu Asp Arg Ser Ala Asn Pro Val Ile Val Leu Gly
             195                 200                 205

Pro Asp Val Asp Ala Ala Arg Ala Asn Ala His Ala Val Arg Leu Ala
         210                 215                 220

Glu Arg Leu Lys Ala Pro Val Trp Val Ala Ser Ala Pro Arg Cys
225                 230                 235                 240

Pro Phe Pro Thr Thr His Pro Asn Phe Arg Gly Leu Leu Thr Ala Ser
                 245                 250                 255

Met Ala Asp Ile Ser Arg Gln Leu Glu Gly His Asp Leu Val Leu Val
             260                 265                 270

Ala Gly Ala Pro Val Phe Arg Tyr His Gln Tyr Glu Pro Gly Pro Leu
         275                 280                 285

Leu Pro Pro Gly Ala Glu Leu Ile Gln Ile Thr Cys Asp Ala Asp Glu
     290                 295                 300

Ala Ala Arg Ala Pro Met Gly Asp Ala Val Gly Asp Val Gly Arg
305                 310                 315                 320

Ile Leu Ala Ala Leu Ala Asp Lys Ile Gly Glu Ala Ala Arg Pro Ala
                 325                 330                 335

Pro Gln Pro Arg Glu Thr Pro Ala Pro Ser Ala Pro Gly Ser Val Pro
                 340                 345                 350

Leu Ala Ala Glu Arg Val Leu Asp Leu Met Asp Glu Leu Ala Pro Ser
             355                 360                 365

Asp Ala Ile Tyr Val Asn Glu Ser Thr Ser Thr Ile Glu Ala Met Trp
     370                 375                 380

Glu Arg Met Arg Trp Glu His Pro Gly Ser Tyr Tyr Phe Gly Ala Ala
385                 390                 395                 400

Gly Gly Leu Gly Phe Ala Met Pro Ala Ala Val Gly Val Gln Leu Ala
                 405                 410                 415

Glu Pro Asp Arg Gln Val Ile Ala Leu Ile Gly Asp Gly Ser Ala Asn
             420                 425                 430

Tyr Ser Val Thr Ala Leu Trp Thr Ala Ala Gln His Ser Val Pro Val
     435                 440                 445
```

-continued

```
Val Phe Val Ile Leu Arg Asn Gly Thr Tyr Gly Ala Leu Arg Trp Phe
            450                 455                 460

Ala Arg Ala Leu Lys Ala Glu His Val Pro Ala Leu Asp Val Pro Asp
465                 470                 475                 480

Ile Asp Phe Val Ala Ile Ala Thr Gly Tyr Gly Val Glu Ala Val Arg
                485                 490                 495

Val Asp Thr Asp Glu Ala Phe Ala Ser Ala Phe Ala Arg Ala Leu Lys
            500                 505                 510

Ala Gly Lys Pro Ser Leu Ile Glu Val Ala Thr Ala Trp Pro Ala Thr
            515                 520                 525

<210> SEQ ID NO 27
<211> LENGTH: 529
<212> TYPE: PRT
<213> ORGANISM: Arthrobacter sp.

<400> SEQUENCE: 27

Met Thr Thr Val His Ala Ala Tyr Glu Leu Leu Arg Ser Asn Arg
1               5                   10                  15

Leu Thr Thr Ile Phe Gly Asn Pro Gly Ser Asn Glu Leu Pro Phe Leu
            20                  25                  30

Asp Ala Met Pro Ala Asp Phe Arg Tyr Ile Leu Gly Leu His Glu Gly
            35                  40                  45

Val Val Val Gly Met Ala Asp Gly Phe Ala Gln Ala Ser Gly Gln Ala
50                  55                  60

Ala Phe Val Asn Leu His Ala Ala Ser Gly Thr Gly Asn Ala Met Gly
65                  70                  75                  80

Ala Leu Thr Asn Ala Trp Tyr Ser His Thr Pro Leu Val Ile Thr Ala
            85                  90                  95

Gly Gln Gln Val Arg Pro Met Ile Gly Leu Glu Ala Met Leu Ser Asn
            100                 105                 110

Val Asp Ala Ala Ser Leu Pro Arg Pro Leu Val Lys Trp Ser Ala Glu
            115                 120                 125

Pro Ala Gln Ala Pro Asp Val Pro Arg Ala Leu Ser Gln Ala Ile His
            130                 135                 140

Thr Ala Thr Ser Asp Pro Lys Gly Pro Val Tyr Leu Ser Ile Pro Tyr
145                 150                 155                 160

Asp Asp Trp Asn Gln Asp Thr Gly Asn Leu Ser Glu His Leu Ser Ser
                165                 170                 175

Arg Ser Val Ser Arg Ala Gly Asn Pro Ser Ala Glu Gln Leu Asp Asp
            180                 185                 190

Ile Leu Ser Ala Leu Arg Glu Ala Asn Pro Ala Leu Val Phe Gly
            195                 200                 205

Pro Asp Val Asp Ala Ala Arg Ala Asn His His Ala Val Arg Leu Ala
            210                 215                 220

Glu Lys Leu Ala Ala Pro Val Trp Ile Ala Pro Ser Ala Pro Arg Cys
225                 230                 235                 240

Pro Phe Pro Thr Arg His Pro Asn Phe Arg Gly Val Leu Pro Ala Ser
                245                 250                 255

Ile Ala Gly Ile Ser Ala Leu Leu Asn Gly His Asp Leu Ile Val Val
            260                 265                 270

Ile Gly Ala Pro Val Phe Arg Tyr His Gln Tyr Gln Pro Gly Ser Tyr
            275                 280                 285

Leu Pro Glu Asn Ser Arg Leu Ile His Ile Thr Cys Asp Ala Gly Glu
            290                 295                 300
```

```
Ala Ala Arg Ala Pro Met Gly Asp Ala Leu Val Ala Asp Ile Gly Gln
305                 310                 315                 320

Thr Leu Arg Ala Leu Ala Asp Ile Ile Pro Gln Ser Lys Arg Pro Pro
                325                 330                 335

Leu Arg Pro Arg Val Ile Pro Val Pro Asp Ser Gln Asp Asp Leu
            340                 345                 350

Leu Ala Pro Asp Ala Val Phe Glu Val Met Asn Glu Val Ala Pro Glu
            355                 360                 365

Asp Val Val Tyr Val Asn Glu Ser Thr Ser Thr Val Thr Ala Leu Trp
            370                 375                 380

Glu Arg Val Glu Leu Lys His Pro Gly Ser Tyr Tyr Phe Pro Ala Ser
385                 390                 395                 400

Gly Gly Leu Gly Phe Gly Met Pro Ala Ala Val Gly Val Gln Leu Ala
                405                 410                 415

Asn Asp Arg Arg Arg Val Ile Ala Val Ile Gly Asp Gly Ser Ala Asn
                420                 425                 430

Tyr Gly Ile Thr Ala Leu Trp Thr Ala Ala Gln Glu Lys Ile Pro Val
            435                 440                 445

Val Phe Ile Ile Leu Asn Asn Gly Thr Tyr Gly Ala Leu Arg Ala Phe
            450                 455                 460

Ala Lys Leu Leu Asn Ala Glu Asn Ala Ala Gly Leu Asp Val Pro Gly
465                 470                 475                 480

Ile Cys Phe Cys Ala Ile Ala Glu Gly Tyr Gly Val Glu Ala His Arg
                485                 490                 495

Ile Thr Ser Leu Glu Asn Phe Lys Asp Lys Leu Ser Ala Ala Leu Gln
                500                 505                 510

Ser Asp Thr Pro Thr Leu Leu Glu Val Pro Thr Ser Thr Thr Ser Pro
            515                 520                 525

Phe

<210> SEQ ID NO 28
<211> LENGTH: 528
<212> TYPE: PRT
<213> ORGANISM: Chromohalobacter salexigens

<400> SEQUENCE: 28

Met Pro Thr Val His Ser Ala Thr Tyr Asp Leu Leu Arg Arg Gln Gly
1               5                   10                  15

Met Thr Thr Ile Phe Gly Asn Pro Gly Ser Asn Glu Leu Pro Phe Leu
                20                  25                  30

Lys Asn Phe Pro Ala Asp Phe Arg Tyr Ile Leu Gly Leu His Glu Gly
            35                  40                  45

Val Val Val Gly Met Ala Asp Gly Phe Ala Leu Ser Gly Ala Pro
        50                  55                  60

Ala Leu Val Asn Leu His Ala Ala Ala Gly Ser Gly Asn Ala Met Gly
65                  70                  75                  80

Ala Leu Thr Asn Ala Trp Tyr Ser His Ser Pro Leu Val Leu Thr Ala
                85                  90                  95

Gly Gln Gln Ala Arg Ser Met Ile Gly Val Glu Ser Met Leu Ala Asn
            100                 105                 110

Val Asp Ala Pro Gln Leu Pro Arg Pro Leu Val Lys Trp Ser Tyr Glu
        115                 120                 125

Pro Ala Cys Pro Glu Asp Val Pro Arg Ala Leu Ser Gln Ala Ile His
        130                 135                 140
```

Thr Ala Cys Leu Pro Ala Arg Gly Pro Val Tyr Val Ser Ile Pro His
145                 150                 155                 160

Asp Asp Trp Gly His Ala Val Asp Asp Ala Ala Leu Leu Ser Ala
            165                 170                 175

Arg Gln Val Ala Ser Ala Gln Pro Ala Glu Thr Gln Val Glu Ala
            180                 185                 190

Leu Val Glu Arg Leu Asn Ala Ala Arg Asn Pro Val Leu Val Leu Gly
            195                 200                 205

Pro Asp Val Asp Ala Tyr Gly Ala Asn Ala Leu Ala Val Thr Leu Ala
210                 215                 220

Glu Arg Leu Asn Ala Pro Ala Trp Val Ala Pro Ser Ala Ser Arg Cys
225                 230                 235                 240

Pro Phe Pro Thr Arg His Ala Cys Phe Arg Gly Val Leu Pro Ala Ala
            245                 250                 255

Ile Gln Gly Ile Ser Asp Arg Leu Asp Gly His Asp Leu Ile Val Val
            260                 265                 270

Ile Gly Ala Pro Val Phe Arg Tyr His Gln Tyr Ala Pro Gly Arg Tyr
        275                 280                 285

Leu Pro Asp Gly Ala Glu Leu Val His Leu Thr Cys Asp Met Gln Glu
        290                 295                 300

Ala Ala Arg Ala Pro Met Gly Asp Ala Leu Val Gly Asp Ile His Ala
305                 310                 315                 320

Met Leu Asp Leu Leu Val Pro Arg Val Arg Gln Ser Gly Arg Ala Arg
                325                 330                 335

Pro Glu Pro Gln Ala Ala Pro Glu Pro Gln Val Asp Pro Glu Gly Met
            340                 345                 350

Leu Thr Pro Glu Thr Val Phe Asp Val Met Asn Ala Met Ala Pro Glu
            355                 360                 365

Asp Ala Ile Tyr Val Lys Glu Ser Thr Ser Thr Val Thr Ala Phe Trp
370                 375                 380

Glu Arg Val Glu Met Arg His Pro Gly Ser Tyr Phe Phe Pro Ala Ala
385                 390                 395                 400

Gly Gly Leu Gly Phe Gly Leu Pro Ala Ala Val Gly Val Gln Leu Ala
                405                 410                 415

Cys Pro Glu Arg Arg Val Ile Gly Val Ile Gly Asp Gly Ser Ala Asn
            420                 425                 430

Tyr Ala Ile Thr Ala Leu Trp Ser Ala Ala Gln Tyr Arg Ile Pro Val
            435                 440                 445

Val Phe Val Ile Leu Lys Asn Gly Thr Tyr Gly Ala Leu Arg Trp Phe
450                 455                 460

Ser Arg Leu Leu Asp Ala Glu Asp Ser Pro Gly Leu Asp Val Pro Gly
465                 470                 475                 480

Leu Asp Phe Cys Ala Leu Ala Glu Gly Tyr Gly Val Glu Ala Glu Gln
                485                 490                 495

Ala Ala Ser Arg Glu Ala Phe Glu Ala Ala Leu Lys Ala Ala Leu Ala
            500                 505                 510

Asp Asp Arg Pro Arg Val Ile Glu Val Pro Thr Thr Thr Ile Glu Pro
            515                 520                 525

<210> SEQ ID NO 29
<211> LENGTH: 528
<212> TYPE: PRT
<213> ORGANISM: Rhodococcus jostii

```
<400> SEQUENCE: 29

Met Ala Thr Val Ser Glu Val Thr Tyr Glu Leu Leu Arg Ala Arg Gly
1               5                   10                  15

Leu Thr Thr Val Phe Gly Asn Pro Gly Ser Asn Glu Leu Pro Phe Leu
            20                  25                  30

Ser Gly Met Pro Asp Asp Phe Arg Tyr Val Leu Gly Leu His Glu Gly
        35                  40                  45

Ala Val Leu Ser Met Ala Asp Gly Tyr Ser Leu Val Thr Gly Glu Ala
    50                  55                  60

Thr Leu Val Asn Leu His Ala Ala Ser Gly Ser Gly Asn Ala Met Gly
65                  70                  75                  80

Ala Leu Thr Asn Ser Val Tyr Ser His Ser Pro Leu Val Val Thr Ala
                85                  90                  95

Gly Gln Gln Val Arg Ser Thr Ile Gly Gln Glu Val Met Leu Ser Asn
            100                 105                 110

Val Asp Ala Gly Thr Leu Met Lys Pro Leu Val Lys Trp Ser Ser Glu
        115                 120                 125

Pro Thr Cys Ala Glu Asp Val Pro Arg Thr Ile Asn Gln Ala Ile His
    130                 135                 140

Thr Ala Leu Leu Pro Ala Lys Gly Pro Val Tyr Val Ser Val Pro Tyr
145                 150                 155                 160

Asp Asp Trp Ala Glu Ala Pro Pro Glu Ser Ala Gly Leu Leu Ala
                165                 170                 175

Arg Glu Val His Ser Ala Ala Ser Leu Ser Gly Asp Gln Ile Asn Asp
            180                 185                 190

Leu Ile Glu Thr Leu Glu Ser Ala Thr Asn Pro Val Leu Val Leu Gly
        195                 200                 205

Pro Ala Val Asp Ala Asp Arg Ala Asn Ala Asp Ala Val Leu Leu Ala
    210                 215                 220

Glu Lys Leu Arg Ala Pro Val Trp Ile Ala Pro Ser Pro Ser Arg Cys
225                 230                 235                 240

Pro Phe Pro Thr Arg His Pro Ser Phe Arg Gly Val Leu Pro Ala Gly
                245                 250                 255

Val Ala Asp Leu Ser Lys Thr Leu Glu Gly His Asp Leu Ile Leu Val
            260                 265                 270

Val Gly Ala Pro Val Phe Arg Tyr His Gln Tyr Val Pro Gly Asn Tyr
        275                 280                 285

Leu Pro Gly Gly Ala Arg Leu Ile His Val Thr Asp Asp Gly Gly Glu
    290                 295                 300

Ala Ala Arg Ala Pro Ile Gly Glu Ala Tyr Val Ala Pro Val Gly Ser
305                 310                 315                 320

Thr Leu Glu Ile Leu Ala Asn Met Val Lys Pro Ser Asp Arg Ser Pro
                325                 330                 335

Leu Pro Pro Leu Gly Asp Phe Glu Glu Ala Val Ser Val Gly Ala Gly
            340                 345                 350

Leu Asp Pro Ala Gln Leu Phe Ala Leu Val Arg Ala Gly Ala Pro Asp
        355                 360                 365

Asp Ala Ile Tyr Val Asn Glu Ser Thr Ser Thr Ser Ala Phe Trp
    370                 375                 380

Ser Gln Met Asp Leu Ser His Gln Gly Ser Tyr Tyr Phe Pro Ala Ser
385                 390                 395                 400

Gly Gly Leu Gly Phe Gly Leu Pro Ala Ala Val Gly Ala Gln Leu Ala
                405                 410                 415
```

```
Ser Pro Asp Arg Gln Val Ile Gly Leu Ile Gly Asp Gly Ser Ala Asn
            420                 425                 430

Tyr Gly Ile Thr Ala Leu Trp Ser Ala Ala Gln Tyr Lys Ile Pro Val
            435                 440                 445

Val Ile Ile Ile Leu Asn Asn Gly Thr Tyr Gly Ala Leu Arg Gly Phe
            450                 455                 460

Ser Lys Ile Leu Asn Thr Gly Glu Thr Pro Gly Leu Asp Val Pro Gly
465                 470                 475                 480

Ile Asp Phe Val His Leu Ala Glu Gly Tyr Gly Val Arg Gly Thr Ala
            485                 490                 495

Val Ala Thr Ala Glu Asp Phe Thr Thr Ala Phe Lys Ser Ala Leu Ala
            500                 505                 510

Ala Asp Ala Pro Thr Leu Ile Glu Val Arg Thr Asn Phe Asp Glu Ser
            515                 520                 525

<210> SEQ ID NO 30
<211> LENGTH: 527
<212> TYPE: PRT
<213> ORGANISM: Rhodococcus jostii

<400> SEQUENCE: 30

Met Ala Thr Val Ser Glu Val Thr Tyr Glu Leu Leu Arg Ala Arg Gly
1               5                   10                  15

Leu Thr Thr Val Phe Gly Asn Pro Gly Ser Asn Glu Leu Pro Phe Leu
            20                  25                  30

Ser Gly Met Pro Asp Asp Phe Arg Tyr Val Leu Gly His Glu Gly Ala
            35                  40                  45

Val Leu Ser Met Ala Asp Gly Tyr Ser Leu Val Thr Gly Glu Ala Thr
            50                  55                  60

Leu Val Asn Leu His Ala Ala Ser Gly Ser Gly Asn Ala Met Gly Ala
65              70                  75                  80

Leu Thr Asn Ser Val Tyr Ser His Ser Pro Leu Val Val Thr Ala Gly
            85                  90                  95

Gln Gln Val Arg Ser Thr Ile Gly Gln Glu Val Met Leu Ser Asn Val
            100                 105                 110

Asp Ala Gly Thr Leu Met Lys Pro Leu Val Lys Trp Ser Ser Glu Pro
            115                 120                 125

Thr Cys Ala Glu Asp Val Pro Arg Thr Ile Asn Gln Ala Ile His Thr
130                 135                 140

Ala Leu Leu Pro Ala Lys Gly Pro Val Tyr Val Ser Val Pro Tyr Asp
145                 150                 155                 160

Asp Trp Ala Ala Glu Ala Pro Pro Glu Ser Ala Gly Leu Leu Ala Arg
            165                 170                 175

Glu Val His Ser Ala Ala Ser Leu Ser Gly Asp Gln Ile Asn Asp Leu
            180                 185                 190

Ile Glu Thr Leu Glu Ser Ala Thr Asn Pro Val Leu Val Leu Gly Pro
            195                 200                 205

Ala Val Asp Ala Asp Arg Ala Asn Ala Asp Ala Val Leu Leu Ala Glu
            210                 215                 220

Lys Leu Arg Ala Pro Val Trp Ile Ala Pro Ser Pro Ser Arg Cys Pro
225                 230                 235                 240

Phe Pro Thr Arg His Pro Ser Phe Arg Gly Val Leu Pro Ala Gly Val
            245                 250                 255

Ala Asp Leu Ser Lys Thr Leu Glu Gly His Asp Leu Ile Leu Val Val
```

```
              260                 265                 270
Gly Ala Pro Val Phe Arg Tyr His Gln Tyr Val Pro Gly Asn Tyr Leu
        275                 280                 285

Pro Gly Gly Ala Arg Leu Ile His Val Thr Asp Asp Gly Gly Glu Ala
        290                 295                 300

Ala Arg Ala Pro Ile Gly Glu Ala Tyr Val Ala Pro Val Gly Ser Thr
305                 310                 315                 320

Leu Glu Ile Leu Ala Asn Met Val Lys Pro Ser Asp Arg Ser Pro Leu
                325                 330                 335

Pro Pro Leu Gly Asp Phe Glu Glu Ala Val Ser Val Gly Ala Gly Leu
        340                 345                 350

Asp Pro Ala Gln Leu Phe Ala Leu Val Arg Ala Gly Ala Pro Asp Asp
        355                 360                 365

Ala Ile Tyr Val Asn Glu Ser Thr Ser Thr Ser Asp Ala Phe Trp Ser
        370                 375                 380

Gln Met Asp Leu Ser His Gln Gly Ser Tyr Tyr Phe Pro Ala Ser Gly
385                 390                 395                 400

Gly Leu Gly Phe Gly Leu Pro Ala Ala Val Gly Ala Gln Leu Ala Ser
                405                 410                 415

Pro Asp Arg Gln Val Ile Gly Leu Ile Gly Asp Gly Ser Ala Asn Tyr
        420                 425                 430

Gly Ile Thr Ala Leu Trp Ser Ala Ala Gln Tyr Lys Ile Pro Val Val
        435                 440                 445

Ile Ile Ile Leu Asn Asn Gly Thr Tyr Gly Ala Leu Arg Gly Phe Ser
450                 455                 460

Lys Ile Leu Asn Thr Gly Glu Thr Pro Gly Leu Asp Val Pro Gly Ile
465                 470                 475                 480

Asp Phe Val His Leu Ala Glu Gly Tyr Gly Val Arg Gly Thr Ala Val
                485                 490                 495

Ala Thr Ala Glu Asp Phe Thr Thr Ala Phe Lys Ser Ala Leu Ala Ala
        500                 505                 510

Asp Ala Pro Thr Leu Ile Glu Val Arg Thr Asn Phe Asp Glu Ser
        515                 520                 525

<210> SEQ ID NO 31
<211> LENGTH: 476
<212> TYPE: PRT
<213> ORGANISM: Saccharopolyspora erythraea

<400> SEQUENCE: 31

Met Ala Asp Gly Tyr Ala Leu Ala Arg Gly Gly Pro Ala Leu Val Asn
1               5                   10                  15

Leu His Ala Ala Gly Thr Gly Asn Ala Leu Gly Ala Leu Thr Asn
                20                  25                  30

Ser Val Tyr Ser His Ser Pro Leu Val Ile Thr Ala Gly Gln Gln Val
        35                  40                  45

Arg Ser Thr Ile Gly Gln Glu Val Met Leu Ala Asn Val Asp Ala Ala
        50                  55                  60

Ser Leu Pro Lys Pro Leu Val Lys Trp Ser Ala Glu Pro Ser Cys Ala
65                  70                  75                  80

Gln Asp Val Pro Arg Thr Ile Ser Gln Ala Ile His Thr Ala Asn Leu
                85                  90                  95

Pro Ala Lys Gly Pro Val Tyr Val Ser Val Pro Tyr Asp Asp Trp Asp
        100                 105                 110
```

Gly Glu Ala Pro Arg Glu Ala Gly His Leu Leu Arg Ser Thr Thr
            115                 120                 125

Ser Ala Gly Ser Leu Gly Ser Glu Gln Leu Ala Asp Leu Val Gln Ala
    130                 135                 140

Val Asp Ser Ala Arg Asn Pro Val Leu Val Leu Gly Pro Asp Val Asp
145                 150                 155                 160

Ala Gln His Ala Asn Asp His Ala Val Arg Leu Ala Asp Lys Leu Asn
                165                 170                 175

Ala Pro Val Trp Val Ala Pro Ser Pro Ser Arg Cys Pro Phe Pro Thr
            180                 185                 190

Arg His Arg Ser Phe Arg Gly Val Leu Pro Ala Val Gln Gly Val
        195                 200                 205

Thr Asp Ala Leu Asp Gly His Asp Leu Val Leu Val Ala Gly Ala Pro
    210                 215                 220

Val Phe Arg Tyr His Gln Tyr Val Pro Gly Glu Tyr Leu Pro Glu Gly
225                 230                 235                 240

Ala Arg Leu Val His Leu Thr Ser Asp Pro Gly Glu Ala Ala Arg Ala
                245                 250                 255

Pro Met Gly Glu Ala Leu Val Cys Asp Ile Ala Asp Ala Leu Ser Arg
            260                 265                 270

Leu Ala Asp Glu Ala Ala Asp Thr Asp Arg Pro Arg Leu Pro Pro Leu
        275                 280                 285

Pro Asp Phe Pro Ser Val Ser Gly Ser Gly Ala Val His Pro Ala
    290                 295                 300

Glu Leu Phe Ala Thr Leu Arg Asp Ile Ala Pro Glu Asp Ala Val Tyr
305                 310                 315                 320

Val Lys Glu Ser Thr Ala Thr Thr Gly Thr Phe Trp Ser Gln Met Asp
                325                 330                 335

Leu Ser Arg Gln Gly Ser Tyr Phe Phe Pro Ala Ser Gly Gly Leu Gly
            340                 345                 350

Phe Gly Leu Pro Ala Ala Val Gly Ala Gln Leu Ala His Pro Glu Arg
        355                 360                 365

Gln Val Val Gly Leu Ile Gly Asp Gly Ser Ala Asn Tyr Gly Ile Thr
    370                 375                 380

Ala Leu Trp Thr Ala Ala Gln Tyr Arg Ile Pro Val Ser Ile Val Ile
385                 390                 395                 400

Leu Lys Asn Gly Thr Tyr Gly Ala Leu Arg Trp Phe Ala Lys Val Leu
                405                 410                 415

Asp Ala Gly Glu Thr Pro Gly Met Asp Val Pro Gly Ile Asp Phe Val
            420                 425                 430

Arg Ile Ala Gly Gly Tyr Gly Val Glu Ala Thr Ser Val Arg Thr Ala
        435                 440                 445

Ala Asp Phe Ala Thr Ala Phe Glu Asp Ala Leu Gly Ala Gly Arg Pro
    450                 455                 460

Ala Leu Ile Glu Val Glu Thr Glu Leu Thr Glu Pro
465                 470                 475

<210> SEQ ID NO 32
<211> LENGTH: 526
<212> TYPE: PRT
<213> ORGANISM: Streptomyces lividans

<400> SEQUENCE: 32

Met Pro Ser Val Arg Arg Val Ser His Glu Phe Leu Glu Arg Gln Gly
1               5                   10                  15

```
Leu Thr Thr Val Phe Gly Asn Pro Gly Ser Asn Glu Leu Pro Phe Leu
             20                  25                  30

Ala Gly Leu Pro Asp Gly Phe Arg Tyr Val Leu Gly Leu His Glu Gly
         35                  40                  45

Ala Val Val Gly Met Ala Asp Gly Tyr Ala Gln Ala Thr Gly Arg Pro
     50                  55                  60

Val Leu Val Asn Leu His Ala Ala Ser Gly Ser Gly Asn Ala Met Gly
 65                  70                  75                  80

Ala Leu Thr Asn Ala Val Ala Ser Arg Thr Pro Leu Val Val Val Ala
                 85                  90                  95

Gly Gln Gln Val Arg Pro Ala Ile Gly Pro Glu Ala Asn Leu Ala Ser
                100                 105                 110

Val Asp Ala Pro Ala Leu Met Lys Pro Leu Val Gly Trp Ala Ala Glu
             115                 120                 125

Pro Ala Cys Ala Gly Asp Val Pro Arg Ala Leu Ala Gln Ala Val Phe
130                 135                 140

Glu Ala Arg Leu Gln Arg Arg Pro Thr Tyr Leu Ser Val Pro Tyr Asp
145                 150                 155                 160

Asp Trp Ser Ala Asp Val Asp Asp Asn Ala Leu Ala Val Leu Asp Arg
                165                 170                 175

Arg Val Leu Arg Ala Ala Val Pro Gly Gly Glu Gln Arg Arg Trp Leu
            180                 185                 190

Val Glu Gln Val Ala Ser Ala Arg Arg Pro Ala Leu Val Leu Gly Gly
        195                 200                 205

Asp Ile Asp Ser Ala Gly Arg Phe Asp Ala Val Arg Leu Ala Glu
    210                 215                 220

Arg Leu Gly Gly Pro Val Trp Ala Ala Pro Ser Gln Phe Arg Leu Pro
225                 230                 235                 240

Phe Pro Asn Arg His Pro Leu Phe Arg Gly Val Leu Pro Ala Gly Ile
                245                 250                 255

Ala Pro Val Ser Ala Ala Phe Glu Gly His Asp Leu Val Leu Val Leu
            260                 265                 270

Gly Ala Pro Val Phe Arg Tyr His Glu His Leu Pro Gly Arg Tyr Leu
        275                 280                 285

Pro Glu Gly Thr Arg Leu Ile Gln Val Thr Glu Asp Ala Ser Ala Ala
290                 295                 300

Ala Arg Ala Pro Met Gly Glu Ala Leu Val Ala Asp Pro Gly Ala Val
305                 310                 315                 320

Ile Asp Ile Leu Leu Glu Ala Leu Gly Ala Ala Asp Arg Pro Ala Gly
                325                 330                 335

Pro Tyr Arg Pro Val Pro Glu Pro Leu Thr Ala Glu Gly Pro Ala Leu
            340                 345                 350

His Pro Glu Gln Val Phe Ala Ala Leu Arg Glu Glu Met Pro Glu Asp
        355                 360                 365

Thr Ala Tyr Val Val Glu Ser Thr Ser Thr Asn Ala Ala Trp Trp Arg
370                 375                 380

Gln Thr Asp Leu Arg Arg Gln Gly Ser Tyr Tyr Phe Pro Ala Ala Gly
385                 390                 395                 400

Gly Leu Gly Phe Gly Leu Pro Gly Ala Val Gly Val Ala Met Ala Gln
                405                 410                 415

Pro Gly Arg Pro Val Val Gly Val Ile Gly Asp Gly Ser Ala Asn Tyr
            420                 425                 430
```

```
Gly Ile Thr Ala Leu Trp Thr Ala Ala Gln His Arg Val Pro Leu Thr
            435                 440                 445

Val Val Leu Leu Arg Asn Gly Ala Tyr Gly Ala Leu Arg Trp Phe Gly
450                 455                 460

Gly Leu Leu Gly Val Pro Asp Ala Pro Gly Leu Asp Ile Pro Gly Leu
465                 470                 475                 480

Asp Phe Thr Arg Ile Ala Glu Gly Tyr Gly Val Arg Ala Gln His Val
                485                 490                 495

Gly Ser Val Ala Glu Leu Arg Ala Ala Leu Ala Glu Thr Pro Glu His
                500                 505                 510

Pro Arg Leu Ile Gln Val Asp Thr Ala Leu Thr Thr Pro Ser
            515                 520                 525

<210> SEQ ID NO 33
<211> LENGTH: 526
<212> TYPE: PRT
<213> ORGANISM: Streptomyces coelicolor

<400> SEQUENCE: 33

Met Pro Ser Val Arg Arg Val Ser His Glu Phe Leu Glu Arg Gln Gly
1               5                   10                  15

Leu Thr Thr Val Phe Gly Asn Pro Gly Ser Asn Glu Leu Pro Phe Leu
                20                  25                  30

Ala Gly Leu Pro Asp Gly Phe Arg Tyr Val Leu Gly Leu His Glu Gly
            35                  40                  45

Ala Val Val Gly Met Ala Asp Gly Tyr Ala Gln Ala Thr Gly Arg Pro
        50                  55                  60

Val Leu Val Asn Leu His Ala Ala Ser Gly Ser Gly Asn Ala Met Gly
65                  70                  75                  80

Ala Leu Thr Asn Ala Val Ala Ser Arg Thr Pro Leu Val Val Val Ala
                85                  90                  95

Gly Gln Gln Val Arg Pro Ala Ile Gly Pro Glu Ala Asn Leu Ala Ser
            100                 105                 110

Val Asp Ala Pro Ala Leu Met Lys Pro Leu Val Gly Trp Ala Ala Glu
        115                 120                 125

Pro Ala Cys Ala Gly Asp Val Pro Arg Ala Leu Ala Gln Ala Val Phe
130                 135                 140

Glu Ala Arg Leu Gln Arg Arg Pro Thr Tyr Leu Ser Val Pro Tyr Asp
145                 150                 155                 160

Asp Trp Ser Ala Asp Val Asp Asn Ala Leu Ala Val Leu Asp Arg
                165                 170                 175

Arg Val Leu Arg Ala Ala Val Pro Gly Gly Glu Gln Arg Arg Trp Leu
            180                 185                 190

Val Glu Gln Val Ala Ser Ala Arg Arg Pro Ala Leu Val Leu Gly Gly
        195                 200                 205

Asp Ile Asp Ser Ala Gly Arg Phe Asp Ala Val Arg Leu Ala Glu
210                 215                 220

Arg Leu Gly Gly Pro Val Trp Ala Ala Pro Ser Gln Phe Arg Leu Pro
225                 230                 235                 240

Phe Pro Asn Arg His Pro Leu Phe Arg Gly Val Leu Pro Ala Gly Ile
                245                 250                 255

Ala Pro Val Ser Ala Ala Phe Glu Gly His Asp Leu Val Leu Val Leu
            260                 265                 270

Gly Ala Pro Val Phe Arg Tyr His Glu His Leu Pro Gly Arg Tyr Leu
        275                 280                 285
```

```
Pro Glu Gly Thr Arg Leu Ile Gln Val Thr Glu Asp Ala Ser Ala Ala
    290                 295                 300

Ala Arg Ala Pro Met Gly Glu Ala Leu Val Ala Asp Pro Gly Ala Val
305                 310                 315                 320

Ile Asp Val Leu Leu Glu Ala Leu Gly Ala Ala Asp Arg Pro Ala Gly
                325                 330                 335

Pro Tyr Arg Pro Val Pro Glu Pro Leu Thr Ala Glu Gly Pro Ala Leu
            340                 345                 350

His Pro Glu Gln Val Phe Ala Ala Leu Arg Glu Glu Met Pro Glu Asp
        355                 360                 365

Thr Ala Tyr Val Val Glu Ser Thr Ser Thr Asn Ala Ala Trp Trp Arg
    370                 375                 380

Gln Thr Asp Leu Arg Arg Gln Gly Ser Tyr Tyr Phe Pro Ala Ala Gly
385                 390                 395                 400

Gly Leu Gly Phe Gly Leu Pro Gly Ala Val Gly Val Ala Met Ala Gln
                405                 410                 415

Pro Gly Arg Pro Val Gly Val Ile Gly Asp Gly Ser Ala Asn Tyr
            420                 425                 430

Gly Ile Thr Ala Leu Trp Thr Ala Ala Gln His Arg Val Pro Leu Thr
        435                 440                 445

Val Val Leu Leu Arg Asn Gly Ala Tyr Gly Ala Leu Arg Trp Phe Gly
    450                 455                 460

Gly Leu Leu Gly Val Pro Asp Ala Pro Gly Leu Asp Ile Pro Asp Leu
465                 470                 475                 480

Asp Phe Thr Arg Ile Ala Glu Gly Tyr Gly Val Arg Ala Gln His Val
                485                 490                 495

Gly Ser Val Ala Glu Leu Arg Ala Ala Leu Ala Glu Thr Pro Glu His
            500                 505                 510

Pro Arg Leu Ile Gln Val Asp Thr Ala Leu Thr Thr Pro Ser
        515                 520                 525

<210> SEQ ID NO 34
<211> LENGTH: 523
<212> TYPE: PRT
<213> ORGANISM: Streptomyces lividans

<400> SEQUENCE: 34

Met Arg Arg Val Ser His Glu Phe Leu Glu Arg Gln Gly Leu Thr Thr
1               5                   10                  15

Val Phe Gly Asn Pro Gly Ser Asn Glu Leu Pro Phe Leu Ala Gly Leu
            20                  25                  30

Pro Asp Gly Phe Arg Tyr Val Leu Gly Leu His Glu Gly Ala Val Val
        35                  40                  45

Gly Met Ala Asp Gly Tyr Ala Gln Ala Thr Gly Arg Pro Val Leu Val
    50                  55                  60

Asn Leu His Ala Ala Ser Gly Ser Gly Asn Ala Met Gly Ala Leu Thr
65                  70                  75                  80

Asn Ala Val Ala Ser Arg Thr Pro Leu Val Val Val Ala Gly Gln Gln
                85                  90                  95

Val Arg Pro Ala Ile Gly Pro Glu Ala Asn Leu Ala Ser Val Asp Ala
            100                 105                 110

Pro Ala Leu Met Lys Pro Leu Val Gly Trp Ala Ala Glu Pro Ala Cys
        115                 120                 125

Ala Gly Asp Val Pro Arg Ala Leu Ala Gln Ala Val Phe Glu Ala Arg
```

```
          130                 135                 140
Leu Gln Arg Arg Pro Thr Tyr Leu Ser Val Pro Tyr Asp Asp Trp Ser
145                 150                 155                 160

Ala Asp Val Asp Asn Ala Leu Ala Val Leu Asp Arg Arg Val Leu
                165                 170                 175

Arg Ala Ala Val Pro Gly Gly Glu Gln Arg Arg Trp Leu Val Glu Gln
                180                 185                 190

Val Ala Ser Ala Arg Arg Pro Ala Leu Val Leu Gly Gly Asp Ile Asp
                195                 200                 205

Ser Ala Gly Arg Phe Asp Asp Ala Val Arg Leu Ala Glu Arg Leu Gly
            210                 215                 220

Gly Pro Val Trp Ala Ala Pro Ser Gln Phe Arg Leu Pro Phe Pro Asn
225                 230                 235                 240

Arg His Pro Leu Phe Arg Gly Val Leu Pro Ala Gly Ile Ala Pro Val
                245                 250                 255

Ser Ala Ala Phe Glu Gly His Asp Leu Val Leu Val Leu Gly Ala Pro
                260                 265                 270

Val Phe Arg Tyr His Glu His Leu Pro Gly Arg Tyr Leu Pro Glu Gly
                275                 280                 285

Thr Arg Leu Ile Gln Val Thr Glu Asp Ala Ser Ala Ala Arg Ala
            290                 295                 300

Pro Met Gly Glu Ala Leu Val Ala Asp Pro Gly Ala Val Ile Asp Ile
305                 310                 315                 320

Leu Leu Glu Ala Leu Gly Ala Ala Asp Arg Pro Ala Gly Pro Tyr Arg
                325                 330                 335

Pro Val Pro Glu Pro Leu Thr Ala Glu Gly Pro Ala Leu His Pro Glu
                340                 345                 350

Gln Val Phe Ala Ala Leu Arg Glu Glu Met Pro Glu Asp Thr Ala Tyr
                355                 360                 365

Val Val Glu Ser Thr Ser Thr Asn Ala Ala Trp Trp Arg Gln Thr Asp
            370                 375                 380

Leu Arg Arg Gln Gly Ser Tyr Tyr Phe Pro Ala Ala Gly Gly Leu Gly
385                 390                 395                 400

Phe Gly Leu Pro Gly Ala Val Gly Val Ala Met Ala Gln Pro Gly Arg
                405                 410                 415

Pro Val Val Gly Val Ile Gly Asp Gly Ser Ala Asn Tyr Gly Ile Thr
                420                 425                 430

Ala Leu Trp Thr Ala Ala Gln His Arg Val Pro Leu Thr Val Val Leu
            435                 440                 445

Leu Arg Asn Gly Ala Tyr Gly Ala Leu Arg Trp Phe Gly Gly Leu Leu
450                 455                 460

Gly Val Pro Asp Ala Pro Gly Leu Asp Ile Pro Gly Leu Asp Phe Thr
465                 470                 475                 480

Arg Ile Ala Glu Gly Tyr Gly Val Arg Ala Gln His Val Gly Ser Val
                485                 490                 495

Ala Glu Leu Arg Ala Ala Leu Ala Glu Thr Pro Glu His Pro Arg Leu
                500                 505                 510

Ile Gln Val Asp Thr Ala Leu Thr Thr Pro Ser
            515                 520

<210> SEQ ID NO 35
<211> LENGTH: 526
<212> TYPE: PRT
<213> ORGANISM: Streptomyces ambofaciens
```

<400> SEQUENCE: 35

```
Met Pro Ser Val Arg Arg Val Ser His Ala Phe Leu Glu Arg Gln Gly
1               5                   10                  15
Leu Thr Thr Val Phe Gly Asn Pro Gly Ser Asn Glu Leu Pro Phe Leu
                20                  25                  30
Ala Asp Leu Pro Asp Gly Phe Arg Tyr Val Leu Gly Leu His Glu Gly
            35                  40                  45
Ala Val Val Gly Met Ala Asp Gly Tyr Ala Gln Ala Thr Gly Arg Pro
        50                  55                  60
Val Leu Val Asn Leu His Ala Ala Ser Gly Ser Gly Asn Ala Met Gly
65                  70                  75                  80
Ala Leu Thr Asn Ala Val Ala Ser Arg Thr Pro Leu Val Val Ala
                85                  90                  95
Gly Gln Gln Val Arg Pro Ala Ile Gly Pro Glu Ala Asn Leu Ala Ser
                100                 105                 110
Val Asp Ala Gln Thr Leu Met Lys Pro Leu Val Gly Trp Ala Ala Glu
            115                 120                 125
Pro Ala Cys Ala Glu Asp Val Pro Arg Ala Leu Ala Gln Ala Val Phe
        130                 135                 140
Glu Ala Arg Leu Gln Arg Arg Pro Thr Tyr Leu Ser Val Pro Tyr Asp
145                 150                 155                 160
Asp Trp Ser Ala Glu Val Asp Asp Asn Ala Leu Ala Val Leu Asp Arg
                165                 170                 175
Arg Val Glu Arg Ala Ser Val Pro Asp Ala Val Gln Ser Arg Arg Leu
                180                 185                 190
Ala Glu Arg Val Ala Ala Arg Arg Pro Ala Leu Val Leu Gly Gly
            195                 200                 205
Asp Ile Asp Ser Pro Gly Leu Phe Asp Asp Ala Val Arg Leu Ala Glu
        210                 215                 220
Arg Leu Gly Cys Pro Val Trp Ala Ala Pro Ser Leu Phe Arg Leu Pro
225                 230                 235                 240
Phe Pro Asn Arg His Pro Gln Phe Arg Gly Val Leu Pro Ala Gly Ile
                245                 250                 255
Ala Pro Val Cys Glu Ala Phe Glu Gly His Asp Leu Val Leu Val Leu
                260                 265                 270
Gly Ala Pro Val Phe Arg Tyr His Glu Tyr Leu Pro Gly Arg Tyr Leu
            275                 280                 285
Pro Glu Gly Thr Arg Leu Val Gln Val Thr Asp Asp Ala Ser Ala Ala
        290                 295                 300
Ala Arg Ala Pro Met Gly Glu Ala Leu Val Ala Asp Pro Gly Ala Val
305                 310                 315                 320
Val Gly Leu Leu Leu Arg Ser Leu Asp Ala Pro Gly Glu Pro Ala Gly
                325                 330                 335
Pro Tyr Arg Pro Ala Pro Glu Leu Thr Ala Gly Pro Ser Leu
                340                 345                 350
His Pro Glu Gln Val Phe Ala Ala Leu Arg Glu Gly Leu Pro Ala Asp
            355                 360                 365
Thr Ala Tyr Val Val Glu Ser Thr Ser Thr Asn Ser Ala Trp Trp Arg
        370                 375                 380
Gln Met Asp Leu Arg Arg Pro Gly Ser Tyr Tyr Phe Pro Ala Ala Gly
385                 390                 395                 400
Gly Leu Gly Phe Gly Leu Pro Gly Ala Val Gly Val Ala Met Ala Gln
```

```
                    405                 410                 415
Pro Asp Arg Pro Val Gly Val Ile Gly Asp Gly Ser Ala Asn Tyr
            420                 425                 430
Gly Ile Thr Ala Leu Trp Thr Ala Ala Gln His Gly Val Pro Leu Thr
            435                 440                 445
Ile Val Leu Leu Arg Asn Gly Thr Tyr Gly Ala Leu Arg Trp Phe Gly
            450                 455                 460
Gly Leu Leu Gly Val Pro Asp Ala Pro Gly Leu Asp Ile Pro Gly Leu
465                 470                 475                 480
Asp Phe Thr Arg Val Ala Glu Gly Tyr Gly Val Arg Ala Arg His Val
            485                 490                 495
Gly Gly Val Glu Glu Leu Arg Ala Val Leu Ala Glu Gln Pro Gly His
            500                 505                 510
Pro Arg Leu Ile Gln Val Asp Thr Ala Leu Thr Thr Pro Ser
            515                 520                 525

<210> SEQ ID NO 36
<211> LENGTH: 538
<212> TYPE: PRT
<213> ORGANISM: Streptomyces sp.

<400> SEQUENCE: 36

Met Leu Arg Thr Ala Gly Glu Glu Ser Gly Val Lys Val Arg Asp Ala
1               5                   10                  15
Phe Phe Glu Val Leu Arg Ser His Gly Ile Thr Thr Val Phe Gly Asn
            20                  25                  30
Pro Gly Ser Asn Glu Leu Pro Leu Leu Arg Asp Phe Pro Asp Asp Phe
        35                  40                  45
Arg Tyr Val Leu Ala Leu His Glu Gly Ala Ala Ile Ala Met Ala Asp
    50                  55                  60
Gly Tyr Ala Leu Ala Thr Gly Arg Pro Ser Leu Val Asn Leu His Ala
65              70                  75                  80
Ala Ala Gly Thr Gly Asn Ala Met Gly Asn Leu Thr Asn Thr Gln Ser
            85                  90                  95
Gly His Val Pro Val Val Thr Ser Gly Gln Gln Ala Arg Arg Tyr
            100                 105                 110
Thr Ala Leu Asn Ala Leu Leu Thr Asn Val Asp Ala Thr Ala Leu Ala
        115                 120                 125
Glu Pro Leu Val Lys Trp Ser Cys Glu Pro Leu Arg Pro Glu Asp Val
    130                 135                 140
Pro Gln Ala Leu Ser Gln Gly Ile Leu Leu Ala Gly Ser Ala Pro Ala
145                 150                 155                 160
Gly Pro Val Tyr Leu Ser Leu Pro Leu Asp Asp Trp Asp His Gln Ala
            165                 170                 175
Asp Pro Gly Ala Leu Lys His Leu Lys Ala Arg Thr Val Gln Gly Asp
            180                 185                 190
Pro Val Val Ser Glu Pro Ala Leu Asp Leu Leu Arg Arg Arg Leu Thr
            195                 200                 205
Gly Ala Ala Asn Pro Val Met Val Val Gly Pro Gly Ile Asp Asp Ala
        210                 215                 220
Thr Gly Trp Asp Gly Ala Cys Arg Leu Ala Asp Arg Leu Ala Leu Pro
225                 230                 235                 240
Val Phe Val Ala Pro Ser Pro Ser Arg Cys Pro Phe Pro Thr Arg His
            245                 250                 255
```

```
Pro Gly Tyr Arg Gly Val Leu Pro Ser Asp Ile Pro Ala Val Ala Arg
            260                 265                 270

His Phe Asp Gly His Asp Leu Val Val Ala Phe Gly Ala Ala Ile Phe
            275                 280                 285

Arg Tyr His Ala Phe Glu Glu Gly Asp Tyr Leu Pro Pro Gly Thr Glu
            290                 295                 300

Leu Trp Ala Val Thr Ser Asp Pro Asp Glu Ala Thr Arg Ala Pro Phe
305                 310                 315                 320

Gly Arg Ile Leu Val Gly Asn Pro Ser Asp Ala Leu Ala Arg Leu Thr
                325                 330                 335

Glu Thr Val Pro Ala Arg His Arg Pro Pro Pro Pro Leu Glu Arg
            340                 345                 350

Thr Ser Arg Leu Asn Glu Ala Gly Pro Ala Phe Ser Ala Glu Ala Ile
            355                 360                 365

Val Asp Ala Leu Asp Ala Ala Lys Asp Glu Ser Thr Val Leu Ala His
            370                 375                 380

Glu Trp Thr Ser Val Asp Thr Thr Trp Asp Arg Phe Asp Ile Ser Arg
385                 390                 395                 400

Pro Gly Ser Leu Tyr Phe Pro Ala Ser Gly Gly Leu Gly Trp Gly Leu
                405                 410                 415

Pro Ala Ala Ile Gly Leu Gln Leu Gly Asp Pro Ser Arg Arg Val Leu
            420                 425                 430

Ala Met Leu Gly Asp Gly Ala Leu His Tyr Thr Val Ser Ala Leu Trp
            435                 440                 445

Thr Ala Ala Arg Tyr Arg Val Pro Val Val Phe Val Val Ala Arg Asn
450                 455                 460

Gly Glu Tyr Gly Ala Leu Lys Lys Phe Thr Gln Ala Met Gln Ala Pro
465                 470                 475                 480

Gly Val Pro Gly Leu Glu Leu Pro Gly Ile Asp Ile Thr Gly Ile Ala
                485                 490                 495

Ser Ala Tyr Gly Ile Ser Ala Thr Arg Ile Asp Thr Leu Asp Ala Leu
            500                 505                 510

Thr Ala Ala Val Thr Ala Ala Leu Ala Thr Asp Glu Pro His Leu Ile
            515                 520                 525

Glu Val Pro Gln Gln Pro Leu Thr Ala Ser
530                 535

<210> SEQ ID NO 37
<211> LENGTH: 535
<212> TYPE: PRT
<213> ORGANISM: Brevibacterium linens

<400> SEQUENCE: 37

Met Thr Ala Thr Gly Lys Thr Val Leu Gln Ala Ser Leu Asp Val Phe
1               5                   10                  15

Arg Thr His Gly Met Thr Thr Ile Phe Gly Asn Pro Gly Ser Asn Glu
            20                  25                  30

Leu Pro Phe Leu Ala Gly Leu Gly Asp Asp Phe Arg Phe Val Leu Gly
            35                  40                  45

Leu His Glu Gln Val Val Gly Met Ala Glu Gly Phe Ala Arg Ala
    50                  55                  60

Thr Gly Arg Pro Val Leu Val Asn Leu His Ala Ala Ser Gly Ser Gly
65                  70                  75                  80

Asn Gly Met Gly Ala Leu Thr Asn Ala His Tyr Gly His Val Pro Leu
                85                  90                  95
```

-continued

```
Val Val Leu Ala Gly Gln Gln Val Arg Arg Thr Val Gly Gln Glu Thr
            100                 105                 110

Met Leu Ala Ser Ala Asp Ala Ala Thr Leu Pro Thr Pro Leu Val Lys
            115                 120                 125

Tyr Ser His Glu Pro Leu Ser Ala Thr Asp Val Pro Arg Thr Leu Ser
            130                 135                 140

Gln Ala Ala Phe Glu Ala Thr Thr Gln Pro Ser Gly Pro Val Tyr Val
145                 150                 155                 160

Ser Val Pro Leu Asp Asp Trp Asp Glu Glu Ala Leu Asp Asp Asp Asp
                165                 170                 175

Leu Leu Thr Thr Arg Thr Val Ser Thr Gly Arg Gly Leu Asp Pro Gln
            180                 185                 190

Leu Gln Glu Glu Leu Leu Ala Ser Leu Asp Gly Ala Lys Arg Pro Ala
            195                 200                 205

Leu Val Val Gly Pro Gln Val Asp Ala Ala Val Ser Asp Pro Glu
            210                 215                 220

Val Leu Glu Ala Val Gln Ala Leu Ala Glu Lys Leu Asp Ala Ser Val
225                 230                 235                 240

Tyr Val Ala Pro Ser Pro Thr Arg Cys Pro Phe Pro Thr Thr His Pro
                245                 250                 255

Asn Phe Glu Gly Val Met Val Pro Gly Ile Gly Ser Val Arg Asp Arg
            260                 265                 270

Leu Ala Asp His Asp Val Val Leu Val Leu Gly Ala Ala Val Phe Arg
            275                 280                 285

Tyr His Arg Trp Glu Pro Ser Asn Tyr Leu Ser Pro Gly Thr Glu Val
            290                 295                 300

Ile Gln Ile Thr Gln Asp Pro Arg Glu Ala Thr Arg Ala Pro Phe Gly
305                 310                 315                 320

Arg Ala Val Ile Thr Asp Val Ala Ser Thr Ala Ala Thr Leu Ala Asp
                325                 330                 335

Gly Val Thr Asp Arg Gly Thr Arg Arg Gly Glu Arg Gly Ser Arg Ile
            340                 345                 350

Met Ser Pro Ala Ala Thr Ser Ala Glu Gly Met Thr Gly Gly Glu Ile
            355                 360                 365

Leu Glu Val Leu Asn Glu His Val Asn Asp Ser Val Ser Tyr Val Asn
            370                 375                 380

Glu Thr Thr Thr Leu Asp Leu Asp Tyr Leu Glu Arg Val Ala Ile Asp
385                 390                 395                 400

Arg Pro Gly Met Tyr Ser Phe Pro Ala Ser Gly Leu Gly Phe Gly
                405                 410                 415

Leu Pro Val Ala Val Gly Met Ser Ile Gly Ala Pro Glu Asn Thr Val
            420                 425                 430

Val Ala Thr Val Gly Asp Gly Ser Ala Asn Tyr Gly Ile Thr Ala Leu
            435                 440                 445

Tyr Thr Ala Ala Gln Leu Gln Thr Arg Thr Val Phe Val Ile Ile Asn
            450                 455                 460

Asn Ser Gly Tyr Gly Ala Leu Ala Gly Phe Ala Gln Arg Met Gly Val
465                 470                 475                 480

Pro Lys Val Pro Gly Leu Ala Leu Gly Ile Asp Phe Val Ser Leu
                485                 490                 495

Ala Lys Gly Tyr Gly Val Pro Ala Lys Gln Thr Ser Thr Arg Ala Glu
            500                 505                 510
```

```
Phe Ala Ala Ala Tyr Arg Glu Ala Leu Asp Ala Thr Gly Pro Val Leu
            515                 520                 525

Ile Asp Ala Ser Ile Val Ser
    530                 535
```

<210> SEQ ID NO 38
<211> LENGTH: 537
<212> TYPE: PRT
<213> ORGANISM: Mycobacterium smegmatis str.

<400> SEQUENCE: 38

```
Met Ser Asp Gln Lys Thr Val His Asp Val Thr Tyr Asp Leu Leu Arg
1               5                   10                  15

Lys Leu Gly Leu Thr Thr Val Phe Gly Asn Pro Gly Ser Thr Glu Glu
            20                  25                  30

Ser Phe Leu Arg Asp Phe Pro Glu Asp Phe Thr Tyr Val Leu Ser Leu
        35                  40                  45

Gln Glu Ala Ser Ala Leu Ala Met Ala Asp Gly Phe Ala Gln Ala Thr
    50                  55                  60

Gly Lys Pro Ala Leu Val Asn Leu His Thr Ala Ala Gly Thr Gly Asn
65                  70                  75                  80

Ala Met Gly Ser Leu Val Ala Ala Tyr Arg Ala Asn Thr Pro Leu Ile
                85                  90                  95

Ile Thr Ala Gly Gln Gln Thr Arg Glu Met Ser Val Val Asp Pro Tyr
            100                 105                 110

Leu Asn Asn Pro Asp Ala Thr Thr Met Pro Lys Pro Trp Val Lys Trp
        115                 120                 125

Ser Tyr Glu Pro Ala Arg Ala Glu Asp Val Pro Ala Ala Phe Met Gln
    130                 135                 140

Ala Tyr Ala Val Ala Met Gln Pro Pro Met Gly Pro Val Phe Leu Ser
145                 150                 155                 160

Ile Pro Leu Asp Asp Trp Asp Lys Pro Ala Leu Gly Pro Ala Ala Val
                165                 170                 175

Arg Ser Val Ser Thr Arg Val Ala Pro Asp Ala Glu Arg Leu Ala Gln
            180                 185                 190

Phe Ala Glu Arg Ile Asn Ala Ala Lys His Pro Met Leu Val Leu Gly
        195                 200                 205

Pro Glu Val Asp Arg Ala Gly Ala Trp Asp Ala Gly Ile Glu Phe Ala
    210                 215                 220

Glu Lys Leu Gly Ala Pro Val His Ala Ser Ala Leu Pro Asp Arg Met
225                 230                 235                 240

Ser Phe Pro Glu Asp His Pro Leu Tyr Ala Gly Pro Leu Pro Met Thr
                245                 250                 255

Ile Ala Gly Val Glu Gln Ala Val Ser Ala Tyr Asp Leu Val Val Val
            260                 265                 270

Val Gly Ala Glu Val Phe Arg Tyr Tyr Pro Tyr Val Pro Gly Glu Tyr
        275                 280                 285

Leu Pro Glu Gly Thr Asp Leu Leu Gln Ile Thr Ala Asp Pro His Arg
    290                 295                 300

Ser Ala Val Ala Pro Val Gly Asp Ser Leu Val Gly Val Gly Ile
305                 310                 315                 320

Ala Leu Ser Arg Leu Thr Glu Leu Ile Asp Thr Pro Asp Asp Arg Val
                325                 330                 335

Pro Pro Lys Pro Leu Val Arg Gln Arg His Ser Asp Ile Pro Ser Thr
            340                 345                 350
```

```
Ala Pro Met Thr Ser Asn Ala Val Tyr Glu Val Leu Ser Asn Val Lys
        355                 360                 365

Pro Asp Asp Ala Ala Val Val Met Glu Ser Thr Ser Thr Met Leu Asp
370                 375                 380

Leu Phe Thr Trp Leu Pro Thr Thr His Pro Ala Ser Phe Phe Ala Thr
385                 390                 395                 400

Gly Ser Gly Gly Ile Gly Trp Gly Val Pro Ala Ala Val Gly Ile Ala
                405                 410                 415

Leu Gly Asp Arg Ala Arg Gly Val Asp Arg Thr Val Val Ala Thr Ile
                420                 425                 430

Gly Asp Gly Ser Phe Gln Tyr Ser Ile Gln Ala Ile Trp Thr Ala Ala
                435                 440                 445

Gln His Lys Leu Pro Ile Val Phe Val Val Leu Arg Asn Gly Glu Tyr
                450                 455                 460

Ala Ile Leu Lys Ser Phe Ala Asp Leu Glu Lys Thr Pro Asn Val Pro
465                 470                 475                 480

Gly Leu Gln Leu Pro Gly Leu Asp Ile Ser Ser Ile Ala Ala Gly Phe
                485                 490                 495

Gly Cys Arg Thr Ala Thr Val Glu Ser Thr Asp Met Leu Glu Ala Glu
                500                 505                 510

Leu Lys Thr Ala Leu Gln Ala Asp Gly Pro Thr Val Leu Val Val Pro
                515                 520                 525

Thr Leu Pro Gln Leu Pro Gln Leu Gly
                530                 535

<210> SEQ ID NO 39
<211> LENGTH: 543
<212> TYPE: PRT
<213> ORGANISM: Providencia rustigianii

<400> SEQUENCE: 39

Met Lys Lys Thr Ile Arg Gln Val Thr Phe Asp Leu Leu Arg Glu Leu
1               5                   10                  15

Asp Ile Thr Thr Ile Phe Gly Asn Pro Gly Ser Thr Glu Glu Thr Phe
                20                  25                  30

Leu Lys Asp Phe Pro Ser Asp Phe Arg Tyr Ile Gln Thr Leu His Glu
            35                  40                  45

Ala Ser Ala Val Ala Ala Ala Asp Gly Tyr Ala Gln Gly Met Arg Lys
        50                  55                  60

Val Ala Met Val Asn Leu His Thr Ser Ala Gly Leu Ser Asn Gly Met
65                  70                  75                  80

Ser Asn Ile Leu Thr Ala Tyr Met Asn Arg Thr Pro Leu Ile Ile Thr
                85                  90                  95

Ala Gly Asn Gln Thr Arg Glu Met Leu Leu Met Glu Pro Trp Leu Thr
            100                 105                 110

Asn Ile Glu Pro Glu Asn Leu Pro Lys Pro Trp Val Lys Trp Ser Tyr
        115                 120                 125

Gln Pro Ala Arg Ala Glu Asp Val Pro Ala Ala Phe Met Arg Ala Tyr
    130                 135                 140

Ala Met Ala Leu Gln Pro Pro Ala Gly Pro Val Phe Leu Ser Ile Pro
145                 150                 155                 160

Leu Asp Asp Trp Asp Lys Pro Ala Glu Lys Asp Ala Ala Val Val Arg
                165                 170                 175

Thr Val Ser Glu Arg Ile Gly Tyr Asp Pro Ile Arg Leu Lys Ser Phe
```

```
                180                 185                 190
Ala Asp Val Leu Ser Gln Ala Lys Asn Pro Val Leu Ile Tyr Gly Ser
            195                 200                 205

Ala Ile Ala Arg Gly Gln Gly Trp Asp Ala Gly Ile Ala Leu Ala Glu
            210                 215                 220

Lys Leu Asn Ile Pro Val Trp Ala Ala Pro Ala Ser Glu Arg Pro Pro
225                 230                 235                 240

Phe Pro Glu Thr His Pro Leu Tyr Ala Gly Gly Leu Pro Phe Ala Ile
            245                 250                 255

Gln Pro Leu Ala Asp Lys Leu Lys Gly His Asp Leu Ala Leu Ile Ile
            260                 265                 270

Gly Ala Pro Val Phe Arg Tyr Tyr Pro Tyr Val Ala Gly Glu Tyr Leu
            275                 280                 285

Pro Asp Gly Leu Arg Leu Leu His Ile Thr Asp Pro Ile Glu Val
            290                 295                 300

Gly Arg Ala Pro Val Gly Asp Ser Met Leu Ser Asp Ala Val Leu Ala
305                 310                 315                 320

Val Glu Gly Leu Thr Gln Leu Val Ser Ala Arg Ala Ala Ser Gln Ala
            325                 330                 335

Lys Val Val Lys Gln Pro His Gly Met Ala Pro Tyr Pro Ala Ala Pro
            340                 345                 350

Glu Thr Val Asn Asn Ala Thr Thr Leu Ser Ala Ala Gln Leu Phe Arg
            355                 360                 365

Ala Leu Arg Glu Val Ser Pro Lys Gly Thr Val Leu Val Glu Glu Ser
            370                 375                 380

Pro Ser Asn Leu Gly Glu Leu His Arg Glu Trp Pro Ile Glu His Pro
385                 390                 395                 400

Asp Ser Phe Tyr Thr Phe Ala Ser Gly Ser Leu Gly Trp Asn Leu Pro
            405                 410                 415

Ala Ser Val Gly Ile Ala Leu Ala Glu Arg Asp Ser Gly Arg Asn Arg
            420                 425                 430

Pro Val Leu Ser Ile Ile Gly Asp Gly Ser Met Gln Tyr Ser Ile Gln
            435                 440                 445

Gly Leu Trp Ser Ala Ala Gln His Asn Leu Pro Ile Val Phe Val Ile
            450                 455                 460

Pro Arg Asn Ser Glu Tyr Ala Ile Leu Lys Ser Phe Ala Val Leu Glu
465                 470                 475                 480

Glu Thr Pro Gly Val Pro Gly Leu Asp Ile Pro Asn Leu Asp Ile Val
            485                 490                 495

Ala Leu Gly Lys Gly Tyr Gly Cys Thr Ala Val Lys Ala Thr Thr Val
            500                 505                 510

Glu Glu Val Gln Gln Ala Cys Lys Glu Ala Tyr Lys Arg Gln Gly Pro
            515                 520                 525

Thr Val Ile Glu Val Pro Ile Leu Pro Gln Ile Pro Pro Leu Ile
            530                 535                 540

<210> SEQ ID NO 40
<211> LENGTH: 545
<212> TYPE: PRT
<213> ORGANISM: Acidobacterium capsulatum

<400> SEQUENCE: 40

Met Ser Ala Gly Asn Ala Phe Thr Val Trp Glu Ala Thr Tyr Asp Leu
1               5                   10                  15
```

```
Leu Arg Lys Leu Gly Leu Thr Thr Val Phe Gly Asn Pro Gly Ser Thr
            20                  25                  30

Glu Gln Pro Phe Leu Lys Asn Phe Pro Ser Asp Phe Asp Tyr Ile Leu
        35                  40                  45

Ala Leu Gln Glu Ala Ser Ala Val Ala Met Ala Asp Gly Phe Ala Gln
 50                  55                  60

Ala Thr Gly Ser Pro Ala Leu Val Asn Leu His Thr Asn Ala Gly Thr
 65                  70                  75                  80

Gly Asn Gly Met Gly Ser Ile Met Thr Ala Phe Gln Asn Lys Thr Pro
                85                  90                  95

Leu Ile Ile Thr Ala Gly Gln Gln Thr Arg Glu Met Ile Ile Cys Asp
            100                 105                 110

Pro Leu Leu Thr Asn Arg Asp Glu Thr Met Leu Pro Arg Pro Tyr Val
        115                 120                 125

Lys Trp Ala Tyr Glu Pro Lys Arg Ala Gln Asp Val Pro Arg Ala Ile
130                 135                 140

Met Arg Ala Tyr Ala Leu Ala Leu Gln Pro Pro Ala Gly Pro Val Phe
145                 150                 155                 160

Leu Ser Ile Pro Leu Asp Asp Trp Asp Gln Pro Ala Leu Gly Ile Ala
                165                 170                 175

Asp Val Arg Thr Val Ser Ser Arg Val Ala Pro Asp Pro Asp Arg Ile
            180                 185                 190

Arg Glu Phe Ala Ser Arg Ile Ser Gly Ala Lys Lys Pro Ala Leu Ile
        195                 200                 205

Tyr Gly Pro Glu Ile Glu Lys Ala Gly Gly Trp Glu Ala Gly Ile Ala
210                 215                 220

Leu Ala Glu Lys Leu Arg Ala Pro Val Phe Arg Ala Pro Ala Ser Glu
225                 230                 235                 240

Arg Met Ser Ile Ser Glu Thr His Pro Leu Phe Gln Met Gln Leu Pro
                245                 250                 255

Gln Ala Met Gly Pro Ile Ser Thr Ile Leu Ala Gly Tyr Asp Leu Ile
            260                 265                 270

Val Val Ile Gly Ala Pro Val Phe Arg Tyr Tyr Pro Tyr Val Pro Gly
        275                 280                 285

Pro Val Val Pro Ala Gly Ala Glu Leu Leu Gln Ile Thr Asn Asp Pro
290                 295                 300

Thr Asp Ala Gly Ser Ala Leu Ile Gly Asp Ser Leu Leu Ser Asp Ala
305                 310                 315                 320

Lys Leu Ala Leu Leu Ala Leu His Asp Leu Val Glu Asp Arg Ser Ser
                325                 330                 335

Leu Pro Leu Pro Ala Arg Arg Glu Lys Lys Thr Pro Pro Ala Ser Ser
            340                 345                 350

Thr Gly Met Pro Leu Thr Ala Glu Glu Leu Tyr Ala Ala Leu Gly Glu
        355                 360                 365

Val Arg Pro Glu Asp Ala Ile Val Val Glu Ser Pro Ser Asn Phe
370                 375                 380

Met Gln Phe Arg Asp Tyr Trp Pro Ala Leu Lys Pro Met Arg Tyr Phe
385                 390                 395                 400

Thr Tyr Ala Ser Gly Gly Leu Gly His Asn Ala Pro Ser Ser Val Gly
                405                 410                 415

Val Ala Leu Ala Gln Lys Lys Leu Gly Thr Gly Leu Pro Val Val Met
            420                 425                 430

Leu Ile Gly Asp Gly Ser Leu Gln Tyr Ser Val Gln Ser Leu Ala Ser
```

```
            435                 440                 445
Ala Ala Gln His Asn Leu Lys Ile Ile Tyr Ile Val Pro Cys Asn Arg
        450                 455                 460

Glu Tyr Ala Ile Leu Lys Glu Phe Ala Val Leu Glu Arg Thr Pro Asn
465                 470                 475                 480

Val Pro Ala Leu Asp Leu Pro Tyr Leu Asp Ile Val Ser Leu Ala Gln
                485                 490                 495

Gly Tyr Gly Val Arg Gly Ile Lys Ala Asp Thr Lys Glu Gln Ile Gln
                500                 505                 510

Ala Ala Phe Arg Gln Ala Leu Ala Ala Glu Gly Pro Thr Leu Ile Ala
            515                 520                 525

Val Pro Ile Lys Gln Glu Leu Lys Pro Leu Ile Pro Pro Ser Val Lys
        530                 535                 540

Ala
545

<210> SEQ ID NO 41
<211> LENGTH: 539
<212> TYPE: PRT
<213> ORGANISM: Desulfovibrio magneticus

<400> SEQUENCE: 41

Met Pro Thr Val Arg Asp Val Thr Phe Ala Leu Leu Arg Arg Leu Gly
1               5                   10                  15

Leu Thr Thr Val Val Gly Asn Pro Gly Ser Thr Glu Glu Thr Phe Leu
                20                  25                  30

Lys Asn Phe Pro Asp Asp Phe Thr Tyr Ile Leu Ala Leu Gln Glu Ser
            35                  40                  45

Ser Val Val Gly Ile Ala Asp Gly Leu Ala Gln Gly Leu Gly Lys Pro
        50                  55                  60

Val Leu Val Asn Val His Thr Gly Ala Gly Met Gly Asn Ala Met Gly
65                  70                  75                  80

Cys Ile Leu Thr Ala Tyr Leu Asn Lys Thr Pro Leu Ile Ile Thr Ala
                85                  90                  95

Gly Gln Gln Thr Arg Asp Met Leu Leu Gly Glu Pro Phe Leu Thr Asn
            100                 105                 110

Ile Asp Glu Thr Met Leu Pro Lys Pro Trp Val Lys Trp Ser Tyr Glu
        115                 120                 125

Pro Lys Arg Pro Gln Asp Val Pro Gly Ala Phe Met Arg Ala Tyr Ala
    130                 135                 140

Met Ala Met Gln Gln Pro Gln Gly Pro Val Phe Leu Ser Leu Pro Leu
145                 150                 155                 160

Asp Asp Trp Glu Lys Asp Met Asp Ala Val Asp Val Tyr Arg Thr Val
                165                 170                 175

Ser Val Arg His Ala Pro Asp Pro Ala Arg Ile Ala Glu Phe Ala Ala
            180                 185                 190

Arg Ile Asn Ala Ser Ala Asn Pro Val Leu Val Tyr Gly Ala Asp Leu
        195                 200                 205

Ser Arg Ser Gln Ala Trp Glu Gln Gly Ile Ala Leu Ala Glu Ala Val
    210                 215                 220

Gln Ala Pro Val Trp Leu Gly Pro Phe Thr Glu Arg Val Pro Phe Pro
225                 230                 235                 240

His Asn His Pro Leu Tyr Ala Gly Val Leu Pro Pro Ala Val Gly Pro
                245                 250                 255
```

```
Leu Ser Lys Ala Leu Ala Gly His Asp Leu Val Val Val Gly Ala
            260                 265                 270

Pro Val Phe Arg Tyr Tyr Pro Trp Val Ala Gly Glu Thr Leu Pro Ala
        275                 280                 285

Gly Ala Lys Leu Leu Gln Ile Ile Asp Asp Pro Tyr Glu Ala Gly Lys
    290                 295                 300

Ala Val Val Gly Asp Ser Leu Val Ala Asp Ser Leu Leu Ala Val Glu
305                 310                 315                 320

Ala Leu Leu Pro Leu Val Ala Lys Arg Pro Ala Arg Gly Pro Val Arg
                325                 330                 335

Pro Glu Arg Ala Lys Val Ala Val Pro Asp Asp Ala Pro Leu Pro Leu
            340                 345                 350

Thr Pro Arg Gln Ile Phe Gly Val Leu Ser Glu Val Ile Val Gly Gly
        355                 360                 365

Asp Cys Ile Leu Val Asn Glu Ser Pro Ser Asn Met Ala Asp Leu Ala
    370                 375                 380

Ala Thr Pro Leu Gly Val Val Thr Gln Pro Asp Ser Ser Phe Val Met
385                 390                 395                 400

Ala Ser Gly Gly Leu Gly Trp Gly Met Pro Ala Ala Val Gly Leu Ala
                405                 410                 415

Leu Ala Glu Lys Ala Ser Gly Arg Gly Lys Pro Val Val Ala Val Ile
            420                 425                 430

Gly Asp Gly Ser Phe Gln Tyr Ser Leu Gln Ser Ile Trp Thr Gly Val
        435                 440                 445

Gln His Gly Ala His Val Val Tyr Val Val Leu Arg Asn Asp Glu Tyr
    450                 455                 460

Gly Ile Leu Lys Ser Phe Ala Arg Leu Glu Glu Thr Pro Gly Val Pro
465                 470                 475                 480

Gly Leu Asp Leu Pro Gly Leu Asp Ile Val Ser Leu Gly Lys Gly Tyr
                485                 490                 495

Gly Ala Ala Thr Ala Lys Val Asp Thr Pro Ala Ala Ile Arg Glu Ala
            500                 505                 510

Phe Ala Asp Ala Leu Ala Phe Lys Gly Val Ser Val Ile Glu Ile Ala
        515                 520                 525

Ala Asp Lys His Val Gly Asp Leu Ile Pro Lys
    530                 535

<210> SEQ ID NO 42
<211> LENGTH: 536
<212> TYPE: PRT
<213> ORGANISM: Burkholderia multivorans

<400> S

```
Tyr Lys Asn Arg Thr Pro Leu Ile Val Thr Ala Gly Gln Gln Ala Arg
            100                 105                 110
Ala Ile Leu Pro Phe Glu Pro Phe Leu Gly Ala Ala Gln Ala Thr Glu
            115                 120                 125
Leu Pro Lys Pro Tyr Val Lys Trp Ser Ile Glu Pro Ala Arg Ala Gln
            130                 135                 140
Asp Val Pro Ala Ala Ile Ala Arg Ala Tyr Arg Ile Ala Met Gln Glu
145                 150                 155                 160
Pro Arg Gly Pro Val Phe Val Ser Ile Pro Val Asp Trp Asp Gln
                    165                 170                 175
Pro Ala Glu Leu Leu Pro Pro Arg Asp Val Ser Gln Val Val Arg Pro
            180                 185                 190
Asp Pro Asp Ala Leu Ala Arg Leu Gly Asp Ala Leu Asp Ala Ala Gln
            195                 200                 205
Arg Pro Ala Phe Val Val Gly Ala Ala Leu Asp Arg Ala Gly Ala Trp
            210                 215                 220
Asp Glu Ala Val Arg Leu Ala Glu Arg His Arg Ala Arg Val Tyr Val
225                 230                 235                 240
Ala Pro Met Ser Gly Arg Cys Ser Phe Pro Glu Asp His Pro Leu Phe
                    245                 250                 255
Ala Gly Phe Leu Pro Ala Ile Arg Glu Gln Ile Val Ala Arg Leu Asp
            260                 265                 270
Gly His Asp Leu Val Phe Ala Phe Gly Ala Pro Ala Phe Thr Tyr His
            275                 280                 285
Ile Glu Gly Phe Gly Pro His Val Pro Pro Gly Ala Thr Leu Val Gln
            290                 295                 300
Leu Val Asp Asp Pro Gly Thr Ala Ala Trp Thr Pro Gln Gly Asp Ala
305                 310                 315                 320
Val Val Gly Asn Leu Lys Leu Ala Ala Arg Asp Leu Leu Ala Arg Pro
                    325                 330                 335
Ala Pro Ala Glu Arg Pro Met Pro Ala Ala Arg Ala Pro Arg Gln Arg
            340                 345                 350
Val Ala Pro Pro Val Ala Gly Glu Arg Met Ser Ala Ala Phe Ala Leu
            355                 360                 365
Gln Thr Leu Ala Asp Leu Arg Asp Val His Asp Ile Val Val Glu Glu
            370                 375                 380
Ala Pro Ser Ala Arg Pro Ile Met Gln Glu His Leu Pro Phe Thr Arg
385                 390                 395                 400
Ser Gly Thr Phe Tyr Thr Met Asp Ser Gly Leu Gly Tyr Gly Met
                    405                 410                 415
Pro Ala Ala Val Gly Val Ala Leu Ala Gln Pro Glu Arg Arg Val Ile
            420                 425                 430
Ala Leu Ile Gly Asp Gly Ser Ser Leu Tyr Ser Ile Gln Ala Leu Trp
            435                 440                 445
Ser Ala Ala Gln Leu Gly Leu Pro Ile Thr Phe Val Ile Leu Asn Asn
            450                 455                 460
Arg Arg Tyr Ala Ala Leu Gln Asp Phe Ala Pro Val Phe Gly Phe Gly
465                 470                 475                 480
Pro Asp Asp Pro Val Gln Gly Thr Asp Leu Pro Asp Leu Asp Phe Val
                    485                 490                 495
Ala Leu Ala Ala Gly Phe Gly Cys Arg Gly Val Arg Val Gly Asp Pro
            500                 505                 510
```

```
Ala Arg Leu Arg Asp Thr Leu Ala Asp Ala Leu Arg Ala Thr Ala Pro
            515                 520                 525

Val Val Val Asp Val Glu Ile Ala
        530                 535

<210> SEQ ID NO 43
<211> LENGTH: 536
<212> TYPE: PRT
<213> ORGANISM: Burkholderia multivorans

<400> SEQUENCE: 43

Met Ser Gly Gln Pro His Ala Ala Thr Pro Ala Thr Thr Val Arg
1               5                   10                  15

Asp Ala Val Ile His Leu Phe Arg Gln Phe Gly Ile Asp Arg Val Phe
                20                  25                  30

Gly Asn Pro Gly Ser Thr Gl

```
Ile Ala Pro Pro Ala Gly Glu Arg Met Ser Ala Ala Phe Val Leu
        355                 360                 365

Gln Thr Leu Ala Asp Leu Arg Asp Ala His Asp Ile Val Val Glu Glu
370                 375                 380

Ala Pro Ser Ala Arg Pro Ile Met Gln Ala His Leu Pro Phe Thr Arg
385                 390                 395                 400

Ser Gly Thr Phe Tyr Thr Met Asp Ser Gly Leu Gly Tyr Gly Met
                405                 410                 415

Pro Ala Ala Val Gly Val Ala Leu Ala Gln Pro Gly Arg Arg Val Ile
                420                 425                 430

Gly Leu Ile Gly Asp Gly Ser Ser Leu Tyr Ser Ile Gln Ala Leu Trp
            435                 440                 445

Ser Ala Ala Gln Leu Arg Leu Pro Ile Thr Phe Val Ile Leu Asn Asn
        450                 455                 460

Arg Arg Tyr Ala Ala Leu Gln Asp Phe Ala Pro Val Phe Gly Phe Gly
465                 470                 475                 480

Pro Asp Asp Pro Val Gln Gly Thr Asp Leu Pro Asp Leu Asp Phe Val
                485                 490                 495

Ala Leu Ala Ala Ala Phe Gly Cys Arg Gly Val Arg Val Asp Asp Pro
                500                 505                 510

Ala Arg Leu Arg Asp Thr Leu Ala Asp Ala Leu Arg Ala Thr Ala Pro
            515                 520                 525

Val Val Val Asp Val Asp Ile Ala
        530                 535

<210> SEQ ID NO 44
<211> LENGTH: 536
<212> TYPE: PRT
<213> ORGANISM: Burkholderia multivorans

<400> SEQUENCE: 44

Met Ser Gly Gln Pro His Ala Ala Ala Thr Pro Ala Thr Thr Val Arg
1               5                   10                  15

Asp Ala Val Ile His Leu Phe Arg Gln Phe Gly Ile Asp Arg Val Phe
            20                  25                  30

Gly Asn Pro Gly Ser Thr Glu Leu Pro Met Phe Arg Asp Phe Pro Asp
        35                  40                  45

Asp Phe Arg Tyr Val Leu Gly Leu Gln Glu Ala Val Val Val Gly Met
    50                  55                  60

Ala Asp Gly Tyr Ala Gln Ala Ser Gly Asn Ala Ala Val Val Asn Leu
65                  70                  75                  80

His Ser Ala Ala Gly Val Gly Asn Ala Met Gly Asn Leu Phe Thr Ala
                85                  90                  95

Tyr Lys Asn Arg Thr Pro Leu Ile Val Thr Ala Gly Gln Gln Ala Arg
            100                 105                 110

Ala Ile Leu Pro Phe Glu Pro Phe Leu Gly Ala Ala Gln Ala Thr Glu
        115                 120                 125

Leu Pro Lys Pro Tyr Val Lys Trp Ser Ile Glu Pro Ala Arg Ala Gln
    130                 135                 140

Asp Val Pro Ala Ala Ile Ala Arg Ala Tyr Arg Ile Ala Met Gln Glu
145                 150                 155                 160

Pro Arg Gly Pro Val Phe Val Ser Ile Pro Val Asp Asp Trp Asp Gln
                165                 170                 175

Pro Ala Glu Leu Leu Pro Ala Arg Glu Val Ser Gln Val Val Arg Pro
```

```
                180             185             190
Asp Pro Asp Ala Leu Ala Arg Leu Gly Asp Ala Leu Asp Ala Ala Gln
            195                 200                 205

Arg Pro Ala Phe Val Val Gly Ala Ala Ile Asp Arg Ala Gly Ala Trp
    210                 215                 220

Asp Glu Ala Val Arg Leu Ala Glu Arg His Arg Ala Arg Val Tyr Val
225                 230                 235                 240

Ala Pro Met Ser Gly Arg Cys Ser Phe Pro Glu Asp His Pro Leu Phe
                245                 250                 255

Ala Gly Phe Leu Pro Ala Ile Arg Glu Lys Ile Val Ala Arg Leu Asp
            260                 265                 270

Gly His Asp Leu Val Phe Ala Phe Gly Ala Pro Ala Phe Thr Tyr His
        275                 280                 285

Ile Glu Gly Phe Gly Pro His Val Pro Pro Gly Ala Thr Leu Val Gln
    290                 295                 300

Leu Val Asp Asp Pro Gly Thr Ala Ala Trp Thr Pro Gln Gly Asp Ala
305                 310                 315                 320

Val Val Gly Asn Leu Lys Leu Ala Ala Arg Asp Leu Leu Ala Arg Pro
                325                 330                 335

Ala Pro Ala Glu Arg Pro Met Pro Ala Ala Arg Ala Pro Arg Glu Arg
            340                 345                 350

Val Ala Pro Pro Ala Ala Gly Glu Arg Met Ser Ala Ala Phe Val Leu
        355                 360                 365

Gln Thr Leu Ala Asp Leu Arg Asp Ala His Asp Ile Val Val Glu Glu
    370                 375                 380

Ala Pro Ser Ala Arg Pro Ile Met Gln Ala His Leu Pro Phe Thr Gln
385                 390                 395                 400

Ser Gly Thr Phe Tyr Thr Met Asp Ser Gly Leu Gly Tyr Gly Met
                405                 410                 415

Pro Ala Ala Val Gly Val Ala Leu Ala Gln Pro Gly Arg Arg Val Ile
            420                 425                 430

Gly Leu Ile Gly Asp Gly Ser Ser Leu Tyr Ser Ile Gln Ala Leu Trp
        435                 440                 445

Ser Ala Ala Gln Leu Arg Leu Pro Ile Thr Phe Val Ile Leu Asn Asn
    450                 455                 460

Arg Arg Tyr Ala Ala Leu Gln Asp Phe Ala Pro Val Phe Gly Phe Gly
465                 470                 475                 480

Pro Asp Asp Pro Val Gln Gly Thr Asp Leu Pro Asp Leu Asp Phe Val
                485                 490                 495

Ala Leu Ala Ala Ala Phe Gly Cys Arg Gly Val Arg Val Asp Asp His
            500                 505                 510

Ala Arg Leu Arg Asp Thr Leu Ala Asp Ala Leu Arg Ala Thr Ala Pro
        515                 520                 525

Val Val Val Asp Val Glu Ile Ala
    530                 535

<210> SEQ ID NO 45
<211> LENGTH: 540
<212> TYPE: PRT
<213> ORGANISM: Bradyrhizobium sp.

<400> SEQUENCE: 45

Met Ala Lys Thr Thr Lys Thr Thr Thr Lys Pro Val Thr Val Lys Gln
1               5                   10                  15
```

```
Ala Thr Phe Glu Leu Leu Arg Ala Phe Gly Ile Lys Lys Val Phe Gly
             20                  25                  30

Asn Pro Gly Ser Thr Glu Leu Pro Phe Leu Ser Asp Trp Pro Asp Asp
             35                  40                  45

Ile Asp Tyr Val Leu Gly Leu Gln Glu Ala Ser Val Val Gly Met Ala
 50                  55                  60

Asp Gly Tyr Ala Gln Ala Thr Arg Asn Ala Gly Phe Val Asn Leu His
 65                  70                  75                  80

Ser Ala Ala Gly Val Gly Asn Ala Leu Gly Asn Ile Tyr Thr Ala His
                 85                  90                  95

Arg Asn Gln Thr Pro Leu Val Ile Thr Ala Gly Gln Gln Ala Arg Ala
             100                 105                 110

Ile Leu Pro Leu Gln Ala Phe Leu Tyr Ala Glu Arg Ala Ser Glu Phe
             115                 120                 125

Pro Arg Pro Tyr Val Lys Tyr Ser Val Glu Pro Ala Arg Pro Glu Asp
             130                 135                 140

Val Pro Gly Ala Ile Ala Arg Ala Tyr Tyr Thr Ala Met Gln Pro Pro
145                 150                 155                 160

Cys Gly Pro Thr Phe Val Ser Ile Pro Ile Asp Asp Trp Met His Pro
                 165                 170                 175

Ala Gln Pro Val Ser Ala Arg Lys Val Ser Arg Glu Leu Gly Pro Asp
             180                 185                 190

Arg Ala Ala Met Asp Glu Leu Val Ala Ala Leu Thr Ala Ala Arg Asn
             195                 200                 205

Pro Ala Leu Val Val Gly Pro Gly Val Asp Arg Ala Gly Cys Val Thr
210                 215                 220

Leu Met Val Gln Leu Ala Glu Arg Ala Lys Ala Gly Val Trp Val Ser
225                 230                 235                 240

Pro Phe Ser Ala Arg Cys Ser Phe Pro Glu Arg His Pro Leu Phe Gln
                 245                 250                 255

Gly Phe Leu His Ala Ser Pro Gly Gln Leu Ser Asp Ala Leu Lys Pro
             260                 265                 270

His Asp Leu Val Leu Val Ile Gly Ala Pro Val Phe Thr Phe His Val
             275                 280                 285

Glu Gly His Ala Ala Ile Phe Asp Gly Ala Thr Ala Ile Tyr Gln Ile
290                 295                 300

Thr Asp Asp Ala Asp Gly Ala Ala Val Pro Pro Ile Ser Thr Ser Ile
305                 310                 315                 320

Ile Ala Thr Met Arg Pro Ala Leu Leu Leu Leu Glu Leu Leu Pro
                 325                 330                 335

Glu Thr Lys Arg Ala Ala Pro Gln Ala Arg Val Leu Pro Glu Ala Pro
             340                 345                 350

Lys Pro Ser Asp Pro Ile Pro Val Asp Tyr Leu Leu His Thr Leu Gly
             355                 360                 365

Gln Ala Leu Pro Ala Gly Ala Ala Leu Val Glu Glu Ile Pro Ser His
             370                 375                 380

Arg Pro Leu Met His Lys Phe Met Pro Met Pro Gly Ala Asp Ser Phe
385                 390                 395                 400

Tyr Thr Met Ser Ser Gly Gly Leu Gly Tyr Ser Leu Pro Ala Ala Val
                 405                 410                 415

Gly Met Ala Leu Gly Arg Pro Lys Asp Arg Ile Val Cys Leu Ile Gly
                 420                 425                 430

Asp Gly Ser Ala Met Tyr Ser Leu Gln Ala Leu Trp Thr Ala Ala Gln
```

```
            435                 440                 445
Arg Arg Leu Pro Met Thr Val Val Ile Asn Asn Ser Gly Tyr Gly
    450                 455                 460

Ala Met Arg Ser Phe Ser Gln Val Met Gln Val Arg Asn Val Pro Gly
465                 470                 475                 480

Leu Glu Leu Pro Gly Leu Asp Phe Val Lys Leu Ala Glu Gly Met Gly
                485                 490                 495

Cys Glu Ala Val Arg Val Ser Arg Ser Ala Glu Leu Pro Ala Ala Leu
                500                 505                 510

Ala Arg Gly Leu Ala His Asp Gly Pro Ser Leu Val Glu Val Met Val
                515                 520                 525

Asp Ser Ala Val Pro Leu Leu Tyr Ala Gln Lys Ser
                530                 535                 540

<210> SEQ ID NO 46
<211> LENGTH: 540
<212> TYPE: PRT
<213> ORGANISM: Bradyrhizobium japonicm

<400> SEQUENCE: 46

Met Ser Lys Asn Gly Lys Thr Gly Ser Lys Ser Val Thr Val Lys Gln
1               5                   10                  15

Ala Thr Ile Asp Leu Leu Arg Ala Phe Gly Ile Asp Arg Val Phe Gly
                20                  25                  30

Asn Pro Gly Ser Thr Glu Leu Pro Phe Leu Ser Asp Trp Pro Asp Asp
            35                  40                  45

Ile Asp Tyr Val Leu Ala Leu Gln Glu Ala Ser Ala Val Gly Met Ala
50                  55                  60

Asp Gly Tyr Ala Gln Ala Thr Arg Asn Ala Gly Phe Val Asn Leu His
65                  70                  75                  80

Ser Ala Ala Gly Val Gly Asn Ala Leu Gly Asn Ile Tyr Thr Ala His
                85                  90                  95

Arg Asn Gln Thr Pro Leu Val Ile Thr Ala Gly Gln Gln Ala Arg Ser
                100                 105                 110

Ile Leu Pro Leu Gln Ala Phe Leu Tyr Ala Glu Arg Ala Ser Glu Phe
            115                 120                 125

Pro Arg Pro Tyr Val Lys Tyr Ser Val Glu Pro Ala Arg Pro Glu Asp
130                 135                 140

Val Pro Ala Ala Ile Ala Arg Ala Tyr Tyr Thr Ala Met Gln Pro Pro
145                 150                 155                 160

Cys Gly Pro Thr Phe Val Ser Ile Pro Ile Asp Asp Trp Thr His Ala
                165                 170                 175

Thr Ala Pro Val Glu Ala Arg Lys Val Ser Arg Glu Ile Gly Pro Glu
            180                 185                 190

Arg Glu Ala Met Lys Ala Leu Val Ala Ala Phe Gly Ser Ala Lys His
        195                 200                 205

Pro Ala Leu Val Val Gly Pro Gly Val Asp Arg Ala Gly Ala Val Asp
    210                 215                 220

Leu Met Val Arg Val Ala Glu Lys Ala Lys Ala Ser Val Trp Val Ser
225                 230                 235                 240

Pro Phe Ser Ala Arg Cys Ser Phe Pro Glu Arg His Pro Gln Phe Ala
                245                 250                 255

Gly Phe Leu His Ala Ser Pro Ala Gln Leu Ser Asp Ala Leu Arg Glu
            260                 265                 270
```

-continued

```
His Asp Leu Val Val Val Val Gly Ala Pro Val Phe Thr Phe His Val
        275                 280                 285

Glu Gly His Ala Ala Ile Phe Asp Gly Gly Ala Thr Ile Phe Gln Ile
    290                 295                 300

Thr Asp Asp Pro Asp Ala Ala Ala Val Thr Pro Val Gly Thr Ser Ile
305                 310                 315                 320

Val Ala Thr Met Lys Pro Ala Leu Ser Leu Leu Leu Asp Leu Leu Pro
                325                 330                 335

Glu Ser Lys Arg Ala Thr Pro Lys Gly Arg Thr Leu Pro Pro Ala Pro
            340                 345                 350

Gln Ala Ala Asp Pro Leu Pro Val Glu Phe Leu Leu His Ser Leu Ala
        355                 360                 365

Gln Ala Met Pro Asp Gly Thr Ser Leu Val Glu Glu Val Pro Ser His
    370                 375                 380

Arg Pro Ala Met Gln Lys Phe Met Pro Met Leu Gly Gln Asp Ser Phe
385                 390                 395                 400

Tyr Thr Met Ser Ser Gly Gly Leu Gly Tyr Ser Leu Pro Ala Ala Val
                405                 410                 415

Gly Met Ala Leu Gly Lys Pro Lys Ser Arg Thr Val Cys Leu Ile Gly
            420                 425                 430

Asp Gly Ser Ala Met Tyr Ser Ile Gln Ala Leu Trp Thr Ala Ala Gln
        435                 440                 445

Arg Lys Leu Pro Leu Thr Val Val Val Ile Asn Asn Ser Gly Tyr Gly
    450                 455                 460

Ala Met Arg Ser Phe Ser Gln Val Met Gln Val Arg Asn Val Pro Gly
465                 470                 475                 480

Leu Glu Leu Pro Gly Ile Asp Phe Val Arg Leu Ala Glu Gly Met Gly
                485                 490                 495

Cys His Ala Val Arg Val Ser Arg Ala Ala Glu Leu Gly Glu Thr Leu
            500                 505                 510

Lys Arg Gly Met Ala Phe Glu Gly Thr Ser Leu Val Glu Val Ile Val
        515                 520                 525

Asp Ser Ala Val Pro Val Leu Tyr Gly Gln Lys His
    530                 535                 540

<210> SEQ ID NO 47
<211> LENGTH: 534
<212> TYPE: PRT
<213> ORGANISM: Burkholderia cenocepacia

<400> SEQUENCE: 47

Met Ser Gly His Pro Pro Pro Ser Ala Ser Ile Thr Val Arg Asp Ala
1               5                   10                  15

Val Val Asp Leu Leu Arg Gln Phe Gly Ile Asp Arg Val Phe Gly Asn
            20                  25                  30

Pro Gly Ser Thr Glu Leu Pro Met Phe Arg Asp Phe Pro Asp Asp Phe
        35                  40                  45

Arg Tyr Val Leu Gly Leu His Glu Ala Val Val Val Gly Met Ala Asp
    50                  55                  60

Gly His Ala Gln Ala Thr Gly Asn Ala Ala Val Val Asn Leu His Ser
65                  70                  75                  80

Ala Ala Gly Val Gly Asn Ala Met Gly Asn Leu Phe Thr Ala Phe Lys
                85                  90                  95

Asn Arg Thr Pro Leu Ile Val Thr Ala Gly Gln Gln Ala Arg Ala Ile
            100                 105                 110
```

```
Leu Pro Phe Asp Pro Phe Leu Gly Ala Thr Gln Ala Ala Glu Leu Pro
            115                 120                 125

Lys Pro Tyr Val Lys Trp Ser Ile Glu Pro Ala Arg Ala Gln Asp Val
130                 135                 140

Pro Ala Ala Ile Ala Arg Ala Tyr Arg Ile Ala Met Gln Glu Pro Arg
145                 150                 155                 160

Gly Pro Val Phe Val Ser Ile Pro Val Asp Asp Trp Asp Gln Pro Ala
                165                 170                 175

Glu Arg Leu Pro Arg Arg Asp Val Ser Ser Ile Val Arg Pro Asp Pro
            180                 185                 190

Asp Ala Leu Ala Arg Leu Gly Asp Ala Leu Asp Ala Ala Arg Arg Pro
        195                 200                 205

Ala Phe Val Val Gly Ala Ala Val Asp Arg Ala Gly Ala Trp Asp Asp
    210                 215                 220

Val Val Arg Leu Ala Glu Arg His Arg Ala Arg Val Tyr Val Ala Pro
225                 230                 235                 240

Met Ser Gly Arg Cys Ser Phe Pro Glu Asp His Pro Leu Phe Ala Gly
                245                 250                 255

Phe Leu Pro Ala Ile Arg Glu Lys Ile Ile Ala Arg Leu Asp Gly His
            260                 265                 270

Asp Leu Val Phe Ala Phe Gly Ala Pro Ala Phe Thr Tyr His Ile Glu
        275                 280                 285

Gly Phe Gly Pro His Val Pro Pro Gly Ala Thr Leu Val Gln Leu Val
    290                 295                 300

Asp Asp Pro Gly Val Ala Ala Trp Thr Pro Ser Gly Asp Ala Val Val
305                 310                 315                 320

Gly Asn Leu Arg Leu Ala Ala Arg Asp Leu Leu Ala Arg Pro Ala Pro
                325                 330                 335

Pro Glu Arg Pro Met Pro Ala Ala Arg Ala Pro Arg Val Arg Val Asp
            340                 345                 350

Ala Pro Ala Ala Gly Glu Arg Met Ser Val Ala Phe Ala Leu Gln Thr
        355                 360                 365

Leu Ala Asp Val Arg Asp Ala Ser Asp Ile Val Glu Glu Ala Pro
    370                 375                 380

Ser Ala Arg Pro Val Met Gln Glu His Leu Pro Phe Thr Arg Ser Gly
385                 390                 395                 400

Thr Phe Tyr Thr Met Asp Ser Gly Leu Gly Tyr Gly Met Pro Ala
                405                 410                 415

Ala Val Gly Val Ala Leu Ala Gln Pro Gly Arg Arg Val Ile Gly Leu
                420                 425                 430

Ile Gly Asp Gly Ser Ser Leu Tyr Ser Ile Gln Ala Leu Trp Ser Ala
            435                 440                 445

Ala Gln Leu Lys Leu Pro Ile Thr Phe Val Ile Leu Asn Asn Arg Arg
        450                 455                 460

Tyr Ala Ala Leu Gln Asp Phe Ala Pro Val Phe Gly Phe Gly Pro Gly
465                 470                 475                 480

Asp Pro Val Gln Gly Thr Glu Leu Pro Asp Leu Asp Phe Val Ala Leu
                485                 490                 495

Ala Gln Gly Met Gly Cys Arg Gly Val Arg Val Ala Glu Ala Ala Lys
            500                 505                 510

Leu Arg Asp Thr Leu Thr Asp Ala Leu Arg Ala Ala Thr Pro Val Val
        515                 520                 525
```

```
Val Glu Val Glu Ile Ala
    530

<210> SEQ ID NO 48
<211> LENGTH: 555
<212> TYPE: PRT
<213> ORGANISM: Burkholderia cenocepacia

<400> SEQUENCE: 48

Met Asn Gly Leu Arg Phe Asp Thr Val Glu Thr Ala Lys Pro Ser Arg
1               5                   10                  15

Arg Arg Pro Ser Met Ser Gly Thr Pro Ser Gln Ser Ala Ala Pro Val
            20                  25                  30

Thr Val Arg Asp Ala Val Ile Asp Leu Phe Arg Gln Phe Gly Ile Asp
        35                  40                  45

Arg Val Phe Gly Asn Pro Gly Ser Thr Glu Leu Pro Met Phe Arg Asp
    50                  55                  60

Phe Pro Ala Asp Phe Arg Tyr Val Leu Gly Leu Gln Glu Ala Val Val
65                  70                  75                  80

Val Gly Met Ala Asp Gly His Ala Gln Ala Thr Gly Asn Ala Ala Val
                85                  90                  95

Val Asn Leu His Ser Ala Ala Gly Val Gly Asn Ala Met Gly Asn Leu
            100                 105                 110

Phe Thr Ala Phe Lys Asn Arg Ser Pro Leu Ile Val Thr Ala Gly Gln
        115                 120                 125

Gln Ala Arg Ala Ile Leu Pro Phe Asp Pro Phe Leu Gly Ala Thr Gln
    130                 135                 140

Ala Ala Glu Leu Pro Lys Pro Tyr Val Lys Trp Ser Ile Glu Pro Ala
145                 150                 155                 160

Arg Ala Gln Asp Val Pro Ala Ala Ile Ala Arg Ala Tyr Arg Ile Ala
                165                 170                 175

Met Gln Glu Pro Arg Gly Pro Val Phe Val Ser Ile Pro Val Asp Asp
            180                 185                 190

Trp Asp Gln Pro Ala Glu Leu Leu Pro Arg Arg Asp Val Ser Ser Ile
        195                 200                 205

Val Arg Pro Asp Pro Asp Ala Leu Ala Arg Leu Gly Asp Val Leu Asp
    210                 215                 220

Ala Ala Arg Arg Pro Ala Phe Val Gly Ala Ala Val Asp Arg Ala
225                 230                 235                 240

Gly Ala Trp Asp Val Val Arg Leu Ala Glu Arg His Arg Ala Arg
                245                 250                 255

Val Tyr Val Ala Pro Met Ser Gly Arg Cys Ser Phe Pro Glu Asp His
            260                 265                 270

Pro Leu Phe Ala Gly Phe Leu Pro Ala Ile Arg Glu Lys Ile Val Ala
        275                 280                 285

Arg Leu Asp Gly His Asp Leu Val Phe Ala Phe Gly Ala Pro Ala Phe
    290                 295                 300

Thr Tyr His Ile Glu Gly Phe Gly Pro His Val Pro Pro Gly Ala Thr
305                 310                 315                 320

Leu Val Gln Leu Val Asp Asp Pro Gly Val Ala Ala Trp Thr Pro Ser
                325                 330                 335

Gly Asp Ala Val Val Gly Asn Val Arg Leu Ala Ala Arg Asp Leu Leu
            340                 345                 350

Ala Arg Pro Ala Pro Pro Glu Arg Pro Met Pro Ala Pro Arg Ala Pro
        355                 360                 365
```

```
Arg Leu Arg Val Asp Ala Pro Ala Gly Glu Arg Met Ser Val Ala
        370                 375                 380

Phe Ala Leu Gln Thr Leu Ala Asp Val Arg Asp Ala His Asp Ile Val
385                 390                 395                 400

Val Glu Glu Ala Pro Ser Ala Arg Pro Val Met Gln Glu His Leu Pro
                405                 410                 415

Phe Thr Arg Ser Gly Thr Phe Tyr Thr Met Asp Ser Gly Leu Gly
            420                 425                 430

Tyr Gly Met Pro Ala Ala Val Gly Val Ala Leu Ala Gln Pro Gly Arg
            435                 440                 445

Arg Val Ile Ala Leu Ile Gly Asp Gly Ser Ser Leu Tyr Ser Ile Gln
    450                 455                 460

Ala Leu Trp Ser Ala Ala Gln Leu Lys Leu Pro Ile Thr Phe Val Ile
465                 470                 475                 480

Leu Asn Asn Arg Arg Tyr Ala Ala Leu Gln Asp Phe Ala Pro Val Phe
                485                 490                 495

Gly Phe Gly Pro Gly Asp Pro Val Gln Gly Thr Asp Leu Pro Asp Leu
            500                 505                 510

Asp Phe Val Ala Leu Ala Gln Gly Met Gly Cys Arg Gly Val Arg Val
            515                 520                 525

Ala Glu Ala Ala Lys Leu Arg Asp Ala Leu Thr Asp Ala Leu Arg Ala
    530                 535                 540

Ala Thr Pro Val Ile Val Glu Val Glu Ile Ala
545                 550                 555

<210> SEQ ID NO 49
<211> LENGTH: 535
<212> TYPE: PRT
<213> ORGANISM: Burkholderia cenocepacia

<400> SEQUENCE: 49

Met Ser Gly Thr Pro Ser Gln Ser Ala Ala Pro Val Thr Val Arg Asp
1               5                   10                  15

Ala Val Ile Asp Leu Phe Arg Gln Phe Gly Ile As

```
                180             185             190
Pro Asp Ala Leu Ala Arg Leu Gly Asp Ala Leu Asp Ala Ala Arg Arg
            195                 200                 205

Pro Ala Phe Val Val Gly Ala Ala Val Asp Arg Ala Gly Ala Trp Asp
            210                 215                 220

Asp Val Val Arg Val Ala Glu Arg His Arg Ala Arg Val Tyr Val Ala
225                 230                 235                 240

Pro Met Ser Gly Arg Cys Ser Phe Pro Glu Asp His Pro Leu Phe Ala
            245                 250                 255

Gly Phe Leu Pro Ala Ile Arg Glu Lys Ile Val Ala Arg Leu Asp Gly
            260                 265                 270

His Asp Leu Val Phe Ala Phe Gly Ala Pro Ala Phe Thr Tyr His Ile
            275                 280                 285

Glu Gly Phe Gly Pro His Val Pro Pro Gly Ala Thr Leu Val Gln Leu
            290                 295                 300

Val Asp Asp Pro Gly Val Ala Ala Trp Thr Pro Ser Gly Asp Ala Val
305                 310                 315                 320

Val Gly Asn Leu Arg Leu Ala Ala Arg Asp Leu Leu Ala Arg Pro Ala
                325                 330                 335

Pro Pro Glu Arg Pro Met Pro Ala Pro Arg Ala Pro Arg Leu Arg Val
            340                 345                 350

Asp Ala Pro Ala Ala Gly Glu Arg Met Ser Val Ala Phe Ala Leu Gln
            355                 360                 365

Thr Leu Ala Asp Val Arg Asp Ala His Asp Ile Val Val Glu Glu Ala
370                 375                 380

Pro Ser Ala Arg Pro Val Met Gln Glu His Leu Pro Phe Thr Arg Ser
385                 390                 395                 400

Gly Thr Phe Tyr Thr Met Asp Ser Gly Gly Leu Gly Tyr Gly Met Pro
                405                 410                 415

Ala Ala Val Gly Val Ala Leu Ala Gln Pro Gly Arg Arg Val Ile Ala
                420                 425                 430

Leu Ile Gly Asp Gly Ser Ser Leu Tyr Ser Ile Gln Ala Leu Trp Ser
                435                 440                 445

Ala Ala Gln Leu Lys Leu Pro Ile Thr Phe Val Ile Leu Asn Asn Arg
            450                 455                 460

Arg Tyr Ala Ala Leu Gln Asp Phe Ala Pro Val Phe Gly Phe Gly Pro
465                 470                 475                 480

Gly Asp Pro Val Gln Gly Thr Asp Leu Pro Asp Leu Asp Phe Val Ala
                485                 490                 495

Leu Ala Gln Gly Met Gly Cys Arg Gly Val Arg Val Ala Glu Ala Ala
            500                 505                 510

Arg Leu Arg Asp Ala Leu Thr Asp Ala Leu Arg Ala Ala Thr Pro Val
            515                 520                 525

Val Val Glu Val Glu Ile Ala
530                 535

<210> SEQ ID NO 50
<211> LENGTH: 535
<212> TYPE: PRT
<213> ORGANISM: Burkholderia cenocepacia

<400> SEQUENCE: 50

Met Ser Gly Thr Pro Ser Gln Ser Ala Ala Pro Val Thr Val

```
Ala Val Ile Asp Leu Phe Arg Gln Phe Gly Ile Asp Arg Val Phe Gly
             20                  25                  30

Asn Pro Gly Ser Thr Glu Leu Pro Met Phe Arg Asp Phe Pro Ala Asp
         35                  40                  45

Phe Arg Tyr Val Leu Gly Leu Gln Glu Ala Val Val Val Gly Met Ala
 50                  55                  60

Asp Gly His Ala Gln Ala Thr Gly Asn Ala Ala Val Val Asn Leu His
 65                  70                  75                  80

Ser Ala Ala Gly Val Gly Asn Ala Met Gly Asn Leu Phe Thr Ala Phe
                 85                  90                  95

Lys Asn Arg Thr Pro Leu Ile Val Thr Ala Gly Gln Gln Ala Arg Ala
            100                 105                 110

Ile Leu Pro Phe Asp Pro Phe Leu Gly Ala Thr Gln Ala Ala Glu Leu
            115                 120                 125

Pro Lys Pro Tyr Val Lys Trp Ser Ile Glu Pro Ala Arg Ala Gln Asp
        130                 135                 140

Val Pro Ala Ala Ile Ala Arg Ala Tyr Arg Ile Ala Met Gln Glu Pro
145                 150                 155                 160

Arg Gly Pro Val Phe Val Ser Ile Pro Val Asp Asp Trp Asp Gln Pro
                165                 170                 175

Ala Glu Leu Leu Pro Arg Arg Asp Val Ser Ser Ile Val Arg Pro Asp
            180                 185                 190

Pro Asp Ala Leu Ala Arg Leu Gly Asp Ala Leu Asp Ala Ala Arg Arg
        195                 200                 205

Pro Ala Phe Val Val Gly Ala Val Asp Arg Ala Gly Ala Trp Asp
210                 215                 220

Asp Val Val Arg Leu Ala Glu Arg His Arg Ala Arg Val Tyr Val Ala
225                 230                 235                 240

Pro Met Ser Gly Arg Cys Ser Phe Pro Glu Asp His Pro Leu Phe Ala
                245                 250                 255

Gly Phe Leu Pro Ala Ile Arg Glu Lys Ile Val Ala Arg Leu Asp Gly
            260                 265                 270

His Asp Leu Val Phe Ala Phe Gly Ala Pro Ala Phe Thr Tyr His Ile
        275                 280                 285

Glu Gly Phe Gly Pro His Val Pro Pro Gly Ala Thr Leu Val Gln Leu
290                 295                 300

Val Asp Asp Pro Gly Val Ala Ala Trp Thr Pro Ser Gly Asp Ala Val
305                 310                 315                 320

Val Gly Asn Leu Arg Leu Ala Ala Arg Asp Leu Leu Ala Arg Pro Ala
                325                 330                 335

Pro Pro Glu Arg Pro Met Pro Ala Pro Arg Ala Pro Arg Leu Arg Val
            340                 345                 350

Asp Ala Pro Ala Ala Gly Glu Arg Met Ser Val Ala Phe Ala Leu Gln
        355                 360                 365

Thr Leu Ala Asp Val Arg Asp Ala His Asp Ile Val Val Glu Glu Ala
    370                 375                 380

Pro Ser Ala Arg Pro Val Met Gln Glu His Leu Pro Phe Thr Arg Ser
385                 390                 395                 400

Gly Thr Phe Tyr Thr Met Asp Ser Gly Leu Gly Tyr Gly Met Pro
                405                 410                 415

Ala Ala Val Gly Val Ala Phe Ala Gln Pro Gly Arg Arg Val Ile Ala
            420                 425                 430

Leu Ile Gly Asp Gly Ser Ser Leu Tyr Ser Ile Gln Ala Leu Trp Ser
```

```
                435             440             445
Ala Ala Gln Leu Lys Leu Pro Ile Thr Phe Val Ile Leu Asn Asn Arg
    450             455             460

Arg Tyr Ala Ala Leu Gln Asp Phe Ala Pro Val Phe Gly Phe Gly Pro
465             470             475             480

Gly Asp Pro Val Gln Gly Thr Asp Leu Pro Asp Leu Asp Phe Val Ala
                485             490             495

Leu Ala Gln Gly Met Gly Cys Arg Gly Val Arg Val Ala Glu Ala Ala
            500             505             510

Arg Leu Arg Asp Ala Leu Thr Asp Ala Leu Arg Ala Ala Thr Pro Val
        515             520             525

Val Val Glu Val Glu Ile Ala
    530             535

<210> SEQ ID NO 51
<211> LENGTH: 542
<212> TYPE: PRT
<213> ORGANISM: Bradyrhizobium japonicum

<400> SEQUENCE: 51

Met Ala Thr Gly Thr Asp Thr Phe Glu Gln Arg Arg Val Thr Ala Pro
1               5                   10                  15

Thr Val Arg Asp Ala Val Val Asp Leu Leu Arg Arg Leu Asn Met Thr
                20                  25                  30

Ser Val Phe Ala Asn Pro Gly Ser Thr Glu Leu Pro Leu Phe Arg Asn
            35                  40                  45

Phe Pro Asp Asp Phe Arg Tyr Val Leu Gly Leu Gln Glu Ala Val Val
    50                  55                  60

Val Gly Met Ala Asp Gly Phe Ala Gln Ala Thr Arg Asn Ala Ala Phe
65                  70                  75                  80

Val Asn Leu His Ser Ala Ala Gly Val Gly Asn Ala Met Gly Asn Ile
                85                  90                  95

Phe Thr Ala Phe Lys Asn Arg Thr Pro Leu Val Ile Thr Ala Gly Gln
            100                 105                 110

Gln Ala Arg Ser Ile Leu Pro Phe Asp Pro Phe Leu Ala Ser Arg Glu
    115                 120                 125

Ala Thr Glu Leu Pro Lys Pro Tyr Val Lys Trp Ser Ile Glu Pro Ala
130                 135                 140

Arg Ala Glu Asp Val Pro His Ala Ile Ala Arg Ala Tyr Tyr Ile Ala
145                 150                 155                 160

Met Thr Gln Pro Cys Gly Pro Val Leu Val Ser Val Pro Val Asp Asp
                165                 170                 175

Trp Asp Arg Pro Ala Glu Tyr Leu Pro Thr Arg Thr Val Ser Gln Gln
            180                 185                 190

Val Arg Pro Asp Pro Ala Ile Leu Asp Gln Ile Gly Ser Ala Leu Asp
    195                 200                 205

Arg Ser Lys Arg Pro Ala Phe Val Val Gly Ala Ala Ala Asp Arg Asp
210                 215                 220

Gly Ala Phe Asn Glu Val Arg Gln Leu Ala Glu Ala His Asn Ala Arg
225                 230                 235                 240

Val Phe Thr Ala Pro Met Ser Gly Arg Cys Ser Phe Pro Glu Asp His
                245                 250                 255

Arg Leu Phe Ala Gly Phe Leu Pro Ala Ile Arg Glu Lys Ile Val Arg
            260                 265                 270
```

```
Leu Leu Asp Gly His Asp Leu Val Phe Ala Ile Gly Ala Pro Ala Phe
            275                 280                 285

Ser Tyr His Val Glu Gly Phe Gly Pro His Leu Pro Asp Gly Ala Glu
        290                 295                 300

Leu Phe Gln Leu Thr Asp Asp Pro Gln Thr Ala Ala Trp Thr Pro Glu
305                 310                 315                 320

Gly Met Ala Ala Val Gly Ser Val Arg Leu Gly Leu Leu Asp Leu Leu
                325                 330                 335

Ala Arg Ala Thr Pro Pro Ile Arg Val Thr Pro Pro Ala Arg Thr Ile
            340                 345                 350

Ala Arg Arg Val Glu Pro Thr Thr Pro Leu Ser Thr Ala Phe Val Met
        355                 360                 365

Gln Thr Ile Ala Asp Met Lys Pro Ala Asp Gly Ile Ile Val Glu Glu
    370                 375                 380

Ala Pro Gly Ala Arg Ser Val Met Gln Ala His Leu Pro Ile Thr Gln
385                 390                 395                 400

Ser Glu Ala Phe Tyr Thr Met Asp Ser Gly Leu Gly Tyr Gly Met
                405                 410                 415

Pro Ala Ala Val Gly Val Ala Leu Gly Lys Pro Gly Arg Pro Val Ile
                420                 425                 430

Ala Leu Met Gly Asp Gly Ser Ser Leu Tyr Ser Ile Gln Ala Ile Trp
            435                 440                 445

Ser Ala Ala Gln Leu Ser Leu Pro Val Thr Phe Val Ile Leu Lys Asn
        450                 455                 460

Gly Arg Tyr Ala Ala Leu Gln Asp Phe Ala Pro Val Phe Gly Phe Gly
465                 470                 475                 480

Ser Gln Glu His Val Gln Gly Thr Asp Leu Pro Gly Leu Asp Phe Val
                485                 490                 495

Ser Ile Ala Arg Gly Leu Gly Cys Ser Ala Ile His Val Glu Thr Ala
            500                 505                 510

Lys Gly Leu His Asp Ala Leu Val Lys Ala Phe Ser Ser Lys Arg Pro
        515                 520                 525

Thr Leu Val Glu Val Glu Val Glu Asp Arg Asp Leu Gln Lys
    530                 535                 540

<210> SEQ ID NO 52
<211> LENGTH: 542
<212> TYPE: PRT
<213> ORGANISM: Rhodopseudomonas palustris

<400> SEQUENCE: 52

Met Pro Ala Lys Lys Ser Lys Gln Pro Ser Ala Ala Val Thr Thr Val
1               5                   10                  15

Lys Ser Ala Thr Leu Asp Leu Leu Arg Ala Phe Lys Ile Asp Lys Val
            20                  25                  30

Phe Gly Asn Pro Gly Ser Thr Glu Leu Pro Phe Leu Ser Asp Trp Pro
        35                  40                  45

Asp Asp Ile Asp Tyr Val Leu Ala Leu Gln Glu Ala Ser Ala Val Ala
    50                  55                  60

Met Ala Asp Gly Tyr Ala Gln Ala Thr Arg Asn Ala Gly Phe Val Asn
65                  70                  75                  80

Leu His Ser Ala Ala Gly Val Gly Asn Ala Leu Gly Asn Ile Tyr Ser
                85                  90                  95

Ala Phe Lys Asn Gln Thr Pro Leu Val Ile Thr Ala Gly Gln Gln Ala
                100                 105                 110
```

```
Arg Ser Leu Leu Pro Leu Gln Ala Phe Leu Gly Ala Glu Arg Ala Ser
        115                 120                 125

Glu Phe Pro Arg Pro Tyr Val Lys Tyr Ser Val Glu Pro Ala Arg Ala
    130                 135                 140

Glu Asp Val Pro Ala Ala Ile Ala Arg Ala Tyr Tyr Val Ala Met Gln
145                 150                 155                 160

Pro Pro Cys Gly Pro Thr Phe Val Ser Val Pro Ile Asp Asp Trp Ala
                165                 170                 175

Arg Pro Ala Ala Pro Val Pro Pro Arg Thr Ile Thr Arg Glu Ile Gly
                180                 185                 190

Pro Asp Arg Ser Ala Met Gln Val Leu Ala Asp Thr Leu Ala Asn Ala
            195                 200                 205

Lys Lys Pro Ala Leu Val Val Gly Pro Ala Ile Asp Arg Ala Ala Ala
        210                 215                 220

Val Gly Leu Met Ala Arg Leu Ala Glu Arg Ala Lys Ala Pro Val Trp
225                 230                 235                 240

Val Ser Pro Phe Ser Ala Arg Cys Ser Phe Pro Glu Arg His Pro Leu
                245                 250                 255

Phe Ala Gly Phe Leu Pro Ala Ser Pro Gly Gln Leu Ser Glu Thr Leu
                260                 265                 270

Gly Ala Tyr Asp Val Ile Val Leu Ile Gly Ala Pro Val Phe Thr Phe
            275                 280                 285

His Val Glu Gly His Ala Ala Ile Phe Asp Gly Ala Ser Gln Leu Phe
        290                 295                 300

Gln Ile Thr Asp Asp Ala Glu Ala Ala Ser Val Thr Pro Leu Gly Ala
305                 310                 315                 320

Ser Ile Ile Ala Thr Met Thr Pro Ala Leu Thr Leu Leu Glu Leu
                325                 330                 335

Leu Pro Glu Thr Lys Arg Ala Ala Pro Pro Ala Arg Ala Val Pro Pro
                340                 345                 350

Ala Pro Arg Pro Ala Glu Pro Met Pro Val Glu Tyr Leu Leu His Thr
            355                 360                 365

Leu Arg Ala Ala Met Pro Glu Ser Ala Met Leu Val Glu Glu Ala Pro
    370                 375                 380

Ser His Arg Pro Ala Met Gln Thr Tyr Met Pro Met Pro Gly Gln Asp
385                 390                 395                 400

Ser Phe Ala Thr Met Ala Ser Gly Gly Leu Gly Trp Ser Leu Pro Ala
                405                 410                 415

Ser Val Gly Phe Ala Leu Ala His Pro Asn Arg Arg Thr Val Cys Leu
                420                 425                 430

Ile Gly Asp Gly Ser Ala Met Tyr Ser Ile Gln Ala Leu Trp Thr Ala
            435                 440                 445

Ala Gln Arg Lys Leu Pro Leu Thr Val Val Leu Asn Asn Gly Gly
        450                 455                 460

Tyr Gly Ala Met Arg Ser Phe Ser Gln Val Met Gln Val Arg Asn Val
465                 470                 475                 480

Pro Gly Leu Glu Leu Pro Gly Ile Asp Phe Thr Ala Leu Ala Gln Ser
                485                 490                 495

Leu Gly Cys Asp Ala Val Arg Val Thr Arg Ser Glu Glu Leu Ala Pro
            500                 505                 510

Ala Leu Thr Arg Ala Leu Ala Trp Asp Gly Val Ser Leu Val Glu Val
        515                 520                 525
```

```
Met Leu Asp Thr Ser Val Pro Met Leu Tyr Ala Arg Asn Gly
    530                 535                 540

<210> SEQ ID NO 53
<211> LENGTH: 535
<212> TYPE: PRT
<213> ORGANISM: Burkholderia sp.

<400> SEQUENCE: 53

Met Ser Gly Tyr Gln Pro Pro Ser Ala Ala Pro Ile Thr Val Arg Asp
1               5                   10                  15

Ala Val Ile Asp Leu Leu Arg Gln Phe Gly Ile Asp Arg Val Phe Gly
            20                  25                  30

Asn Pro Gly Ser Thr Glu Leu Pro Met Phe Arg Asp Phe Pro Asp Asp
            35                  40                  45

Phe Arg Tyr Val Leu Gly Leu His Glu Ala Val Val Gly Met Ala
    50                  55                  60

Asp Gly His Ala Gln Ala Thr Gly Asn Ala Ala Val Val Asn Leu His
65                  70                  75                  80

Ser Ala Ala Gly Val Gly Asn Ala Met Gly Asn Leu Phe Thr Ala Phe
                85                  90                  95

Lys Asn Arg Thr Pro Leu Ile Val Thr Ala Gly Gln Gln Ala Arg Ala
            100                 105                 110

Ile Leu Pro Phe Asp Pro Phe Leu Gly Ala Thr Gln Ala Ala Glu Leu
        115                 120                 125

Pro Lys Pro Tyr Val Lys Trp Ser Ile Glu Pro Ala Arg Ala Gln Asp
    130                 135                 140

Val Pro Ala Ala Ile Ala Arg Ala Tyr Arg Ile Ala Met Gln Glu Pro
145                 150                 155                 160

Arg Gly Pro Val Phe Val Ser Ile Pro Val Asp Asp Trp Asp Gln Pro
                165                 170                 175

Ala Glu Leu Leu Pro Arg Arg Asp Val Ser Ser Val Val Arg Pro Asp
            180                 185                 190

Pro Asp Ala Leu Ala Arg Leu Gly Asp Thr Leu Asp Ala Ala Arg Arg
        195                 200                 205

Pro Ala Phe Val Val Gly Ala Ala Val Asp Arg Ala Gly Ala Trp Asp
    210                 215                 220

Asp Val Val Arg Leu Ala Glu Arg His Arg Ala Arg Val Tyr Val Ala
225                 230                 235                 240

Pro Met Ser Gly Arg Cys Ser Phe Pro Glu Asp His Pro Leu Phe Ala
                245                 250                 255

Gly Phe Leu Pro Ala Ile Arg Glu Lys Ile Val Ala Arg Leu Asp Gly
            260                 265                 270

His Asp Leu Val Phe Ala Phe Gly Ala Pro Ala Phe Thr Tyr His Ile
        275                 280                 285

Glu Gly Phe Gly Pro His Val Pro Pro Gly Ala Thr Leu Val Gln Leu
    290                 295                 300

Val Asp Asp Pro Gly Ile Ala Ala Trp Thr Pro Ser Gly Asp Ala Val
305                 310                 315                 320

Val Gly Asn Leu Arg Leu Ala Ala Arg Asp Leu Leu Ala Arg Pro Ala
                325                 330                 335

Pro Pro Glu Arg Pro Met Pro Ala Pro Arg Pro Arg Ala Arg Val
            340                 345                 350

Glu Pro Pro Ala Ala Gly Glu Arg Met Ser Val Ala Phe Ala Leu Gln
        355                 360                 365
```

```
Thr Leu Ala Asp Val Arg Asp Ala His Asp Ile Val Glu Glu Ala
    370                 375                 380

Pro Ser Ala Arg Ala Val Met Gln Glu His Leu Pro Phe Thr His Ser
385                 390                 395                 400

Gly Thr Phe Tyr Thr Met Asp Ser Gly Leu Gly Tyr Gly Met Pro
                405                 410                 415

Ala Ala Val Gly Val Ala Leu Ala His Pro Gly Arg Val Ile Gly
                420                 425                 430

Leu Ile Gly Asp Gly Ser Ser Leu Tyr Ser Ile Gln Ala Leu Trp Ser
                435                 440                 445

Ala Ala Gln Leu Lys Leu Pro Ile Thr Phe Val Ile Leu Asn Asn Arg
    450                 455                 460

Arg Tyr Ala Ala Leu Gln Asp Phe Ala Pro Val Phe Gly Phe Gly Pro
465                 470                 475                 480

Asp Asp Pro Val Gln Gly Thr Asp Leu Pro Asn Leu Asp Phe Val Ala
                485                 490                 495

Leu Ala Gln Gly Met Gly Cys Arg Gly Val Arg Val Thr Asp Ala Ala
                500                 505                 510

His Leu Arg Asp Thr Leu Thr Glu Ala Leu Arg Ala Ala Thr Pro Val
    515                 520                 525

Val Val Glu Val Glu Ile Ala
    530                 535

<210> SEQ ID NO 54
<211> LENGTH: 548
<212> TYPE: PRT
<213> ORGANISM: Delftia acidovorans

<400> SEQUENCE: 54

Met Gln Ala Pro Thr Thr Pro Arg Ser Gln Pro Ala Glu Ala Ser Ser
1               5                   10                  15

Ser Thr Ala Thr Ser Thr Ala Thr Tyr Thr Val Arg His Ala Val Ile
                20                  25                  30

Ala Met Leu Arg Glu Leu Gly Met Thr Arg Ile Phe Gly Asn Pro Gly
            35                  40                  45

Ser Thr Glu Leu Pro Leu Phe Arg Asp Tyr Pro Glu Asp Phe Ser Tyr
        50                  55                  60

Val Leu Gly Leu Gln Glu Thr Val Val Val Gly Met Ala Asp Gly His
65                  70                  75                  80

Ala Gln Ala Thr Arg Asn Ala Ser Phe Val Asn Leu His Ser Ala Ala
                85                  90                  95

Gly Val Gly His Ala Met Ala Asn Ile Phe Thr Ala Phe Lys Asn Arg
            100                 105                 110

Thr Pro Leu Val Ile Thr Ala Gly Gln Gln Ala Arg Ser Leu Leu Gln
        115                 120                 125

Phe Asp Pro Phe Leu His Ser Ser Gln Ala Ala Glu Leu Pro Lys Pro
    130                 135                 140

Tyr Val Lys Trp Ser Cys Glu Pro Ala Arg Ala Glu Asp Val Pro Gln
145                 150                 155                 160

Ala Leu Ala Arg Ala Tyr Tyr Ile Ala Met Gln Glu Pro Arg Gly Pro
                165                 170                 175

Val Leu Val Ser Ile Pro Ala Asp Asp Trp Asp Lys Pro Ala Glu Pro
            180                 185                 190

Val Thr Leu Arg His Val Gly Phe Glu Thr Arg Pro Asp Pro Arg Thr
```

```
            195                 200                 205
Leu Asp Leu Ile Gly Gln Ala Leu Asp Ala Ala Arg Ala Pro Ala Leu
210                 215                 220

Val Val Gly Ala Ala Val Asp Arg Ala Gln Gly Trp Asp Ala Val Val
225                 230                 235                 240

Ala Leu Ala Glu Arg His Gln Ala Arg Val Phe Val Ala Pro Met Ser
                245                 250                 255

Gly Arg Cys Ser Phe Pro Glu Asp His Pro Leu Phe Ala Gly Phe Leu
            260                 265                 270

Pro Ala Met Arg Glu Arg Ile Val Gln Leu Leu Ser Gly His Asp Val
                275                 280                 285

Val Phe Ala Val Gly Ala Ala Phe Thr Tyr His Val Glu Gly Glu
290                 295                 300

Gly Pro His Ile Pro Glu Gly Thr Ala Leu Tyr Gln Leu Ile Glu Asp
305                 310                 315                 320

Pro Ala Ile Ala Ala Trp Ala Pro Val Gly Thr Ala Ala Val Gly Asn
                325                 330                 335

Val Arg Met Gly Val Glu Glu Leu Leu Gln Arg Pro Ala Pro Ala Pro
                340                 345                 350

Arg Gln Ala Pro Ala Pro Arg Pro Ala Ala Pro Val Pro Ala Ala Pro
                355                 360                 365

Ala Ala Gly Asp Arg Met Ser Val Ala Phe Ala Met His Thr Leu Ala
370                 375                 380

Gln Val Arg Asp Arg His Ser Ile Val Val Glu Glu Ala Pro Ser Ser
385                 390                 395                 400

Arg Ser Thr Ile Gln Thr Tyr Leu Pro Ile Phe His Ser Gly Thr Phe
                405                 410                 415

Tyr Thr Met Cys Ser Gly Gly Leu Gly His Ser Met Pro Ala Ala Val
                420                 425                 430

Gly Val Ala Leu Ala Lys Pro Glu Ala Lys Val Val Ala Val Ile Gly
                435                 440                 445

Asp Gly Ser Ala Met Tyr Ala Ile Gln Ala Leu Trp Ser Ala Ala Gln
450                 455                 460

Leu Arg Leu Pro Ile Ser Phe Val Ile Leu Lys Asn Arg Arg Tyr Ala
465                 470                 475                 480

Ala Leu Gln Asp Phe Ala His Val Phe Gly Tyr Arg Glu Gly Glu Lys
                485                 490                 495

Val Glu Gly Thr Glu Leu Pro Asp Ile Asp Phe Val Ala Leu Ala Arg
                500                 505                 510

Gly Gln Gly Cys Asp Gly Val His Val Glu Asn Ala Ala Glu Leu Ala
                515                 520                 525

Asp Val Leu Glu Arg Ala Leu Ala His Pro Lys Pro Ile Val Val Glu
                530                 535                 540

Val Glu Val Ala
545

<210> SEQ ID NO 55
<211> LENGTH: 560
<212> TYPE: PRT
<213> ORGANISM: Bradyrhizobium sp.

<400> SEQUENCE: 55

Met Pro Gly Thr Leu Asp Cys Phe Val Ala Ser Leu Leu Ala Met Thr
1               5                   10                  15
```

-continued

```
Ala Ile Arg Gly Thr Pro Leu Ala Lys Lys Thr Thr Lys Pro Val
            20                  25                  30

Thr Val Lys Gln Ala Thr Phe Asp Leu Leu Arg Ala Phe Gly Ile Lys
        35                  40                  45

Lys Val Phe Gly Asn Pro Gly Ser Thr Glu Leu Pro Phe Leu Ser Asp
 50                  55                  60

Trp Pro Asp Asp Ile Asp Tyr Val Leu Gly Leu Gln Glu Ala Ser Val
 65                  70                  75                  80

Val Gly Met Ala Asp Gly Tyr Ala Gln Ala Thr Arg Asn Ala Gly Phe
                85                  90                  95

Val Asn Leu His Ser Ala Ala Gly Val Gly Asn Ala Leu Gly Asn Ile
            100                 105                 110

Tyr Thr Ala His Arg Asn Gln Thr Pro Leu Val Ile Thr Ala Gly Gln
        115                 120                 125

Gln Ala Arg Ser Ile Leu Pro Leu Gln Ala Phe Leu Tyr Ala Glu Arg
    130                 135                 140

Pro Ser Glu Phe Pro Arg Pro Tyr Val Lys Tyr Ser Val Glu Pro Ala
145                 150                 155                 160

Arg Pro Glu Asp Val Pro Gly Ala Ile Ala Arg Ala Tyr Tyr Thr Ala
                165                 170                 175

Met Gln Pro Pro Cys Gly Pro Thr Phe Val Ser Ile Pro Ile Asp Asp
            180                 185                 190

Trp Met His Pro Ala Gln Pro Val Ala Ala Arg Lys Val Ser Arg Glu
        195                 200                 205

Leu Gly Pro Asp Arg Ala Ala Ile Glu Glu Leu Val Ala Ala Leu Gly
    210                 215                 220

Ala Ala Lys Asn Pro Ala Leu Val Val Gly Pro Gly Ile Asp Arg Ala
225                 230                 235                 240

Ala Cys Val Asp Leu Met Val Gln Val Ala Glu Lys Ala Lys Ala Gly
                245                 250                 255

Val Trp Val Ser Pro Phe Ser Ala Arg Cys Ser Phe Pro Glu Arg His
            260                 265                 270

Pro Gln Phe Gln Gly Phe Leu His Ala Ser Pro Gly Gln Leu Ser Glu
        275                 280                 285

Ala Leu Lys Pro Tyr Asp Ile Val Val Ile Gly Ala Pro Val Phe
    290                 295                 300

Thr Phe His Val Glu Gly His Ala Ala Ile Phe Asp Gly Ala Thr Thr
305                 310                 315                 320

Leu Tyr Gln Ile Thr Asp Asp Ala Glu Gly Ala Ser Val Pro Pro Ile
                325                 330                 335

Gly Thr Ser Ile Val Ala Thr Met Arg Pro Ala Leu Ser Leu Leu Arg
            340                 345                 350

Glu Leu Leu Pro Glu Ser Gln Arg Ala Ala Pro Lys Gly Arg Val Met
        355                 360                 365

Pro Glu Pro Pro Asp Ala Ser Asp Pro Ile Pro Val Asp Tyr Leu Leu
    370                 375                 380

His Thr Leu Ser Gln Ala Leu Pro Pro Gly Ala Ala Ile Val Glu Glu
385                 390                 395                 400

Ile Pro Ser His Arg Pro Val Met Tyr Lys Tyr Met Pro Met Pro Gly
                405                 410                 415

Ala Asp Ser Phe Tyr Thr Met Ala Ser Gly Gly Leu Gly Tyr Ser Leu
            420                 425                 430

Pro Ala Ser Val Gly Met Ala Leu Gly Arg Pro Asn Asp Arg Ile Val
```

```
            435                 440                 445
Cys Leu Ile Gly Asp Gly Ser Ala Met Tyr Ser Leu Gln Ala Leu Trp
450                 455                 460

Thr Ala Ala Gln Arg Lys Leu Arg Leu Thr Ile Val Val Ile Asn Asn
465                 470                 475                 480

Ser Gly Tyr Gly Ala Met Arg Ser Phe Ser Gln Val Met Gln Val Arg
                485                 490                 495

Asn Val Pro Gly Leu Glu Leu Pro Gly Leu Asp Phe Val Lys Leu Ala
                500                 505                 510

Glu Gly Leu Gly Cys Asp Ala Val Arg Val Ser Arg Ser Ala Asp Leu
            515                 520                 525

Pro Ala Ala Leu Ala Arg Gly Leu Ala His Asp Gly Thr Ser Leu Val
530                 535                 540

Glu Val Met Val Asp Ser Ala Val Pro Leu Leu Tyr Ala Gln Lys Arg
545                 550                 555                 560

<210> SEQ ID NO 56
<211> LENGTH: 346
<212> TYPE: PRT
<213> ORGANISM: Escherichia coli

<400> SEQUENCE: 56

Met Gln Asn Ile Ile Arg Lys Gly Gly Thr Met Lys Ala Ala Val Val
1               5                   10                  15

Thr Lys Asp His His Val Asp Val Thr Asp Lys Thr Leu Arg Ser Leu
                20                  25                  30

Lys His Gly Glu Ala Leu Leu Lys Met Glu Cys Cys Gly Val Cys His
            35                  40                  45

Thr Asp Leu His Val Lys Asn Gly Asp Phe Gly Asp Lys Thr Gly Val
50                  55                  60

Ile Leu Gly His Glu Gly Ile Gly Val Val Ala Glu Val Gly Pro Gly
65                  70                  75                  80

Val Thr Ser Leu Lys Pro Gly Asp Arg Ala Ser Val Ala Trp Phe Tyr
                85                  90                  95

Glu Gly Cys Gly His Cys Glu Tyr Cys Asn Ser Gly Asn Glu Thr Leu
            100                 105                 110

Cys Arg Ser Val Lys Asn Ala Gly Tyr Ser Val Asp Gly Gly Met Ala
        115                 120                 125

Glu Glu Cys Ile Val Ala Asp Tyr Ala Val Lys Val Pro Asp Gly
130                 135                 140

Leu Asp Ser Ala Ala Ser Ser Ile Thr Cys Ala Gly Val Thr Thr
145                 150                 155                 160

Tyr Lys Ala Val Lys Leu Ser Lys Ile Arg Pro Gly Gln Trp Ile Ala
                165                 170                 175

Ile Tyr Gly Leu Gly Gly Leu Gly Asn Leu Ala Leu Gln Tyr Ala Lys
            180                 185                 190

Asn Val Phe Asn Ala Lys Val Ile Ala Ile Asp Val Asn Asp Glu Gln
        195                 200                 205

Leu Lys Leu Ala Thr Glu Met Gly Ala Asp Leu Ala Ile Asn Ser Arg
210                 215                 220

Thr Glu Asp Ala Ala Lys Ile Val Gln Glu Lys Thr Gly Gly Ala His
225                 230                 235                 240

Ala Ala Val Val Thr Ala Val Ala Lys Ala Ala Phe Asn Ser Ala Val
                245                 250                 255
```

```
Asp Ala Val Arg Ala Gly Gly Arg Val Ala Val Gly Leu Pro Pro
            260                 265                 270

Glu Ser Met Ser Leu Asp Ile Pro Arg Leu Val Leu Asp Gly Ile Glu
        275                 280                 285

Val Val Gly Ser Leu Val Gly Thr Arg Gln Asp Leu Thr Glu Ala Phe
    290                 295                 300

Gln Phe Ala Ala Glu Gly Lys Val Val Pro Lys Val Ala Leu Arg Pro
305                 310                 315                 320

Leu Ala Asp Ile Asn Thr Ile Phe Thr Glu Met Glu Glu Gly Lys Ile
                325                 330                 335

Arg Gly Arg Met Val Ile Asp Phe Arg Arg
            340                 345

<210> SEQ ID NO 57
<211> LENGTH: 346
<212> TYPE: PRT
<213> ORGANISM: Escherichia coli

<400> SEQUENCE: 57

Met Gln Asn Ile Ile Arg Lys Gly Gly Thr Met Lys Ala Ala Val Val
1               5                   10                  15

Thr Lys Asp His His Val Asp Val Thr Asp Lys Thr Leu Arg Ser Leu
                20                  25                  30

Lys His Gly Glu Ala Leu Leu Lys Met Glu Cys Cys Gly Val Cys His
            35                  40                  45

Thr Asp Leu His Val Lys Asn Gly Asp Phe Gly Asp Lys Thr Gly Val
        50                  55                  60

Ile Leu Gly His Glu Gly Ile Gly Val Val Ala Glu Val Gly Pro Gly
65                  70                  75                  80

Val Thr Ser Leu Lys Pro Gly Asp Arg Ala Ser Val Ala Trp Phe Tyr
                85                  90                  95

Glu Gly Cys Gly His Cys Glu Tyr Cys Asn Ser Gly Asn Glu Thr Leu
            100                 105                 110

Cys Arg Ser Val Lys Asn Ala Gly Tyr Ser Val Asp Gly Gly Met Ala
        115                 120                 125

Glu Glu Cys Ile Val Val Ala Asp Tyr Ala Val Lys Val Pro Asp Gly
    130                 135                 140

Leu Asp Ser Ala Ala Ala Asn Ser Ile Thr Cys Ala Gly Val Thr Thr
145                 150                 155                 160

Tyr Lys Ala Val Lys Leu Ser Lys Ile Arg Pro Gly Gln Trp Ile Ala
                165                 170                 175

Ile Tyr Gly Leu Gly Gly Leu Gly Asn Leu Ala Leu Gln Tyr Ala Lys
            180                 185                 190

Asn Val Phe Asn Ala Lys Val Ile Ala Ile Asp Val Asn Asp Glu Gln
        195                 200                 205

Leu Lys Leu Ala Thr Glu Met Gly Ala Asp Leu Ala Ile Asn Ser Arg
    210                 215                 220

Thr Glu Asp Ala Ala Lys Ile Val Gln Glu Lys Thr Gly Gly Ala His
225                 230                 235                 240

Ala Ala Val Val Thr Ala Val Ala Lys Ala Ala Phe Asn Ser Ala Val
                245                 250                 255

Asp Ala Val Arg Ala Gly Gly Arg Val Ala Val Gly Leu Pro Pro
            260                 265                 270

Glu Ser Met Ser Leu Asp Ile Pro Arg Leu Val Leu Asp Gly Ile Glu
        275                 280                 285
```

```
Val Val Gly Ser Leu Val Gly Thr Arg Gln Asp Leu Thr Glu Ala Phe
        290                 295                 300

Gln Phe Ala Ala Glu Gly Lys Val Val Pro Lys Val Ala Leu Arg Pro
305                 310                 315                 320

Leu Ala Asp Ile Asn Thr Ile Phe Thr Glu Met Glu Glu Gly Lys Ile
                325                 330                 335

Arg Gly Arg Met Val Ile Asp Phe Arg Arg
                340                 345

<210> SEQ ID NO 58
<211> LENGTH: 346
<212> TYPE: PRT
<213> ORGANISM: Escherichia coli

<400> SEQUENCE: 58

Met Gln Asn Ile Ile Arg Lys Gly Gly Thr Met Lys Ala Ala Val Val
1               5                   10                  15

Thr Lys Asp His His Val Asp Val Thr Asp Lys Thr Leu Arg Ser Leu
                20                  25                  30

Lys His Gly Glu Ala Leu Leu Lys Met Glu Cys Cys Gly Val Cys His
            35                  40                  45

Thr Asp Leu His Val Lys Asn Gly Asp Phe Gly Asp Lys Thr Gly Val
    50                  55                  60

Ile Leu Gly His Glu Gly Ile Gly Val Val Ala Glu Val Gly Pro Gly
65                  70                  75                  80

Val Thr Ser Leu Lys Pro Gly Asp Arg Ala Ser Val Ala Trp Phe Tyr
                85                  90                  95

Glu Gly Cys Gly His Cys Glu Tyr Cys Asn Ser Gly Asn Glu Thr Leu
            100                 105                 110

Cys Arg Ser Val Lys Asn Ala Gly Tyr Ser Val Asp Gly Gly Met Ala
        115                 120                 125

Glu Glu Cys Ile Val Val Ala Asp Tyr Ala Val Lys Val Pro Asp Gly
    130                 135                 140

Leu Asp Ser Ala Ala Ala Ser Ser Ile Thr Cys Ala Gly Val Thr Thr
145                 150                 155                 160

Tyr Lys Ala Val Lys Leu Ser Lys Ile Arg Pro Gly Gln Trp Ile Ala
                165                 170                 175

Ile Tyr Gly Leu Gly Gly Leu Gly Asn Leu Ala Leu Gln Tyr Ala Lys
            180                 185                 190

Asn Val Phe Asn Ala Lys Val Ile Ala Ile Asp Val Asn Asp Glu Gln
        195                 200                 205

Leu Lys Leu Ala Thr Glu Met Gly Ala Asp Leu Ala Ile Asn Ser Arg
    210                 215                 220

Thr Glu Asp Ala Ala Lys Ile Val Gln Glu Lys Thr Gly Gly Ala His
225                 230                 235                 240

Ala Ala Val Val Thr Ala Val Ala Lys Ala Ala Phe Asn Ser Ala Val
                245                 250                 255

Asp Ala Val Arg Ala Gly Gly Arg Val Val Ala Val Gly Leu Pro Pro
            260                 265                 270

Glu Ser Met Ser Leu Asp Ile Pro Arg Leu Val Leu Asp Gly Ile Glu
        275                 280                 285

Val Val Ser Ser Leu Val Gly Thr Arg Gln Asp Leu Thr Glu Ala Phe
    290                 295                 300

Gln Phe Ala Ala Glu Gly Lys Val Val Pro Lys Val Ala Leu Arg Pro
```

```
            305                 310                 315                 320
Leu Ala Asp Ile Asn Thr Ile Phe Thr Glu Met Glu Glu Gly Lys Ile
                325                 330                 335
Arg Gly Arg Met Val Ile Asp Phe Arg Arg
                340                 345

<210> SEQ ID NO 59
<211> LENGTH: 346
<212> TYPE: PRT
<213> ORGANISM: Escherichia coli

<400> SEQUENCE: 59

Met Gln Asn Ile Ile Arg Lys Gly Gly Thr Met Lys Ala Ala Val Val
1               5                   10                  15

Thr Lys Asp His His Val Asp Val Thr Asp Lys Thr Leu Arg Ser Leu
                20                  25                  30

Lys His Gly Glu Ala Leu Leu Lys Met Glu Cys Cys Gly Val Cys His
            35                  40                  45

Thr Asp Leu His Val Lys Asn Gly Asp Phe Gly Asp Lys Thr Gly Val
        50                  55                  60

Ile Leu Gly His Glu Gly Ile Gly Val Val Ala Glu Val Gly Pro Gly
65                  70                  75                  80

Val Thr Ser Leu Lys Pro Gly Asp Arg Ala Ser Val Ala Trp Phe Tyr
                85                  90                  95

Glu Gly Cys Gly His Cys Glu Tyr Cys Asn Ser Gly Asn Glu Thr Leu
            100                 105                 110

Cys Arg Ser Val Lys Asn Ala Gly Tyr Ser Val Asp Gly Gly Met Ala
        115                 120                 125

Glu Glu Cys Ile Val Val Ala Asp Tyr Ala Val Lys Val Pro Asp Gly
130                 135                 140

Leu Asp Ser Ala Ala Ser Ser Ile Thr Cys Ala Gly Val Thr Thr
145                 150                 155                 160

Tyr Lys Ala Val Lys Leu Ser Lys Ile Arg Pro Gly Gln Trp Ile Ala
                165                 170                 175

Ile Tyr Gly Leu Gly Gly Leu Gly Asn Leu Ala Leu Gln Tyr Ala Lys
            180                 185                 190

Asn Val Phe Asn Ala Lys Val Ile Ala Ile Asp Val Asn Asp Glu Gln
        195                 200                 205

Leu Lys Leu Ala Thr Glu Met Gly Ala Asp Leu Ala Ile Asn Ser Arg
210                 215                 220

Thr Glu Asp Ala Ala Arg Ile Val Gln Glu Lys Ala Gly Gly Ala His
225                 230                 235                 240

Ala Ala Val Val Thr Ala Val Ala Lys Ala Ala Phe Asn Ser Ala Val
                245                 250                 255

Asp Ala Val Arg Ala Gly Gly Arg Val Val Ala Val Gly Leu Pro Pro
            260                 265                 270

Glu Ser Met Ser Leu Asp Ile Pro Arg Leu Val Leu Asp Gly Ile Glu
        275                 280                 285

Val Val Gly Ser Leu Val Gly Thr Arg Gln Asp Leu Thr Glu Ala Phe
290                 295                 300

Gln Phe Ala Ala Glu Gly Lys Val Val Pro Lys Val Ala Leu Arg Pro
305                 310                 315                 320

Leu Ala Asp Ile Asn Thr Ile Phe Thr Glu Met Glu Glu Gly Lys Ile
                325                 330                 335
```

Arg Gly Arg Met Val Ile Asp Phe Arg Arg
            340                 345

<210> SEQ ID NO 60
<211> LENGTH: 375
<212> TYPE: PRT
<213> ORGANISM: Shigella dysenteriae

<400> SEQUENCE: 60

Met Gln Asn Ile Ile Arg Lys Gly Gly Thr Met Lys Ala Ala Val Val
1               5                   10                  15

Thr Lys Asp His His Val Asp Val Thr Asp Lys Thr Leu Arg Ser Leu
            20                  25                  30

Lys His Asp Glu Ala Leu Leu Lys Met Glu Cys Cys Gly Val Cys His
        35                  40                  45

Thr Asp Leu His Val Lys Asn Gly Asp Phe Gly Asp Lys Thr Ser Val
    50                  55                  60

Ile Leu Gly His Glu Gly Ile Gly Val Val Ala Glu Val Gly Pro Gly
65              70                  75                  80

Val Thr Ser Leu Lys Pro Gly Asp Arg Ala Ser Val Ala Trp Phe Tyr
                85                  90                  95

Glu Gly Cys Gly His Cys Glu Tyr Cys Asn Ser Gly Asn Glu Thr Leu
            100                 105                 110

Cys Arg Ser Val Lys Asn Ala Gly Tyr Ser Val Asp Gly Gly Met Ala
        115                 120                 125

Gln Glu Cys Ile Val Ala Asp Tyr Ala Val Lys Val Pro Asp Gly
    130                 135                 140

Leu Asp Ser Ala Ala Ala Ser Ser Ile Thr Cys Ala Gly Val Thr Thr
145                 150                 155                 160

Tyr Lys Ala Val Lys Leu Ser Lys Ile Arg Pro Gly Gln Trp Ile Ala
                165                 170                 175

Ile Tyr Gly Leu Gly Gly Leu Gly Asn Leu Ala Leu Gln Tyr Ala Lys
            180                 185                 190

Asn Val Phe Asn Ala Lys Val Ile Ala Ile Asp Val Asn Asp Glu Gln
        195                 200                 205

Leu Lys Leu Ala Thr Glu Met Gly Ala Asp Leu Ala Ile Asn Ser Arg
    210                 215                 220

Thr Glu Asp Ala Ala Lys Ile Val Gln Glu Lys Thr Gly Gly Ala His
225                 230                 235                 240

Ala Ala Val Val Thr Ala Val Ala Lys Ala Ala Phe Asn Ser Ala Val
                245                 250                 255

Asp Ala Val Arg Ala Gly Gly His Val Val Ala Val Gly Leu Pro Pro
            260                 265                 270

Glu Ser Met Ser Leu Asp Ile Pro Arg Leu Val Leu Asp Gly Ile Glu
        275                 280                 285

Val Val Gly Ser Leu Val Gly Thr Arg Gln Asp Leu Thr Glu Ala Phe
    290                 295                 300

Gln Phe Ala Ala Glu Gly Lys Val Val Pro Lys Val Ala Leu Arg Pro
305                 310                 315                 320

Leu Ala Asp Ile Asn Thr Ile Phe Thr Glu Met Glu Glu Gly Lys Ile
                325                 330                 335

Arg Gly Arg Met Val Ile Asp Phe Arg Arg Ser Glu Ala Phe Ala Ala
            340                 345                 350

Thr Ala Ser Pro Gly Val Ala Ala Ser His Thr Leu Gln His Glu Met
        355                 360                 365

```
Ala Lys Trp Ile Ile Val Ala
    370             375

<210> SEQ ID NO 61
<211> LENGTH: 336
<212> TYPE: PRT
<213> ORGANISM: Escherichia coli

<400> SEQUENCE: 61

Met Lys Ala Ala Val Val Thr Lys Asp His His Val Asp Val Thr Tyr
1               5                   10                  15

Lys Thr Leu Arg Ser Leu Lys His Gly Glu Ala Leu Leu Lys Met Glu
            20                  25                  30

Cys Cys Gly Val Cys His Thr Asp Leu His Val Lys Asn Gly Asp Phe
        35                  40                  45

Gly Asp Lys Thr Gly Val Ile Leu Gly His Glu Gly Ile Gly Val Val
    50                  55                  60

Ala Glu Val Gly Pro Gly Val Thr Ser Leu Lys Pro Gly Asp Arg Ala
65                  70                  75                  80

Ser Val Ala Trp Phe Tyr Glu Gly Cys Gly His Cys Glu Tyr Cys Asn
                85                  90                  95

Ser Gly Asn Glu Thr Leu Cys Arg Ser Val Lys Asn Ala Gly Tyr Ser
            100                 105                 110

Val Asp Gly Gly Met Ala Glu Cys Ile Val Val Ala Asp Tyr Ala
        115                 120                 125

Val Lys Val Pro Asp Gly Leu Asp Ser Ala Ala Ser Ser Ile Thr
        130                 135                 140

Cys Ala Gly Val Thr Thr Tyr Lys Ala Val Lys Leu Ser Lys Ile Arg
145                 150                 155                 160

Pro Gly Gln Trp Ile Ala Ile Tyr Gly Leu Gly Gly Leu Gly Asn Leu
                165                 170                 175

Ala Leu Gln Tyr Ala Lys Asn Val Phe Asn Ala Lys Val Ile Ala Ile
            180                 185                 190

Asp Val Asn Asp Glu Gln Leu Lys Leu Ala Thr Glu Met Gly Ala Asp
        195                 200                 205

Leu Ala Ile Asn Ser His Thr Glu Asp Ala Ala Lys Ile Val Gln Glu
    210                 215                 220

Lys Thr Gly Gly Ala His Ala Ala Val Val Thr Ala Val Ala Lys Ala
225                 230                 235                 240

Ala Phe Asn Ser Ala Val Asp Ala Val Arg Ala Gly Gly Arg Val Val
                245                 250                 255

Ala Val Gly Leu Pro Pro Glu Ser Met Ser Leu Asp Ile Pro Arg Leu
            260                 265                 270

Val Leu Asp Gly Ile Glu Val Val Gly Ser Leu Val Gly Thr Arg Gln
        275                 280                 285

Asp Leu Thr Glu Ala Phe Gln Phe Ala Ala Glu Gly Lys Val Val Pro
    290                 295                 300

Lys Val Ala Leu Arg Pro Leu Ala Asp Ile Asn Thr Ile Phe Thr Glu
305                 310                 315                 320

Met Glu Glu Gly Lys Ile Arg Gly Arg Met Val Ile Asp Phe Arg His
                325                 330                 335

<210> SEQ ID NO 62
<211> LENGTH: 336
<212> TYPE: PRT
```

<213> ORGANISM: Escherichia coli

<400> SEQUENCE: 62

Met Lys Ala Ala Val Val Thr Lys Asp His His Val Asp Val Thr Asp
1               5                   10                  15

Lys Thr Leu Arg Ser Leu Lys His Gly Glu Ala Leu Leu Lys Met Glu
            20                  25                  30

Cys Cys Gly Val Cys His Thr Asp Leu His Val Lys Asn Gly Asp Phe
        35                  40                  45

Gly Asp Lys Thr Gly Val Ile Leu Gly His Glu Gly Ile Gly Val Val
    50                  55                  60

Ala Glu Val Gly Pro Gly Val Thr Ser Leu Lys Pro Gly Asp Arg Ala
65                  70                  75                  80

Ser Val Ala Trp Phe Tyr Glu Gly Cys Gly His Cys Glu Tyr Cys Asn
                85                  90                  95

Ser Gly Asn Glu Thr Leu Cys Arg Ser Val Lys Asn Ala Gly Tyr Ser
            100                 105                 110

Val Asp Gly Gly Met Ala Glu Cys Ile Val Val Ala Asp Tyr Ala
        115                 120                 125

Val Lys Val Pro Asp Gly Leu Asp Ser Ala Ala Ala Ser Ser Ile Thr
    130                 135                 140

Cys Ala Gly Val Thr Thr Tyr Lys Ala Val Lys Leu Ser Lys Ile Arg
145                 150                 155                 160

Pro Gly Gln Trp Ile Ala Ile Tyr Gly Leu Gly Gly Leu Gly Asn Leu
                165                 170                 175

Ala Leu Gln Tyr Ala Lys Asn Val Phe Asn Ala Lys Val Ile Ala Ile
            180                 185                 190

Asp Val Asn Asp Glu Gln Leu Lys Leu Ala Thr Glu Met Gly Ala Asp
        195                 200                 205

Leu Ala Ile Asn Ser Arg Thr Glu Asp Ala Ala Lys Ile Val Gln Glu
    210                 215                 220

Lys Thr Gly Gly Ala His Ala Ala Val Val Thr Ala Val Ala Lys Ala
225                 230                 235                 240

Ala Phe Asn Ser Ala Val Asp Ala Val Arg Ala Gly Gly Arg Val Val
                245                 250                 255

Ala Val Gly Leu Pro Pro Glu Ser Met Ser Leu Asp Ile Pro Arg Leu
            260                 265                 270

Val Leu Asp Gly Ile Glu Val Val Gly Ser Leu Val Gly Thr Arg Gln
    275                 280                 285

Asp Leu Thr Glu Ala Phe Gln Phe Ala Ala Glu Gly Lys Val Val Pro
290                 295                 300

Lys Val Ala Leu Arg Pro Leu Ala Asp Ile Asn Thr Ile Phe Thr Glu
305                 310                 315                 320

Met Glu Glu Gly Lys Ile Arg Gly Arg Met Val Ile Asp Phe Arg Arg
                325                 330                 335

<210> SEQ ID NO 63
<211> LENGTH: 336
<212> TYPE: PRT
<213> ORGANISM: Escherichia coli

<400> SEQUENCE: 63

Met Lys Ala Ala Val Val Thr Lys Asp His His Val Asp Val Thr Asp
1               5                   10                  15

Lys Thr Leu Arg Ser Leu Lys His Gly Glu Ala Leu Leu Lys Met Glu

```
            20                  25                  30
Cys Cys Gly Val Cys His Thr Asp Leu His Val Lys Asn Gly Asp Phe
         35                  40                  45

Gly Asp Lys Thr Gly Val Ile Leu Gly His Glu Gly Ile Gly Val Val
 50                  55                  60

Ala Glu Val Gly Pro Gly Val Thr Ser Leu Lys Pro Gly Asp Arg Ala
 65                  70                  75                  80

Ser Val Ala Trp Phe Tyr Glu Gly Cys Gly His Cys Glu Tyr Cys Asn
                 85                  90                  95

Ser Gly Asn Glu Thr Leu Cys Arg Ser Val Lys Asn Ala Gly Tyr Ser
            100                 105                 110

Val Asp Gly Gly Met Ala Glu Cys Ile Val Val Ala Asp Tyr Ala
            115                 120                 125

Val Lys Val Pro Asp Gly Leu Asp Ser Ala Ala Asn Ser Ile Thr
            130                 135                 140

Cys Ala Gly Val Thr Thr Tyr Lys Ala Val Lys Leu Ser Lys Ile Arg
145                 150                 155                 160

Pro Gly Gln Trp Ile Ala Ile Tyr Gly Leu Gly Gly Leu Gly Asn Leu
                165                 170                 175

Ala Leu Gln Tyr Ala Lys Asn Val Phe Asn Ala Lys Val Ile Ala Ile
            180                 185                 190

Asp Val Asn Asp Glu Gln Leu Lys Leu Ala Thr Glu Met Gly Ala Asp
            195                 200                 205

Leu Ala Ile Asn Ser Arg Thr Glu Asp Ala Ala Lys Ile Val Gln Glu
            210                 215                 220

Lys Thr Gly Gly Ala His Ala Ala Val Val Thr Ala Val Ala Lys Ala
225                 230                 235                 240

Ala Phe Asn Ser Ala Val Asp Ala Val Arg Ala Gly Gly Arg Val Val
                245                 250                 255

Ala Val Gly Leu Pro Pro Glu Ser Met Ser Leu Asp Ile Pro Arg Leu
            260                 265                 270

Val Leu Asp Gly Ile Glu Val Val Gly Ser Leu Val Gly Thr Arg Gln
            275                 280                 285

Asp Leu Thr Glu Ala Phe Gln Phe Ala Ala Glu Gly Lys Val Val Pro
 290                 295                 300

Lys Val Ala Leu Arg Pro Leu Ala Asp Ile Asn Thr Ile Phe Thr Glu
305                 310                 315                 320

Met Glu Glu Gly Lys Ile Arg Gly Arg Met Val Ile Asp Phe Arg Arg
                325                 330                 335

<210> SEQ ID NO 64
<211> LENGTH: 336
<212> TYPE: PRT
<213> ORGANISM: Escherichia fergusonii

<400> SEQUENCE: 64

Met Lys Ala Ala Val Val Thr Lys Asp His His Val Asp Val Thr Asp
 1               5                  10                  15

Lys Thr Leu Arg Ser Leu Lys His Gly Glu Ala Leu Leu Lys Met Glu
            20                  25                  30

Cys Cys Gly Val Cys His Thr Asp Leu His Val Lys Asn Gly Asp Phe
         35                  40                  45

Gly Asp Lys Thr Gly Val Ile Leu Gly His Glu Gly Ile Gly Val Val
 50                  55                  60
```

Ala Glu Val Gly Pro Gly Val Thr Ser Leu Lys Pro Gly Asp Arg Ala
65                  70                  75                  80

Ser Val Ala Trp Phe Tyr Glu Gly Cys Gly His Cys Glu Tyr Cys Asn
            85                  90                  95

Ser Gly Asn Glu Thr Leu Cys Arg Ser Val Lys Asn Ala Gly Tyr Ser
        100                 105                 110

Val Asp Gly Gly Met Ala Glu Cys Ile Val Val Ala Asp Tyr Ala
        115                 120                 125

Val Lys Val Pro Asp Gly Leu Asp Ser Ala Ala Ser Ser Ile Thr
    130                 135                 140

Cys Ala Gly Val Thr Thr Tyr Lys Ala Val Lys Leu Ser Lys Ile Arg
145                 150                 155                 160

Pro Gly Gln Trp Ile Ala Ile Tyr Gly Leu Gly Gly Leu Gly Asn Leu
                165                 170                 175

Ala Leu Gln Tyr Ala Lys Asn Val Phe Asn Ala Lys Val Ile Ala Ile
                180                 185                 190

Asp Val Asn Asp Glu Gln Leu Lys Leu Ala Thr Glu Ile Gly Ala Asp
                195                 200                 205

Leu Ala Ile Asn Ser Arg Thr Glu Asp Ala Ala Lys Ile Val Gln Glu
210                 215                 220

Lys Thr Gly Gly Ala His Ala Ala Val Val Thr Ala Val Ala Lys Ala
225                 230                 235                 240

Ala Phe Asn Ser Ala Val Asp Ala Val Arg Ala Gly Gly Arg Val Val
                245                 250                 255

Ala Val Gly Leu Pro Pro Glu Ser Met Ser Leu Asp Ile Pro Arg Leu
                260                 265                 270

Val Leu Asp Gly Ile Glu Val Val Gly Ser Leu Val Gly Thr Arg Gln
            275                 280                 285

Asp Leu Thr Glu Ala Phe Gln Phe Ala Ala Glu Gly Lys Val Val Pro
            290                 295                 300

Lys Val Ala Leu Arg Pro Leu Ala Asp Ile Asn Thr Ile Phe Thr Glu
305                 310                 315                 320

Met Glu Glu Gly Lys Ile Arg Gly Arg Met Val Ile Asp Phe Arg Arg
                325                 330                 335

<210> SEQ ID NO 65
<211> LENGTH: 336
<212> TYPE: PRT
<213> ORGANISM: Escherichia coli

<400> SEQUENCE: 65

Met Lys Ala Ala Val Val Thr Lys Asp His His Val Asp Val Thr Asp
1               5                   10                  15

Lys Thr Leu Arg Ser Leu Lys His Gly Glu Ala Leu Leu Lys Met Glu
                20                  25                  30

Cys Cys Gly Val Cys His Thr Asp Leu His Val Lys Asn Gly Asp Phe
            35                  40                  45

Gly Asp Lys Thr Gly Val Ile Leu Gly His Glu Gly Ile Gly Val Val
        50                  55                  60

Ala Glu Val Gly Pro Gly Val Thr Ser Leu Lys Pro Gly Asp Arg Ala
65                  70                  75                  80

Ser Val Ala Trp Phe Tyr Glu Gly Cys Gly His Cys Glu Tyr Cys Asn
            85                  90                  95

Ser Gly Asn Glu Thr Leu Cys Arg Ser Val Lys Asn Ala Gly Tyr Ser
        100                 105                 110

```
Val Asp Gly Gly Met Ala Glu Glu Cys Ile Val Val Ala Asp Tyr Ala
            115                 120                 125

Val Lys Val Pro Asp Gly Leu Asp Ser Ala Ala Ser Ser Ile Thr
        130                 135                 140

Cys Ala Gly Val Thr Thr Tyr Lys Ala Val Lys Leu Ser Lys Ile Arg
145                 150                 155                 160

Pro Gly Gln Trp Ile Ala Ile Tyr Gly Leu Gly Gly Leu Gly Asn Leu
                165                 170                 175

Ala Leu Gln Tyr Ala Lys Asn Val Phe Asn Ala Lys Val Ile Ala Ile
                180                 185                 190

Asp Val Asn Asp Glu Gln Leu Lys Leu Ala Thr Glu Met Gly Ala Asp
            195                 200                 205

Leu Ala Ile Asn Ser Arg Thr Glu Asp Ala Ala Arg Ile Val Gln Glu
        210                 215                 220

Lys Ala Gly Gly Ala His Ala Ala Val Val Thr Ala Val Ala Lys Ala
225                 230                 235                 240

Ala Phe Asn Ser Ala Val Asp Ala Val Arg Ala Gly Gly Arg Val Val
                245                 250                 255

Ala Val Gly Leu Pro Pro Glu Ser Met Ser Leu Asp Ile Pro Arg Leu
            260                 265                 270

Val Leu Asp Gly Ile Glu Val Val Gly Ser Leu Val Gly Thr Arg Gln
        275                 280                 285

Asp Leu Thr Glu Ala Phe Gln Phe Ala Ala Glu Gly Lys Val Val Pro
    290                 295                 300

Lys Val Ala Leu Arg Pro Leu Ala Asp Ile Asn Thr Ile Phe Thr Glu
305                 310                 315                 320

Met Glu Glu Gly Lys Ile Arg Gly Arg Met Val Ile Asp Phe Arg Arg
                325                 330                 335

<210> SEQ ID NO 66
<211> LENGTH: 336
<212> TYPE: PRT
<213> ORGANISM: Escherichia coli

<400> SEQUENCE: 66

Met Lys Ala Ala Val Val Thr Lys Asp His His Val Asp Val Thr Asp
1               5                   10                  15

Lys Thr Leu Arg Ser Leu Lys His Gly Glu Ala Leu Leu Lys Met Glu
                20                  25                  30

Cys Cys Gly Val Cys His Thr Asp Leu His Val Lys Asn Gly Asp Phe
            35                  40                  45

Gly Asp Lys Thr Gly Val Ile Leu Gly His Glu Gly Ile Gly Val Val
        50                  55                  60

Ala Glu Val Gly Ser Gly Val Thr Ser Leu Lys Pro Gly Asp Arg Ala
65                  70                  75                  80

Ser Val Ala Trp Phe Tyr Glu Gly Cys Gly His Cys Glu Tyr Cys Asn
                85                  90                  95

Ser Gly Asn Glu Thr Leu Cys Arg Ser Val Lys Asn Ala Gly Tyr Ser
            100                 105                 110

Val Asp Gly Gly Met Ala Glu Glu Cys Ile Val Val Ala Asp Tyr Ala
            115                 120                 125

Val Lys Val Pro Asp Gly Leu Asp Ser Ala Ala Ser Ser Ile Thr
        130                 135                 140

Cys Ala Gly Val Thr Thr Tyr Lys Ala Val Lys Leu Ser Lys Ile Arg
```

```
              145                 150                 155                 160
Pro Gly Gln Trp Ile Ala Ile Tyr Gly Leu Gly Gly Leu Gly Asn Leu
                165                 170                 175

Ala Leu Gln Tyr Ala Lys Asn Val Phe Asn Ala Lys Val Ile Ala Ile
            180                 185                 190

Asp Val Asn Asp Glu Gln Leu Lys Leu Ala Thr Glu Met Gly Ala Asp
            195                 200                 205

Leu Ala Ile Asn Ser Arg Thr Glu Asp Ala Ala Lys Ile Val Gln Glu
            210                 215                 220

Lys Thr Ser Gly Ala His Ala Ala Val Val Thr Ala Val Ala Lys Ala
225                 230                 235                 240

Ala Phe Asn Ser Ala Val Asp Ala Val Arg Ala Gly Gly Arg Val Val
                245                 250                 255

Ala Val Gly Leu Pro Pro Glu Ser Met Ser Leu Asp Ile Pro Arg Leu
            260                 265                 270

Val Leu Asp Gly Ile Glu Val Val Gly Ser Leu Val Gly Thr Arg Gln
            275                 280                 285

Asp Leu Thr Glu Ala Phe Gln Phe Ala Ala Glu Gly Lys Val Val Pro
            290                 295                 300

Lys Val Ala Leu Arg Pro Leu Ala Asp Ile Asn Thr Ile Phe Thr Glu
305                 310                 315                 320

Met Glu Glu Gly Lys Ile Arg Gly Arg Met Val Ile Asp Phe Arg Arg
                325                 330                 335

<210> SEQ ID NO 67
<211> LENGTH: 336
<212> TYPE: PRT
<213> ORGANISM: Shigella flexneri

<400> SEQUENCE: 67

Met Lys Thr Ala Val Val Thr Lys Asp His His Val Asp Val Thr Asp
1               5                   10                  15

Lys Thr Leu Arg Ser Leu Lys His Gly Glu Ala Leu Leu Lys Met Glu
            20                  25                  30

Cys Cys Gly Val Cys His Thr Asp Leu His Val Lys Asn Gly Asp Phe
        35                  40                  45

Gly Asp Lys Thr Gly Val Ile Leu Gly His Glu Gly Ile Gly Val Val
    50                  55                  60

Ala Glu Val Gly Pro Gly Val Thr Ser Leu Lys Pro Gly Asp Arg Ala
65                  70                  75                  80

Ser Val Ala Trp Phe Tyr Glu Gly Cys Gly His Cys Glu Tyr Cys Asn
                85                  90                  95

Ser Gly Asn Glu Thr Leu Cys Arg Ser Val Lys Asn Ala Gly Tyr Ser
            100                 105                 110

Val Asp Gly Gly Met Glu Glu Glu Cys Ile Val Val Ala Asp Tyr Ala
            115                 120                 125

Val Lys Val Pro Asp Gly Leu Asp Ser Ala Ala Pro Ser Ser Ile Thr
            130                 135                 140

Cys Ala Gly Val Thr Thr Tyr Lys Ala Val Lys Leu Ser Lys Ile Arg
145                 150                 155                 160

Pro Gly Gln Trp Ile Ala Ile Tyr Gly Leu Gly Gly Leu Gly Asn Leu
                165                 170                 175

Ala Leu Gln Tyr Ala Lys Asn Val Phe Asn Ala Lys Val Ile Ala Ile
            180                 185                 190
```

```
Asp Val Asn Asp Glu Gln Leu Lys Leu Ala Thr Glu Met Asp Ala Asp
            195                 200                 205

Leu Ala Ile Asn Ser Arg Thr Glu Asp Ala Ala Lys Ile Val Gln Glu
        210                 215                 220

Lys Thr Gly Gly Ala His Ala Ala Val Val Thr Ala Val Ala Lys Ala
225                 230                 235                 240

Ala Phe Asn Ser Ala Val Asp Ala Val Arg Ala Gly Arg Val Val
                245                 250                 255

Ala Val Gly Leu Pro Pro Glu Ser Met Ser Leu Asp Ile Pro Arg Leu
            260                 265                 270

Val Leu Asp Gly Ile Glu Val Val Gly Ser Leu Val Gly Thr Arg Gln
        275                 280                 285

Asp Leu Thr Glu Ala Phe Gln Phe Ala Ala Glu Gly Lys Val Val Pro
    290                 295                 300

Lys Val Ala Leu Arg Pro Leu Ala Asp Ile Asn Thr Ile Phe Thr Glu
305                 310                 315                 320

Met Glu Glu Gly Lys Ile Arg Gly Arg Met Val Ile Asp Phe Arg His
                325                 330                 335

<210> SEQ ID NO 68
<211> LENGTH: 336
<212> TYPE: PRT
<213> ORGANISM: Escherichia coli

<400> SEQUENCE: 68

Met Lys Ala Ala Val Val Thr Lys Asp His Val Asp Val Thr Asp
1               5                   10                  15

Lys Thr Leu Arg Ser Leu Lys His Gly Glu Ala Leu Leu Lys Met Glu
                20                  25                  30

Cys Cys Gly Val Cys His Thr Asp Leu His Val Lys Asn Gly Asp Phe
            35                  40                  45

Gly Asp Lys Thr Gly Val Ile Leu Gly His Glu Gly Ile Gly Val Val
        50                  55                  60

Ala Glu Val Gly Pro Gly Val Thr Ser Leu Lys Pro Gly Asp Arg Ala
65                  70                  75                  80

Ser Val Ala Trp Phe Tyr Glu Gly Cys Gly His Cys Glu Tyr Cys Asn
                85                  90                  95

Ser Gly Asn Glu Thr Leu Cys Arg Ser Val Lys Asn Ala Gly Tyr Ser
            100                 105                 110

Val Asp Gly Gly Met Ala Glu Glu Cys Ile Val Val Ala Asp Tyr Ala
        115                 120                 125

Val Lys Val Pro Asp Gly Leu Asp Ser Ala Ala Ala Ser Ser Ile Thr
130                 135                 140

Cys Ala Gly Val Thr Thr Tyr Lys Ala Val Lys Leu Ser Lys Ile Arg
145                 150                 155                 160

Pro Gly Gln Trp Ile Ala Ile Tyr Gly Leu Gly Gly Leu Gly Asn Leu
                165                 170                 175

Ala Leu Gln Tyr Ala Lys Asn Val Phe Asn Ala Lys Val Ile Ala Ile
            180                 185                 190

Asp Val Asn Asp Glu Gln Leu Lys Leu Ala Thr Glu Met Gly Ala Asp
        195                 200                 205

Leu Ala Ile Asn Ser Arg Thr Glu Asp Ala Ala Arg Ile Val Gln Glu
    210                 215                 220

Lys Ala Gly Gly Ala His Ala Ala Val Val Thr Ala Val Ala Lys Ala
225                 230                 235                 240
```

```
Ala Phe Asn Ser Ala Val Asp Ala Val Arg Ala Gly Gly Arg Val Val
                245                 250                 255

Ala Val Gly Leu Pro Pro Glu Ser Met Ser Leu Asp Ile Pro Arg Leu
            260                 265                 270

Val Leu Asp Gly Ile Glu Val Val Gly Ser Leu Val Gly Thr Arg Gln
        275                 280                 285

Asp Leu Thr Glu Ala Phe Gln Phe Ala Ala Glu Gly Lys Val Val Pro
    290                 295                 300

Lys Val Ala Leu Arg Pro Leu Glu Asp Ile Asn Thr Ile Phe Thr Glu
305                 310                 315                 320

Met Glu Glu Gly Lys Ile Arg Gly Arg Met Val Ile Asp Phe Arg Arg
                325                 330                 335

<210> SEQ ID NO 69
<211> LENGTH: 336
<212> TYPE: PRT
<213> ORGANISM: Escherichia coli

<400> SEQUENCE: 69

Met Lys Ala Ala Val Val Thr Lys Asp His Val Asp Val Thr Asp
1               5                   10                  15

Lys Thr Leu Arg Ser Leu Lys His Gly Glu Ala Leu Leu Lys Met Glu
                20                  25                  30

Cys Cys Gly Val Cys His Thr Asp Leu His Val Lys Asn Gly Asp Phe
            35                  40                  45

Gly Asp Lys Thr Gly Val Ile Leu Gly His Glu Gly Ile Gly Val Val
        50                  55                  60

Ala Glu Val Gly Pro Gly Val Thr Ser Leu Lys Pro Gly Asp Arg Ala
65                  70                  75                  80

Ser Val Ala Trp Phe Tyr Glu Gly Cys Gly His Cys Glu Tyr Cys Asn
                85                  90                  95

Ser Gly Asn Glu Thr Leu Cys Arg Ser Val Lys Asn Ala Gly Tyr Ser
                100                 105                 110

Val Asp Gly Gly Met Ala Glu Glu Cys Ile Val Val Ala Asp Tyr Ala
            115                 120                 125

Val Lys Val Pro Asp Gly Leu Asp Ser Ala Ala Ala Ser Ser Ile Thr
    130                 135                 140

Cys Ala Gly Val Thr Thr Tyr Lys Ala Val Lys Leu Ser Lys Ile Arg
145                 150                 155                 160

Pro Gly Gln Trp Ile Ala Ile Tyr Gly Leu Gly Gly Leu Gly Asn Leu
                165                 170                 175

Ala Leu Gln Tyr Ala Lys Asn Val Phe Asn Ala Lys Val Ile Ala Ile
                180                 185                 190

Asp Val Asn Asp Glu Gln Leu Lys Leu Ala Thr Lys Met Gly Ala Asp
            195                 200                 205

Leu Ala Ile Asn Ser Arg Thr Glu Asp Ala Ala Lys Ile Val Gln Glu
    210                 215                 220

Lys Ala Gly Gly Ala His Ala Ala Val Val Thr Ala Val Ala Lys Ala
225                 230                 235                 240

Ala Phe Asn Ser Ala Val Asp Ala Val Arg Ala Gly Gly Arg Val Val
                245                 250                 255

Ala Val Gly Leu Pro Pro Glu Ser Met Ser Leu Asp Ile Pro Arg Leu
            260                 265                 270

Val Leu Asp Gly Ile Glu Val Val Gly Ser Leu Val Gly Thr Arg Gln
```

```
            275                 280                 285
Asp Leu Thr Glu Ala Phe Gln Phe Ala Ala Glu Gly Lys Val Val Pro
    290                 295                 300
Lys Val Ala Leu Arg Pro Leu Glu Asp Ile Asn Thr Ile Phe Thr Glu
305                 310                 315                 320
Met Glu Glu Gly Lys Ile Arg Gly Arg Met Val Ile Asp Phe Arg Arg
                325                 330                 335

<210> SEQ ID NO 70
<211> LENGTH: 336
<212> TYPE: PRT
<213> ORGANISM: Escherichia coli

<400> SEQUENCE: 70

Met Lys Ala Ala Val Val Thr Lys Ala His His Val Asp Val Thr Asp
1               5                   10                  15
Lys Thr Leu Arg Ser Leu Lys His Gly Glu Ala Leu Leu Lys Met Glu
                20                  25                  30
Cys Cys Gly Val Cys His Thr Asp Leu His Val Lys Asn Gly Asp Phe
            35                  40                  45
Gly Asp Lys Thr Gly Val Ile Leu Gly His Glu Gly Ile Gly Val Val
    50                  55                  60
Ala Glu Val Gly Pro Gly Val Thr Ser Leu Lys Pro Gly Asp Arg Ala
65              70                  75                  80
Ser Val Ala Trp Phe Tyr Glu Gly Cys Gly His Cys Glu Tyr Cys Asn
                85                  90                  95
Ser Gly Asn Glu Thr Leu Cys Arg Ser Val Lys Asn Ala Gly Tyr Ser
                100                 105                 110
Val Asp Gly Gly Met Ala Glu Glu Cys Ile Val Val Ala Asp Tyr Ala
            115                 120                 125
Val Lys Val Pro Asp Gly Leu Asp Ser Ala Ala Ala Ser Ser Ile Thr
    130                 135                 140
Cys Ala Gly Val Thr Thr Tyr Lys Ala Val Lys Leu Ser Lys Ile Arg
145                 150                 155                 160
Pro Gly Gln Trp Ile Ala Ile Tyr Gly Leu Gly Gly Leu Gly Asn Leu
                165                 170                 175
Ala Leu Gln Tyr Ala Lys Asn Val Phe Asn Ala Lys Val Ile Ala Ile
                180                 185                 190
Asp Val Asn Asp Glu Gln Leu Lys Leu Ala Thr Glu Met Gly Ala Asp
            195                 200                 205
Leu Ala Ile Asn Ser Arg Thr Glu Asp Ala Ala Arg Ile Val Gln Glu
    210                 215                 220
Lys Ala Gly Gly Ala His Ala Ala Val Val Thr Ala Val Ala Lys Ala
225                 230                 235                 240
Ala Phe Asn Ser Ala Val Asp Ala Val Arg Ala Gly Gly Arg Val Val
                245                 250                 255
Ala Val Gly Leu Pro Pro Glu Ser Met Ser Leu Asp Ile Pro Arg Leu
                260                 265                 270
Val Leu Asp Gly Ile Glu Val Val Gly Ser Leu Val Gly Thr Arg Gln
            275                 280                 285
Asp Leu Thr Glu Ala Phe Gln Phe Ala Ala Glu Gly Lys Val Val Pro
    290                 295                 300
Lys Val Ala Leu Arg Pro Leu Glu Asp Ile Asn Thr Ile Phe Thr Glu
305                 310                 315                 320
```

```
Met Glu Glu Gly Lys Ile Arg Gly Arg Met Val Ile Asp Phe Arg Arg
            325                 330                 335
```

<210> SEQ ID NO 71
<211> LENGTH: 365
<212> TYPE: PRT
<213> ORGANISM: Shigella dysentariae

<400> SEQUENCE: 71

```
Met Lys Ala Ala Val Val Thr Lys Asp His Val Asp Val Thr Asp
1               5                   10                  15

Lys Thr Leu Arg Ser Leu Lys His Asp Glu Ala Leu Leu Lys Met Glu
            20                  25                  30

Cys Cys Gly Val Cys His Thr Asp Leu His Val Lys Asn Gly Asp Phe
        35                  40                  45

Gly Asp Lys Thr Ser Val Ile Leu Gly His Glu Gly Ile Gly Val Val
    50                  55                  60

Ala Glu Val Gly Pro Gly Val Thr Ser Leu Lys Pro Gly Asp Arg Ala
65                  70                  75                  80

Ser Val Ala Trp Phe Tyr Glu Gly Cys Gly His Cys Glu Tyr Cys Asn
                85                  90                  95

Ser Gly Asn Glu Thr Leu Cys Arg Ser Val Lys Asn Ala Gly Tyr Ser
            100                 105                 110

Val Asp Gly Gly Met Ala Gln Glu Cys Ile Val Ala Asp Tyr Ala
        115                 120                 125

Val Lys Val Pro Asp Gly Leu Asp Ser Ala Ala Ala Ser Ser Ile Thr
    130                 135                 140

Cys Ala Gly Val Thr Thr Tyr Lys Ala Val Lys Leu Ser Lys Ile Arg
145                 150                 155                 160

Pro Gly Gln Trp Ile Ala Ile Tyr Gly Leu Gly Gly Leu Gly Asn Leu
                165                 170                 175

Ala Leu Gln Tyr Ala Lys Asn Val Phe Asn Ala Lys Val Ile Ala Ile
            180                 185                 190

Asp Val Asn Asp Glu Gln Leu Lys Leu Ala Thr Glu Met Gly Ala Asp
        195                 200                 205

Leu Ala Ile Asn Ser Arg Thr Glu Asp Ala Ala Lys Ile Val Gln Glu
    210                 215                 220

Lys Thr Gly Gly Ala His Ala Ala Val Val Thr Ala Val Ala Lys Ala
225                 230                 235                 240

Ala Phe Asn Ser Ala Val Asp Ala Val Arg Ala Gly Gly His Val Val
                245                 250                 255

Ala Val Gly Leu Pro Pro Glu Ser Met Ser Leu Asp Ile Pro Arg Leu
            260                 265                 270

Val Leu Asp Gly Ile Glu Val Val Gly Ser Leu Val Gly Thr Arg Gln
        275                 280                 285

Asp Leu Thr Glu Ala Phe Gln Phe Ala Ala Glu Gly Lys Val Val Pro
    290                 295                 300

Lys Val Ala Leu Arg Pro Leu Ala Asp Ile Asn Thr Ile Phe Thr Glu
305                 310                 315                 320

Met Glu Glu Gly Lys Ile Arg Gly Arg Met Val Ile Asp Phe Arg Arg
                325                 330                 335

Ser Glu Ala Phe Ala Ala Thr Ala Ser Pro Gly Val Ala Ala Ser His
            340                 345                 350

Thr Leu Gln His Glu Met Ala Lys Trp Ile Ile Val Ala
        355                 360                 365
```

<210> SEQ ID NO 72
<211> LENGTH: 336
<212> TYPE: PRT
<213> ORGANISM: Salmonella enterica

<400> SEQUENCE: 72

Met Lys Ala Ala Val Val Thr Gln Asp His Gln Val Asp Val Thr Glu
1               5                   10                  15

Lys Thr Leu Arg Pro Leu Arg His Gly Glu Ala Leu Leu Lys Met Glu
            20                  25                  30

Cys Cys Gly Val Cys His Thr Asp Leu His Val Lys Asn Gly Asp Phe
        35                  40                  45

Gly Asp Lys Thr Gly Val Ile Leu Gly His Glu Gly Ile Gly Val Val
50                  55                  60

Ala Glu Val Gly Pro Gly Val Thr Ser Leu Lys Pro Gly Asp Arg Ala
65                  70                  75                  80

Ser Val Ala Trp Phe Tyr Glu Gly Cys Gly His Cys Glu Tyr Cys Asn
                85                  90                  95

Thr Gly Asn Glu Thr Leu Cys Arg Asn Val Lys Asn Ala Gly Tyr Thr
            100                 105                 110

Val Asp Gly Gly Met Ala Glu Glu Cys Ile Val Val Ala Asp Tyr Ala
        115                 120                 125

Val Lys Val Pro Glu Gly Leu Asp Ser Ala Ala Ser Ser Ile Thr
130                 135                 140

Cys Ala Gly Val Thr Thr Tyr Lys Ala Val Lys Ile Ser His Ile Lys
145                 150                 155                 160

Pro Gly Gln Trp Ile Ala Ile Tyr Gly Leu Gly Gly Leu Gly Asn Leu
                165                 170                 175

Ala Leu Gln Tyr Ala Lys Asn Val Phe Asn Ala Lys Val Ile Ala Ile
            180                 185                 190

Asp Val Asn Asp Gly Gln Leu Lys Leu Ala Glu Met Gly Ala Asp
        195                 200                 205

Leu Thr Ile Asn Ser Arg Thr Glu Asp Ala Ala Lys Ile Val Gln Glu
210                 215                 220

Lys Thr Gly Gly Ala His Ala Ala Val Val Thr Ala Val Ala Lys Ala
225                 230                 235                 240

Ala Phe Asn Ser Ala Val Asp Ala Val Arg Ala Gly Gly Arg Val Val
                245                 250                 255

Ala Val Gly Leu Pro Pro Glu Ala Met Asn Leu Asp Ile Pro Arg Leu
            260                 265                 270

Val Leu Asp Gly Ile Gln Val Val Gly Ser Leu Val Gly Thr Arg Gln
        275                 280                 285

Asp Leu Thr Glu Ala Phe Gln Phe Ala Ala Glu Gly Lys Val Val Pro
290                 295                 300

Lys Val Ala Leu Arg Pro Leu Asp Ile Asn Val Ile Phe Lys Glu
305                 310                 315                 320

Met Glu Gln Gly Gln Ile Arg Gly Arg Met Val Ile Asp Phe Arg Arg
                325                 330                 335

<210> SEQ ID NO 73
<211> LENGTH: 336
<212> TYPE: PRT
<213> ORGANISM: Salmonella enterica

<400> SEQUENCE: 73

```
Met Lys Ala Ala Val Val Thr Gln Asp His Gln Val Asp Val Thr Glu
1               5                   10                  15

Lys Thr Leu Arg Pro Leu Arg His Gly Glu Ala Leu Leu Lys Met Glu
            20                  25                  30

Cys Cys Gly Val Cys His Thr Asp Leu His Val Lys Asn Gly Asp Phe
        35                  40                  45

Gly Asp Lys Thr Gly Val Ile Leu Gly His Glu Gly Ile Gly Val Val
        50                  55                  60

Ala Glu Val Gly Pro Gly Val Thr Ser Leu Lys Pro Gly Asp Arg Ala
65                  70                  75                  80

Ser Val Ala Trp Phe Tyr Glu Gly Cys Gly His Cys Glu Tyr Cys Asn
                85                  90                  95

Thr Gly Asn Glu Thr Leu Cys Arg Asn Val Lys Asn Ala Gly Tyr Thr
            100                 105                 110

Val Asp Gly Gly Met Ala Glu Glu Cys Ile Val Val Ala Asp Tyr Ala
        115                 120                 125

Val Lys Val Pro Glu Gly Leu Asp Ser Ala Ala Ala Ser Ser Ile Thr
130                 135                 140

Cys Ala Gly Val Thr Thr Tyr Lys Ala Val Lys Ile Ser His Ile Lys
145                 150                 155                 160

Pro Gly Gln Trp Ile Ala Ile Tyr Gly Leu Gly Gly Leu Gly Asn Leu
                165                 170                 175

Ala Leu Gln Tyr Ala Lys Asn Val Phe Asn Ala Lys Val Ile Ala Ile
            180                 185                 190

Asp Val Asn Asp Gly Gln Leu Lys Leu Ala Glu Met Gly Ala Asp
        195                 200                 205

Leu Thr Ile Asn Ser Arg Thr Glu Asp Ala Ala Lys Ile Val Gln Glu
        210                 215                 220

Lys Thr Gly Gly Ala His Ala Ala Val Val Thr Ala Val Ala Lys Ala
225                 230                 235                 240

Ala Phe Asn Ser Ala Val Asp Ala Val Arg Ala Gly Gly Arg Val Val
                245                 250                 255

Ala Val Gly Leu Pro Pro Glu Ala Met Asn Leu Asp Ile Pro Arg Leu
            260                 265                 270

Val Leu Asp Gly Ile Gln Val Val Gly Ser Leu Val Gly Thr Arg Gln
        275                 280                 285

Asp Leu Thr Glu Ala Phe Gln Phe Ala Ala Glu Gly Lys Val Val Pro
290                 295                 300

Lys Val Ala Leu Arg Pro Leu Glu Asp Ile Asn Ala Ile Phe Lys Glu
305                 310                 315                 320

Met Glu Gln Gly Gln Ile Arg Gly Arg Met Val Ile Asp Phe Arg Arg
                325                 330                 335

<210> SEQ ID NO 74
<211> LENGTH: 336
<212> TYPE: PRT
<213> ORGANISM: Salmonella enterica

<400> SEQUENCE: 74

Met Lys Ala Val Val Thr Gln Asp His Gln Val Asp Val Thr Glu
1               5                   10                  15

Lys Thr Leu Arg Pro Leu Arg His Gly Glu Ala Leu Leu Lys Met Glu
            20                  25                  30

Cys Cys Gly Val Cys His Thr Asp Leu His Val Lys Asn Gly Asp Phe
```

```
            35                  40                  45
Gly Asp Lys Thr Gly Val Ile Leu Gly His Glu Gly Ile Gly Val Val
 50                  55                  60

Ala Glu Val Gly Pro Gly Val Thr Ser Leu Lys Pro Gly Asp Arg Ala
 65                  70                  75                  80

Ser Val Ala Trp Phe Tyr Glu Gly Cys Gly His Cys Glu Tyr Cys Asn
                 85                  90                  95

Thr Gly Asn Glu Thr Leu Cys Arg Asn Val Lys Asn Ala Gly Tyr Thr
            100                 105                 110

Val Asp Gly Gly Met Ala Glu Glu Cys Ile Val Val Ala Asp Tyr Ala
            115                 120                 125

Val Lys Val Pro Glu Gly Leu Asp Ser Ala Ala Ser Ser Ile Thr
130                 135                 140

Cys Ala Gly Val Thr Thr Tyr Lys Ala Val Lys Ile Ser His Ile Lys
145                 150                 155                 160

Pro Gly Gln Trp Ile Ala Ile Tyr Gly Leu Gly Gly Leu Gly Asn Leu
                165                 170                 175

Ala Leu Gln Tyr Ala Lys Asn Val Phe Asn Ala Lys Val Ile Ala Ile
            180                 185                 190

Asp Val Asn Asp Gly Gln Leu Lys Leu Ala Glu Glu Met Gly Ala Asp
            195                 200                 205

Leu Thr Ile Asn Ser Arg Thr Glu Asp Ala Ala Lys Ile Val Gln Glu
210                 215                 220

Lys Thr Gly Gly Ala His Ala Ala Val Val Thr Ala Val Ala Lys Ala
225                 230                 235                 240

Ala Phe Asn Ser Ala Val Asp Ala Val Arg Ala Gly Gly Arg Val Val
                245                 250                 255

Ala Val Gly Leu Pro Pro Glu Ala Met Asn Leu Asp Ile Pro Arg Leu
            260                 265                 270

Val Leu Asp Gly Ile Gln Val Val Gly Ser Leu Val Gly Thr Arg Gln
            275                 280                 285

Asp Leu Thr Glu Ala Phe Gln Phe Ala Ala Glu Gly Lys Val Val Pro
290                 295                 300

Lys Val Ala Leu Arg Pro Leu Glu Asp Ile Asn Val Ile Phe Lys Glu
305                 310                 315                 320

Met Glu Gln Gly Gln Ile Arg Gly Arg Met Val Ile Asp Phe Arg Arg
                325                 330                 335

<210> SEQ ID NO 75
<211> LENGTH: 336
<212> TYPE: PRT
<213> ORGANISM: Salmonella enterica

<400> SEQUENCE: 75

Met Lys Ala Ala Val Val Thr Gln Asp His Gln Val Asp Val Thr Glu
 1               5                  10                  15

Lys Thr Leu Arg Pro Leu Arg His Gly Glu Ala Leu Leu Lys Met Glu
                20                  25                  30

Cys Cys Gly Val Cys His Thr Asp Leu His Val Lys Asn Gly Asp Phe
            35                  40                  45

Gly Asp Lys Thr Gly Val Ile Leu Gly His Glu Gly Ile Gly Val Val
 50                  55                  60

Ala Glu Val Gly Pro Gly Val Thr Ser Leu Lys Pro Gly Asp Arg Ala
 65                  70                  75                  80
```

Ser Val Ala Trp Phe Tyr Glu Gly Cys Gly His Cys Glu Tyr Cys Asn
            85                  90                  95

Thr Gly Asn Glu Thr Leu Cys Arg Asn Val Lys Asn Ala Gly Tyr Thr
        100                 105                 110

Val Asp Gly Gly Met Ala Glu Glu Cys Ile Val Val Ala Asp Tyr Ala
        115                 120                 125

Val Lys Val Pro Glu Gly Leu Asp Ser Ala Ala Ser Ser Ile Thr
        130                 135                 140

Cys Ala Gly Val Ala Thr Tyr Lys Ala Val Lys Ile Ser His Ile Lys
145                 150                 155                 160

Pro Gly Gln Trp Ile Ala Ile Tyr Gly Leu Gly Gly Leu Gly Asn Leu
                165                 170                 175

Ala Leu Gln Tyr Ala Lys Asn Val Phe Asn Ala Lys Val Ile Ala Ile
                180                 185                 190

Asp Val Asn Asp Gly Gln Leu Lys Leu Ala Glu Glu Met Gly Ala Asp
            195                 200                 205

Leu Thr Ile Asn Ser Arg Thr Glu Asp Ala Ala Lys Ile Val Gln Glu
        210                 215                 220

Lys Thr Gly Gly Ala His Ala Ala Val Val Thr Ala Val Ala Lys Ala
225                 230                 235                 240

Ala Phe Asn Ser Ala Val Asp Ala Val Arg Ala Gly Gly Arg Val Val
                245                 250                 255

Ala Val Gly Leu Pro Pro Glu Ala Met Asn Leu Asp Ile Pro Arg Leu
                260                 265                 270

Val Leu Asp Gly Ile Gln Val Val Gly Ser Leu Val Gly Thr Arg Gln
            275                 280                 285

Asp Leu Thr Glu Ala Phe Gln Phe Ala Ala Glu Gly Lys Val Val Pro
        290                 295                 300

Lys Val Ala Leu Arg Pro Leu Glu Asp Ile Asn Val Ile Phe Lys Glu
305                 310                 315                 320

Met Glu Gln Gly Gln Ile Arg Gly Arg Met Val Ile Asp Phe Arg Arg
                325                 330                 335

<210> SEQ ID NO 76
<211> LENGTH: 336
<212> TYPE: PRT
<213> ORGANISM: Salmonella enterica

<400> SEQUENCE: 76

Met Lys Ala Ala Val Val Thr Gln Asp His Gln Val Asp Val Thr Glu
1               5                   10                  15

Lys Thr Leu Arg Pro Leu Arg His Gly Glu Ala Leu Leu Lys Met Glu
            20                  25                  30

Cys Cys Gly Val Cys His Thr Asp Leu His Val Lys Asn Gly Asp Phe
        35                  40                  45

Gly Asp Lys Thr Gly Val Ile Leu Gly His Glu Gly Ile Gly Val Val
        50                  55                  60

Ala Glu Val Gly Pro Gly Val Thr Ser Leu Lys Pro Gly Asp Arg Ala
65                  70                  75                  80

Ser Val Ala Trp Phe Tyr Glu Gly Cys Gly His Cys Glu His Cys Asn
            85                  90                  95

Thr Gly Asn Glu Thr Leu Cys Arg Asn Val Lys Asn Ala Gly Tyr Thr
        100                 105                 110

Val Asp Gly Gly Met Ala Glu Glu Cys Ile Val Val Ala Asp Tyr Ala
        115                 120                 125

```
Val Lys Val Pro Glu Gly Leu Asp Ser Ala Ala Ser Ser Ile Thr
    130                 135                 140

Cys Ala Gly Val Thr Thr Tyr Lys Ala Val Lys Ile Ser His Ile Lys
145                 150                 155                 160

Pro Gly Gln Trp Ile Ala Ile Tyr Gly Leu Gly Gly Leu Gly Asn Leu
                165                 170                 175

Ala Leu Gln Tyr Ala Lys Asn Val Phe Asn Ala Lys Val Ile Ala Ile
            180                 185                 190

Asp Val Asn Asp Gly Gln Leu Lys Leu Ala Glu Glu Met Gly Ala Asp
        195                 200                 205

Leu Thr Ile Asn Ser Arg Thr Glu Asp Ala Ala Lys Ile Val Gln Glu
    210                 215                 220

Lys Thr Gly Gly Ala His Ala Ala Val Val Thr Ala Val Ala Lys Ala
225                 230                 235                 240

Ala Phe Asn Ser Ala Val Asp Ala Val Arg Ala Gly Gly Arg Val Val
                245                 250                 255

Ala Val Gly Leu Pro Pro Glu Ala Met Asn Leu Asp Ile Pro Arg Leu
            260                 265                 270

Val Leu Asp Gly Ile Gln Val Val Gly Ser Leu Val Gly Thr Arg Gln
        275                 280                 285

Asp Leu Thr Glu Ala Phe Gln Phe Ala Ala Glu Gly Lys Val Val Pro
    290                 295                 300

Lys Val Ala Leu Arg Pro Leu Glu Asp Ile Asn Val Ile Phe Lys Glu
305                 310                 315                 320

Met Glu Gln Gly Gln Ile Arg Gly Arg Met Val Ile Asp Phe Arg Arg
                325                 330                 335

<210> SEQ ID NO 77
<211> LENGTH: 336
<212> TYPE: PRT
<213> ORGANISM: Salmonella enterica

<400> SEQUENCE: 77

Met Lys Ala Ala Val Val Thr Gln Asp His Gln Val Asp Val Thr Glu
1               5                   10                  15

Lys Thr Leu Arg Pro Leu Arg His Gly Glu Ala Leu Leu Lys Met Glu
                20                  25                  30

Cys Cys Gly Val Cys His Thr Asp Leu His Val Lys Asn Gly Asp Phe
            35                  40                  45

Gly Asp Lys Thr Gly Val Ile Leu Gly His Glu Gly Ile Gly Val Val
        50                  55                  60

Ala Glu Val Gly Pro Gly Val Thr Ser Leu Lys Pro Gly Asp Arg Ala
65                  70                  75                  80

Ser Val Ala Trp Phe Tyr Glu Gly Cys Gly His Cys Glu Tyr Cys Asn
                85                  90                  95

Thr Gly Asn Glu Thr Leu Cys Cys Asn Val Lys Asn Ala Gly Tyr Thr
            100                 105                 110

Val Asp Gly Gly Met Ala Glu Glu Cys Ile Val Val Ala Asp Tyr Ala
        115                 120                 125

Val Lys Val Pro Glu Gly Leu Asp Ser Ala Ala Ser Ser Ile Thr
    130                 135                 140

Cys Ala Gly Val Thr Thr Tyr Lys Ala Val Lys Ile Ser His Ile Lys
145                 150                 155                 160

Pro Gly Gln Trp Ile Ala Ile Tyr Gly Leu Gly Gly Leu Gly Asn Leu
```

```
                165                 170                 175
Ala Leu Gln Tyr Ala Lys Asn Val Phe Asn Ala Lys Val Ile Ala Ile
            180                 185                 190

Asp Val Asn Asp Gly Gln Leu Lys Leu Ala Glu Glu Met Gly Ala Asp
            195                 200                 205

Leu Thr Ile Asn Ser Arg Thr Glu Asp Ala Ala Lys Ile Val Gln Glu
        210                 215                 220

Lys Thr Gly Gly Ala His Ala Ala Val Val Thr Ala Val Ala Lys Ala
225                 230                 235                 240

Ala Phe Asn Ser Ala Val Asp Ala Val Arg Ala Gly Gly Arg Val Val
                245                 250                 255

Ala Val Gly Leu Pro Pro Glu Ala Met Asn Leu Asp Ile Pro Arg Leu
            260                 265                 270

Val Leu Asp Gly Ile Gln Val Val Gly Ser Leu Val Gly Thr Arg Gln
            275                 280                 285

Asp Leu Thr Glu Ala Phe Gln Phe Ala Ala Glu Gly Lys Val Val Pro
        290                 295                 300

Lys Val Ala Leu Arg Pro Leu Glu Asp Ile Asn Val Ile Phe Lys Glu
305                 310                 315                 320

Met Glu Gln Gly Gln Ile Arg Gly Arg Met Val Ile Asp Phe Arg Arg
                325                 330                 335
```

<210> SEQ ID NO 78
<211> LENGTH: 347
<212> TYPE: PRT
<213> ORGANISM: Enterobacter cancerogenus

<400> SEQUENCE: 78

```
Met Gln Met His Ile Met Asn Lys Glu Lys Gln Met Lys Ala Ala Val
1               5                   10                  15

Val Thr Gln Asp His Gln Val Asn Val Thr Glu Lys Thr Leu Arg Pro
            20                  25                  30

Leu Lys His Gly Glu Ala Leu Leu Lys Met Glu Cys Cys Gly Val Cys
        35                  40                  45

His Thr Asp Leu His Val Lys Asn Gly Asp Phe Gly Asp Lys Thr Gly
    50                  55                  60

Val Ile Leu Gly His Glu Gly Ile Gly Ile Val Lys Glu Ile Gly Pro
65                  70                  75                  80

Gly Val Asn Ser Leu Lys Val Gly Asp Arg Ala Ser Val Ala Trp Phe
                85                  90                  95

Phe Glu Gly Cys Gly His Cys Glu Tyr Cys Asn Ala Gly Asn Glu Thr
            100                 105                 110

Leu Cys Arg Ser Val Lys Asn Ala Gly Tyr Ser Val Asp Gly Gly Met
        115                 120                 125

Ala Glu Glu Cys Ile Val Thr Ala Asp Tyr Ala Val Lys Val Pro Asp
    130                 135                 140

Gly Leu Gly Ser Ala Ala Ala Ser Ser Ile Thr Cys Ala Gly Val Thr
145                 150                 155                 160

Thr Tyr Lys Ala Val Lys Ile Ser Thr Ile Lys Pro Gly Gln Trp Ile
                165                 170                 175

Ala Ile Tyr Gly Leu Gly Gly Leu Gly Asn Leu Ala Leu Gln Tyr Ala
            180                 185                 190

Lys Asn Val Phe Asn Ala Lys Val Ile Ala Ile Asp Val Asn Asp Glu
        195                 200                 205
```

-continued

```
Gln Leu Lys Leu Ala Ala Ser Met Gly Ala Asp Leu Thr Ile Asn Ser
    210                 215                 220

Arg Asn Glu Asp Ala Ala Lys Val Ile Gln Glu Lys Thr Gly Gly Ala
225                 230                 235                 240

His Ala Ala Val Val Thr Ala Val Ala Lys Ala Ala Phe Asn Ser Ala
                245                 250                 255

Val Asp Ala Val Arg Ala Gly Gly Arg Val Val Ala Val Gly Leu Pro
                260                 265                 270

Pro Glu Ala Met Ser Leu Asp Ile Pro Arg Leu Val Leu Asp Gly Ile
            275                 280                 285

Gln Val Val Gly Ser Leu Val Gly Thr Arg Gln Asp Leu Val Glu Ala
    290                 295                 300

Phe Gln Phe Ala Ala Glu Gly Lys Val Val Pro Lys Val Thr Met Arg
305                 310                 315                 320

Pro Leu Glu Asp Ile Asn Ala Ile Phe Lys Glu Met Glu Gln Gly Gln
                325                 330                 335

Ile Arg Gly Arg Met Val Ile Asp Leu Arg Ala
                340                 345
```

The embodiments of the invention in which an exclusive property or privilege is claimed are defined as follows:

1. A recombinant prokaryotic microorganism metabolically engineered from a parental prokaryotic microorganism to produce 1,4-butanediol, said recombinant prokaryotic microorganism comprising genes encoding the following:
   a. a xylonate dehydrogenase that catalyzes the conversion of xylose to xylonic acid, wherein said xylonate dehydrogenase comprises an amino acid sequence having at least 90% sequence identity to the amino acid sequence of SEQ ID NO: 2 or to the amino acid sequence of SEQ ID NO: 4;
   b. a xylonate dehydratase that catalyzes the conversion of xylonic acid to 3-deoxy-D-glycero-pentulosonic acid, wherein said xylonate dehydratase comprises an amino acid sequence having at least 90% sequence identity to the amino acid sequence of SEQ ID NO: 6 or to the amino acid sequence of SEQ ID NO: 8;
   c. a decarboxylase that catalyzes conversion of 3-deoxy-D-glycero-pentulosonic acid to 3,4-dihydroxy-D-butanal, wherein said decarboxylase comprises an amino acid sequence having at least 90% sequence identity to SEQ ID NO: 9;
   d. a first alcohol dehydrogenase that catalyzes conversion of 3,4-dihydroxy-D-butanal to 1,2,4-butanetriol, wherein said first alcohol dehydrogenase comprises an amino acid sequence having at least 90% sequence identity to the amino acid sequence of SEQ ID NO:10;
   e. a diol dehydratase that catalyzes conversion of 1,2,4-butanetriol to 4-hydroxybutanal, wherein said diol dehydratase is selected from the group consisting of GldABC from Klebsiella, PddABC from Klebsiella, or DhaB123 from Clostridium; and
   f. a second alcohol dehydrogenase that catalyzes conversion of 4-hydroxybutanal to 1,4-butanediol, wherein said second alcohol dehydrogenase comprises an amino acid sequence having at least 90% sequence identity to the amino acid sequence of SEQ ID NO: 10; wherein at least one of the genes encoding said xylonate dehydrogenase, said xylonate dehydratase, said decarboxylase, said first alcohol dehydrogenase, said diol dehydratase, and said second alcohol dehydrogenase is heterologous to said recombinant prokaryotic microorganism and is associated with a heterologous expression control sequence resulting in the overexpression thereof.

2. The recombinant prokaryotic microorganism of claim 1, wherein the microorganism over-expresses one or more of the xylonate dehydrogenase, the xylonate dehydratase, the decarboxylase, the first alcohol dehydrogenase, the diol dehydratase, and the second alcohol dehydrogenase, as compared to the parental microorganism.

3. The recombinant prokaryotic microorganism of claim 1, wherein said gene encoding the xylonate dehydrogenase is heterologous to the parental microorganism.

4. The recombinant prokaryotic microorganism of claim 1, wherein said xylonate dehydrogenase comprises the amino acid sequence of SEQ ID NO:2 or SEQ ID NO:4.

5. The recombinant prokaryotic microorganism of claim 1, wherein said gene encoding said xylonate dehydratase is heterologous to the parental microorganism.

6. The recombinant prokaryotic microorganism of claim 1, wherein said xylonate dehydratase is a heterologous D-xylonate dehydratase comprising the amino acid sequence of SEQ ID NO:6 or SEQ ID NO:8.

7. The recombinant prokaryotic microorganism of claim 1, wherein said gene encoding said decarboxylase is heterologous to the parental microorganism.

8. The recombinant prokaryotic microorganism of claim 1, wherein said decarboxylase is a heterologous decarboxylase comprising the amino acid sequence of SEQ ID NO:9.

9. The recombinant prokaryotic microorganism of claim 1, wherein said gene encoding said first alcohol dehydrogenase or said gene encoding said second alcohol dehydrogenase is heterologous to the parental microorganism.

10. The recombinant prokaryotic microorganism of claim 9, wherein said first alcohol dehydrogenase or said second alcohol dehydrogenase comprises the amino acid sequence of SEQ ID NO: 10.

11. The recombinant prokaryotic microorganism of claim 1, wherein said first alcohol dehydrogenase is the same as said second alcohol dehydrogenase.

12. The recombinant prokaryotic microorganism of claim 1, wherein said first alcohol dehydrogenase is different from said second alcohol dehydrogenase.

13. The recombinant prokaryotic microorganism of claim 1, wherein said microorganism further reduces expression of a polypeptide compared to the expression of said polypeptide in the parental prokaryotic organism, wherein said polypeptide produces a flux in the parental prokaryotic organism that competes with one or more metabolic intermediates for the production of 1,4-butanediol, wherein said polypeptide is selected from the group consisting of a D-xylose isomerase, a 2-keto acid aldolase, a 2-keto acid transaminase, a 2-keto acid dehydrogenase, and any combination thereof.

14. The recombinant prokaryotic microorganism of claim 1, wherein said microorganism is selected from *Escherichia, Corynebacterium, Lactobacillus*, and *Bacillus*.

15. The recombinant prokaryotic microorganism of claim 14, wherein said microorganism is *Escherichia coli*.

16. A method of producing 1,4-butanediol, comprising:
   a. providing the recombinant prokaryotic microorganism of claim 1;
   b. culturing said recombinant prokaryotic microorganism in the presence of xylose under conditions suitable for the conversion of xylose to 1,4-butanediol; and
   c. isolating the 1,4-butanediol.

* * * * *